United States Patent
Kawakami et al.

(10) Patent No.: US 9,266,840 B2
(45) Date of Patent: Feb. 23, 2016

(54) BICYCLIC HETEROCYCLIC COMPOUND

(71) Applicant: Astellas Pharma Inc., Tokyo (JP)

(72) Inventors: Shimpei Kawakami, Tokyo (JP);
Minoru Sakurai, Ibaraki (JP); Noriyuki Kawano, Ibaraki (JP); Takayuki Suzuki, Tokyo (JP); Nobuyuki Shiraishi, Tokyo (JP); Wataru Hamaguchi, Tokyo (JP); Ryuichi Sekioka, Tokyo (JP); Hiroyuki Moritomo, Tokyo (JP); Ayako Moritomo, Tokyo (JP)

(73) Assignee: ASTELLAS PHARMA INC., Tokyo (JP)

( * ) Notice: Subject to any disclaimer, the term of this patent is extended or adjusted under 35 U.S.C. 154(b) by 0 days.

(21) Appl. No.: 14/351,965

(22) PCT Filed: Oct. 17, 2012

(86) PCT No.: PCT/JP2012/076771
§ 371 (c)(1),
(2) Date: Apr. 15, 2014

(87) PCT Pub. No.: WO2013/058258
PCT Pub. Date: Apr. 25, 2013

(65) Prior Publication Data
US 2014/0249151 A1    Sep. 4, 2014

(30) Foreign Application Priority Data

Oct. 18, 2011   (JP) ................................ 2011-228822

(51) Int. Cl.
| | | |
|---|---|---|
| C07D 417/14 | (2006.01) | |
| C07D 239/80 | (2006.01) | |
| C07D 401/12 | (2006.01) | |
| C07D 237/28 | (2006.01) | |
| C07D 403/12 | (2006.01) | |
| C07D 401/14 | (2006.01) | |
| C07D 405/14 | (2006.01) | |
| C07D 231/56 | (2006.01) | |
| C07D 403/14 | (2006.01) | |
| C07D 405/12 | (2006.01) | |
| C07D 409/12 | (2006.01) | |
| C07D 409/14 | (2006.01) | |
| C07D 413/12 | (2006.01) | |
| C07D 471/04 | (2006.01) | |

(52) U.S. Cl.
CPC ............ *C07D 237/28* (2013.01); *C07D 231/56* (2013.01); *C07D 239/80* (2013.01); *C07D 401/12* (2013.01); *C07D 401/14* (2013.01); *C07D 403/12* (2013.01); *C07D 403/14* (2013.01); *C07D 405/12* (2013.01); *C07D 405/14* (2013.01); *C07D 409/12* (2013.01); *C07D 409/14* (2013.01); *C07D 413/12* (2013.01); *C07D 417/14* (2013.01); *C07D 471/04* (2013.01)

(58) Field of Classification Search
CPC ... C07D 417/14; C07D 239/80; C07D 401/12
See application file for complete search history.

(56) References Cited

U.S. PATENT DOCUMENTS

| | | | |
|---|---|---|---|
| 5,075,303 A | 12/1991 | Cliffe et al. | |
| 5,194,439 A | 3/1993 | Cliffe et al. | |
| 5,776,945 A | 7/1998 | Nagase et al. | |
| 2009/0088428 A1 | 4/2009 | Saeed et al. | |
| 2009/0111800 A1 | 4/2009 | Aicher et al. | |
| 2009/0264650 A1 | 10/2009 | Cho et al. | |
| 2010/0197662 A1 | 8/2010 | Ogawa et al. | |

FOREIGN PATENT DOCUMENTS

| | | |
|---|---|---|
| CN | 1165513 A | 11/1997 |
| CN | 101426780 A | 5/2009 |
| CN | 101426783 A | 5/2009 |
| EP | 0 395 244 A1 | 10/1990 |
| EP | 0 787 721 A1 | 8/1997 |
| EP | 1 864 971 A1 | 12/2007 |
| EP | 1 894 919 A1 | 3/2008 |

(Continued)

OTHER PUBLICATIONS

Extended European Search Report issued Feb. 20, 2015 in Patent Application No. 12840990.1.
Combined Office Action and Search Report issued Jan. 12, 2015 in Chinese Patent Application No. 201280051414.6 (with English language translation).
International Search Report issued Dec. 4, 2012 in PCT/JP2012/076771 with English Translation.

(Continued)

*Primary Examiner* — Shawquia Jackson
(74) *Attorney, Agent, or Firm* — Oblon, McClelland, Maier & Neustadt, L.L.P

(57) ABSTRACT

To provide a compound useful as an active ingredient of a pharmaceutical composition for treating 11β-hydroxysteroid dehydrogenase type 1-related diseases such as dementia, schizophrenia, depression, pain (particularly, neuropathic pain or fibromyalgia), diabetes (particularly, type II diabetes mellitus), insulin resistance and the like.
[Means for Solution] A bicyclic heterocyclic compound (the bicyclic heterocycle is formed when a cyclohexane ring is fused with a 5- to 6-membered monocyclic heterocycle that has only a nitrogen atom as a hetero atom) substituted with an acylamino group such as a (hetero)aroylamino group or the like or a pharmaceutically acceptable salt thereof was found to have an excellent selective inhibitory action against 11β-HSD1. Accordingly, the bicyclic heterocyclic compound of the present invention can be used for treating dementia, schizophrenia, depression, pain (particularly, neuropathic pain or fibromyalgia), diabetes (particularly, type II diabetes mellitus), insulin resistance, and the like.

16 Claims, No Drawings

(56) References Cited

FOREIGN PATENT DOCUMENTS

| EP | 2 614 824 A1 | 7/2013 |
|---|---|---|
| JP | 2-290852 A | 11/1990 |
| WO | WO 97/03968 A1 | 2/1997 |
| WO | WO 01/68652 A1 | 9/2001 |
| WO | WO 03/082826 A1 | 10/2003 |
| WO | WO 2004/089470 A2 | 10/2004 |
| WO | WO 2006/104280 A1 | 10/2006 |
| WO | WO 2006/105289 A1 | 10/2006 |
| WO | WO 2006/132197 A1 | 12/2006 |
| WO | WO 2006/138508 A2 | 12/2006 |
| WO | WO 2007/050124 A1 | 5/2007 |
| WO | WO 2007/069773 A1 | 6/2007 |
| WO | WO 2007/124254 A2 | 11/2007 |
| WO | WO 2007/124329 A1 | 11/2007 |
| WO | WO 2007/127726 A2 | 11/2007 |
| WO | WO 2007/145834 A2 | 12/2007 |
| WO | WO 2007/145835 A2 | 12/2007 |
| WO | WO 2008/088540 A2 | 7/2008 |
| WO | WO 2011/090738 A2 | 7/2011 |
| WO | WO 2012/033070 A1 | 3/2012 |
| WO | WO 2012/080727 A2 | 6/2012 |
| WO | WO 2012/080729 A2 | 6/2012 |

OTHER PUBLICATIONS

M. S. Cooper et al., "Expression and Functional Consequences of 11β-Hydroxysteroid Dehydrogenase Activity in Human Bone", Bone, vol. 27, 2000, pp. 375-381.
Saaeha Rauz et al. "Expression and Putative Role of 11β-Hydroxysteroid Dehydrogenase Isozymes within the Human Eye", Investigative Opthalmology & Visual Science, vol. 42, 2001, pp. 2037-2042.
Thekkepat C. Sandeep et al., "11 β-Hydroxysteroid Dehydrogenase Inhibition Improves Cognitive Function in Healthy Elderly Men and Type 2 Diabetics", Proceeding of the National Academy of Science, vol. 101, 2004, pp. 6734-6739.
F. Giubilei et al., "Altered Circadian Cortisol Secretion in Alzheimer's Disease: Clinical and Neuroradiological Aspects", Journal of neuroscience research, vol. 66, 2001, pp. 262-265.
Zeynel A. Erkut et al., "Stress of Dying is not Suppressed by High-dose Morphine or by Dementia", Neuropsychopharmacology, vol. 29, 2004, pp. 152-157.
John G. Csernansky, M.D. et al., "Plasma Cortisol and Progression of Dementia in Subjects With Alzheimer-Type Dementia", The American journal of Psychiatry, vol. 163, 2006,pp. 2164-2169.
A.H. Young et al., "The Effects of Chronic Administration of Hydrocortisone on Cognitive Function in Normal Male Volunteers", Psychopharmacology, vol. 145, 1999, pp. 260-266.
P. S. Aisen, M.D. et al., "A Randomized Controlled Trial of Prednisone in Alzheimer's Disease", Neurology, vol. 54, 2000, pp. 588-593.
Joyce L. W. Yau et al., "Lack of Tissue Glucocorticoid, Reactivation in 11 β-hydroxysteroid Dehydrogenase Type 1knockout Mice Ameliorates Age-related Learning Impairments", Proceeding of the National Academy of Science, vol. 98, 2001, pp. 4716-4721.
Xiang Yang Zhang et al., "Cortisol and Cytokines in Chronic and Treatment-Resistant Patients with Schizophrenia: Association with Psychopathology and Response to Antipsychotics", Neuropsychopharmacology, vol. 30, 2005, pp. 1532-1538.
Bernard J. Carroll, MB, PhD, et al., "A Specific Laboratory Test for the Diagnosis of Melancholia", Archives of General Psychiatry, vol. 38, 1981, pp. 15-22.
Gerthe Veen et al., "Salivary Cortisol, Serum Lipids, and Adiposity in Patients with Depressive and Anxiety Disorders", Metabolism, vol. 58, 2009, pp. 821-827.
Dennis 5. Charney, MD, et al., "Psychobiologic Mechanisms of Posttraumatic Stress Disorder", Archives of General Psychiatry, vol. 50, 1993, pp. 294-305.
Hyun Ju Hong et al., "Hypothalamic-Pituitary-Adrenal Reactivity in Boys with Attention Deficit Hyperactivity Disorder", Yonsei Medical Journal, vol. 44, No. 4, 2003, pp. 608-614.
Angelika Erhardtl et al., "Regulation of the Hypothalamic-Pituitary-Adrenocortical System in Patients with Panic Disorder", Neuropsychopharmacology, vol. 31, 2006, pp. 2515-2522.
Monica L. Andersen et al., "Endocrinological and Catecholaminergic Alterations During Sleep Deprivation and Recovery in Male Rats", Journal of Sleep Research, vol. 14, 2005, pp. 83-90.
Eva Rask et al., "Tissue-specific dysregulation of cortisol metabolism in human obesity", The Journal of Clinical Endocrinology & Metabolism, vol. 86, 2001, pp. 1418-1421.
Robert S. Lindsay et al., Subcutaneous Adipose IIfl-Hydroxysteroid Dehydrogenase Type 1 Activity and Messenger Ribonucleic Acid Levels Are Associated with Adiposity and Insulinemia in Pima Indians and Caucasians, The Journal of Clinical Endocrinology & Metabolism, vol. 88, 2003, pp. 2738-2744.
Hiroaki Masuzaki et al., "A Transgenic Model of Visceral Obesity and the Metabolic Syndrome", Science, vol. 294, 2001, pp. 2166-2170.
Hiroaki Masuzaki et al., "Transgenic Amplification of Glucocorticoid Action in Adipose Tissue Causes High Blood Pressure in Mice", The Journal of Clinical Investigation, vol. 112, 2003, pp. 83-90.
Nicholas M. Morton et al., "Improved Lipid and Lipoprotein Profile, Hepatic Insulin Sensitivity, and Glucose Tolerance in 11β-Hydroxysteroid Dehydrogenase Type 1 Null Mice", The Journal of Biological Chemistry, vol. 276, 2001, pp. 41293-41300.
Behrous Davani et al., "Type 1 11β-Hydroxysteroid Dehydrogenase Mediates Glucocorticoid Activation and Insulin Release in Pancreatic Islets", The Journal of Biological Chemistry, vol. 275, 2000, pp. 34841-34844.
I. Klinkenberg et al., Neuroscience and Biobehavioral Reviews, vol. 34, pp. 1307-1350 (2010).

BICYCLIC HETEROCYCLIC COMPOUND

CROSS REFERENCES TO RELATED APPLICATIONS

This application is a 371 of International Patent Application No. PCT/JP2012/076771, filed on Oct. 17, 2012, and claims priority to Japanese Patent Application No. 2011-228822, filed on Oct. 18, 2011.

TECHNICAL FIELD

The present invention relates to a bicyclic heterocyclic compound or a pharmaceutically acceptable salt thereof that is useful as an active ingredient of a pharmaceutical composition, for example, a pharmaceutical composition for treating 11β-hydroxysteroid dehydrogenase type 1 (11β-HSD1)-related diseases such as dementia (particularly, Alzheimer's type dementia), schizophrenia, depression, pain (particularly, neuropathic pain or fibromyalgia), diabetes (particularly, type II diabetes mellitus), and insulin resistance.

BACKGROUND ART

Glucocorticoid is produced from the adrenal gland. In addition, glucocorticoid is converted into an active form from an inactive form at tissue level and acts via its receptor thereof.

11β-hydroxysteroid dehydrogenase (11β-HSD) is an enzyme that catalyzes this conversion, and it is known that there are two subtypes of the enzyme. 11β-hydroxysteroid dehydrogenase type 1 (11β-HSD1) is an enzyme that converts the inactive form into the active form and is highly expressed in the liver, and 11β-hydroxysteroid dehydrogenase type 2 (11β-HSD2) is an enzyme that converts the active form into the inactive form and is highly expressed in the kidneys.

11β-HSD1 is also known to be highly expressed in the brain, but the 11β-HSD2 is practically not expressed in the brain (Thekkepat C. Sandeep et al., Proceedings of the National Academy of Science, 2004, Vol. 101, p. 6734-6739).

As the relationship between glucocorticoid and patients with dementia, the increase in the level of active glucocorticoid (cortisol) in the saliva or blood in patients with Alzheimer's disease (Giubilei F. et al., Journal of neuroscience research, 2001, Vol. 66, p. 262-265, Zeynel A Erkut et al., Neuropsychopharmacology, 2004, Vol. 29, p. 152-157), correlation between HPA axis disorder (John G Csernansky et al., The American journal of Psychiatry, 2006, Vol. 163, p. 2164-2169) as well as cortisol level and the value of bran atrophy index, and the like have been confirmed (Giubilei F. et al., Journal of neuroscience research, 2001, Vol. 66, p. 262-265). In addition, it has been confirmed that the administration of a cortisol or glucocorticoid preparation to a healthy individual or a patient with Alzheimer's disease induces language disorder or memory disorder (A. H. Young et al., Psychopharmacology, 1999, Vol. 145, p. 260-266, P. S. Aisen et al., Neurology, 2000, Vol. 54, p. 588-593). Moreover, as the relationship between 11β-HSD1 and cognition, they reported an action of improving verbal memory by the administration of non-selective 11β-HSD inhibitor to a patient with type II diabetes mellitus (Thekkepat C. Sandeep et al., Proceeding of National Academy of Science, 2004, Vol. 101, p. 6734-6739), as well as an action of ameliorating cognitive disorder in an aged 11β-HSD1 knockout mouse (Joyce L., W. Yau et al., Proceeding of the National Academy of Science, 2001, Vol. 98, p. 4716-4721), and the like.

In this respect, the 11β-HSD1 inhibitor is expected to suppress the action of glucocorticoid in the brain by inhibiting the conversion of glucocorticoid to the active type, and accordingly remedy cognitive disorder induced by glucocorticoid.

In addition to dementia, the 11β-HSD1 inhibitor is also expected to ameliorate central disorders such as schizophrenia (X. Y. Zhang et al., Neuropsychopharmacology, 2005, Vol. 30, p. 1532-1538), depression (Bernard J. Carroll et al., Archives of General Psychiatry, 1981, Vol. 38, p. 15-22), anxiety (Veen G. et al., Metabolism, 2009, Vol. 58, p. 821-827), Post-Traumatic Stress Disorder (PTSD) (Charney D. S. et al., Archives of General Psychiatry, 1993, Vol. 50, p. 295-305), Attention Deficit/Hyperactivity Disorder (AD/HD) (Hong H. J. et al., Yonsei Medical Journal, 2003, Vol. 44, p. 608-614), panic disorder (Angelika E. et al., Neuropsychopharmacology, 2006, Vol. 31, p. 2515-2522), sleep disorder (Andersen M. L. et al., Journal of sleep research, 2005, Vol. 14, p. 83-90), which are closely related to stress and show HPA axis disorder or the increase in plasma cortisol level.

In addition, as the relationship between 11β-HSD1 and metabolic diseases, increased activity of 11β-HSD1 in the adipose tissue of an obese individual is known (Rask E. et al., The Journal of Clinical Endocrinology & Metabolism, 2001, Vol. 86, p. 1418-1421), and it is reported that the activity of 11β-HSD1 is closely correlated with BMI as the index of obesity, HOMA-IR as the index of insulin resistance, and the fasting blood glucose level (Lindsay R. S. et al., The Journal of Clinical Endocrinology & Metabolism, 2003, Vol. 88, p. 2738-2744). It is also reported that a transgenic mouse over-expressing 11β-HSD1 in an adipose tissue-selective manner shows increase in the level of glucocorticoid in the adipose tissue and insulin resistance, visceral fat obesity, hyperlipidemia, and hypertension (Masuzaki H. et al., Science, 2001, Vol. 294, p. 2166-2170, Masuzaki H. et al., The Journal of Clinical Investigation, 2003, Vol. 112, p. 83-90), and that a 11β-HSD1 knockout mouse shows improvement in glucose tolerance, decrease in blood triglyceride levels, and increase in HDL-cholesterol levels (Morton N. M. et al., The Journal of Biological Chemistry, 2001, Vol. 276, p. 41293-41300).

In this respect, a selective inhibitor of 11β-HSD1 is expected to suppress the action of glucocorticoid in a tissue by inhibiting the conversion of glucocorticoid to the active type, and consequently remedy metabolic abnormality such as hyperglycemia, insulin resistance, obesity, hyperlipidemia, and hypertension induced by glucocorticoid.

It is also reported that a non-selective 11β-HSD inhibitor, carbenoxolone, ameliorates deficient secretion of insulin caused by the addition of inactive glucocorticoid in rat pancreatic β-cells (Davani B. et al., The Journal of Biological Chemistry, 2000, Vol. 275, p. 34841-34844), so the 11β-HSD1 inhibitor has a possibility of ameliorating not only insulin resistance but also hyperglycemia by promoting insulin secretion.

In addition, it is reported that a triazole compound having the 11β-HSD1 inhibitory action is effective in a spinal nerve ligation model as an animal model of neuropathic pain and an animal model of fibromyalgia caused by repeated reserpine administration (Patent Document 1), so the 11β-HSD1 inhibitor is expected to be effective for treating pain, particularly neuropathic pain and fibromyalgia.

Examples of other 11β-HSD1-related diseases include osteoporosis (Cooper M. S. et al., Bone, 2000, Vol. 27, p. 375-381) and glaucoma (Rauz S. et al., Investigative Opthalmology & Visual Science, 2001, Vol. 42, p. 2037-2042), and the 110-HSD1 inhibitor is expected to be effective for ameliorating these diseases.

Patent Document 2 discloses that a compound represented by the following formula (A) has the 11β-HSD1 inhibitory action and is useful for treating diseases such as diabetic diseases and metabolic syndrome. However, in the compound, the moiety corresponding to amide of the present application is cyclic amide.

[Chem. 1]

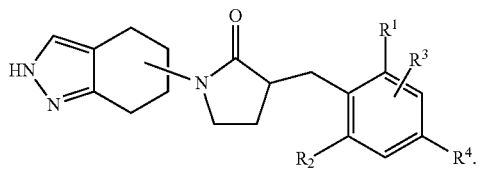

(A)

(see the corresponding gazette for symbols in the formula)

Patent Document 3 discloses that a compound represented by the following formula (B) has the action of regulating hydroxysteroid dehydrogenases such as 11β-HSD1 and is useful for treating a large number of diseases including diabetes, metabolic syndrome, and dementia. However, this compound does not include a ring corresponding to the ring A of the present application.

[Chem. 2]

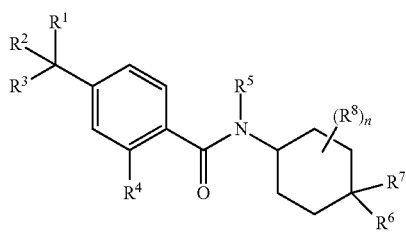

(B)

(see the corresponding gazette for symbols in the formula)

Patent Document 4 discloses that a compound represented by the following formula (C) has an inhibitory action against 11β-HSD1, 11β-HSD2, 17β-HSD3, and the like and is useful for treating a large number of diseases including diabetes, metabolic syndrome, and dementia. However, this compound does not include a ring corresponding to the ring A of the present application.

[Chem. 3]

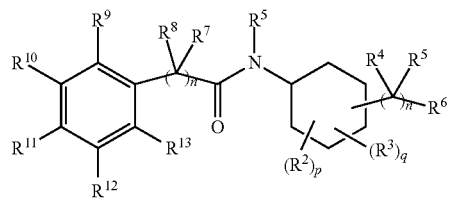

(C)

(see the corresponding gazette for symbols in the formula)

Patent Document 5 discloses that a compound represented by the following formula (D) has the action of regulating a TRPV1 receptor and is useful for treating pain. However, this document does not disclose the 11β-HSD1 inhibitory action and the usefulness of the compound with respect to dementia.

[Chem. 4]

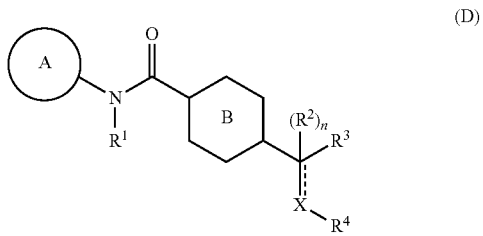

(D)

(see the corresponding gazette for symbols in the formula)

Patent Document 6 discloses that a compound represented by the following formula (E) has the action of regulating a histamine H3 receptor and is useful for treating a large number of diseases including obesity, diabetes, and Alzheimer's disease.

[Chem. 5]

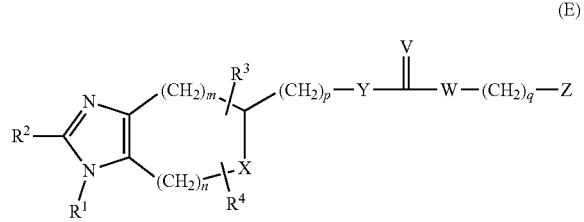

(E)

(see the corresponding gazette for symbols in the formula)

Patent Document 7 discloses that a compound represented by the following formula (F) has the action of regulating stearoyl-CoA desaturase and is useful for treating hyperlipidemia, circulatory diseases, diabetes, obesity, metabolic syndrome and the like. However, the document does not make disclosures about the 11β-HSD1 inhibitory action and usefulness of the compound with respect to dementia.

[Chem. 6]

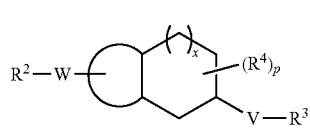

(F)

(see corresponding gazette for symbols in the formula)

Patent Document 8 discloses that a compound represented by the following formula (G) has the action of regulating a C5A receptor and is useful for treating various inflammatory diseases and immunological diseases. However, the document does not disclose the 11β-HSD1 inhibitory action.

[Chem. 7]

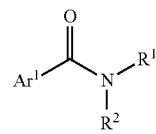

(G)

(see the corresponding gazette for symbols in the formula)

Patent Document 9 discloses that a compound represented by the following formula (H) has an antibacterial activity and is useful for treating infection. However, the document does not disclose the 11β-HSD1 inhibitory action and the usefulness of the compound with respect to dementia.

[Chem. 8]

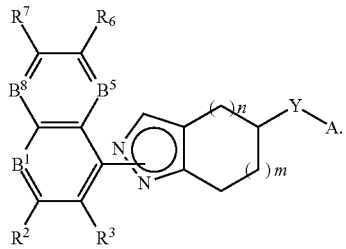
(H)

(see the corresponding gazette for symbols in the formula)

RELATED ART

Patent Document

Patent Document 1: Pamphlet of International Publication WO2012/033070
Patent Document 2: Pamphlet of International Publication WO2007/124254
Patent Document 3: Pamphlet of International Publication WO2007/145834
Patent Document 4: Pamphlet of International Publication WO2008/088540
Patent Document 5: Pamphlet of International Publication WO2007/069773
Patent Document 6: Pamphlet of International Publication WO01/068652
Patent Document 7: Pamphlet of International Publication WO2007/050124
Patent Document 8: Pamphlet of International Publication WO03/082826
Patent Document 9: Pamphlet of International Publication WO2006/105289

DISCLOSURE OF INVENTION

Technical Problem

Problems to Be Solved by the Invention

The present invention provides a novel compound that is useful as an active ingredient of a pharmaceutical composition, for example, a pharmaceutical composition for treating 11β-hydroxysteroid dehydrogenase type 1-related diseases such as dementia (particularly, Alzheimer's type dementia), schizophrenia, depression, pain (particularly, neuropathic pain or fibromyalgia), diabetes (particularly, type II diabetes mellitus), insulin resistance and the like.

Means for Solving the Problems

The present inventors conducted thorough research regarding a compound having 11β-HSD1 inhibitory action that can be expected to ameliorate dementia (particularly, Alzheimer's type dementia), schizophrenia, depression, pain (particularly, neuropathic pain or fibromyalgia), diabetes (particularly, type II diabetes mellitus), and insulin resistance. As a result, they found that a bicyclic heterocyclic compound (the bicyclic heterocycle is formed when a cyclohexane ring is fused with a 5- to 6-membered monocyclic heterocycle having only a nitrogen atom as a hetero atom) substituted with an acylamino group such as a (hetero)aroylamino group or a pharmaceutically acceptable salt thereof has an excellent selective inhibitory action against 11β-HSD1, thereby completing the present invention.

That is, the present invention relates to a compound of the formula (I) or a salt thereof and a pharmaceutical composition containing the compound of the formula (I) or a salt thereof and an excipient.

[Chem. 9]

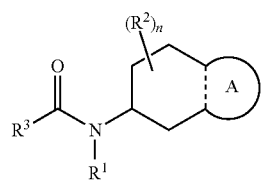
(I)

[symbols in the formula represent the following:
ring A: a 5- to 6-membered monocyclic heterocycle which may be substituted and has only the nitrogen atoms as the hetero atom; wherein the atoms in the position where the ring is fused with the adjacent ring are carbon atoms,
$R^1$: lower alkyl, halogeno-lower alkyl, or cycloalkyl which may be substituted,
$R^2$: halogen or lower alkyl,
$R^3$: aryl, heteroaryl, or lower alkylene-heteroaryl; wherein each of the aryl and heteroaryl represented by $R^3$ may be substituted,
n: an integer of 0 to 3, and
a dotted line represents a single bond or a double bond].

In addition, the present invention relates to a pharmaceutical composition which contains the compound of the formula (I) or a salt thereof and is for treating dementia (particularly, Alzheimer's type dementia), schizophrenia, depression, pain (particularly, neuropathic pain or fibromyalgia), diabetes (particularly, type II diabetes mellitus), and insulin resistance. In addition, the pharmaceutical composition includes an agent which containing the compound of the formula (I) or a salt thereof and for treating dementia (particularly, Alzheimer's type dementia), schizophrenia, depression, pain (particularly, neuropathic pain or fibromyalgia), diabetes (particularly, type II diabetes mellitus), and insulin resistance.

Moreover, the present invention relates to use of the compound of the formula (I) or a salt thereof for the manufacture of a pharmaceutical composition for treating dementia (particularly, Alzheimer's type dementia), schizophrenia, depression, pain (particularly, neuropathic pain or fibromyalgia), diabetes (particularly, type II diabetes mellitus), and insulin resistance; use of the compound of the formula (I) or a salt thereof for treating dementia, schizophrenia, depression, pain (particularly, neuropathic pain or fibromyalgia), diabetes (particularly, type II diabetes mellitus), and insulin resistance; the compound of the formula (I) or a salt thereof for treating dementia (particularly, Alzheimer's type dementia), schizophrenia, depression, pain (particularly, neuropathic pain or fibromyalgia), diabetes (particularly, type II diabetes mellitus), and insulin resistance; and a method of treating dementia, schizophrenia, depression, pain (particularly, neuropathic pain or fibromyalgia), diabetes (particularly, type II diabetes mellitus), and insulin resistance, which includes administering the effective amount of the compound of the formula (I) or a salt thereof to a subject. In addition, the "subject" refers to human being or other animals that require the prevention or treatment of the above diseases. As another embodiment, the "subject" refers to a human being who requires the prevention or treatment of the above diseases.

That is, the present invention relates to (1) A pharmaceutical composition including the compound of the formula (I) or a pharmaceutically acceptable salt thereof and a pharmaceutically acceptable carrier;
(2) The pharmaceutical composition according to (1), which is an inhibitor of 11β-hydroxysteroid dehydrogenase type 1;
(3) The pharmaceutical composition according to (1), which is an agent for preventing or treating dementia, schizophrenia, depression, or pain;
(4) The pharmaceutical composition according to (1), which is an agent for preventing or treating dementia;
(5) The pharmaceutical composition according to (1), which is an agent for preventing or treating pain;
(6) Use of the compound of the formula (I) or a pharmaceutically acceptable thereof for the manufacture of an inhibitor of 11β-hydroxysteroid dehydrogenase type 1 or an agent for preventing or treating dementia, schizophrenia, depression, or pain;
(7) Use of the compound of the formula (I) or a pharmaceutically acceptable salt thereof for preventing or treating dementia, schizophrenia, depression, or pain;
(8) The compound of the formula (I) or a pharmaceutically acceptable salt thereof for preventing or treating dementia, schizophrenia, depression, or pain;
(9) A method of preventing or treating dementia, schizophrenia, depression, or pain, including administering an effective amount of the compound of the formula (I) or a salt thereof to a patient.

Effects of the Invention

The compound of the formula (I) or a salt thereof has a 11β-HSD1 inhibitory action and can be used as an agent for preventing and/or treating dementia (particularly, Alzheimer's type dementia), schizophrenia, depression, pain (particularly, neuropathic pain or fibromyalgia), diabetes (particularly, type II diabetes mellitus), insulin resistance, and the like.

EMBODIMENTS FOR CARRYING OUT THE INVENTION

Hereafter, the present invention will be described in detail.

In the present specification, "lower alkyl" refers to linear or branched alkyl having 1 to 6 carbon atoms (hereinafter, abbreviated to $C_{1-6}$), for example, methyl, ethyl, n-propyl, isopropyl, n-butyl, isobutyl, sec-butyl, tert-butyl, n-pentyl, n-hexyl or the like. As another embodiment, the lower alkyl is $C_{1-4}$ alkyl, and as still another embodiment, the lower alkyl is methyl, ethyl, n-propyl, or isopropyl.

"Lower alkylene" refers to linear or branched $C_{1-6}$ alkylene, for example, methylene, ethylene, trimethylene, tetramethylene, pentamethylene, hexamethylene, propylene, methyl methylene, ethyl ethylene, 1,2-dimethyl ethylene, 1,1,2,2-tetramethyl ethylene or the like. As another embodiment, the lower alkylene is $C_{1-4}$ alkylene, and as still another embodiment, the lower alkylene is methylene, ethylene, or trimethylene.

"Halogen" refers to F, Cl, Br, or I.

"Halogeno-lower alkyl" refers to lower alkyl substituted with one or more halogen atoms. As another embodiment, the halogeno-lower alkyl is lower alkyl substituted with 1 to 5 halogen atoms, and as still another embodiment, the halogeno-lower alkyl is fluoromethyl, difluoromethyl, trifluoromethyl, 2-fluoroethyl, 1,1-difluoroethyl, 2,2-difluoroethyl, 2,2,2-trifluoroethyl, pentafluoroethyl, or the like.

"Cycloalkyl" refers to a saturated $C_{3-10}$ hydrocarbon ring group which may have a bridge. The cycloalkyl is, for example, cyclopropyl, cyclobutyl, cyclopentyl, cyclohexyl, cycloheptyl, cyclooctyl, adamantyl or the like. As another embodiment, the cycloalkyl is $C_{3-8}$ cycloalkyl, and as still another embodiment, the cycloalkyl is cyclopropyl, cyclobutyl, cyclopentyl, or cyclohexyl.

"Aryl" refers to a mono- to tri-cyclic $C_{6-14}$ aromatic hydrocarbon ring group, for example, phenyl, naphthyl, 5-tetrahydronaphthyl, 6-tetrahydronaphthyl, 4-indenyl, 1-fluorenyl or the like. As another embodiment, the aryl is phenyl or naphthyl, and as still another embodiment, the aryl is phenyl.

A "heterocycle" refers to a 3- to 15-membered, or, as another embodiment, 5- to 10-membered mono- to tri-cyclic heterocyclic group containing 1 to 4 hetero atoms selected from oxygen, sulfur, and nitrogen. The heterocycle includes a saturated ring, an aromatic ring, and cyclic groups formed when these rings are partially hydrogenated. Sulfur or nitrogen as a ring atom may be oxidized to form oxide or dioxide. The heterocycle is specifically pyridyl, pyrrolyl, pyrazinyl, pyrimidinyl, pyridazinyl, imidazolyl, triazolyl, triazinyl, tetrazolyl, thiazolyl, pyrazolyl, isothiazolyl, oxazolyl, isoxazolyl, thiadiazolyl, oxadiazolyl, thienyl, furyl, indolyl, isoindolyl, benzimidazolyl, indazolyl, quinolyl, isoquinolyl, quinazolinyl, quinoxalinyl, naphthylidyl, cinnolinyl, phthalazinyl, benzothiazolyl, benzisothiazolyl, benzothiadiazolyl, benzoxazolyl, benzisoxazolyl, benzofuranyl, benzothienyl, carbazolyl, dibenzo[b,d]furanyl, dibenzo[b,d]thienyl, azetidinyl, pyrrolidinyl, piperidyl, piperazinyl, azepanyl, diazepanyl, morpholinyl, thiomorpholinyl, tetrahydropyridinyl, oxetanyl, tetrahydrofuranyl, tetrahydropyranyl, dioxolanyl, dioxanyl, tetrahydrothiopyranyl, indolinyl, tetrahydroquinolyl, tetrahydroisoquinolyl, dihydrobenzimidazolyl, tetrahydrobenzimidazolyl, tetrahydroindazolyl, tetrahydroquinoxalinyl, tetrahydrocinnolinyl, dihydroquinoxalinyl, dihydrobenzoxazolyl, dihydrobenzoxazinyl, dihydrobenzofuryl, 1,3-benzodioxolyl, chromanyl, chromenyl, methylenedioxyphenyl, ethylenedioxyphenyl, quinuclidinyl or the like. As another embodiment, the heterocycle is 5- to 10-membered mono- to bicyclic heterocyclic group, and as still another embodiment, the heterocycle is pyridyl, thiazolyl, thienyl, furyl, indolyl, benzothienyl, indazolyl, pyrrolidinyl, morpholinyl, oxetanyl, or tetrahydropyranyl.

"Heteroaryl" refers to, among the above "heterocycles", a 5- to 15 membered, or, as another embodiment, 5- to 10-membered mono- to tri-cyclic aromatic heterocyclic group containing 1 to 4 hetero atoms selected from oxygen, sulfur, and nitrogen. Sulfur or nitrogen as a ring atom may be oxidized to form oxide or dioxide. The heteroaryl is specifically pyridyl, pyrrolyl, pyrazinyl, pyrimidinyl, pyridazinyl, imidazolyl, triazolyl, triazinyl, tetrazolyl, thiazolyl, pyrazolyl, isothiazolyl, oxazolyl, isoxazolyl, thiadiazolyl, oxadiazolyl, thienyl, furyl, indolyl, isoindolyl, benzimidazolyl, indazolyl, quinolyl, isoquinolyl, quinazolyl, quinoxalinyl, naphthylidyl, cinnolinyl, phthalazinyl, benzothiazolyl, benzisothiazolyl, benzothiadiazolyl, benzoxazolyl, benzisoxazolyl, benzofuranyl, benzothienyl, carbazolyl, benzo[b,d]furanyl, benzo[b,d]thienyl, or the like.

As another embodiment, the heteroaryl is 5- to 10-membered mono- to bicyclic heteroaryl, and as still another embodiment, the heteroaryl is 5- to 6-membered monocyclic heteroaryl. As another embodiment, the heteroaryl is pyridyl, thiazolyl, thienyl, furyl, indolyl, benzothienyl, or indazolyl.

The "5- to 6-membered monocyclic heterocycle having only a nitrogen atom as a hetero atom" refers to, among the above "heterocycles", a 5- to 6-membered monocyclic heterocyclic group having only 1 to 3 nitrogen atoms as hetero atoms, and includes a saturated ring, an aromatic ring, and cyclic groups formed when these rings are partially hydrogenated. Nitrogen as a ring atom may be oxidized to form oxide. The monocyclic heterocycle is specifically pyrrolyl, pyrazolyl, imidazolyl, triazolyl, pyridyl, pyridazinyl, pyrimidinyl, pyrazinyl, or triazinyl. As another embodiment, the monocyclic heterocycle is pyrazolyl, pyridazinyl, or pyrimidinyl.

In the present specification, the words "may be substituted" mean that a group is unsubstituted or has 1 to 5 substituents. In addition, the word "substituted" means that a group has 1 to 5 substituents. When a group has a plurality of substituents, these substituents may be the same as or different from each other.

"$(R^2)_n$—" on a cyclohexane ring or a cyclohexene ring as a bicyclic ring that is formed when the ring A is fused with an adjacent cyclohexane ring or cyclohexene ring means that the ring is substituted with n groups represented by $R^2$ in the portion of a cyclohexane ring or a cyclohexene ring as a bicyclic ring that is formed when the ring A is fused with an adjacent cyclohexane ring or cyclohexene ring (wherein the ring is not substituted when n represents 0). When n represents a plural number, the respective substituents represented by $R^2$ may be the same as or different from each other.

Examples of the substituent in the "5- to 6-membered monocyclic heterocycle having only a nitrogen atom as a hetero atom" that may be substituted in the ring A include a group selected from halogen, lower alkyl, halogeno-lower alkyl, —$OR^0$, —O-halogeno-lower alkyl, and oxo (wherein $R^0$ represents —H or lower alkyl, the same shall apply hereinafter).

Examples of the substituent in the "aryl" or "heteroaryl" that may be respectively substituted in $R^3$ include a group selected from the following Group G Group G: halogen, cyano, lower alkyl, halogeno-lower alkyl, —$N(R^0)_2$, —$OR^0$—, —O-halogeno-lower alkyl, —O-(lower alkyl substituted with cycloalkyl), -(lower alkylene that may be substituted with halogen)-$OR^0$, lower alkylene-O-cycloalkyl, lower alkylene-O-aryl, lower alkylene-O-heterocyclic group, lower)alkylene-$N(R^0)_2$, lower alkylene-$CO_2R^0$, lower) alkylene-$C(O)N(R^0)_2$, —S-lower alkyl, —S(O)-lower alkyl, —$S(O)_2$-lower alkyl, lower alkylene-S-lower alkyl, lower alkylene-S(O)-lower alkyl, lower alkylene-$S(O)_2$-lower alkyl, —$CO_2R^0$, —$C(O)N(R^0)_2$, cycloalkyl, aryl, a heterocyclic group, lower alkylene-cycloalkyl, lower alkylene-aryl, lower alkylene-heterocyclic group, —O-cycloalkyl, —O-aryl, —O-heterocyclic group, —O-lower alkylene-aryl, and —O-lower alkylene-heterocyclic group.

Here, the aryl and heterocyclic group in Group G may be respectively substituted with halogen, cyano, nitro, lower alkyl, halogeno-lower alkyl, —$OR^0$, —O-halogeno-lower alkyl, lower alkylene-$OR^0$, —$S(O)_2$-lower alkyl, cycloalkyl, —$CO_2R^0$, —$C(O)N(R^0)_2$, or oxo, and the cycloalkyl in Group G may be substituted with halogen or lower alkyl.

Alternatively, two groups in Group G may form lower alkylene, —$N(R^0)$-lower alkylene, or lower)alkylene-N($R^0$)— in combination.

Examples of another embodiment of the substituent in the "aryl" or "heteroaryl" that may be respectively substituted in $R^3$ include a group selected from the following Group Q.
Group Q: halogen, lower alkyl, halogeno-lower alkyl, —$OR^0$, lower alkylene-$OR^0$, —S-lower alkyl, aryl, a heterocyclic group, and lower alkylene-heterocyclic group.

Here, the aryl and heterocyclic group in Group Q may be substituted with halogen, cyano, lower alkyl, —$OR^0$, or oxo.

Examples of still another embodiment of the substituent in the "aryl" or "heteroaryl" that may be respectively substituted in $R^3$ include a group selected from (i) phenyl or pyridyl that may be respectively substituted with halogen or cyano, (ii) halogen, (iii) lower alkyl, and (iv) —O-lower alkyl.

Examples of the substituent in "cycloalkyl" that may be substituted in an $R^1$ ring include halogen, lower alkyl, and the like.

Embodiments of the compound of the present invention represented by the formula (I) will be shown below.

(1) A compound in which $R^1$ represents methyl, ethyl, n-propyl, isopropyl or cyclopropyl, as another embodiment, a compound in which $R^1$ represents cyclopropyl (2) A compound in which the bicyclic ring formed when the ring A is fused with an adjacent ring is 4,5,6,7-tetrahydroindazol-5-yl which may be substituted with halogen, lower alkyl, halogeno-lower alkyl, —$OR^0$, or —O-halogeno-lower alkyl, as another embodiment, a compound in which the bicyclic ring formed when the ring A is fused with an adjacent ring is 4,5,6,7-tetrahydroindazol-5-yl (3) A compound in which n represents 0

(4) A compound in which $R^3$ represents aryl or heteroaryl which may be respectively substituted with a group selected from Group Q, as another embodiment, a compound in which $R^3$ represents phenyl, indolyl, or indazolyl which may be respectively substituted with a group selected from Group Q, as another embodiment, a compound in which $R^3$ represents phenyl that may be substituted with a group selected from (i) phenyl or pyridyl which may be respectively substituted with halogen or cyano, (ii) halogen, (iii) lower alkyl, and (iv) —O-lower alkyl; as still another embodiment, a compound in which $R^3$ represents phenyl which may be substituted with phenyl substituted with halogen or cyano and may be further substituted with halogen; as another embodiment, a compound in which $R^3$ represents phenyl which may be substituted with phenyl substituted with halogen or cyano at a 4-position and may be further substituted with halogen; and as another embodiment, a compound in which $R^3$ represents phenyl that may be substituted with 2-cyanophenyl which may be substituted with halogen at a 4-position and may be further substituted with halogen, as another embodiment, a compound in which $R^3$ represents phenyl substituted with lower alkyl or —O-lower alkyl; and as another embodiment, a compound in which $R^3$ represents phenyl substituted with —O-lower alkyl, as another embodiment, a compound in which $R^3$ represents indolyl which may be substituted with lower alkyl or —O-lower alkyl, and as another embodiment, a compound in which $R^3$ represents indol-4-yl which may be substituted with lower alkyl or —O-lower alkyl (6) A compound which is a combination of two or more groups according to the above embodiments (1) to (5)

As specific embodiments of the combination of two or more groups according to the above embodiments (1) to (5) of embodiment (6), the following (a) to (f) are exemplified.

(a) The compound represented by the formula (I) in which n represents 0

(b) The compound according to (a), in which $R^1$ represents cyclopropyl (c) The compound according to (b), in which the bicyclic group formed when the ring A is fused with an adjacent ring is 4,5,6,7-tetrahydroindazol-5-yl (d) The compound according to (c), in which $R^3$ represents phenyl, indolyl, or indazolyl which may be respectively substituted with a group selected from the Group Q (e) The compound according to (d), in which $R^3$ represents phenyl which may be substituted with a group selected from a group consisting of (i) phenyl or pyridyl that which be respectively substituted with halogen or cyano, (ii) halogen, (iii) lower alkyl, and (iv) —O-lower alkyl (f) The compound according to (d), in which $R^3$ represents indolyl which may be substituted with lower alkyl or —O-lower alkyl Examples of specific compounds included in the present invention include the following compounds:

A compound selected from a group consisting of (−)-N-cyclopropyl-4-isopropoxy-N-(4,5,6,7-tetrahydro-1H-indazol-5-yl)benzamide, (−)-2'-cyano-N-cyclopropyl-6'-fluoro-N-(4,5,6,7-tetrahydro-1H-indazol-5-yl)biphenyl-4-carboxamide, N-cyclopropyl-1-methyl-N-(4,5,6,7-tetrahydro-1H-indazol-5-yl)-1H-indole-4-carboxamide, N-cyclopropyl-7-methoxy-1-methyl-N-(4,5,6,7-tetrahydro-1H-indazol-5-yl)-1H-indole-4-carboxamide, 2'-cyano-N-cyclopropyl-4'-fluoro-N-(4,5,6,7-tetrahydro-1H-indazol-5-yl)biphenyl-4-carboxamide, 2'-cyano-N-cyclopropyl-3-fluoro-N-(4,5,6,7-tetrahydro-1H-indazol-5-yl)biphenyl-4-carboxamide, N-cyclopropyl-2',6'-difluoro-N-(4,5,6,7-tetrahydro-1H-indazol-5-yl)biphenyl-4-carboxamide, N-cyclopropyl-4-(3,5-difluoropyridin-4-yl)-N-(4,5,6,7-tetrahydro-2H-indazol-5-yl)benzamide, and N-cyclopropyl-4-isopropoxy-2-methoxy-N-(4,5,6,7-tetrahydro-1H-indazol-5-yl)benzamide The compound of the formula (I) may have tautomers or geometric isomers depending on the type of substituents. In the present specification, the compound of the formula (I) is described only in one form of isomer in some cases. However, the present invention includes other isomers, separated isomers, or a mixture of these. For example, 4,5,6,7-tetrahydroindazol-5-yl is described as a tautomer of one of the following (A) and (B) in the present specification, but tautomers of both the (A) and (B) are also included in the present invention.

[Chem. 10]

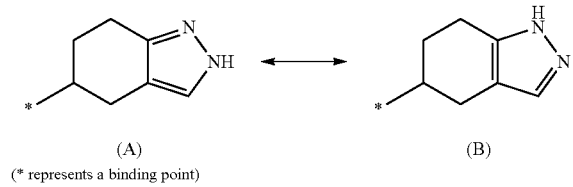

(A)          (B)
(* represents a binding point)

In addition, the compound of the formula (I) has asymmetric carbon atoms or axis chirality in some cases, and there may be optical isomers based on this case. The present invention includes separated optical isomers of the compound of the formula (I) or a mixture of these.

The present invention also includes pharmaceutically acceptable prodrugs of the compound represented by the formula (I). The pharmaceutically acceptable prodrugs refer to compounds having a group that can be converted into an amino group, a hydroxyl group, a carboxyl group, or the like by solvolysis or under physiological conditions. Examples of groups that form the prodrugs include the groups disclosed in Prog. Med., 5, 2157-2161 (1985) or in "Pharmaceutical Research and Development", (Hirokawa Publishing Company, 1990), Vol. 7, Drug Design 163-198.

The salt of the compound of the formula (I) refers to a pharmaceutically acceptable salt of the compound of the formula (I), and forms an acid addition salt or a salt with a base depending on the type of substituents. Specific examples of the salt include acid addition salts with an inorganic acid such as hydrochloric acid, hydrobromic acid, hydriodic acid, sulfuric acid, nitric acid, or phosphoric acid or with an organic acid such as formic acid, acetic acid, propionic acid, oxalic acid, malonic acid, succinic acid, fumaric acid, maleic acid, lactic acid, malic acid, mandelic acid, tartaric acid, dibenzoyl tartrate, ditoluoyl tartrate, citric acid, methanesulfonic acid, ethanesulfonic acid, benzenesulfonic acid, p-toluenesulfonic acid, aspartic acid, or glutamic acid, salts with an inorganic base such as sodium, potassium, magnesium, calcium, or aluminum, or with an organic base such as methylamine, ethylamine, ethanolamine, lysine, or ornithine, salts with various amino acids and amino acid derivatives such as acetylleucine, ammonium salts, and the like.

(Preparation Process)

The compound of the formula (I) or a salt thereof can be prepared by applying various known synthesis processes, by using characteristics based on the basic structure thereof or the type of substituents. At this time, depending on the type of functional groups, it is in some cases effective to substitute the functional group in advance with an appropriate protective group (group that can be easily converted into the functional group) during the period from the stage of a starting material to the stage of an intermediate. Examples of the protective group include the protective groups disclosed in Wuts (P. G M. Wuts) and Greene (T. W. Greene), "Greene's Protective Groups in Organic Synthesis (4th edition, 2006)", and the like. The protective group may be used by being appropriately selected according to the reaction conditions thereof. In this method, the protective group is introduced to cause a reaction, and then the protective group is optionally removed, whereby a desired compound can be obtained.

In addition, a prodrug of the compound of the formula (I) can be prepared by introducing a specific group during the period from the stage of a starting material to the stage of an intermediate just like the above protective group, or by further causing a reaction by using the obtained compound of the formula (I). The reaction can be performed by applying methods known to a person skilled in the art, such as general esterification, amidation, and dehydration.

Hereinafter, a typical preparation process of the compound of the formula (I) will be described. Each preparation process can be performed with reference to the reference document included in the corresponding description. Moreover, the preparation process of the present invention is not limited to the following examples.

(Preparation Process 1)

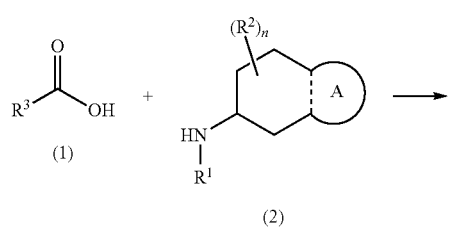

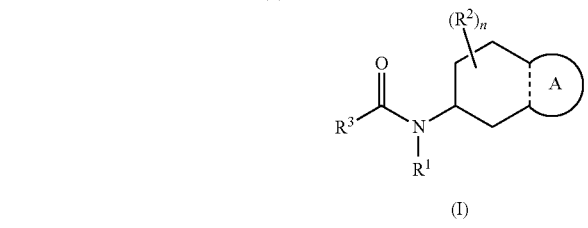

A compound (1) of the present invention can be obtained from an amidation reaction between a compound (1) and a compound (2).

In this reaction, the compounds (1) and (2) are used in an equal amount, or one of the compounds used in an excess amount than the other. A mixture of these is generally stirred for 0.1 hours to 5 days under cooling to heating preferably at −20° C. to 60° C. in a solvent inactive to the reaction in the presence of a condensing agent. Though not particularly limited, examples of the solvent used herein include aromatic hydrocarbons such as benzene, toluene, and xylene, halogenated hydrocarbons such as dichloromethane, 1,2-dichloroethane, and chloroform, ethers such as diethylether, tetrahydrofuran (THF), dioxane, and dimethoxyethane, N,N-dimethylformamide (DMF), dimethylsulfoxide (DMSO), ethyl acetate, acetonitrile, water, and a mixture of these. Examples of the condensing agent include 1-(3-dimethylaminopropyl)-3-ethylcarbodiimide, dicyclohexylcarbodiimide, 1,1'-carbonyldiimidazole, diphenyl phosphate azide, and phosphorus oxychloride, and N-[(dimethylamino)(3H-[1,2,3]triazo[4,5,-b]pyridin-3-yloxy)methylidene]-N-methyl-methanaminium hexafluorophosphate (HATU), but the present invention is not limited thereto. It is preferable to use an additive (for example, 1-hydroxybenzotriazole) in some cases for the reaction. It is advantageous to perform the reaction in the presence of an organic base such as triethylamine, N,N-diisopropylethylamine, or N-methylmorpholine, or an inorganic base such as potassium carbonate, sodium carbonate, or potassium hydroxide, in terms of causing the reaction to proceed smoothly.

In addition, it is also possible to use a method of converting carboxylic acid (1) into a reactive derivative and then reacting this with amine (2). Examples of the reactive derivative of carboxylic acid include acid halides obtained when the carboxylic acid reacts with a halogenating agent such as phosphorus oxychloride or thionyl chloride, mixed acid anhydrides obtained when the carboxylic acid reacts with isobutyl chloroformate or the like, and active esters obtained when the carboxylic acid is condensed with 1-hydroxybenzotriazole or the like. The reaction between these reactive derivatives and the compound (2) can be performed in a solvent inactive to the reaction, such as halogenated hydrocarbons, aromatic hydrocarbons, or ethers, under cooling to heating preferably at −20° C. to 60° C.

Moreover, if the ring A is pyrazole, it is in some cases effective to perform a reaction by using the compound (2) protected with a protective group such as ethoxycarbonyloxy, tert-butoxycarbonyl, benzyloxycarbonyl, or benzyloxymethyl and then performing deprotection, for obtaining the compound (1) of the present invention. As the deprotection reaction, for example, the method disclosed in Wuts (P. G M. Wuts) and Greene (T. W. Greene), "Greene's Protective Groups in Organic Synthesis (4th edition, 2006)" can be used.

(Preparation Process 2)

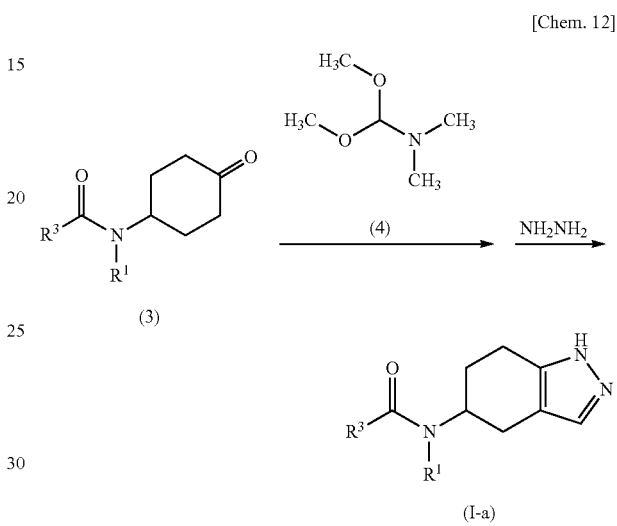

A compound (I-a) of the present invention can be obtained by reacting a compound (3) with a compound (4) and then causing a cyclization reaction between the product and hydrazine.

The reaction between the compound (3) and compound (4) can be performed in the presence of a base such as triethylamine, by using the compound (3) and the compound (4) in an equal amount, or using one of the compounds in an excess amount than the other, without using a solvent or in a solvent inactive to the reaction, under heating. The solvent is not particularly limited as long as it is a solvent inactive to the reaction, but for example, ethers, aromatic hydrocarbons, and the like can be used.

The cyclization reaction between the product obtained from the reaction between the compound (3) and compound (4) and hydrazine can be performed without using a solvent or in a solvent inactive to the reaction, under heating. The solvent is not particularly limited as long as it is a solvent inactive to the reaction, but for example, ethers, aromatic hydrocarbons, alcohols such as methanol and ethanol, water, and the like can be used.

In addition, some of the compounds represented by the formula (I) can also be prepared from the compound of the present invention obtained in the above manner, by arbitrarily combining steps that a person skilled in the art can employ, such as acylation, a substitution reaction, oxidation, reduction, hydrolysis, and amidation.

Starting materials used for preparing the compound of the present invention can be prepared by, for example, the following method, the method described in the preparation example described later, known methods, or methods clearly known to a person skilled in the art, or by applying modified methods of these.

(Starting Material Synthesis 1)

[Chem. 13]

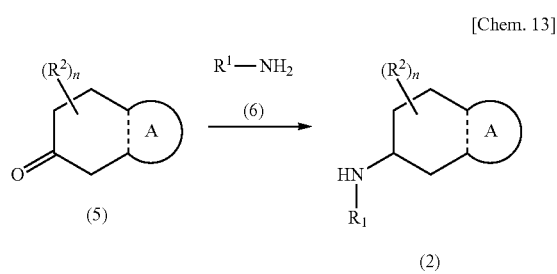

The compound (2) can be obtained from a reductive amination reaction between a compound (5) and a compound (6).

In this reaction, the compound (5) and the compound (6) are used in an equal amount, or one of these compounds is used in an excess amount than the other. A mixture of these is generally stirred for 0.1 hours to 5 days at −45° C. to heating under reflux preferably at 0° C. to room temperature in a solvent inactive to the reaction, in the presence of a reductant. Though not particularly limited, examples of the solvent used herein include alcohols such as methanol and ethanol, ethers such as diethylether, tetrahydrofuran, dioxane, and dimethoxyethane, and a mixture of these. Examples of the reductant include sodium cyanoborohydride, sodium triacetoxyborohydride, sodium borohydride, and the like. It is preferable to perform the reaction in the presence of a dehydrating agent such as molecular sieves or an acid such as acetic acid, hydrochloric acid, or a titanium(IV) isopropoxide complex in some cases. Depending on the reaction, an imine is generated by the condensation of the compounds (5) and (6) and can be isolated as a stable intermediate in some cases. In this case, the compound (2) can be obtained by a reduction reaction of the imine intermediate. In addition, instead of treating the compounds with the reductant, it is possible to perform the reaction in a solvent such as methanol, ethanol, or ethyl acetate in the presence or absence of an acid such as acetic acid or hydrochloric acid by using a reduction catalyst (for example, palladium carbon or Raney nickel). In this case, it is preferable to perform the reaction in a hydrogen atmosphere under normal pressure to 50 atm, under cooling to heating.

(Starting Material Synthesis 2)

[Chem. 14]

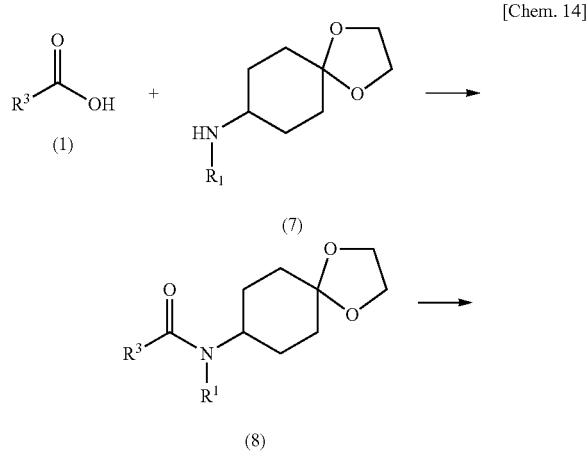

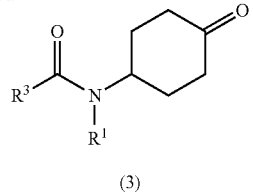

A compound (3) can be obtained by preparing a compound (8) by causing amidation between the compound (1) and the compound (7) and then deprotecting ketal of the compound (8).

The amidation reaction can be performed in the same manner as in Preparation process 1.

For the deprotection of ketal, the method disclosed in Wuts (P. G M. Wuts) and Greene (T. W. Greene), "Greene's Protective Groups in Organic Synthesis (4$^{th}$ edition, 2006)" can be used.

The compound of the formula (I) is isolated as a free compound, a salt thereof, hydrate, solvate, or polymorphic substance and purified. The salt of the compound of the formula (I) can be prepared by a salt preparation reaction using a common method.

Isolation and purification are performed by applying general chemical operations such as extraction, fractionated crystallization, and various types of fractionation chromatography.

Various isomers can be prepared by selecting appropriate starting compounds, or can be separated using difference in physicochemical characteristics between isomers. For example, an optical isomer is obtained by general optical resolution (for example, fractionated crystallization for obtaining a diastereomeric salt with an optically active base or acid or chromatography using a chiral column) of a racemic mixture, or can be prepared from an appropriate starting compound that is optically active.

The pharmacological activity of the compound of the formula (I) was confirmed by the following test.

Test Method 1: Test for Measuring Human 11β-HSD1/11β-HSD2 Inhibitory Activity

11β-HSD1 inhibitory activity was measured in the following order. In addition, an enzymatic reaction and assay was performed using a 384-well plate. The enzyme was prepared according to a document (Walker E. A. et al., Journal of Biological Chemistry, 2001, Vol. 276, p. 21343-21350). The reaction was performed in a manner in which various concentrations of test compounds were added to a reaction liquid including a 10 mM a phosphoric acid buffer (pH 6.6), 200 nM cortisone, 40 μM reduced nicotinamide adenine dinucleotide phosphate (NADPH), and recombinant human 11β-HSD1, followed by incubation for an hour at room temperature (10 μl/well). The test compound was dissolved in dimethylsulfoxide (DMSO), and the DMSO concentration was adjusted so as to be 1% in the reaction liquid. After the enzymatic reaction, cortisol was detected using Homogenous Time-Resolved Fluorescence (HTRF) to measure enzyme inhibitory activity. XL-665-labeled cortisol including 400 μM carbenoxolone and a cryptate-labeled cortisol antibody (CIS bio international) were added respectively to the plate at 5 μl/well, followed by incubation for 2 hours at room temperature, and then fluorescence intensity was measured using a fluorospectrometer (trade name: Discovery, manufactured by PerkinElmer Inc.), thereby calculating enzyme inhibitory activity from the ratio of fluorescence intensity between two wavelengths (665 nm/620 nm).

11β-HSD2 inhibitory activity was measured in the same manner as in the measurement of the 11β-HSD1 inhibitory activity, except for the conditions of the enzymatic reaction. The enzymatic reaction was performed in the manner in which various concentrations of test substances were added to a reaction liquid including 40 mM tris-hydrochloric acid buffer (Tris-HCl) (pH 8.0), 200 nM cortisol, 200 μM nicotinamide adenine dinucleotide (NAD), and recombinant human 11β-HSD2, followed by incubation for 2 hours at 37° C. (10 μl/well).

The results of measurement were calculated by obtaining the average of the values of three wells under the same condition. The ratio obtained when DMSO was added instead of the test compound was regarded as 0%, and the ratio obtained when 11β-HSD1 or 11β-HSD2 was not added was regarded as 100%, whereby a concentration at which the test compound suppresses the enzyme activity by 50% was calculated as $IC_{50}$ of the inhibitory activity of the compound.

The $IC_{50}$ values of typical compounds of the present invention are shown in the following Table 1. In addition, Ex represents example number.

TABLE 1

| Ex | Human 11β-HSD1 ($IC_{50}$/μM) | Human 11β-HSD2 ($IC_{50}$/μM) |
|---|---|---|
| 1 | 0.048 | >30 |
| 5 | 0.056 | |
| 7-1 | 0.018 | >3 |
| 8-1 | 0.026 | >30 |
| 27 | 0.062 | >3 |
| 30 | 0.028 | >3 |
| 81 | 0.024 | >30 |
| 132 | 0.038 | >30 |
| 159 | 0.040 | >30 |
| 176 | 0.088 | |
| 190 | 0.025 | |
| 216 | 0.043 | |
| 228 | 0.053 | |
| 237 | 0.040 | |

From the above results, it was confirmed that some of the compounds of the present invention exhibit potent inhibitory activity against 11β-HSD1, and the 11β-HSD1 inhibitory activity is selective compared to 11β-HSD2.

Test Method 2: Test for Spontaneous Alternation Behavior Disorder Induced by Scopolamine Test drugs were orally administered to 5- to 7-week old male ddY mice. 10 minutes later, scopolamine was intraperitoneally administered to the animals at 0.5 mg/kg. 20 minutes later, the animal was put in Y-maze having arms with the same length and extending in three directions and allowed to freely explore for 8 minutes. During the exploration, spontaneous arm-alternating behavior (entering different arms 3 times consecutively) was counted to calculate the rate of spontaneous alternation (spontaneous alternation behavior/(number of times of entering−2)×100), thereby judging drug efficacy.

Results of typical compounds of the present invention are shown in Table 2.

TABLE 2

| Ex | Dose improving minimum spontaneous alternation rate (mg/kg) |
|---|---|
| 7-1 | 1.0 |
| 8-1 | 0.3 |

From the above results, it was confirmed that some of the compounds of the present invention are effective for treating dementia.

Test Method 3: Test for Spinal Nerve Ligation Model

This test was performed according to Pain, 1992, Vol. 50, p 355-363. The skin and muscle in the lumbar region of rats (SD, male, 5- to 6-week old) were excised under pentobarbital anesthesia, and a lumbar L6 transverse process was removed to expose lumbar nerves. L5 and L6 spinal nerves were ligated with a silk thread, and then the wound was sutured. The procedure was performed in the left side. In addition, in the case of pseudo-operation, the wound was sutured without performing nerve ligation.

The drug efficacy was evaluated on the postoperative days 7 to 12 by von Frey hair test. The threshold of retraction response was calculated according to Journal of Neuroscience Methods, 1994, Vol. 53, p 55-63. By using 8 types of von Frey filaments (0.41 g to 15.14 g), the sole of the rat's hindlimb was stimulated, and the threshold of 50% retraction response was determined by an up-and-down method. The test started from 2.04 g of a filament, and when the limb retraction response was confirmed, this was regarded as "response".

The day before the drug efficacy evaluation, animals showing reduction in the threshold through the von Frey hair test were selected in advance, and the animals were grouped such that the difference in the average of the threshold between the respective groups was reduced.

The test substance was suspended in a 0.5% methyl cellulose solution and orally administered 1 hour before the drug efficacy evaluation. The test substance was evaluated by calculating the improvement rate of the test substance-administered group, under the condition that the threshold of the procedure-performed limb of the pseudo-operation animal group was regarded as 100% and the threshold of the procedure-performed limb of the solvent-administered animal group having undergone operation was regarded as 0%.

The results of typical compounds of the present invention are shown in Table 3.

TABLE 3

| Ex | Improvement rate % (applied dose) |
|---|---|
| 7-1 | 52 (1 mg/kg) |
| 8-1 | 73 (1 mg/kg) |

From the above results, it was confirmed that some of the compounds of the present invention are useful for treating neuropathic pain.

Test Method 4: Test for Model with Fibromyalgia Caused by Repeated Reserpine Administration This test was performed according to Pain, 2009, Vol. 146, p 26-33., by using rats (SD, male, 7-week old).

The threshold of muscle tenderness was measured according to the method of Schafers et al. (Pain, 2003, Vol. 104, p 579-588). A pressure stimulus slowly increasing up to 250 g was applied to the gastrocnemius muscle of the right lower leg of the rat. The magnitude of the minimum pressure stimulus at which the rat exhibited retraction response to the pressure stimulus in the right lower leg was measured as a muscle tenderness threshold (g). The measurement was performed 3 times for each point in time, and the average thereof was taken as a measured value.

A solvent (0.5% aqueous acetic acid) or reserpine (1 mg/kg) was subcutaneously administered to the back of the rat once a day for three days. The dose of both the solvent and reserpine administered was 1 mL per 1 kg of the body weight of the animal. 6 days after the beginning of the administration of the solvent or reserpine, the muscle tenderness threshold of each rat was measured, and the rats were grouped such that the difference in the average of threshold between the respective groups was reduced. The drug efficacy evaluation was performed on the next day. The test substance was suspended in a 0.5% methyl cellulose solution and orally administered. 30, 60, and 120 minutes after the administration, the muscle tenderness threshold was measured. For healthy rats, the drug was not administered, and only the muscle tenderness threshold was measured. The drug efficacy was measured by an experimenter who did not know how the drug was administered to the animals. The test substance was evaluated by calculating improvement rate of the test substance-administered group, under the condition that a muscle tenderness threshold of a healthy rat measured in any point in time 30, 60, and 120 minutes after the administration was regarded as 100%, and a muscle tenderness threshold of a reserpine-administered rat administered with the solvent was regarded as 0%.

The results of typical compounds of the present invention are shown in Table 4.

TABLE 4

| Ex | Maximum improvement rate % (applied dose) | Calculated point in time (min) |
|---|---|---|
| 7-1 | 82 (10 mg/kg) | 60 |
| 8-1 | 104 (10 mg/kg) | 60 |

From the above results, it was confirmed that some of the compounds of the present invention are useful for treating fibromyalgia.

Test Method 5: Pharmacokinetic Test

A 0.5% methyl cellulose suspension including the test substance was orally administered to 5-week old male mice, and the blood and brain were collected after a certain time passed from the administration. The collected blood sample was treated with sodium heparin, and then the plasma was separated, thereby preparing a plasma sample. In addition, a phosphoric acid buffer (pH 7.0) was added to the collected brain sample, in an amount that was 4 times the weight of the brain, thereby preparing 20% brain homogenate. The concentration of the respective test substances in the plasma and brain was measured using LC-MS/MS. An hour after Example 8-1 was administered at 1 mg/kg, the concentration of the substance in the plasma was 153 ng/ml, and the concentration in the brain was 58 ng/ml.

Test Method 6: Pharmacokinetic Test Under Cortisone Load

A 0.5% methyl cellulose solution or a 0.5% methyl cellulose suspension including the test substance was orally administered to 5-week old male ddY mice. After 30 minutes, cortisone was intraperitoneally administered at 1 mg/kg, and 20 minutes later, the brain was collected. A phosphoric acid buffer (pH 7.0) was added to the collected brain sample, in an amount that was 9 times the weight of the brain, thereby preparing 10% brain homogenate. The quantity of cortisol in the brain homogenate was determined by ELISA, and the inhibition rate resulting from the test substance was calculated, under the condition that the amount of cortisol produced from the mouse orally administered with 0.5% methyl cellulose was regarded as 100%. When Example 8-1 was orally administered at 1 mg/kg, an inhibition rate of 43% was obtained.

As a result of the respective tests described above, it was confirmed that the compound of the present invention has a 11β-HSD1 inhibitory action. This result clearly shows that the compound of the present invention is useful as an active ingredient of a pharmaceutical composition for preventing or treating diseases such as dementia (particularly, Alzheimer's type dementia), schizophrenia, depression, pain (particularly, neuropathic pain or fibromyalgia), diabetes (particularly, type II diabetes mellitus), insulin resistance, obesity, hyperlipidemia, hypertension, osteoporosis, and glaucoma, particularly for treating dementia (particularly, Alzheimer's type dementia), schizophrenia, depression, pain (particularly, neuropathic pain or fibromyalgia), diabetes (particularly, type II diabetes mellitus), and insulin resistance. In addition, as another embodiment, the compound of the present invention is useful as an active ingredient of a pharmaceutical composition for preventing and/or treating dementia (particularly, Alzheimer's type dementia), schizophrenia, and depression. As still another embodiment, the compound of the present invention is useful as an active ingredient of a pharmaceutical composition preventing and/or treating dementia (particularly, Alzheimer's type dementia). As still another embodiment, the compound of the present invention is useful as an active ingredient of a pharmaceutical composition preventing and/or treating pain (particularly, neuropathic pain or fibromyalgia).

The pharmaceutical composition containing one or two or more kinds of the compound of the formula (I) or a salt thereof as an active ingredient can be prepared using excipients generally used in the related art, that is, using excipients or carriers for medications, by methods generally used.

The composition can be administered in any forms such as oral administration by using a tablet, a pill, a capsule, granules, powder, or liquid, and parenteral administration by using a preparation for injection such as intra-articular injection, intravenous injection, and intramuscular injection, a suppository, an eye drop, an eye ointment, a transdermal liquid, an ointment, a transdermal patch, a transmucosal liquid, a transmucosal patch, or an inhalation.

As a solid composition for oral administration, a tablet, powder, granules, and the like are used. In such a solid composition, one or two or more kinds of active ingredients are mixed with at least one kind of inactive excipient. The composition may contain inactive additives, for example, a lubricant, a disintegrating agent, a stabilizer, and a dissolution adjuvant according to common methods. The tablet or pill may optionally be coated with sugar or with film of a gastric or enteric material.

A liquid composition for oral administration includes a pharmaceutically acceptable opalizer, solution, suspension, syrup, elixir, or the like, and contains a generally used inactive diluent, for example, purified water or ethanol. The liquid composition may contain an auxiliary agent such as a solubilizer, a moisturizer, or a suspension, a sweetener, a flavor, an aromatic, and a preservative, in addition to the inactive diluent.

The injection preparation for parenteral administration contains a sterile aqueous or non-aqueous solution, a suspension, or an opalizer. Examples of the aqueous solution include distilled water for injection and physiological saline. Examples of the non-aqueous solution include alcohols such as ethanol. These compositions may further contain a tonicity agent, a preservative, a moisturizer, an emulsifier, a dispersant, a stabilizer, or a solubilizer. These are sterilized by, for example, filtering in which they are filtered through a bacteria retentive filter, by being mixed with a germicide, or by irradiation. Moreover, these can be used by being prepared as a sterile solid composition and dissolved or suspended in sterile water or a sterile solvent for injection before use.

Examples of agents for external use include an ointment, a plaster, a cream, a jelly, a cataplasm, a spray, a lotion, eye drops, an eye ointment, and the like. The agent for external use contains generally used substrates of ointments and lotions, an aqueous or non-aqueous liquid formulation, a suspension, an emulsion, and the like.

Transmucosal agents such as an inhalation and a transnasal agent are used in the form of a solid, a liquid or a semisolid, and can be prepared according to methods known in the related art. For example, a known excipient, a pH adjustor, a preservative, a surfactant, a lubricant, a stabilizer, a thickener or the like may be appropriately added thereto. For administration, appropriate devices for inhalation or insufflation can be used. For example, by using a known device such as a metered dose inhaler or an atomizer, the compound can be administered alone or administered as powder of a formulated mixture or as a solution or suspension which is a combination of the compound with a pharmaceutically acceptable carrier. A dry powder inhaler and the like may be for single administration or multiple administration, and dry powder or powder-containing capsules can be used. Alternatively, the compound may be administered in the form of a pressurized aerosol spray using an appropriate ejection agent, for example, a suitable gas such as a chlorofluoroalkane, or carbon dioxide.

Generally, in the case of oral administration, an appropriate daily dose is about 0.001 mg/kg to 100 mg/kg in terms of body weight, preferably 0.1 mg/kg to 30 mg/kg, and more preferably 0.1 mg/kg to 10 mg/kg, which is administered once or two to four times in separate doses. In the case of intravenous administration, an appropriate daily dose is about 0.0001 mg/kg to 10 mg/kg in terms of body weight, which is administered once or plural times in separate doses. In addition, the transmucosal agent is administered once a day or plural times a day in separate doses, in a dose of about 0.001 mg/kg to 100 mg/kg in terms of body weight. The dose is appropriately determined case by case in consideration of the symptoms, age, gender, and the like.

The pharmaceutical composition of the present invention contains one or more kinds of the compound of the formula (I) and a salt thereof as an active ingredient, in an amount of 0.01% by weight to 100% by weight, and 0.01% by weight to 50% by weight as an embodiment, even though the amount varies with the route of administration, dosage forms, site of administration, and the type of excipient or additive.

The compound of the formula (I) can be used concurrently with an agent for treating or preventing various diseases considered to be diseases for which the compound of the formula (I) is effective. In concurrent use, the compound and the agent may be administered simultaneously, administered sequentially one by one, or administered at a desired time interval. The preparation for simultaneous administration may be a combination drug or individual preparations.

EXAMPLES

Hereinafter, the preparation process of the compound of the formula (I) will be described in more detail based on examples, but the present invention is not limited to the compound described in the following examples. In addition, the preparation process of starting compounds will be shown in preparation examples. The preparation process of the compound of the formula (I) is not limited to the preparation processes of the specific examples shown below. The compound of the formula (I) can also be prepared by combining those preparation processes, or by a method that is clearly known to a person skilled in the art.

In addition, in examples, preparation examples, and tables described later, the following abbreviations will be used in some cases.

PEx: preparation example number, Ex: example number, Structure: structural formula (when there is a plurality of structure formulae, this means that a compound is a mixture of those compounds), Data: physical data (EI: EI-MS; ESP+: ESI-MS (Pos); ESN-; ESI-MS (Neg); CI+: CI-MS (Pos); APCI/ESP+: meaning simultaneous measurement of APCI (Pos) and ESI (Pos); NMR-DMSO-$d_6$: δ (ppm) of a characteristic peak in $^1$H-NMR in DMSO-$d_6$, NMR-CDCl$_3$: δ(ppm) of a characteristic peak in $^1$H-NMR in CDCl$_3$, $[\alpha]_D$: specific optical rotation in sodium D-line), Note: notes (Sal: salt (HCl: hydrochloride, if this abbreviation is not indicated for a compound, this means that the compound does not contain HCl, and the number placed before the salt indicates a compositional ratio; for example, if a compound is described 2HCl, this means that the compound is dihydrochloride, Chiral: this means that though the compound described as a planar structure since the steric structure thereof is unclear, the compound is chiral), Syn: preparation method (the number shows that the compound was prepared using the corresponding starting material just like the example compound having the number as the example compound number; when there is P before the number, this means that the compound was prepared using the corresponding starting material in the same manner as the compound of the preparation example having the same number as the preparation example number; when there is a plurality of numbers, this shows that the compound was prepared by performing the preparation methods in order from the preparation method corresponding to the previous number), PSyn: preparation method (this means that the compound was prepared using the corresponding starting material just like the compound of the preparation example having the same number as the preparation example number; when there is a plurality of numbers, this means that the compound was prepared by performing the preparation methods in order from the preparation method corresponding to the previous number.))

Preparation Example 1

N-[(dimethylamino)(3H-[1,2,3]triazolo[4,5-b]pyri din-3-yloxy)methylidene]-N-methyl methanaminium hexafluorophosphate (HATU) (235 mg) and diisopropylethylamine (184 mg) were added to a DMF (2 mL) solution of 4-isopropoxy-2-methoxybenzoic acid (100 mg) and benzyl 5-(cyclopropylamino)-4,5,6,7-tetrahydro-2H-indazole-2-carboxylate hydrochloride (165 mg), followed by stirring overnight at 60° C. Thereafter, water was added to the reaction mixture, extraction was performed using ethyl acetate, followed by washing with water and saturated brine in this order and drying over anhydrous magnesium sulfate, thereby obtaining a crude product. The crude product obtained was purified by silica gel column chromatography (30% to 100%, ethyl acetate/hexane), thereby obtaining benzyl 5-[cyclopropyl(4-isopropoxy-2-methoxybenzoyl)amino]-4,5,6,7-tetrahydro-2H-indazole-2-carboxylate (140 mg).

Preparation Example 2

Oxalyl chloride (0.167 ml) and one drop of DMF were added to a dichloromethane (9 ml) suspension of 2'-cyano-6'-fluorobiphenyl-4-carboxylic acid (470 mg) at 0° C., followed by stirring for 3 hours at room temperature. Thereafter, the reaction liquid was cooled again to 0° C., diisopropylethylamine (0.61 ml) was added thereto, and then a dichloromethane (4.5 ml) solution of tert-butyl 5-(cyclopropylamino)-4,5,6,7-tetrahydro-2H-indazole-2-carboxylate (450 mg) was added dropwise thereto, followed by stirring for 2 hours at room temperature. Water was added to the reaction liquid, extraction was performed using ethyl acetate, followed by washing with a saturated aqueous sodium hydrogen carbonate solution and saturated brine in this order and drying over anhydrous magnesium sulfate, thereby obtaining a crude product. The crude product was purified by silica gel column chromatography (30% to 100%, ethyl acetate/hexane), thereby obtaining tert-butyl 5-{[(2'-cyano-6'-fluorobiphenyl-4-yl)carbonyl] (cyclopropyl)amino}-4,5,6,7-tetrahydro-2H-indazole-2-carboxylate (700 mg).

Preparation Example 3

Thionyl chloride (890 mg) was added to a dichloromethane (2 ml) solution of 1-(2-methoxyethyl)-1H-indole-4-carboxylic acid (125 mg) and 1H-1,2,3-benzotriazole (900 mg) at room temperature. After stirring for 2 hours at room temperature, the insoluble material was removed by filtration, followed by washing with a small amount of toluene. Anhydrous magnesium sulfate was added to the filtrate, followed by stirring, and then the solid was removed by filtration, and the filtrate was concentrated. The residue obtained was dissolved in dichloromethane (3 ml) and added to a dichloromethane (2 ml) solution of tert-butyl 5-(cyclopropylamino)-4,5,6,7-tetrahydro-2H-indazole-2-carboxylate (150 mg) and isopropylethylamine (150 mg), followed by stirring for 16 hours at room temperature. The reaction liquid was diluted with ethyl acetate and washed with saturated aqueous sodium bicarbonate and saturated brine. The obtained organic layer was dried over anhydrous magnesium sulfate, followed by filtration and concentration under reduced pressure. The obtained residue was purified by silica gel column chromatography (hexane:ethyl acetate=10:0 to 4:6), thereby obtaining tert-butyl 5-(cyclopropyl {[1-(2-methoxyethyl)-1H-indol-4-yl]carbonyl}amino)-4,5,6,7-tetrahydro-2H-indazole-2-carboxylate (34 mg) as a colorless oil-like substance.

Preparation Example 4

An aqueous solution (3 ml) of tetrakis triphenylphosphine palladium (115 mg) and sodium carbonate (530 mg) was added to a dioxane (20 ml) solution of 2-bromo-3-fluorobenzonitrile (667 mg) and 4-(methoxycarbonyl)phenyl boronic acid (600 mg), followed by stirring overnight at 100° C. in an argon atmosphere, thereafter, cooling to room temperature, diluting with ethyl acetate, washing with saturated brine, and drying over anhydrous magnesium sulfate. The solvent was evaporated under reduced pressure. The solid of the crude product obtained was washed with diisopropylether and dried under reduced pressure, thereby obtaining methyl 2'-cyano-6'-fluorobiphenyl-4-carboxylate (740 mg).

Preparation Example 5

Under an argon gas atmosphere, tris(dibenzylideneacetone)dipalladium (14 mg) and tri-tert-butylphosphonium tetrafuloroborate (11 mg) were added to a mixture of 2-bromo-3-fluorobenzonitrile (150 mg), 4-methoxycarbonyl-2-methylphenylboronic acid pinacol ester (259 mg), potassium fluoride (144 mg), THF (1.8 mL), and water (0.23 mL), followed by stirring for 14 hours at room temperature. The reaction liquid was concentrated under reduced pressure, and the residue was purified by silica gel column chromatography (hexane/ethyl acetate), thereby obtaining methyl 2'-cyano-6'-fluoro-2-methylbiphenyl-4-carboxylate (70 mg).

Preparation Example 6

A mixture of 4-bromo-3,5-dichloropyridine (357 mg), 4-methoxycarbonylphenyl boronic acid (236 mg), a 1,1'-bis(diphenylphosphino)ferrocene-palladium(II)dichloride-dichloromethane complex (107 mg), cesium fluoride (398 mg), and 1,2-dimethoxyethane (3.5 mL) was stirred under heating for an hour at an oil temperature of 80° C. under an argon gas atmosphere, followed by cooling to room temperature. The reaction liquid was concentrated under reduced pressure, and the residue was purified by silica gel column chromatography (hexane/ethyl acetate), thereby obtaining methyl 4-(3,5-dichloropyridin-4-yl)benzoate (298 mg).

Preparation Example 7

Tris(dibenzylideneacetone)dipalladium (24 mg) and 2-dicyclohexylphosphino-2',6'-dimethoxybiphenyl (43 mg) were added to a mixture of methyl 3,5-dimethyl-4-{[(trifluoromethyl)sulfonyl]oxy}benzoate (409 mg), 2-cyanophenyl boronic acid (385 mg), tripotassium phosphate (835 mg), and toluene (2.6 mL) under an argon gas atmosphere, followed by stirring under heating for 3 hours at an oil temperature of 110° C., and cooling to room temperature. Water was added to the reaction liquid, followed by diluting with ethyl acetate, washing with saturated brine, drying, and then concentrating under reduced pressure. The residue was purified by silica gel column chromatography (hexane/ethyl acetate), thereby obtaining methyl 2'-cyano-2,6-dimethylbiphenyl-4-carboxylate (347 mg).

Preparation Example 8

Lithium diisopropylamide (2.0 M heptane/THF/ethylbenzene solution, 5.57 mL) was added to a THF (7.5 mL) solution of 3,5-difluoropyridine (1.26 g) under an argon gas atmosphere at −78° C. with dry ice/acetone, followed by stirring for 0.5 hours, and then zinc chloride (1.55 g) was added thereto, followed by stirring again for 0.5 hours at the same temperature. After the temperature was elevated to room temperature, a N-methylpyrrolidin-2-one (NMP) (7.5 mL) solution of ethyl 4-bromobenzoate (0.50 g) and tetrakis(triphenylphosphine)palladium (0.50 g) were added thereto, followed by stirring under heating for 8 hours at an oil temperature of 100° C., and cooling to room temperature. 1 M hydrochloric acid was added to the reaction liquid, and then the generated solid was collected by filtration, thereby obtaining 4-(3,5-difluoropyridin-4-yl)benzoic acid (Preparation Example 8-1, 80 mg). The filtrate was diluted with ethyl acetate and then washed with saturated brine, followed by drying and then concentrating under reduced pressure. The residue was purified by silica gel column chromatography (hexane/ethyl acetate), thereby obtaining ethyl 4-(3,5-difluoropyridin-4-yl)benzoate (Preparation Example 8-2, 83 mg).

Preparation Example 9

Under an argon gas atmosphere, n-butyllithium (1.63 M n-hexane solution, 2.41 mL) was added to a THF (3.0 mL) solution of 3-chloro-5-fluoropyridine (517 mg) under cooling at −78° in a dry ice/acetone bath, followed by stirring for 0.5 hours, and then zinc chloride (0.5 M THF solution, 7.86 mL) was added thereto, followed by stirring again for 0.5 hours at the same temperature. After the temperature was elevated to room temperature, a THF (3.0 mL) solution of ethyl 4-bromobenzoate (300 mg) and tetrakis(triphenylphosphine)palladium (303 mg) were added thereto, followed by stirring under heating for 16 hours at an oil temperature of 60° C., and cooling to room temperature. 1 M hydrochloric acid was added to the reaction liquid, followed by diluting with ethyl acetate, washing with saturated brine, drying, and then concentrating under reduced pressure. The residue was purified by silica gel column chromatography (hexane/ethyl acetate), thereby obtaining ethyl 4-(3-chloro-5-fluoropyridin-4-yl) benzoate (194 mg).

Preparation Example 10

(Tributylphosphoranylidene)acetonitrile (1.38 g) was added to a mixture of methyl 1H-indole-4-carboxylate (500 mg), (3-methyloxetan-3-yl)methanol (583 mg), and toluene (15 mL) under an argon gas atmosphere, followed by reflux overnight, and then cooling to room temperature. The reaction liquid was concentrated under reduced pressure, and the residue was purified by silica gel column chromatography (hexane/ethyl acetate), thereby obtaining methyl 1-[(3-methyloxetan-3-yl)]-1H-indole-4-carboxylate (700 mg).

Preparation Example 11

60% sodium hydride (134 mg) was slowly added to a DMF (5 mL) solution of methyl 1H-indole-4-carboxylate (507 mg) in an ice bath under cooling, followed by stirring for 30 minutes. 2-(2-oxopyrrolidin-1-yl)ethyl methanesulfonate (660 mg) was added thereto, and the temperature was slowly elevated to room temperature, followed by stirring for 5 hours. Thereafter, the reaction liquid was poured into water, followed by extracting with ethyl acetate, washing with saturated brine, drying over anhydrous magnesium sulfate, and concentrating under reduced pressure. The residue was purified by a silica gel column, thereby obtaining methyl 1-[2-(2-oxopyrrolidin-1-yl)ethyl]-1H-indole-4-carboxylate (260 mg).

Preparation Example 12

Potassium carbonate (196 mg) and 1-iodopropane (482 mg) were added to a DMF (2.5 mL) solution of methyl 1H-indazole-4-carboxylate (250 mg), followed by stirring overnight at room temperature. Thereafter, water was added to the reaction liquid, followed by extracting with ethyl acetate, and washing with saturated brine, thereby obtaining a crude product. The crude product obtained was purified by silica gel column chromatography (hexane/ethyl acetate), thereby obtaining methyl 1-propyl-1H-indazole-4-carboxylate (130 mg).

Preparation Example 13

2,2'-dimethyloxirane (412 mg) and cesium carbonate (1.4 g) were added to a DMF (10 ml) solution of methyl 1H-indole-4-carboxylate (500 mg), followed by stirring for an hour at 100° C. Thereafter, 2,2'-dimethyloxirane (411 mg) was further added thereto, followed by stirring for an hour, followed by cooling to room temperature. The reaction liquid was concentrated under reduced pressure, and the residue was purified by silica gel column chromatography (hexane/ethyl acetate), thereby obtaining methyl 1-(2-hydroxy-2-methylpropyl)-1H-indole-4-carboxylate (560 mg).

Preparation Example 14

Potassium tert-butoxide (241 mg) was added to a DMF (2.2 mL) solution of methyl 7-methoxy-1H-indole-4-carboxylate (220 mg) under ice cooling, followed by stirring for 30 minutes. Thereafter, iodomethane (183 mg) was added thereto, followed by stirring for 3 hours at room temperature. Water was added to the reaction liquid, followed by extraction with ethyl acetate. The organic layer was washed with saturated brine and dried over anhydrous magnesium sulfate, thereby obtaining a crude product. The obtained crude product was purified by silica gel column chromatography (hexane/ethyl acetate), thereby obtaining methyl 7-methoxy-1-methyl-1H-indole-4-carboxylate (200 mg).

Preparation Example 15

Potassium carbonate (55 mg) was added to an acetone (3 mL) solution of tert-butyl 5-{cyclopropyl[(6-hydroxy-1-benzothiophen-3-yl)carbonyl]amino}-4,5,6,7-tetrahydro-2H-indazole-2-carboxylate (120 mg) at room temperature, followed by stirring for 30 minutes. Iodomethane (25 μL) was added thereto under ice cooling, followed by stirring for 14 hours at room temperature. Water was added to the reaction liquid, followed by extraction with ethyl acetate. The organic layer was washed with saturated brine and dried over anhydrous magnesium sulfate. After the solid was filtered, the solution was concentrated under reduced pressure. The residue obtained was purified by silica gel column chromatography, thereby obtaining tert-butyl 5-{cyclopropyl[(6-methoxy-1-benzothiophen-3-yl)carbonyl]amino}-4,5,6,7-tetrahydro-2H-indazole-2-carboxylate (35 mg).

Preparation Example 16

A THF solution (3.45 mL) of 1 M tetrabutylammonium fluoride was added to a mixture of methyl 5-methoxy-1-(triisopropylsilyl)-1H-indole-4-carboxylate (1.04 g) and THF (10 mL) under ice cooling under an argon gas atmosphere, followed by stirring for an hour at the same temperature. Iodomethane (0.897 mL) was added thereto, followed by stirring for an hour at the same temperature and then for 12 hours at room temperature. The reaction liquid was diluted with ethyl acetate and was washed with water and saturated brine in this order, followed by drying, and concentrating under reduced pressure. The residue was purified by silica gel column chromatography (hexane/ethyl acetate), thereby obtaining methyl 5-methoxy-1-methyl-1H-indole-4-carboxylate (205 mg).

Preparation Example 17

2,6-difluorobenzylamine (0.710 mL) and p-toluenesulfonic acid hydrate (70 mg) were added to a toluene (20 mL) solution of ethyl 2-acetyl-4-oxopentanoate (1.00 g), followed by stirring for 14 hours at 110° C. The reaction mixture was returned to room temperature, and a saturated aqueous sodium hydrogen carbonate solution was added thereto, followed by extraction with ethyl acetate. The organic layer was washed with saturated brine and dried over anhydrous magnesium sulfate, and the solvent was evaporated. The residue obtained was purified by silica gel column chromatography (hexane/ethyl acetate=100/0 to 85/15), thereby obtaining ethyl 1-(2,6-difluorobenzyl)-2,5-dimethyl-1H-pyrrole-3-carboxylate (1.073 g) as a pale yellow solid.

Preparation Example 18

2,4-dichloroaniline (1.37 g) was added to an acetic acid (10 mL) solution of ethyl 2-acetyl-4-oxopentanoate (1.50 g), followed by stirring for 14 hours at 100° C. The reaction mixture was concentrated, and then a saturated aqueous sodium hydrogen carbonate solution was added to the residue, followed by extraction with ethyl acetate. The organic layer was washed with saturated brine and dried over anhydrous magnesium sulfate, and then the solvent was evaporated. The residue obtained was purified by silica gel column chromatography (hexane/ethyl acetate=100/0 to 90/10), thereby obtaining ethyl 1-(2,4-dichlorophenyl)-2,5-dimethyl-1H-pyrrole-3-carboxylate (1.469 g) as a yellow oil-like substance.

Preparation Example 19

A 4 M aqueous lithium hydroxide solution (5 mL) was added to an ethanol (10 mL) solution of ethyl 2-methyl-1-(2-methylphenyl)-1,4,5,6-tetrahydrocyclopenta[b]pyrrole-3-carboxylate (840 mg), followed by stirring for 2.5 days at 80° C. 1 M hydrochloric acid (20 ml) was added to the reaction liquid, followed by extraction with ethyl acetate. The organic layer was washed with saturated brine and dried over anhydrous magnesium sulfate, and then the solvent was evaporated. The residue obtained was purified by silica gel column chromatography (hexane/ethyl acetate=100/0 to 80/20 or 60/40), thereby obtaining 2-methyl-1-(2-methylphenyl)-1,4,5,6-tetrahydrocyclopenta[b]pyrrole-3-carboxylate (225 mg) as a pale yellow solid.

Preparation Example 20

A 5M aqueous sodium hydroxide solution (5.7 ml) was added to an ethanol (11 ml) suspension of methyl 2'-cyano-6'-fluorobiphenyl-4-carboxylate (730 mg) at room temperature, followed by stirring for 30 minutes at 70° C., followed by cooling. The reaction liquid was acidified using 1M hydrochloric acid. The precipitate was collected by filtration, washed with water, and concentrated under reduced pressure, thereby obtaining 2'-cyano-6'-fluorobiphenyl-4-carboxylic acid (560 mg).

Preparation Example 21

A 1M THF solution (1.12 mL) of N,N,N-tributylbutan-1-ammonium fluoride (TBAF) was added dropwise to a THF (2.6 mL) solution of methyl 1-(2-oxopropyl)-1H-indole-4-carboxylate (260 mg) and trimethyl(trifluoro)silane (240 mg) under ice cooling, followed by stirring overnight at room temperature. Thereafter, 1 M hydrochloric acid was added to the reaction liquid, followed by stirring for 30 minutes, and extracting with ethyl acetate. The organic layer was washed with a saturated aqueous sodium hydrogen carbonate solution and saturated brine in this order and dried over anhydrous magnesium sulfate, followed by concentration under reduced pressure, thereby obtaining a crude product. The crude product obtained was purified by silica gel column chromatography (hexane/ethyl acetate), thereby obtaining methyl 1-(3,3,3-trifluoro-2-hydroxy-2-methylpropyl)-1H-indole-4-carboxylate (230 mg).

Preparation Example 22 n-Butyllithium (1.65 M THF solution) (4.1 mL) was added dropwise to a diethylether (20 mL) solution of 3-bromo-4-fluoro-1-benzothiophene (1.4 g) at −70° C. under a nitrogen flow, followed by stirring for 30 minutes at −70° C. Thereafter, the reaction liquid was added to dry ice. After the reaction liquid was returned to room temperature, the solvent was concentrated under reduced pressure. Water was added to the residue, followed by washing with hexane. 1M hydrochloric acid was added to the aqueous layer for neutralization, followed by extraction with ethyl acetate. After the organic layer was dried over anhydrous magnesium sulfate, the solid was removed by filtration, followed by concentration under reduced pressure. Diethylether was added thereto, followed by stirring, and the solid was collected by filtration and dried under reduced pressure at 40° C., thereby obtaining 4-fluoro-1-benzothiophene-3-carboxylic acid (0.57 g).

Preparation Example 23

Borane tribromide (3.76 mL, 1 M solution) was added to a dichloromethane (1.3 mL) solution of N-cyclopropyl-1-(3-methoxypropyl)-N-(4,5,6,7-tetrahydro-1H-indazol-5-yl)-1H-indole-4-carboxamide (130 mg) under ice cooling in an argon atmosphere, followed by stirring for 60 hours at room temperature. Thereafter, water was added thereto, followed by extraction with ethyl acetate. The organic layer was dried over anhydrous magnesium sulfate, the solid was removed by filtration, followed by concentration under reduced pressure. The residue was purified by silica gel column chromatography (chloroform:methanol=10:0 to 9:1), thereby obtaining 1-(3-bromopropyl)-N-cyclopropyl-N-(4,5,6,7-tetrahydro-1H-indazol-5-yl)-1H-indole-4-carboxamide (68 mg).

Preparation Example 24

A mixture of benzyl cyclopropyl(4-oxocyclohexyl)carbamate (18.4 g), 1,1-dimethoxy-N,N-dimethylmethanamine (40 mL), and triethylamine (40 mL) was stirred under heating for 30 minutes at an oil temperature of 140° C., and a volatile substance was evaporated.

Thereafter, 1,1-dimethoxy-N,N-dimethylmethanamine (40 mL) and triethylamine (40 mL) were added thereto, followed by stirring under heating for 30 minutes at 140° C. By using the respective reagents in an amount of 200 mL in total, the above operation was repeated 5 times. The reaction liquid was concentrated under reduced pressure, and ethanol (100 mL) and a hydrazine hydrate (10.1 mL) were added to the residue, followed by stirring for 60 hours at room temperature. After the reaction liquid was diluted with ethyl acetate, followed by washing with water 3 times and then with saturated brine, drying, and concentrating under reduced pressure. The residue was purified by silica gel column chromatography (chloroform/methanol), thereby obtaining benzyl cyclopropyl(4,5,6,7-tetrahydro-1H-indazol-5-yl)carbamate (15.0 g).

Preparation Example 25

Tris(dibenzylideneacetone)dipalladium (18 mg) and 2-dicyclohexylphosphino-2',6'-dimethoxybiphenyl (33 mg) were added to a mixture of 2-bromo-3,5-difluoropyridine (250 mg), [4-(methoxycarbonyl)phenyl]boronate (180 mg), tripotassium phosphate (637 mg), and toluene (1.8 mL) under an argon gas atmosphere, followed by stirring under heating for 4 hours at an oil temperature of 110° C., and then the reaction liquid was cooled to room temperature. Water was added to the reaction liquid, followed by diluting with ethyl acetate, washing with saturated brine, drying, and concentrating under reduced pressure. The residue was purified by silica gel column chromatography (hexane/ethyl acetate), thereby obtaining methyl 4-(3,5-difluoropyridin-2-yl)benzoate (249 mg).

Preparation Example 26

Sodium triacetoxy borohydride (5.41 g) and acetic acid (2.19 mL) were added to a mixture of a mixture (3.45 g) of benzyl 5-oxo-4,5,6,7-tetrahydro-2H-indazole-2-carboxylate and a regioisomer thereof, cyclopropylamine (0.878 mL), and 1,2-dichloroethane (70 mL) under an argon gas atmosphere, followed by stirring for 18 hours at room temperature. Water was added to the reaction liquid, followed by stirring for 2 hours at room temperature, and then pH thereof was adjusted to 8 by using saturated aqueous bicarbonate, followed by liquid separation. The organic layer was dried and then concentrated under reduced pressure. A dioxane solution (4.15 mL) of 4 M hydrogen chloride was added to a mixture of the residue and ethyl acetate (100 mL), followed by stirring for an hour at room temperature. The precipitate was collected by filtration and washed with ethyl acetate, thereby obtaining a mixture (3.26 g) of benzyl 5-(cyclopropylamino)-4,5,6,7-tetrahydro-2H-indazole-2-carboxylate monohydrochloride and a regioisomer thereof.

Preparation Example 27

1 M hydrochloric acid (100 mL) was added to a mixture of benzyl cyclopropyl(1,4-dioxaspiro[4.5]dec-8-yl)carbamate (23.1 g) and THF (200 mL) under ice cooling, followed by stirring for 48 hours at room temperature. Thereafter, 1 M hydrochloric acid (100 mL) was added thereto, followed by stirring again for 10 hours at room temperature. The reaction liquid was diluted with ethyl acetate, followed by liquid separation. The organic layer was washed with a saturated aqueous ammonium chloride solution and saturated brine and dried, followed by concentration under reduced pressure. The residue was purified by silica gel column chromatography (hexane/ethyl acetate), thereby obtaining benzyl cyclopropyl (4-oxocyclohexyl)carbamate (18.4 g).

Preparation Example 28

Diisopropylethylamine (9.59 mL) and benzyloxycarbonyl chloride (6.40 mL) were added to a mixture of 1',4',6',7'-tetrahydrospiro[1,3-dioxolane-2,5'-indazole] (6.73 g) and THF (70 mL) under ice cooling under an argon gas atmosphere, followed by stirring for 3 hours under ice cooling. The reaction liquid was diluted with ethyl acetate and then washed with water and saturated brine in this order, followed by drying, and concentrating under reduced pressure. The residue was purified by silica gel column chromatography (hexane/ethyl acetate), thereby obtaining benzyl 6',7'-dihydrospiro[1,3-dioxolane-2,5'-indazole]-2'(4'H)-carboxylate (11.1 g).

Preparation Example 29

Triethylamine (35.3 mL), benzyl chlorocarbonate (29.0 mL), and 4-dimethylaminopyridine in a catalytic amount were added to a mixture of N-cyclopropyl-1,4-dioxaspiro [4.5]decan-8-amine (20 g) and dichloromethane (200 mL) under ice cooling under an argon gas atmosphere, followed by stirring for an hour under ice cooling and then for 12 hours at room temperature. The reaction liquid was diluted with chloroform, and then the resultant was washed with 1 M hydrochloric acid, water, and saturated aqueous sodium bicarbonate in this order, followed by drying, and concentrating under reduced pressure. The residue was purified by silica gel column chromatography (hexane/ethyl acetate), thereby obtaining benzyl cyclopropyl(1,4-dioxaspiro[4.5]dec-8-yl)carbamate (23.9 g).

Preparation Example 30

A mixture of a mixture (17.1 g) of tert-butyl 5-{[(benzyloxy)carbonyl](cyclopropylamino}-4,5,6,7-tetrahydro-2H-indazole-2-carboxylate and a regioisomer thereof, 10% palladium supported on activated charcoal (1.7 g), and ethanol (200 mL) was stirred for 2 hours at room temperature under a hydrogen atmosphere at 1 atm. The 10% palladium supported on activated charcoal was removed from the reaction liquid by filtration, and then the filtrate was concentrated under reduced pressure. The residue was purified by silica gel column chromatography (chloroform/methanol), thereby obtaining a mixture (10.5 g) of tert-butyl 5-(cyclopropylamino)-4,5,6,7-tetrahydro-2H-indazole-2-carboxylate monohydrochloride and a regioisomer thereof.

Preparation Example 31

A mixture of tert-butyl dicarbonate (13.7 g) and dichloromethane (100 mL) was added to a mixture of benzyl cyclopropyl(4,5,6,7-tetrahydro-1H-indazol-5-yl)carbamate (18.0 g) and dichloromethane (200 mL) under an argon gas atmosphere, followed by stirring for 12 hours at room temperature. Thereafter, a mixture of tert-butyl dicarbonate (5.3 g) and dichloromethane (10 mL) was added thereto, followed by stirring again for 24 hours at room temperature. The reaction liquid was concentrated under reduced pressure. The residue was purified by silica gel column chromatography (chloroform/ethyl acetate), thereby obtaining a mixture (17.1 g) of tert-butyl 5-{[(benzyloxy)carbonyl] (cyclopropylamino}-4, 5,6,7-tetrahydro-2H-indazole-2-carboxylate and a regioisomer thereof.

Preparation Example 32

Triethylamine (635 µL) and di-tert-butyl dicarbonate (597 mg) were added to a THF (3.7 mL) solution of 4'-[cyclopropyl (4,5,6,7-tetrahydro-1H-indazol-5-yl)carbamoyl]biphenyl-2-carboxylic acid (366 mg), followed by stirring for 16 hours at room temperature. Water was added to the reaction liquid, followed by diluting with ethyl acetate, washing with saturated brine, drying, and then concentrating under reduced pressure, thereby obtaining 4'-{[2-(tert-butoxycarbonyl)-4,5, 6,7-tetrahydro-2H-indazol-5-yl](cyclopropyl) carbamoyl}biphenyl-2-carboxylic acid (300 mg). N—[(dimethylamino)(3H-[1,2,3]triazolo[4,5-b]pyridin-3-yloxy) methylidene]-N-methylmethanaminium hexafluorophosphate (HATU) (57 mg), diisopropylethylamine (19 mg), and 4-dimethylaminopyridine in a catalytic amount were added to a DMF (1.2 mL) solution of 4'-{[2-(tert-butoxycarbonyl)-4,5,6,7-tetrahydro-2H-indazol-5-yl] (cyclopropyl)carbamoyl}biphenyl-2-carboxylic acid (50 mg), followed by stirring overnight at 60° C. Thereafter, water was added to the reaction liquid, followed by extracting with ethyl acetate, washing with water and saturated brine in this order, and drying over anhydrous magnesium sulfate, thereby obtaining a crude product. The obtained crude product was purified by silica gel column chromatography (30% to 100%, ethyl acetate/hexane), thereby obtaining tert-butyl 5-(cyclopropyl){[2'-(dimethylcarbamoyl)biphenyl-4-yl] carbonyl}amino)-4,5,6,7-tetrahydro-2H-indazole-2-carboxylate (30 mg).

Preparation Example 33

1-(Chloromethyl)-4-fluoro-1,4-diazoniabicyclo[2,2,2]octane ditetrafluoroborate (2.36 g) was added to a mixture of methyl 2-methyl-1H-indole-4-carboxylate (1.17 g) and acetonitrile (20 mL) under ice cooling, followed by stirring for 3 hours at room temperature. The reaction liquid was diluted with ethyl acetate and washed with a saturated aqueous sodium hydrogen carbonate solution, followed by drying, and concentrating under reduced pressure. The residue was purified by silica gel column chromatography (hexane/ethyl acetate and then hexane/chloroform), thereby obtaining methyl 3-fluoro-2-methyl-1H-indole-4-carboxylate (102 mg).

Preparation Example 34

N-ethyl-N-isopropylpropan-2-amine (4.08 mL) and benzyl chloromethyl ether (0.792 mL) were added to a mixture of 3'-methyl-1',4',6',7'-tetrahydrospiro[1,3-dioxolane-2,5'-indazole] (925 mg) and dichloromethane (20 mL) under ice cooling under an argon gas atmosphere, followed by stirring for 4.5 hours at room temperature. The reaction liquid was diluted with ethyl acetate and then washed with water, saturated aqueous sodium bicarbonate, and saturated brine in this order, followed by drying, and concentrating under reduced pressure. The residue was purified by silica gel column chromatography (hexane/ethyl acetate), thereby obtaining a mixture (1.11 g) of 1'-[(benzyloxy)methyl]-3'-methyl-1',4',6',7'-tetrahydrospiro[1,3-dioxolane-2,5'-indazole] and a regioisomer thereof.

Preparation Example 35

A hydrazine hydrate (0.756 mL) was added to a mixture of 1-(8-hydroxy-1,4-dioxaspiro[4.5]dec-7-en-7-yl)ethanone (1.03 g) and ethanol (10 mL), followed by stirring for 12 hours at room temperature. The reaction liquid was diluted with ethyl acetate and then washed with saturated aqueous sodium bicarbonate and saturated brine in this order, followed by drying, and concentrating under reduced pressure, thereby obtaining 3'-methyl-1',4',6',7'-tetrahydrospiro[1,3-dioxolane-2,5'-indazole] (948 mg).

Preparation Example 36

A mixture of benzyl cyclopropyl(3-oxo-2,3,5,6,7,8-hexahydrocinnolin-6-yl)carbamate (172 mg) and phosphoric trichloride (0.50 mL) was stirred under heating for 3.5 hours at an oil temperature of 100° C. under an argon gas atmosphere and then cooled to room temperature. The reaction liquid was added to ice water, followed by extraction with ethyl acetate. The organic layer was washed with saturated aqueous sodium bicarbonate, followed by drying, and concentrating under reduced pressure. The residue was purified by silica gel column chromatography (chloroform/methanol), thereby obtaining benzyl (3-chloro-5,6,7,8-tetrahydrocinnolin-6-yl)cyclopropyl carbamate (74 mg).

Preparation Example 37

A mixture of benzyl 5-[cyclopropyl(4-hydroxybenzoyl) amino]-4,5,6,7-tetrahydro-2H-indazole-2-carboxylate (80 mg), (R)-(−)-2-butanol (19 μL), triphenylphosphine (63 mg), and THF (1.0 mL) was cooled with ice water under an argon gas atmosphere, and diisopropyl azodicarboxylate (40% toluene solution, 127 μL) was added thereto, and the temperature was elevated to room temperature, followed by stirring for 6 hours. The reaction liquid was concentrated under reduced pressure, and the residue was purified by silica gel column chromatography (hexane/ethyl acetate), thereby obtaining benzyl 5-[{4-[(2S)-butan-2-yloxy]benzoyl}(cyclopropyl) amino]-4,5,6,7-tetrahydro-2H-indazole-2-carboxylate (18 mg).

Preparation Example 38

Tetrabutylammonium fluoride (1 M THF solution, 742 μL) was added to a THF (6.0 mL) solution of benzyl 5-(cyclopropyl{4-[(triethylsilypoxy]benzoyl}amino)-4,5,6,7-tetrahydro-2H-indazole-2-carboxylate (270 mg), followed by stirring for 3 days at room temperature. The reaction liquid was concentrated under reduced pressure, and the residue was purified by silica gel column chromatography (hexane/ethyl acetate), thereby obtaining benzyl 5-[cyclopropyl(4-hydroxybenzoyl)amino]-4,5,6,7-tetrahydro-2H-indazole-2-carboxylate (129 mg).

Preparation Example 39

A mixture of methyl 1H-indazole-4-carboxylate (505 mg), iodobenzene (1.17 g), copper(I) iodide (107 mg), trans-N,N'-dimethylcyclohexane-1,2-diamine (161 mg), tripotassium phosphate (1.22 g), and dioxane (5 mL) was stirred under heating for 8 hours at an oil temperature of 95° C. The reaction liquid was cooled to room temperature, followed by diluting with ethyl acetate, and washing with water and saturated brine. The organic layer was dried and concentrated under reduced pressure, and the residue was purified by silica gel column chromatography (hexane/ethyl acetate), thereby obtaining methyl 1-phenyl-1H-indazole-4-carboxylate (345 mg).

Preparation Example 40

A dichloromethane (0.8 mL) solution of trifluoroacetic acid (111 mg) was added dropwise to diethyl zinc (1 M dichloromethane solution, 0.97 mL) under ice cooling, followed by stirring for 20 minutes. Thereafter, a dichloromethane (0.8 mL) solution of diiodomethane (274 mg) was added dropwise to the reaction liquid, and then the temperature was elevated to room temperature, followed by stirring for 20 minutes. Thereafter, a dichloromethane (0.8 mL) solution of methyl 1-[2-(vinyloxy)ethyl]-1H-indazole-4-carboxylate (120 mg) was added dropwise thereto under ice cooling, and the temperature was slowly elevated to room temperature, followed by stirring overnight. Water was added to the reaction liquid, followed by extraction with chloroform. The organic layer was washed with a saturated aqueous hydrogen carbonate solution and saturated brine in this order and dried over anhydrous magnesium sulfate, followed by concentration under reduced pressure and purification by silica gel column chromatography, thereby obtaining methyl 1-[2-(cyclopropyloxy)ethyl]-1H-indazole-4-carboxylate (30 mg).

Preparation Example 41

N-bromosuccinimide (1.125 g) was added to a chloroform (20 mL) solution of (1-benzothiophen-6-yloxy)(tert-butyl) diphenylsilane (2.34 g) at room temperature, followed by stirring for 60 hours. Thereafter, water was added thereto, followed by extraction with chloroform, and the organic layer was concentrated. Subsequently, the residue was purified by silica gel column chromatography (hexane), thereby obtaining [(3-bromo-1-benzothiophen-6-yl)oxy](tert-butyl)diphenylsilane (1.16 g) as a colorless oil-like substance.

Preparation Example 42 tert-Butyl(chloro)diphenylsilane (4.9 mL) was added dropwise to a dichloromethane (20 ml) solution of 1-benzothiophen-6-ol (2.5 g) and diisopropylethylamine under ice cooling, followed by stirring for 16 hours at room temperature. A saturated aqueous ammonium chloride solution was added thereto, followed by extracting with chloroform, drying over anhydrous magnesium sulfate. Thereafter, the solvent was evaporated. The residue was purified by silica gel column chromatography (hexane/ethyl acetate=10:0 to 95:5), thereby obtaining (1-benzothiophen-6-yloxy)(tert-butyl)diphenylsilane (5.37 g) as a colorless oil-like substance.

Preparation Example 43

A 4 M aqueous sodium hydroxide solution (2 mL) was added to a mixture of methanol (2 mL) and THF (2 mL) of tert-butyl 5-(cyclopropyl{[2'-(methoxycarbonyl)biphenyl-4-yl]carbonyl}amino)-4,5,6,7-tetrahydro-2H-indazole-2-carboxylate (470 mg) at room temperature, followed by stirring overnight. Thereafter, 1 M hydrochloric acid was added to the reaction liquid for neutralization, and the solvent was evaporated under reduced pressure, thereby obtaining 4'-[cyclopropyl(4,5,6,7-tetrahydro-1H-indazol-5-yl)carbamoyl]biphenyl-2-carboxylic acid (366 mg).

Preparation Example 44

Acetyl chloride (0.140 mL) was added to a mixture of N-cyclopropyl-4-isopropyl-N-[4-(pyrrolidin-1-yl)cyclohex-3-en-1-yl benzamide (630 mg), diisopropylethylamine (0.367 mL), and chloroform (17 mL) under an argon gas atmosphere, followed by stirring for 26 hours at room temperature. 1 M hydrochloric acid was added to the reaction liquid, followed by stirring for an hour at room temperature, and ethyl acetate was added thereto to perform liquid separation. The organic layer was washed with water and saturated brine in this order and dried, followed by concentration under reduced pressure. The residue was purified by silica gel column chromatography (chloroform/ethyl acetate), thereby obtaining N-(3-acetyl)-4-hydroxycyclohex-3-en-1-yl)-N-cyclopropyl-4-isopropyl benzamide (203 mg).

Preparation Example 45

Pyrrolidine (0.846 mL) was added to a mixture of N-cyclopropyl-4-isopropyl-N-(4-oxocyclohexyl benzamide (500 mg), anhydrous magnesium sulfate (1.5 g), and toluene (5 mL) under an argon gas atmosphere, followed by stirring for 24 hours at room temperature. Magnesium sulfate was removed from the reaction liquid by filtration, followed by concentrating under reduced pressure and drying, thereby obtaining N-cyclopropyl-4-isopropyl-N-[4-(pyrrolidin-1-yl)cyclohex-3-en-1-yl]benzamide (640 mg).

Preparation Example 46

A mixture of ethyl 2-acetamide-3-oxobutanoate (400 mg), benzylamine (0.700 mL), and acetic acid (4 mL) was heated under reflux for 28 hours. Acetic acid was evaporated from the reaction liquid under reduced pressure, followed by dilution with chloroform, and washing with water. The organic layer was dried and then concentrated under reduced pressure. The residue was purified by silica gel column chromatography (chloroform/methanol), thereby obtaining ethyl 1-benzyl-2,5-dimethyl-1H-imidazole-4-carboxylate (384 mg).

Preparation Example 47

Optical resolution was performed on racemic tert-butyl 5-(cyclopropylamino)-4,5,6,7-tetrahydro-2H-indazole-2-carboxylate (228 mg) by supercritical fluid chromatography (column: Chiralpak AYH 10×250 mm manufactured by DAICEL CORPORATION, mobile phase: liquefied carbon dioxide gas/0.1% diethylamine-containing methanol). As a result, optically active tert-butyl 5-(cyclopropylamino)-4,5,6,7-tetrahydro-2H-indazole-2-carboxylate (Preparation Example 47-1, 80.8 mg) having a retention time of 6.49 min and optically active tert-butyl 5-(cyclopropylamino)-4,5,6,7-tetrahydro-2H-indazole-2-carboxylate (Preparation Example 47-2, 88.8 mg) having a retention time of 9.32 min were obtained.

Preparation Example 48

A mixture of N-cyclopropyl-4-isopropyl-N-(4-oxocyclohexyl)benzamide (1 g), 1,1-dimethoxy-N,N-dimethylmethanamine (2 mL), and triethylamine (2 mL) was stirred under heating for 30 minutes at an oil temperature of 140° C., and a volatile substance was evaporated. Thereafter, 1,1-dimethoxy-N,N-dimethylmethanamine (2 mL) and triethylamine (2 mL) were added thereto, followed by stirring under heating for 30 minutes at an oil temperature of 140° C. By using the respective reagents in an amount of 10 mL in total, the above operation was repeated 5 times. The reaction liquid was concentrated under reduced pressure. Ethanol (10 mL) and O-methylisourea hydrochloride (769 mg) were added to the residue, followed by stirring for an hour at room temperature, heating for 21 hours at an oil temperature of 60° C. and, stirring under heating for 12 hours at an oil temperature of 80° C., and cooling to room temperature. The reaction liquid was diluted with ethyl acetate and then washed with water and saturated brine in this order, followed by drying, and concentrating under reduced pressure. The residue was purified by silica gel column chromatography (chloroform/methanol), thereby obtaining benzyl cyclopropyl(2-methoxy-5,6,7,8-tetrahydroquinazolin-6-yl)carbamate (204 mg).

Preparation Example 49

A hexane solution (6.96 mL) of 1.65 M n-butyllithium was added to a mixture of N-isopropylpropan-2-amine (1.62 mL) and THF (30 mL) while being cooled in an acetone/dry ice bath under an argon gas atmosphere, followed by stirring for 30 minutes at the same temperature. A mixture of benzyl cyclopropyl(4-oxocyclohexyl)carbamate (3 g) and THF (26 mL) was added thereto, and the temperature was slowly elevated to the temperature of ice cooling over 3 hours, followed by stirring for 10 minutes at the same temperature. Hexamethylphosphate triamide (HMPA) (1.83 mL) and ethyl cyanoformate (1.13 mL) were further added thereto while being cooled in an acetone/dry ice bath, followed by stirring for an hour at the same temperature. The reaction liquid was diluted with ethyl acetate and then washed with water and saturated brine in this order, followed by drying, and concentrating under reduced pressure. The residue was purified by silica gel column chromatography (hexane/ethyl acetate), thereby obtaining ethyl 5-{[(benzyloxy)carbonyl] (cyclopropyl)amino}-2-hydroxycyclohexa-1-ene-1-carboxylate (692 mg).

Preparation Example 50

A mixture of benzyl cyclopropyl(4-oxocyclohexyl)carbamate (500 mg) and a glyoxylic acid hydrate (160 mg) was stirred under heating for 23 hours at 50° C. under an argon gas atmosphere. Thereafter, acetic acid (0.5 mL) was added thereto, followed by stirring under heating for 21 hours at an oil temperature 50° C. and then for 7 hours at an oil temperature of 100° C. Subsequently, acetic acid (1 mL) and a hydrazine hydrate (0.127 mL) were added thereto, followed by stirring under heating for 18 hours at an oil temperature of 100° C., and then the reaction liquid was cooled to room temperature. The reaction liquid was diluted with ethyl acetate and then washed with saturated aqueous sodium bicarbonate and saturated brine in this order, followed by drying, and concentrating under reduced pressure. The residue was purified by silica gel column chromatography (chloroform/methanol), thereby obtaining benzyl cyclopropyl(3-oxo-2,3,5,6,7,8-hexahydrocinnolin-6-yl)carbamate (343 mg).

Preparation Example 51

Pyridine (0.030 mL) and ethyl chloroformate (0.036 mL) were added to a mixture of a mixture (117 mg) of benzyl cyclopropyl(2-methyl-3-oxo-2,3,4,5,6,7-hexahydro-1H-indazol-5-yl)carbamate and a regioisomer thereof and dichloromethane (2 mL) under ice cooling under an argon gas atmosphere, followed by stirring for 2 hours at the same temperature. The reaction liquid was diluted with ethyl acetate and then washed with a saturated aqueous ammonium chloride solution and saturated brine in this order, followed by drying, and concentrating under reduced pressure. The residue was purified by silica gel column chromatography (chloroform/methanol), thereby obtaining ethyl 5-{[(benzyloxycarbonyl](cyclopropyl)amino}-2-methyl-3-oxo-2,3,4,5,6,7-tetrahydro-1H-indazole-1-carboxylate (117 mg).

Preparation Example 52

A mixture of ethyl 5-{[(benzyloxy)carbonyl] (cyclopropylamino}-2-hydroxycyclohex-1-ene-1-carboxylate (210 mg), methyl hydrazine (0.062 mL), and ethanol (4 mL) was stirred under heating for 3 hours and then cooled to room temperature. The reaction liquid was concentrated under reduced pressure. The residue was purified by silica gel column chromatography (chloroform/methanol), thereby obtaining a mixture (129 mg) of benzyl cyclopropyl(2-methyl-3-oxo-2,3,4,5,6,7-hexahydro-1H-indazol-5-yl)carbamate and a regioisomer thereof.

Preparation Example 53

Potassium tert-butoxide (0.596 g) was added to a mixture of 4-bromo-5-methoxy-1H-indole (1.0 g) and DMF (10 mL) under ice cooling under an argon gas atmosphere, followed by stirring for an hour at room temperature. After ice cooling, chloro(triisopropyl)silane (1.13 mL) was added thereto, followed by stirring for 2 hours at the same temperature. The reaction liquid was diluted with ethyl acetate and then washed with water (3 times) and saturated brine in this order, followed by drying, and concentrating under reduced pressure. The residue was purified by silica gel column chromatography (hexane/ethyl acetate), thereby obtaining 4-bromo-5-methoxy-1-(triisopropylsilyl)-1H-indole (1.72 g).

Preparation Example 54

A hexane solution (2.85 mL) of 1.62 M n-butyllithium was added to a mixture of 4-bromo-5-methoxy-1-(triisopropylsilyl)-1H-indole (1.47 g) and THF (30 mL) while being cooled in a dry ice/acetone bath under an argon gas atmosphere, followed by stirring for 50 minutes at the same temperature. Dimethyl carbonate (0.647 mL) was added thereto, and the temperature was elevated to the temperature of ice cooling over 8 hours. The reaction liquid was diluted with ethyl acetate and then washed with water and saturated brine in this order, followed by drying, and concentrating under reduced pressure. The residue was purified by silica gel column chromatography (hexane/ethyl acetate), thereby obtaining methyl 5-methoxy-1-(triisopropylsilyl)-1H-indole-4-carboxylate (1.00 g).

Preparation Example 55

A hydrazine hydrate (133 mg) was added to an ethanol (10 mL) solution of ethyl 5-{[(benzyloxy)carbonyl](cyclopropyl)amino}-2-hydroxycyclohexa-1-ene-1-carboxylate (478 mg), followed by heating under reflux for 3 hours. Thereafter, the reaction liquid was poured into water, extraction was performed 3 times by using chloroform. The organic layer was dried over anhydrous magnesium sulfate and concentrated under reduced pressure. The obtained residue was purified by silica gel column chromatography (methanol/chloroform), thereby obtaining benzyl cyclopropyl(3-oxo-2,3,4,5,6,7-hexahydro-1H-indazol-5-yl)carbamate (308 mg).

Preparation Example 56

Potassium tert-butoxide (705 mg) was added to a DMF (5 mL) solution of 3-methyl-1H-indole-4-carboxylate (500 mg) under ice cooling, followed by stirring for 40 minutes. Thereafter, iodomethane (1.2 g) was added thereto, followed by stirring overnight at room temperature. Water was added to the reaction liquid, followed by extraction with ethyl acetate. The organic layer was washed with saturated brine and dried over anhydrous magnesium sulfate, thereby obtaining a crude product. The obtained crude product was purified by silica gel column chromatography (hexane/ethyl acetate), thereby obtaining methyl 3-dimethyl-1H-indole-4-carboxylate (480 mg).

Preparation Example 57

Water (1.5 mL), 2-cyanophenyl boronic acid (231 mg), triphenylphosphine (45 mg), and sodium carbonate (416 mg) were added in this order to a 1,4-dioxane (10 mL) solution of 4-bromo-3-chlorobenzoic acid (308 mg), followed by stirring under heating for 3 hours at 100° C. in an argon atmosphere. Water was added to the reaction liquid, followed by extraction with ethyl acetate. The organic layer was washed with a saturated aqueous sodium chloride solution and dried over magnesium sulfate, thereby obtaining a crude product. The obtained crude product was purified by silica gel column chromatography (hexane/ethyl acetate), thereby obtaining 2-chloro-2'-cyanobiphenyl-4-carboxylic acid (363 mg).

Compounds of Preparation Examples 58 to 432 shown in the table described later were prepared in the same manner as in Preparation Examples 1 to 57. The structures of compounds of the preparation examples are shown in Tables 5 to 81, and physicochemical data and preparation process of the compounds are shown in Tables 82 to 92 respectively.

Example 1

Trifluoroacetic acid (260 mg) was added to a dichloromethane (1.1 mL) solution of tert-butyl 5-{[(2'-cyanobiphenyl-4-yl)carbonyl](cyclopropyl)amino}-4,5,6,7-tetrahydro-2H-indazole-2-carboxylate (110 mg), followed by stirring for 2 hours at room temperature. Thereafter, the solvent was evaporated under reduced pressure, followed by diluting with ethyl acetate and washed with a saturated aqueous sodium hydrogen carbonate solution and saturated brine in this order. The organic layer was dried over anhydrous magnesium sulfate and concentrated under reduced pressure. The obtained residue was purified by a silica gel column (methanol/chloroform), thereby obtaining 2'-cyano-N-cyclopropyl-N-(4,5,6,7-tetrahydro-1H-indazol-5-yl)biphenyl-4-carboxamide (66 mg).

Example 2

A 4 M hydrogen chloride/ethyl acetate solution (2 mL) was added to a mixture of ethyl acetate (1.9 mL) and ethanol (0.48 mL) of tert-butyl 5-(cyclopropyl {[1-(2-fluoroethyl)-1H-indol-4-yl]carbonyl}amino)-4,5,6,7-tetrahydro-2H-indazole-2-carboxylate (95 mg) at room temperature, followed by stirring for 2 hours. Thereafter, the reaction liquid was concentrated under reduced pressure and alkalified using a saturated aqueous sodium hydrogen carbonate solution, followed by extraction with ethyl acetate. The organic layer was washed with saturated brine and dried over anhydrous magnesium sulfate, followed by concentration under reduced pressure. The residue was purified by a silica gel column (0% to 10% methanol/chloroform), and then a 4 M hydrogen chloride/ethyl acetate solution was added thereto, followed by evaporation of the solvent under reduced pressure, thereby obtaining N-cyclopropyl-1-(2-fluoroethyl)-N-(4,5,6,7-tetrahydro-1H-indazol-5-yl)-1H-indole-4-carboxamide hydrochloride (44 mg).

Example 3

A mixture of tert-butyl 5-(cyclopropyl {[1-(1-phenylethyl)-1H-indazol-4-yl]carbonyl}amino)-4,5,6,7-tetrahydro-2H-indazole-2-carboxylate (184 mg), trifluoroacetic acid (0.25 mL), and dichloromethane (5 mL) was stirred overnight at room temperature. The reaction liquid was poured into saturated aqueous sodium bicarbonate, and extraction was performed using chloroform. The organic layer was dried and then concentrated under reduced pressure, and the residue was purified by silica gel column chromatography (chloroform/methanol), followed by dissolving into ethyl acetate. A 4 M hydrogen chloride/ethyl acetate solution was added thereto, and the generated solid was collected by filtration, thereby obtaining N-cyclopropyl-1-(1-phenylethyl)-N-(4,5,6,7-tetrahydro-1H-indazol-5-yl)-1H-indazole-4-carboxamide hydrochloride (60 mg).

Example 4

Oxalyl chloride (100 µl) and DMF (20 µl) were added to a mixture of 1-benzyl-1H-indole-2-carboxylic acid (140 mg) and dichloromethane (5 mL), followed by stirring for an hour at room temperature, and then the solvent was evaporated under reduced pressure. Dichloromethane (5 ml) was added to the residue that was obtained by azeotropy and drying using toluene, and tert-butyl-5-(cyclopropylamino)-4,5,6,7-tetrahydro-2H-indazole-2-carboxylate monohydrochloride (150 mg) and triethylamine (200 µl) were further added thereto at 0° C., followed by stirring for 20 hours at room temperature. The reaction liquid was diluted with ethyl acetate and then washed with saturated aqueous sodium bicarbonate and saturated brine in this order, followed by drying, and concentrating under reduced pressure. A 4 M hydrogen chloride/ethyl acetate solution (5 ml) was added to the residue, followed by stirring for 24 hours at room temperature. The solvent was evaporated from the reaction liquid under reduced pressure, and ethyl acetate was added to the obtained residue, followed by washing with saturated aqueous sodium bicarbonate and saturated brine in this order, drying, and concentrating under reduced pressure. The residue was purified by silica gel column chromatography (chloroform/ethyl acetate), thereby obtaining 1-benzyl-N-cyclopropyl-N-(4,5,6,7-tetrahydro-2H-indazol-5-yl)-1H-indole-2-carboxamide (217 mg).

Example 5

A 5 M aqueous sodium hydroxide solution was added to a tetrahydrofuran (1.4 mL) solution of benzyl 5-[cyclopropyl (4-isopropoxy-2-methoxybenzoyl)amino]-4,5,6,7-tetrahydro-2H-indazole-2-carboxylate (140 mg), followed by stirring for 2 hours at room temperature. Thereafter, the reaction liquid was neutralized by 1 M hydrochloric acid, followed by extraction with chloroform, concentration under reduced pressure, and purification by silica gel column chromatography, thereby obtaining N-cyclopropyl-4-isopropoxy-2-methoxy-N-(4,5,6,7-tetrahydro-1H-indazol-5-yl)benzamide (40 mg).

Example 6

Boron tribromide (1 M THF solution, 5.3 mL) was added dropwise to a dichloromethane (3 mL) solution of benzyl 5-{[(2'-cyano-6'-fluoro-3-methoxybiphenyl-4-yl)carbonyl] (cyclopropyl)amino}-4,5,6,7-tetrahydro-2H-indazole-2-carboxylate (300 mg) under ice cooling, followed by stirring for 3 days at room temperature. Thereafter, the reaction liquid was poured into water and weakly alkalified using a saturated aqueous sodium hydrogen carbonate solution, followed by extraction with chloroform, and concentration under reduced pressure. The residue was purified by silica gel column chromatography (methanol/chloroform), thereby obtaining 2'-cyano-N-cyclopropyl-6'-fluoro-3-hydroxy-N-(4,5,6,7-tetrahydro-1H-indazol-5-yl)biphenyl-4-carboxamide (180 mg).

Example 7

Optical resolution was performed on racemic 2'-cyano-N-cyclopropyl-6'-fluoro-N-(4,5,6,7-tetrahydro-1H-indazol-5-yl)biphenyl-4-carboxamide (500 mg) by supercritical fluid chromatography (column: AS-H, eluting solvent: liquefied carbon dioxide gas/ethanol=80/20, flow rate: 12 mL/min). As a result, (−)-2'-cyano-N-cyclopropyl-6'-fluoro-N-(4,5,6,7-tetrahydro-1H-indazol-5-yl)biphenyl-4-carboxamide (210 mg) (Example 7-1) and (+)-2'-cyano-N-cyclopropyl-6'-fluoro-N-(4,5,6,7-tetrahydro-1H-indazol-5-yl)biphenyl-4-carboxamide (190 mg) (Example 7-2) were obtained.

Example 8

Optical resolution was performed on racemic N-cyclopropyl-4-isopropoxy-N-(4,5,6,7-tetrahydro-1H-indazol-5-yl)

benzamide (450 mg) by supercritical fluid chromatography (column: AY-H, eluting solvent: liquefied carbon dioxide/ethanol=7/3, flow rate: 10 mL/min). As a result, (−)-N-cyclopropyl-4-isopropoxy-N-(4,5,6,7-tetrahydro-1H-indazol-5-yl)benzamide (190 mg) (Example 8-1) and (+)—N-cyclopropyl-4-isopropoxy-N-(4,5,6,7-tetrahydro-1H-indazol-5-yl)benzamide (187 mg) (Example 8-2) were obtained.

Example 9

Silver trifluoroacetate (45 mg) was added to a 1,4-dioxane (1 mL)/water (0.25 mL) solution of 1-(3-bromopropyl)-N-cyclopropyl-N-(4,5,6,7-tetrahydro-1H-indazol-5-yl)-1H-indole-4-carboxamide (65 mg) at room temperature, followed by stirring for 40 hours at room temperature. Ethanol was added thereto, and the insoluble material was removed by filtration by using celite. The solution was concentrated under reduced pressure, a saturated aqueous sodium hydrogen carbonate solution was added thereto, followed by extraction with ethyl acetate. The solvent was concentrated under reduced pressure, and the residue was purified by silica gel column chromatography (chloroform/methanol=10:0 to 9:1), thereby obtaining N-cyclopropyl-1-(3-hydroxypropyl)-N-(4,5,6,7-tetrahydro-1H-indazol-5-yl)-1H-indole-4-carboxamide (18 mg).

Example 10

A mixture of N-cyclopropyl-4-isopropyl-N-(4-oxocyclohexyl)benzamide (500 mg), 1,1-dimethoxy-N,N-dimethylmethanamine (1 mL), and triethylamine (1 mL) was stirred under heating for 30 minutes at an oil temperature of 140° C., and a volatile substance was evaporated. Thereafter, 1,1-dimethoxy-N,N-dimethylmethanamine (1 mL) and triethylamine (1 mL) were added thereto, followed by stirring under heating for 30 minutes at an oil temperature of 140° C. By using the respective reagents in an amount of 5 mL in total, and the above operation was repeated 5 times. The reaction liquid was concentrated under reduced pressure. Ethanol (2.5 mL) and a hydrazine hydrate (0.243 mL) were added to the residue, followed by stirring for 12 hours at room temperature. The reaction liquid was diluted with ethyl acetate and then washed with water (3 times) and saturated brine in this order, followed by drying, and concentrating under reduced pressure. The residue was purified by silica gel column chromatography (chloroform/methanol), thereby obtaining N-cyclopropyl-4-isopropyl-N-(4,5,6,7-tetrahydro-2H-indazol-5-yl)benzamide (380 mg).

Example 11

O-(7-azabenzotriazol-1-yl)-N,N,N',N'-tetramethyluronium hexafluorophosphate (113 mg), diisopropylethylamine (0.127 mL), and 4-dimethylaminopyridine in a catalytic amount were added to a mixture of N-cyclopropyl-5,6,7,8-tetrahydrocinnolin-6-amine monohydrochloride (56 mg), 1-methyl-1H-indole-4-carboxylic acid (52 mg), and DMF (2 mL) under an argon gas atmosphere, followed by stirring under heating for 60 hours at an oil temperature of 60° C., and then the resultant was cooled to room temperature. The reaction liquid was diluted with ethyl acetate and then washed with water (3 times) and saturated brine in this order, followed by drying, and concentrating under reduced pressure. The residue was purified by silica gel column chromatography (chloroform/methanol), thereby obtaining N-cyclopropyl-1-methyl-N-(5,6,7,8-tetrahydrocinnolin-6-yl)-1H-indole-4-carboxamide (9.3 mg).

Example 12

A 1 M aqueous sodium hydroxide solution (3 ml) and 30% aqueous hydrogen peroxide (600 μl) were added to a mixture of 4-cyano-N-cyclopropyl-N-(4,5,6,7-tetrahydro-2H-indazol-5-yl)benzamide (130 mg) and ethanol (5 mL), followed by stirring for 2.5 hours at room temperature. The reaction liquid was diluted with chloroform and washed with water and saturated brine, followed by drying, and concentrating under reduced pressure. A 4 M hydrogen chloride/ethyl acetate solution (5 ml) was added to the residue, followed by stirring for 24 hours at room temperature. Ethyl acetate was added to the residue that was obtained by evaporating the solvent from the reaction liquid under reduced pressure, followed by washing with saturated aqueous sodium bicarbonate and saturated brine in this order, drying, and concentrating under reduced pressure. The residue was purified by NH-silica gel column chromatography (chloroform/methanol), thereby obtaining N-cyclopropyl-N-(4,5,6,7-tetrahydro-2H-indazol-5-yl)terephthalamide (85 mg).

Example 13

A hydrazine hydrate (0.0840 mL) was added to a mixture of N-(3-acetyl)-4-hydroxycyclohex-3-en-1-yl)-N-cyclopropyl-4-isopropyl benzamide (197 mg) and ethanol (2 mL), followed by stirring for 72 hours at room temperature. The reaction liquid was diluted with ethyl acetate and then washed with water and saturated brine in this order, followed by drying, and concentrating under reduced pressure. The residue was purified by silica gel column chromatography (chloroform/ethyl acetate methanol) and made into hydrochloride by using a 4 M hydrogen chloride/ethyl acetate solution, thereby obtaining N-cyclopropyl-4-isopropyl-N-(3-methyl-4,5,6,7-tetrahydro-1H-indazol-5-yl)benzamide monohydrochloride (130 mg).

Example 14

A 5 M aqueous sodium hydroxide solution (0.059 mL) was added to a mixture of ethyl 5-{cyclopropyl[(1-methyl-1H-indol-4-yl)carbonyl]amino}-2-methyl-3-oxo-2,3,4,5,6,7-hexahydro-1H-indazole-1-carboxylate (64 mg), methanol (1 mL), and THF (1 mL), followed by stirring for an hour at room temperature. 1 M hydrochloric acid was added to the reaction liquid for neutralization, followed by concentration under reduced pressure. The residue was diluted with chloroform and washed with water, followed by drying, and concentrating under reduced pressure. The residue was purified by silica gel column chromatography (chloroform/methanol), thereby obtaining N-cyclopropyl-1-methyl-N-(2-methyl-3-oxo-2,3,4,5,6,7-hexahydro-1H-indazol-5-yl)-1H-indole-4-carboxamide (28 mg).

Example 15

10% palladium supported on activated charcoal (20 mg) was added to a mixture of ethanol (4 mL) of N-{1-[(benzyloxy)methyl]-3-methyl-4,5,6,7-tetrahydro-1H-indazol-5-yl]-N-cyclopropyl-5-[2-(trifluoromethyl)phenyl]-2-furamide (199 mg) and 6 M hydrochloric acid (1 mL), followed by stirring for 3.5 hours in a nitrogen atmosphere at 1 atm. The 10% palladium supported on activated charcoal was removed from the reaction liquid by filtration, followed by concentration under reduced pressure. The residue was alkalified using saturated aqueous sodium bicarbonate, followed by extraction with chloroform. The organic layer was dried and then concentrated under reduced pressure. The residue was purified by silica gel column chromatography (chloroform/methanol) and made into hydrochloride by using a 4 M hydrogen chloride/ethyl acetate solution, thereby obtaining N-cyclopropyl-N-(3-methyl-4,5,6,7-tetrahydro-1H-indazol-5-yl)-5-[2-(trifluoromethyl)phenyl]-2-furamide monohydrochloride (147 mg).

Example 16

A mixture of 4-(dimethylamino)benzoic acid (6.5 mg), oxalyl chloride (3.0 μL), dichloromethane (0.5 mL), and DMF (catalytic amount) was stirred for 2 hours at 50° C. and cooled to room temperature. Thereafter, a dichloromethane solution (0.5 mL) of tert-butyl 5-(ethylamino)-4,5,6,7-tetrahydro-2H-indazole-2-carboxylate hydrochloride (9.1 mg) and diisopropylethylamine (16 μL) were added thereto, followed by stirring overnight at room temperature. PS-trisamine (manufactured by Biotage, 3.90 mmol/g, 60 mg) and chloroform (1 mL) were added thereto, followed by stirring for 4 hours at room temperature. After the reaction liquid was filtered, the solvent was evaporated under reduced pressure, followed by dissolving in ethyl acetate (1 mL). A 4 M hydrogen chloride/ethyl acetate solution (0.5 mL) was added thereto, followed by stirring overnight at room temperature, and the solvent was evaporated under reduced pressure. The obtained residue was purified by HPLC (0.1% aqueous formic acid solution/methanol), thereby obtaining 4-(diethylamino)-N-ethyl-N-(4,5,6,7-tetrahydro-1H-indazol-5-yl)benzamide (6.4 mg).

Example 17

A mixture of 2,5-dimethyl-1-(2-thienylmethyl)-1H-pyrrole-3-carboxylic acid (7.8 mg), oxalyl chloride (3.0 μL), dichloromethane (0.5 mL), and DMF (catalytic amount) was stirred for 2 hours at 50° C. After the resultant was cooled to room temperature, a dichloromethane solution (0.5 mL) of tert-butyl 5-(cyclopropylamino)-4,5,6,7-tetrahydro-2H-indazole-2-carboxylate hydrochloride (9.4 mg) and isopropylethylamine (16 μL) were added thereto, followed by stirring overnight at room temperature. PS-trisamine (manufactured by Biotage, 3.90 mmol/g, 60 mg) and chloroform (1 mL) were added thereto, followed by stirring for 6 hours at room temperature. After the reaction liquid was filtered, the solvent was evaporated under reduced pressure, followed by dissolving in ethanol (1 mL). A 4 M hydrogen chloride/ethyl acetate solution (0.5 mL) was added thereto, followed by stirring overnight at room temperature, and the solvent was evaporated under reduced pressure. The obtained residue was purified by HPLC (0.1% aqueous formic acid solution/methanol), thereby obtaining N-cyclopropyl-2,5-dimethyl-N-(4,5,6,7-tetrahydro-1H-indazol-5-yl)-1-(2-thienylmethyl)-1H-pyrrole-3-carboxamide (1.9 mg).

Example 18

A mixture of 2'-(trifluoromethyl)biphenyl-4-carboxylate (8.8 mg), 1-chloro-N,N,2-trimethylpropenylamine (4.0 μl), and dichloromethane (0.8 mL) was stirred for an hour at room temperature. A dichloromethane solution (0.7 mL) of tert-butyl 5-(cyclopropylamino)-4,5,6,7-tetrahydro-2H-indazole-2-carboxylate hydrochloride (9.4 mg) and pyridine (7.3 μl) were added thereto, followed by stirring overnight at room temperature. Water (1.5 mL) was added to the reaction liquid, and extraction was performed using chloroform (2 mL). The solvent was evaporated under reduced pressure, followed by dissolving in ethanol (1 mL). A 4 M hydrogen chloride/ethyl acetate solution (0.5 mL) was added thereto, followed by stirring overnight at room temperature, and the solvent was evaporated under reduced pressure. The obtained residue was purified by HPLC (0.1% aqueous formic acid solution/methanol), thereby obtaining N-cyclopropyl-N-(4,5,6,7-tetrahydro-1H-indazol-5-yl)-2'-(trifluorophenyl)biphenyl-4-carboxamide (1.1 mg).

Example 19

A mixture of 4-(1,3-benzodioxol-5-yl)benzoic acid (8.0 mg), tert-butyl 5-(cyclopropylamino)-4,5,6,7-tetrahydro-2H-indazole-2-carboxylate hydrochloride (9.4 mg), O-(7-azabenzotriazol-1-yl)-N,N,N',N'-tetramethyluronium hexafluorophosphate (11.4 mg), diisopropylethylamine (16 and DMF (1 mL) was stirred overnight at 80° C. After cooling to room temperature, water (1.5 mL) was added to the reaction liquid, followed by extraction with chloroform (2 mL). The solvent was evaporated under reduced pressure, and the resultant was dissolved in ethanol (1 mL). A 4 M hydrogen chloride/ethyl acetate solution (0.5 mL) was added thereto, followed by stirring overnight at room temperature, and the solvent was evaporated under reduced pressure. The obtained residue was purified by HPLC (0.1% aqueous formic acid solution/methanol), thereby obtaining 4-(1,3-benzodioxol-5-yl)-N-cyclopropyl-N-(4,5,6,7-tetrahydro-1H-indazol-5-yl)benzamide (3.8 mg).

Example 20

Boron tribromide (1 M THF solution, 5.3 mL) was added dropwise to a dichloromethane (3 mL) solution of N-cyclopropyl-1-(2-methoxyethyl)-N-(4,5,6,7-tetrahydro-1H-indazol-5-yl)-1H-indole-4-carboxamide (300 mg) under ice cooling, followed by stirring for 3 days at room temperature. Thereafter, the reaction liquid was poured into water and weakly alkalified using a saturated aqueous sodium hydrogen carbonate solution, followed by extraction with chloroform, and concentration under reduced pressure. The residue was purified by silica gel column chromatography (methanol/chloroform), thereby obtaining N-cyclopropyl-1-(2-hydroxyethyl)-N-(4,5,6,7-tetrahydro-1H-indazol-5-yl)-1H-indole-4-carboxamide (69 mg).

Example 21

Boron tribromide (1 M THF solution, 1.5 mL) was added dropwise to a dichloromethane (2 mL) solution of N-cyclopropyl-4'-methoxy-N-(4,5,6,7-tetrahydro-1H-indazol-5-yl)biphenyl-4-carboxamide monohydrochloride (100 mg) under ice cooling, followed by stirring for 3 hours at room temperature. Thereafter, the reaction liquid was poured into water and weakly alkalified using a saturated aqueous sodium hydrogen carbonate, followed by extraction with chloroform, and concentration under reduced pressure. The residue was purified by silica gel column chromatography (methanol/chloroform), thereby obtaining N-cyclopropyl-4'-hydroxy-N-(4,5,6,7-tetrahydro-1H-indazol-5-yl)biphenyl-4-carboxamide (88 mg).

Example 22

Boron tribromide (1 M THF solution, 0.63 mL) was added dropwise to a dichloromethane (5 mL) solution of N-cyclopropyl-N-(2-methoxy-5,6,7,8-tetrahydroquinazolin-6-yl)-1-methyl-1H-indole-4-carboxamide (79 mg) under ice cooling, followed by stirring overnight at room temperature. Thereafter, the reaction liquid was poured into water and weakly alkalified using a saturated aqueous sodium hydrogen carbonate solution, followed by extraction with chloroform, and concentration under reduced pressure. The residue was purified by silica gel column chromatography (methanol/chloroform), thereby obtaining N-cyclopropyl-1-methyl-N-(2-oxo-1,2,5,6,7,8-hexahydroquinazolin-6-yl)-1H-indole-4-carboxamide (23 mg).

Example 23 p-Tosyl acid monohydrate (434 mg) and water (33 mL) were added to an acetone (33 mL) solution of N-cyclopropyl-N-(1,4-dioxaspiro[4.5]dec-8-yl)-4-isopropoxybenzamide (4.1 g), followed by stirring for 2 hours at 70° C., followed by cooling to room temperature, concentrating under reduced pressure, neutralizing with a saturated aqueous sodium hydrogen carbonate solution, extracting with ethyl acetate, washing with saturated brine, drying over anhydrous magnesium sulfate, and concentrating under reduced pressure, thereby obtaining N-cyclopropyl-4-isopropoxy-N-(4-oxocyclohexyl)benzamide (3.5 g). N,N-dimethylformamide dimethylacetal (7.3 mL) and triethylamine (7.3 mL) were added to N-cyclopropyl-4-isopropoxy-N-(4-oxocyclohexyl)benzamide (3.5 g), and a volatile substance was evaporated by distillation at 120° C. This operation was repeated 5 times. Subsequently, ethanol (19 mL) was added to the residue, and hydrazine monohydrate (1.67 g) was added thereto, followed by stirring overnight at room temperature. Thereafter, the reaction liquid was diluted with water, and extraction was performed using ethyl acetate. The organic layer was washed with water and saturated brine and dried over anhydrous magnesium sulfate, followed by concentration under reduced pressure. The residue was purified by silica gel column chromatography (ethyl acetate), thereby obtaining N-cyclopropyl-4-isopropoxy-N-(4,5,6,7-tetrahydro-1H-indazol-5-yl) benzamide (2 g).

Example 24

A THF (1.5 mL) solution of tert-butyl 5-(cyclopropyl{[2'-(methoxycarbonyl)biphenyl-4-yl]carbonyl}amino)-4,5,6,7-tetrahydro-2H-indazole-2-carboxylate (200 mg) was cooled with ice water under an argon gas atmosphere. A THF (1.5 mL) solution of lithium tetrahydroborate (17 mg) was added dropwise thereto, followed by stirring for 4 hours with heating under reflux at an oil temperature of 70° C., cooling to room temperature, diluting with ethyl acetate, washing with saturated brine and dried, and concentrating under reduced pressure. The residue was purified by silica gel column chromatography (hexane/ethyl acetate), thereby obtaining tert-butyl 5-(cyclopropyl{[2'-(hydroxymethyl)biphenyl-4-yl]carbonyl}amino)-4,5,6,7-tetrahydro-2H-indazole-2-carboxylate (189 mg). Trifluoroacetic acid (199 mg) was added to a dichloromethane (2 mL) solution of the obtained tert-butyl 5-(cyclopropyl{[2'-(hydroxymethyl)biphenyl-4-yl]carbonyl}amino)-4,5,6,7-tetrahydro-2H-indazole-2-carboxylate (85 mg), followed by stirring overnight at room temperature, concentrating under reduced pressure, neutralizing with a saturated aqueous sodium hydrogen carbonate solution, extracting with chloroform, and purifying by silica gel column chromatography (0% to 10%, methanol/chloroform), thereby obtaining N-cyclopropyl-2'-(hydroxymethyl)-N-(4,5,6,7-tetrahydro-1H-indazol-5-yl)biphenyl-4-carboxamide (57 mg).

Compounds of Examples 25 to 315 shown in the table described later were prepared in the same manner as in Examples 1 to 24. The structures of the example compounds are shown in Tables 93 to 152, and the physicochemical data and preparation processes of the compounds are shown in Tables 153 to 161 respectively.

TABLE 5

| PEx | Structure | Note |
|-----|-----------|------|
| 1 | 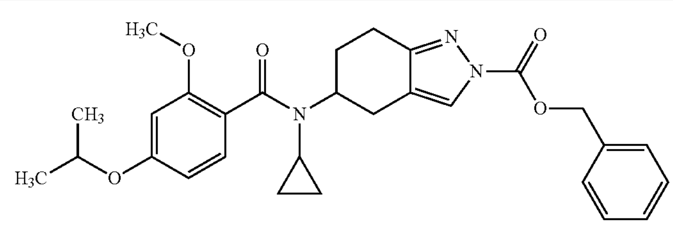 [SMILES: COc1cc(OC(C)C)ccc1C(=O)N(C1CC1)C1CCc2nn(C(=O)OCc3ccccc3)cc2C1] | |
| 2 | 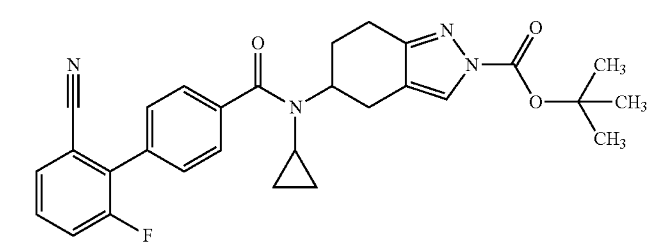 [SMILES: CC(C)(C)OC(=O)n1cc2c(n1)CCC(N(C(=O)c1ccc(-c3c(F)cccc3C#N)cc1)C1CC1)C2] | |

TABLE 5-continued

| PEx | Structure | Note |
|---|---|---|
| 3 | 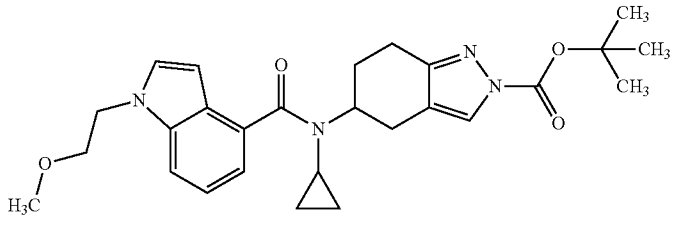 [SMILES: COCCn1ccc2c(C(=O)N(C3CC3)C3CCc4nn(C(=O)OC(C)(C)C)cc4C3)cccc21] | |
| 4 | 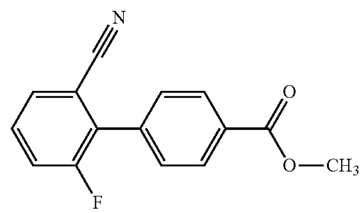 [SMILES: COC(=O)c1ccc(-c2c(F)cccc2C#N)cc1] | |
| 5 | 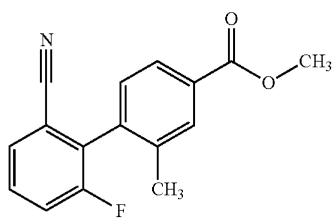 [SMILES: COC(=O)c1ccc(-c2c(F)cccc2C#N)c(C)c1] | |

TABLE 6

| 6 | |
|---|---|
| 7 | |
| 8 | |

TABLE 6-continued

| 9 | |
|---|---|
| 10 | |
| 11 | |

TABLE 7
12 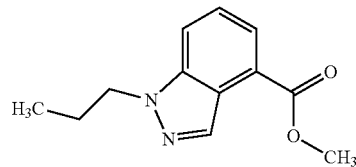 [SMILES: CCCn1ncc2c(C(=O)OC)cccc21]
13 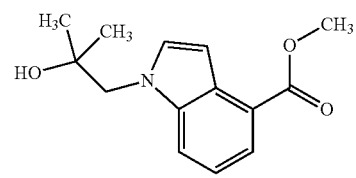 [SMILES: COC(=O)c1cccc2c1ccn2CC(C)(C)O]
14 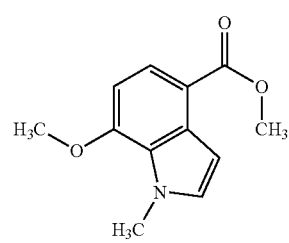
15 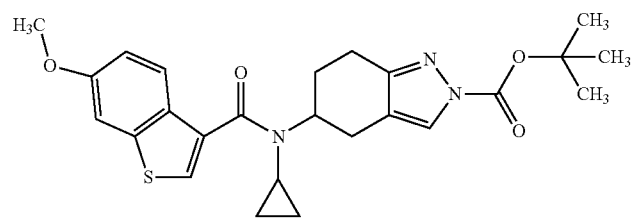 [SMILES: COc1ccc2c(C(=O)N(C3CC3)C3CCc4nn(C(=O)OC(C)(C)C)cc4C3)csc2c1]
16 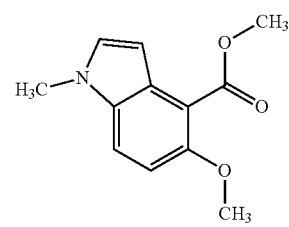
17 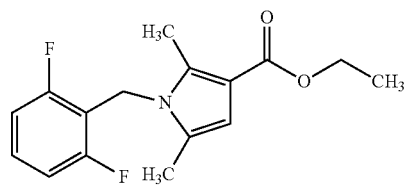 [SMILES: CCOC(=O)c1cc(C)n(Cc2c(F)cccc2F)c1C]
| TABLE 8 | TABLE 8-continued |
|---|---|
| 18 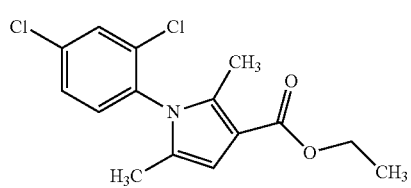 [SMILES: CCOC(=O)c1cc(C)n(-c2ccc(Cl)cc2Cl)c1C] | 19 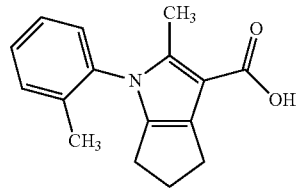 [SMILES: Cc1ccccc1-n1c(C)c(C(=O)O)c2c1CCC2] |

TABLE 8-continued
| | |
|---|---|
| 20 | 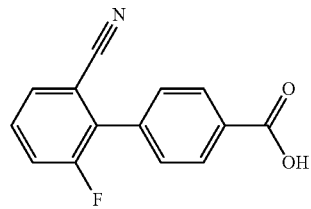 [SMILES: N#Cc1cccc(F)c1-c1ccc(C(=O)O)cc1] |
| 21 | 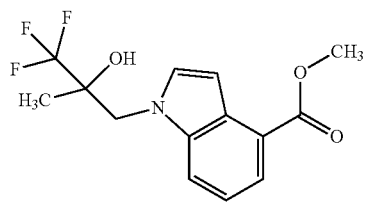 [SMILES: COC(=O)c1cccc2c1ccn2CC(C)(O)C(F)(F)F] |
| 22 | 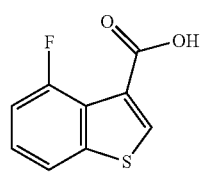 [SMILES: O=C(O)c1csc2cccc(F)c12] |
| 23 | 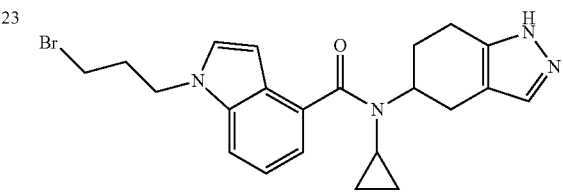 |
TABLE 9
| | |
|---|---|
| 24 | 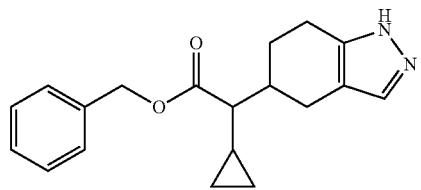 [SMILES: O=C(OCc1ccccc1)C(C1CC1)C1CCc2[nH]ncc2C1] |
TABLE 9-continued
| | | |
|---|---|---|
| 25 | 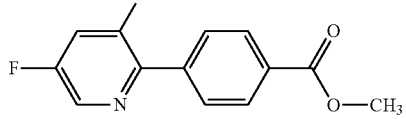 | |
| 26 | 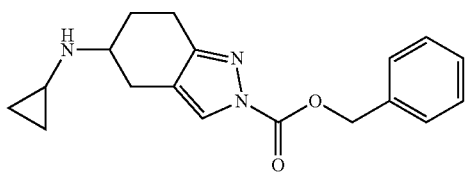 [SMILES: O=C(OCc1ccccc1)n1cc2c(n1)CCC(NC1CC1)C2] | Sal: HCl |
| 27 | 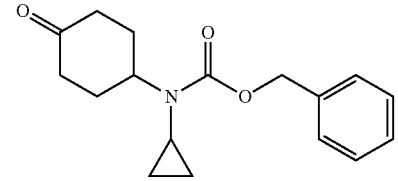 [SMILES: O=C1CCC(N(C(=O)OCc2ccccc2)C2CC2)CC1] | |
| 28 | 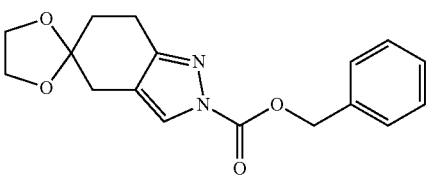 [SMILES: O=C(OCc1ccccc1)n1cc2c(n1)CCC1(C2)OCCO1] | |
| 29 | 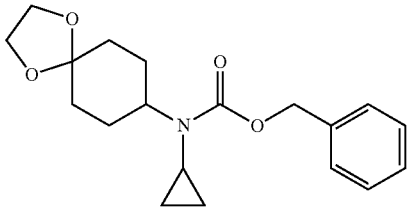 [SMILES: O=C(OCc1ccccc1)N(C1CC1)C1CCC2(CC1)OCCO2] | |
TABLE 10
| | | |
|---|---|---|
| 30 | 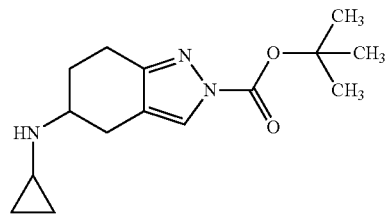 [SMILES: CC(C)(C)OC(=O)n1cc2c(n1)CCC(NC1CC1)C2] | Sal: HCl |
| 31 | 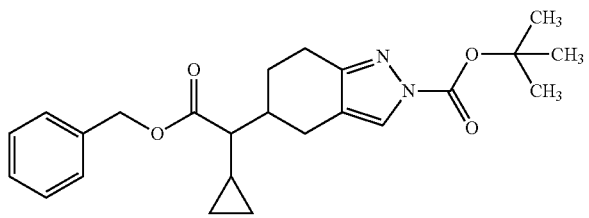 [SMILES: CC(C)(C)OC(=O)n1cc2c(n1)CCC(C(C(=O)OCc1ccccc1)C1CC1)C2] | |

TABLE 10-continued
| | |
|---|---|
| 32 | 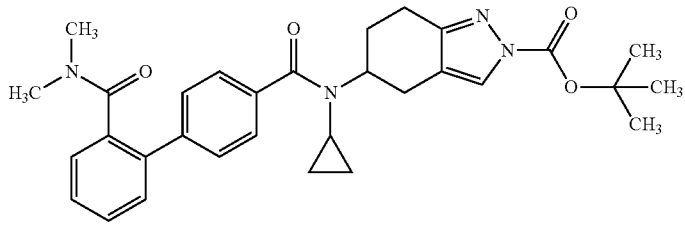 [SMILES: CN(C)C(=O)c1ccccc1-c1ccc(C(=O)N(C2CC2)C2CCc3nn(C(=O)OC(C)(C)C)cc3C2)cc1] |
| 33 | 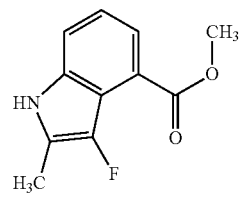 |
| 34 | 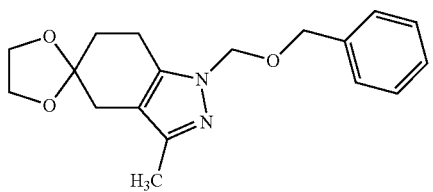 [SMILES: Cc1nn(COCc2ccccc2)c2c1CC1(CC2)OCCO1] |
| 35 | 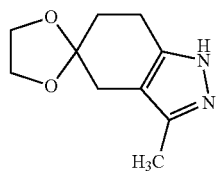 |
TABLE 11
| | |
|---|---|
| 36 | 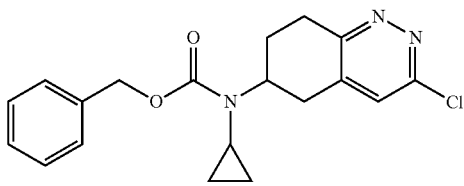 [SMILES: O=C(OCc1ccccc1)N(C1CC1)C1CCc2nnc(Cl)cc2C1] |
| 37 | 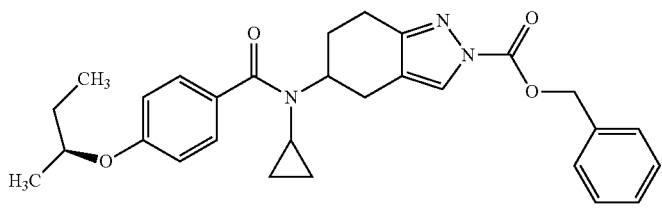 [SMILES: CC[C@H](C)Oc1ccc(C(=O)N(C2CC2)C2CCc3nn(C(=O)OCc4ccccc4)cc3C2)cc1] |
| 38 | 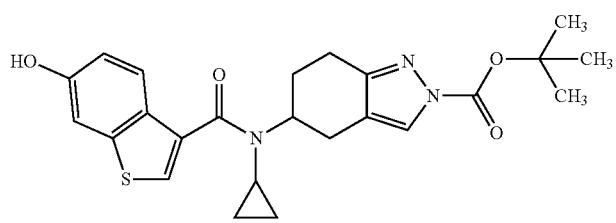 [SMILES: CC(C)(C)OC(=O)n1cc2c(n1)CCC(N(C(=O)c1csc3cc(O)ccc13)C1CC1)C2] |

TABLE 11-continued
39 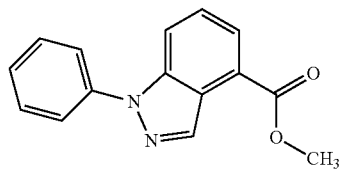 [SMILES: COC(=O)c1cccc2c1cnn2-c1ccccc1]
40 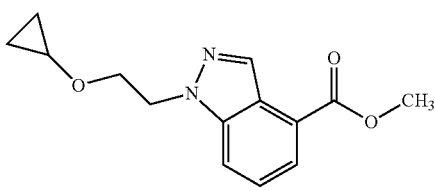 [SMILES: COC(=O)c1cccc2c1cnn2CCOC1CC1]
41 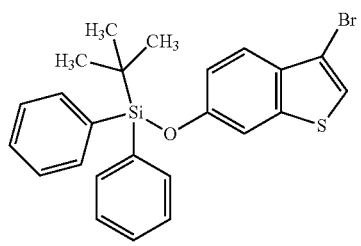 [SMILES: CC(C)(C)[Si](Oc1ccc2c(Br)csc2c1)(c1ccccc1)c1ccccc1]
TABLE 12
42 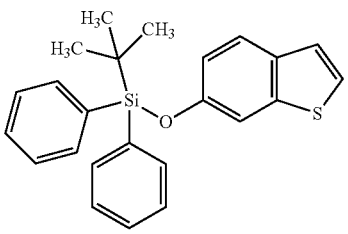 [SMILES: CC(C)(C)[Si](Oc1ccc2ccsc2c1)(c1ccccc1)c1ccccc1]
43 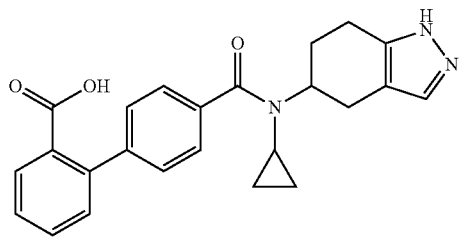
44 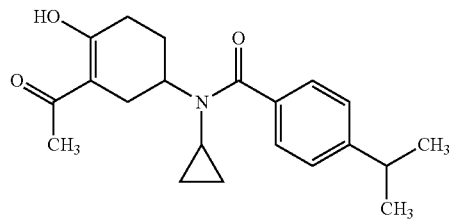 [SMILES: CC(=O)C1=C(O)CCC(N(C(=O)c2ccc(C(C)C)cc2)C2CC2)C1]
TABLE 12-continued
45 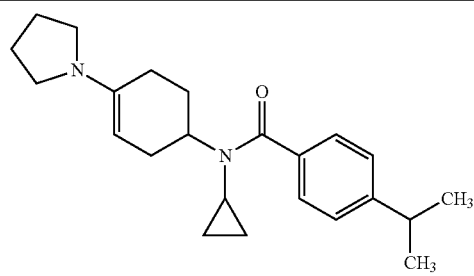
46 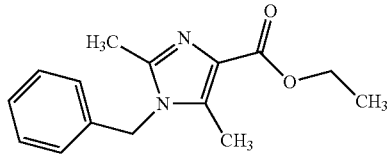 [SMILES: CCOC(=O)c1nc(C)n(Cc2ccccc2)c1C]
TABLE 13
47-1 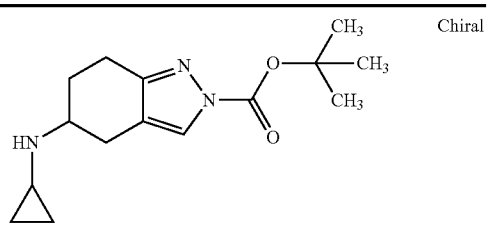  Chiral TABLE 13-continued
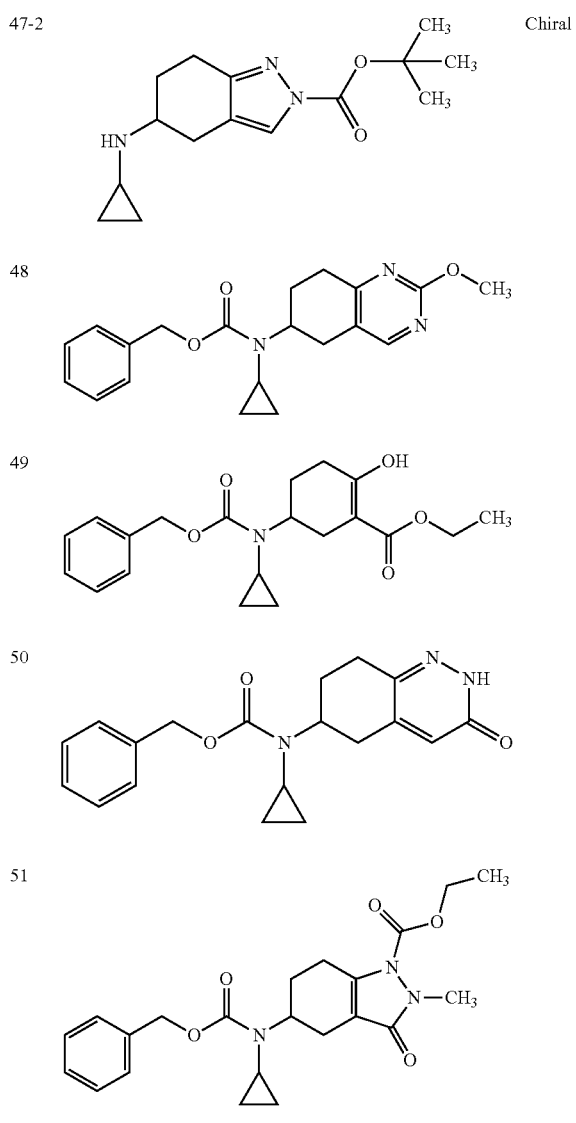
TABLE 14
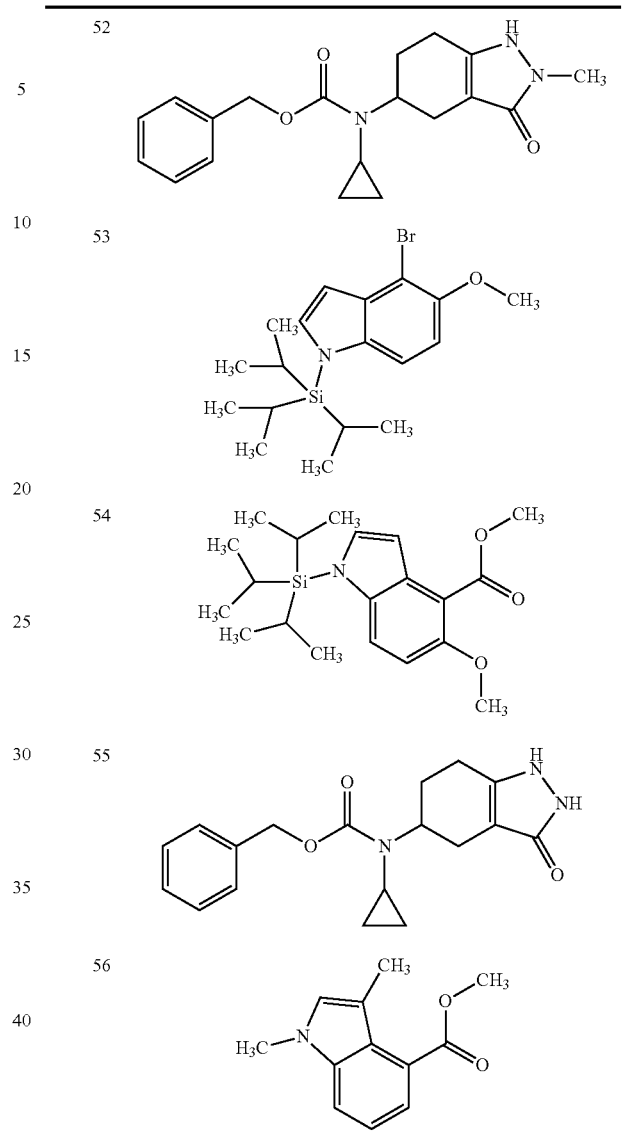
TABLE 15
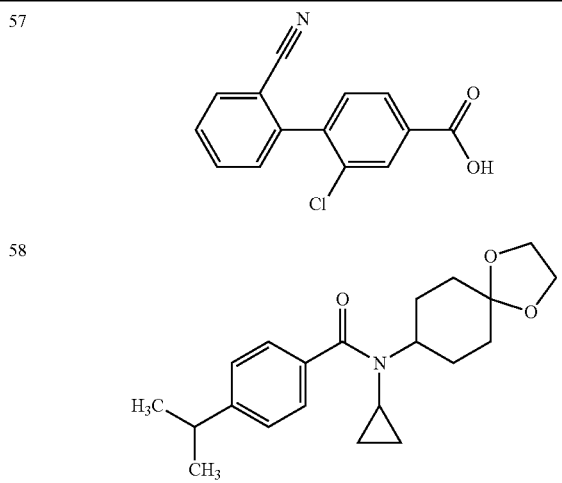

TABLE 15-continued
| | | |
|---|---|---|
| 59 | 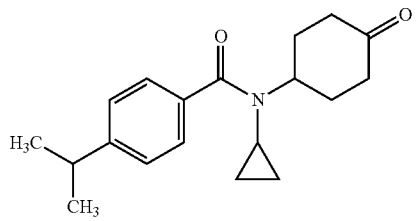 [SMILES: CC(C)c1ccc(C(=O)N(C2CCC(=O)CC2)C2CC2)cc1] | |
| 60 | 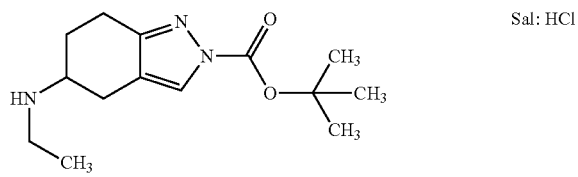 | Sal: HCl |
| 61 | 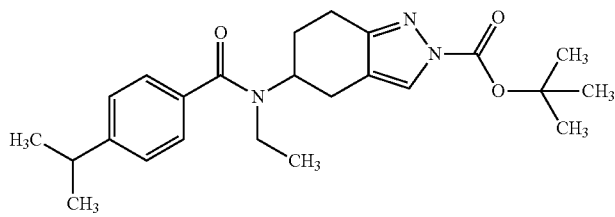 [SMILES: CCN(C(=O)c1ccc(C(C)C)cc1)C1CCc2nn(C(=O)OC(C)(C)C)cc2C1] | |
| 62 |  | |
TABLE 16
| 63 | 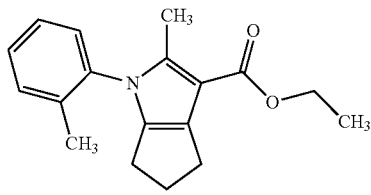 [SMILES: CCOC(=O)c1c2c(n(-c3ccccc3C)c1C)CCC2] |
|---|---|
| 64 | 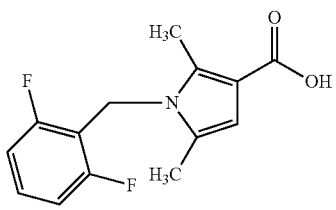 [SMILES: Cc1cc(C(=O)O)c(C)n1Cc1c(F)cccc1F] |
| 65 | 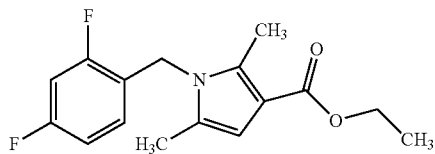 [SMILES: CCOC(=O)c1cc(C)n(Cc2ccc(F)cc2F)c1C] |
TABLE 16-continued
| 66 | 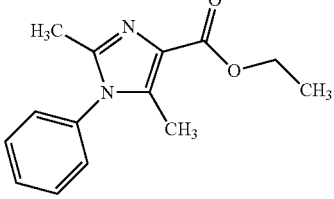 |
|---|---|
| 67 | 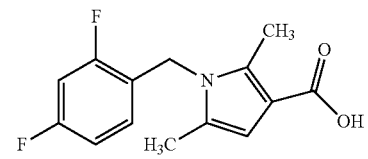 [SMILES: Cc1cc(C(=O)O)c(C)n1Cc1ccc(F)cc1F] |
| 68 | 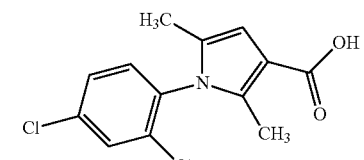 |

TABLE 17
69 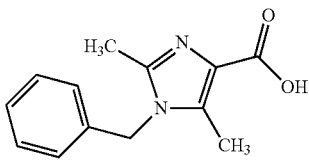 [SMILES: Cc1nc(C(=O)O)c(C)n1Cc1ccccc1]
70 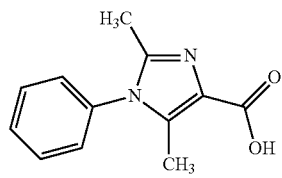
71 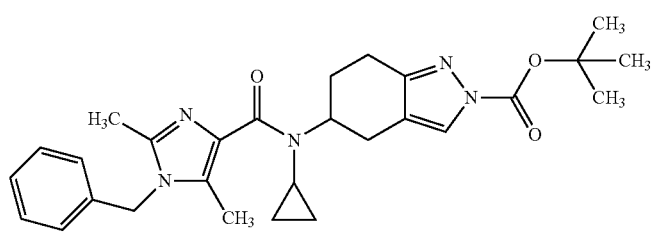 [SMILES: Cc1nc(C(=O)N(C2CC2)C2CCc3nn(C(=O)OC(C)(C)C)cc3C2)c(C)n1Cc1ccccc1]
72 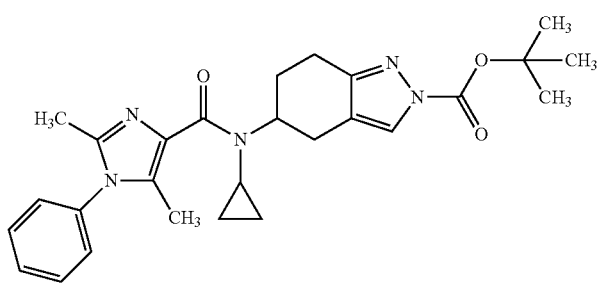 [SMILES: Cc1nc(C(=O)N(C2CC2)C2CCc3nn(C(=O)OC(C)(C)C)cc3C2)c(C)n1-c1ccccc1]
73 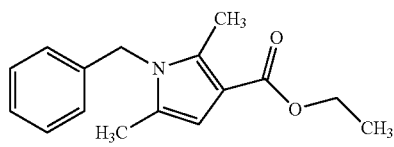 [SMILES: CCOC(=O)c1cc(C)n(Cc2ccccc2)c1C]
74 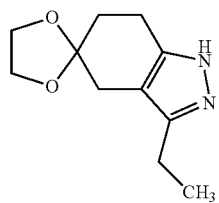
| TABLE 18 | TABLE 18-continued |
|---|---|
| 75 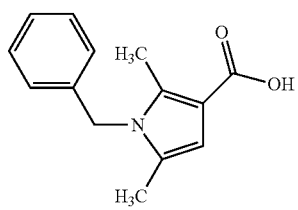 [SMILES: Cc1cc(C(=O)O)c(C)n1Cc1ccccc1] | 76 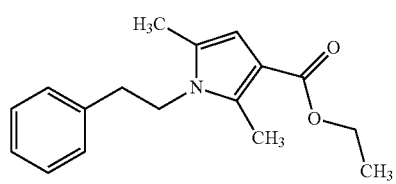 [SMILES: CCOC(=O)c1cc(C)n(CCc2ccccc2)c1C] |

TABLE 18-continued
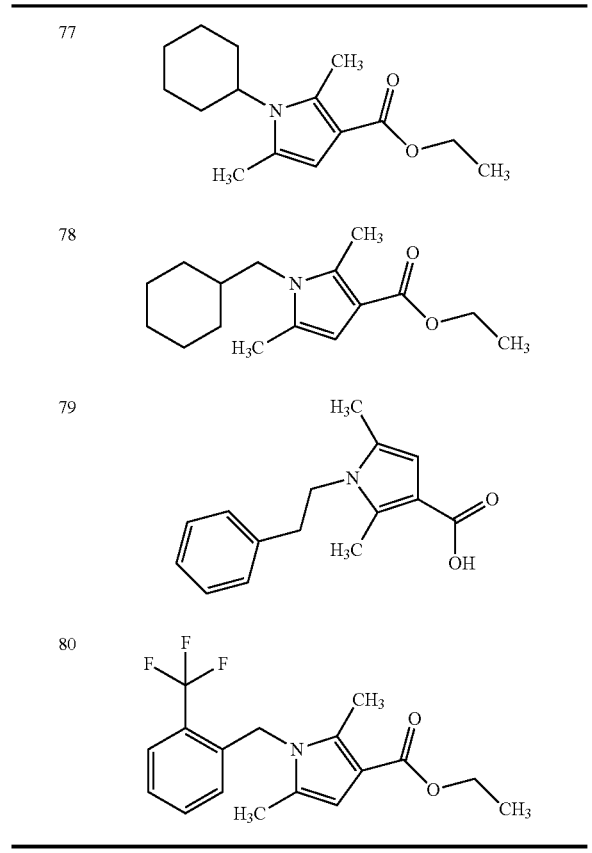
TABLE 19
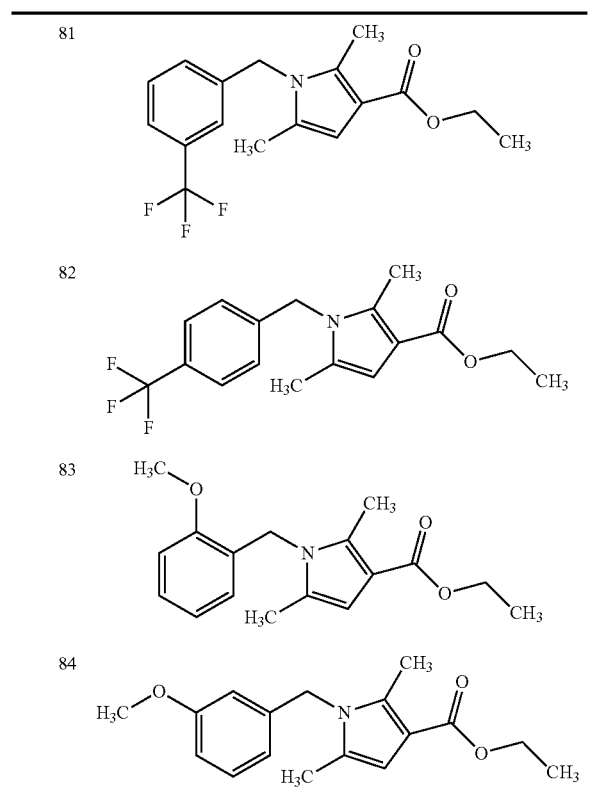
TABLE 19-continued
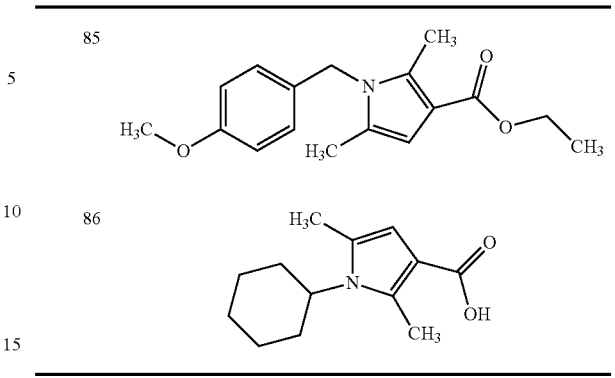
TABLE 20
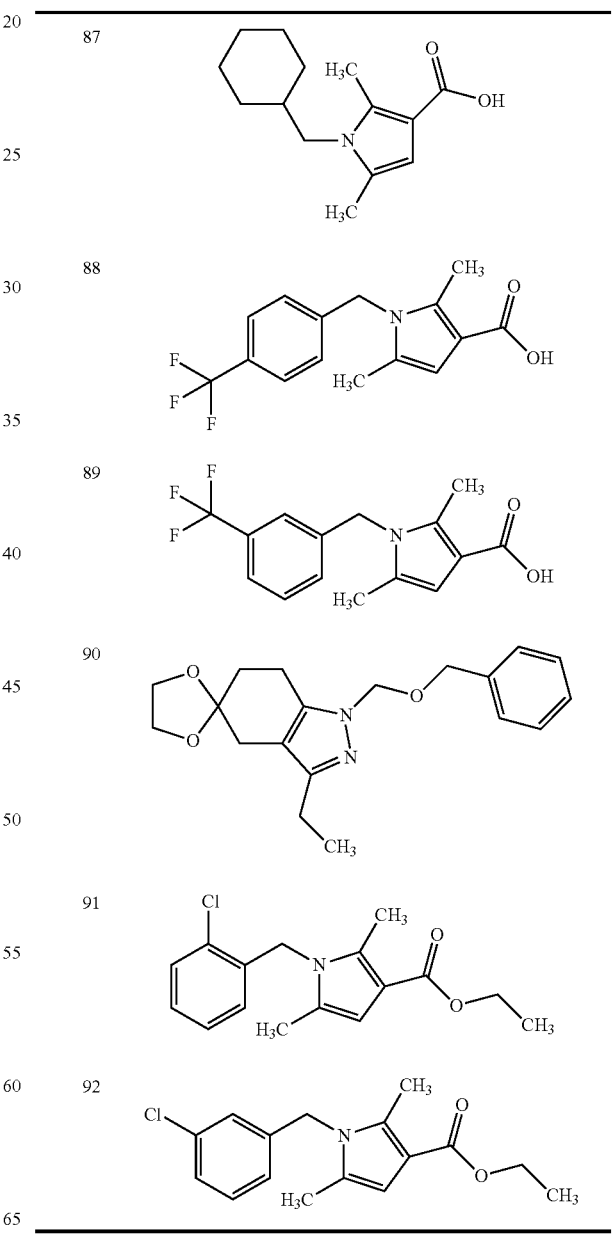

TABLE 21
93 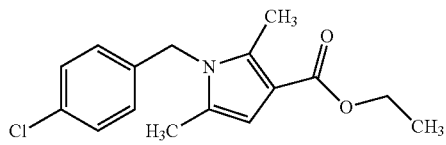 [SMILES: CCOC(=O)c1cc(C)n(Cc2ccc(Cl)cc2)c1C]
94 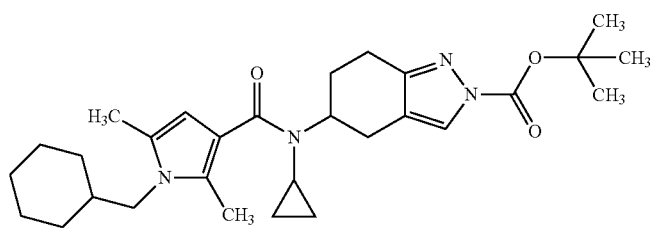 [SMILES: Cc1cc(C(=O)N(C2CC2)C2CCc3nn(C(=O)OC(C)(C)C)cc3C2)c(C)n1CC1CCCCC1]
95 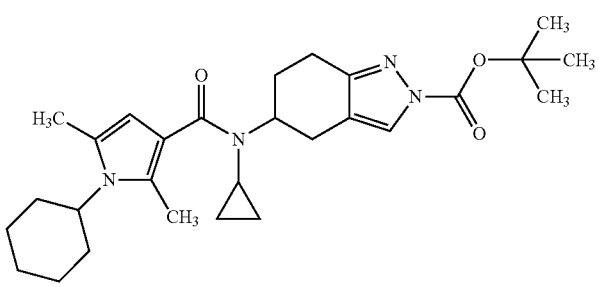 [SMILES: Cc1cc(C(=O)N(C2CC2)C2CCc3nn(C(=O)OC(C)(C)C)cc3C2)c(C)n1C1CCCCC1]
96 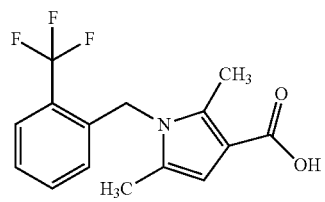 [SMILES: Cc1cc(C(=O)O)c(C)n1Cc1ccccc1C(F)(F)F]
97 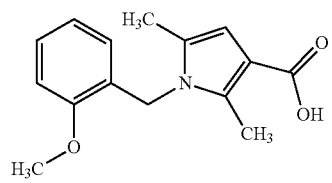
TABLE 22
98 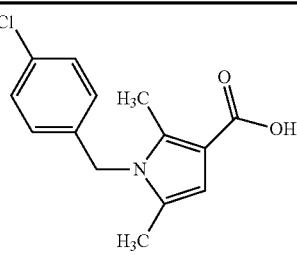
99 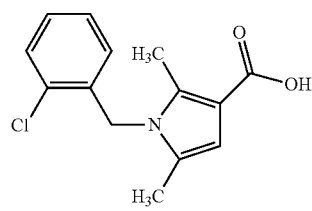 [SMILES: Cc1cc(C(=O)O)c(C)n1Cc1ccccc1Cl]

TABLE 22-continued
100 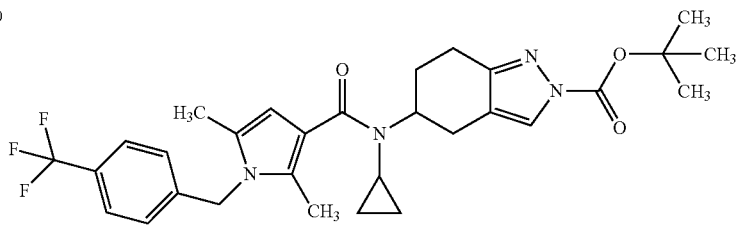
101 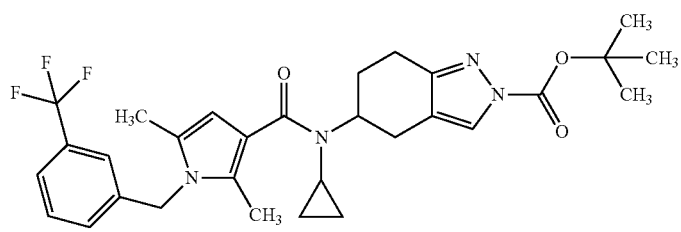 [SMILES: Cc1cc(C(=O)N(C2CC2)C2CCc3nn(C(=O)OC(C)(C)C)cc3C2)c(C)n1Cc1cccc(C(F)(F)F)c1]
102 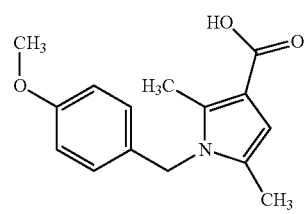 [SMILES: COc1ccc(Cn2c(C)cc(C(=O)O)c2C)cc1]
TABLE 23
103 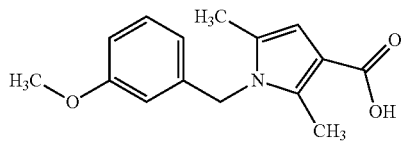 [SMILES: COc1cccc(Cn2c(C)cc(C(=O)O)c2C)c1]
104 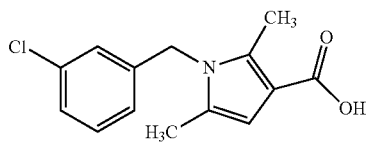 [SMILES: Cc1cc(C(=O)O)c(C)n1Cc1cccc(Cl)c1]
105 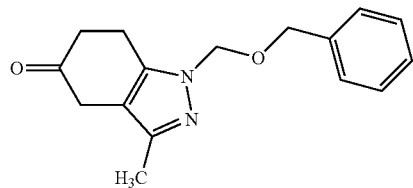 [SMILES: Cc1nn(COCc2ccccc2)c2c1CC(=O)CC2]
TABLE 23-continued
106 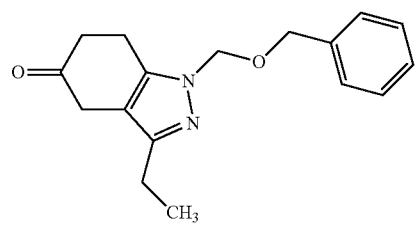 [SMILES: CCc1nn(COCc2ccccc2)c2c1CC(=O)CC2]
107 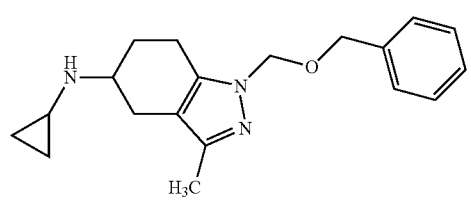 [SMILES: Cc1nn(COCc2ccccc2)c2c1CC(NC1CC1)CC2]
108 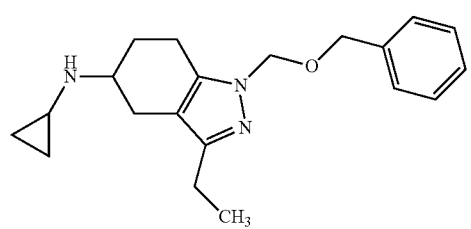 [SMILES: CCc1nn(COCc2ccccc2)c2c1CC(NC1CC1)CC2]

TABLE 24
109
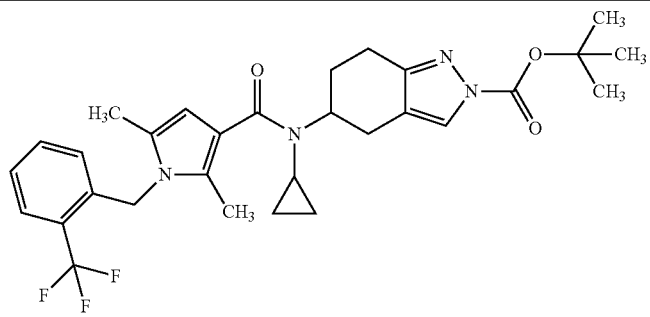
110
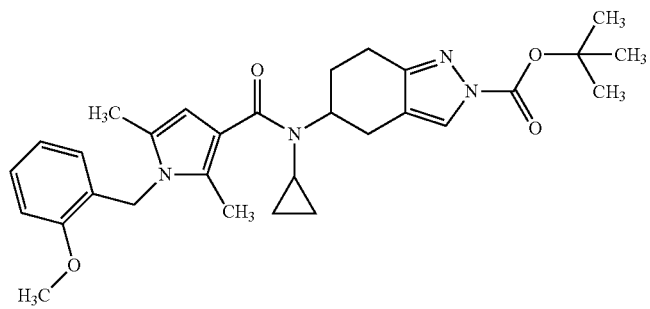 [SMILES: COc1ccccc1Cn1c(C)cc(C(=O)N(C2CC2)C2CCc3nn(C(=O)OC(C)(C)C)cc3C2)c1C]
111
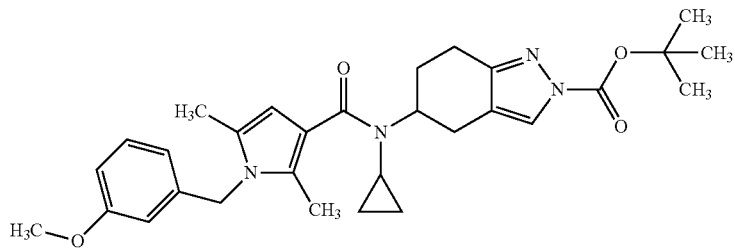 [SMILES: COc1cccc(Cn2c(C)cc(C(=O)N(C3CC3)C3CCc4nn(C(=O)OC(C)(C)C)cc4C3)c2C)c1]
112
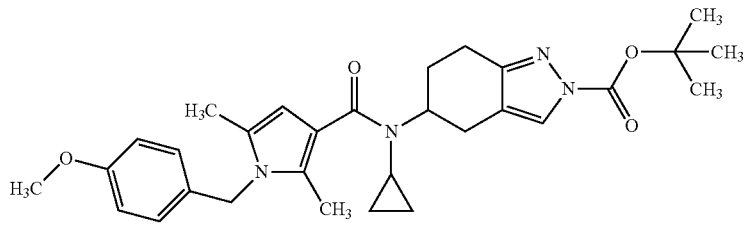 [SMILES: COc1ccc(Cn2c(C)cc(C(=O)N(C3CC3)C3CCc4nn(C(=O)OC(C)(C)C)cc4C3)c2C)cc1]
TABLE 25
113
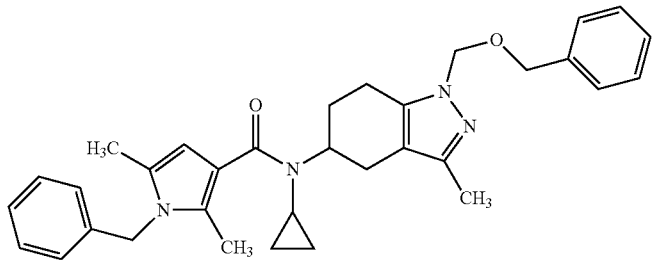 [SMILES: Cc1nn(COCc2ccccc2)c2c1CC(N(C(=O)c1cc(C)n(Cc3ccccc3)c1C)C1CC1)CC2]

TABLE 25-continued
114
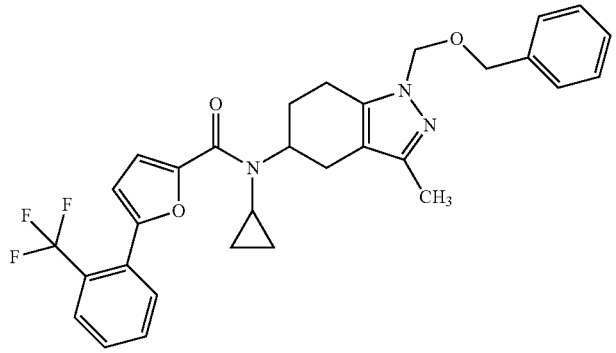 [SMILES: Cc1nn(COCc2ccccc2)c2c1CC(N(C(=O)c1ccc(-c3ccccc3C(F)(F)F)o1)C1CC1)CC2]
115
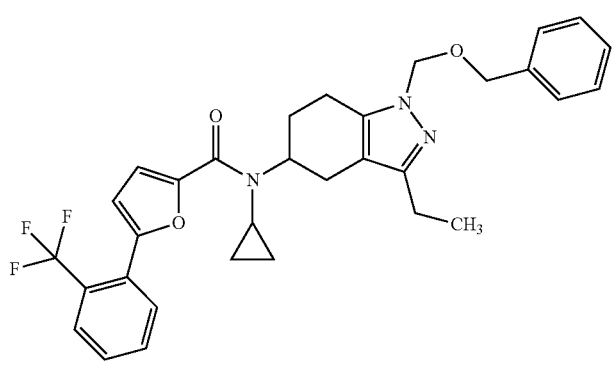 [SMILES: CCc1nn(COCc2ccccc2)c2c1CC(N(C(=O)c1ccc(-c3ccccc3C(F)(F)F)o1)C1CC1)CC2]
116
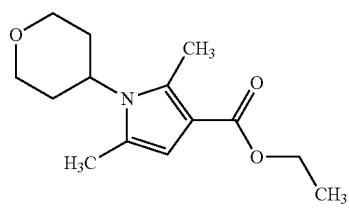 [SMILES: CCOC(=O)c1cc(C)n(C2CCOCC2)c1C]
117
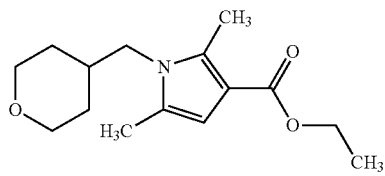 [SMILES: CCOC(=O)c1cc(C)n(CC2CCOCC2)c1C]
TABLE 26
118
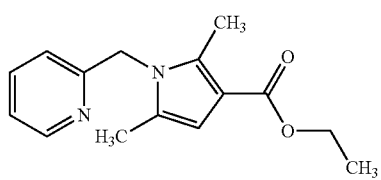 [SMILES: CCOC(=O)c1cc(C)n(Cc2ccccn2)c1C]
119
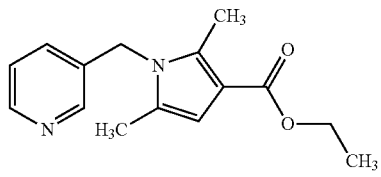
TABLE 26-continued
120
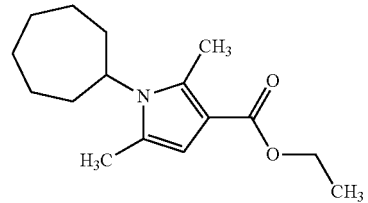 [SMILES: CCOC(=O)c1cc(C)n(C2CCCCCC2)c1C]
121
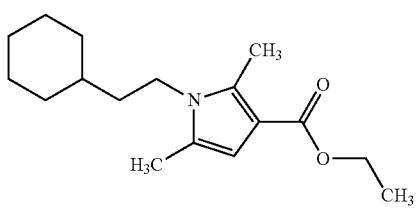 [SMILES: CCOC(=O)c1cc(C)n(CCC2CCCCC2)c1C]

TABLE 26-continued
| 122 | 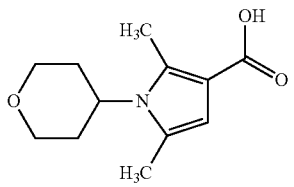 [SMILES: Cc1cc(C(=O)O)c(C)n1C1CCOCC1] |
| --- | --- |
| 123 | 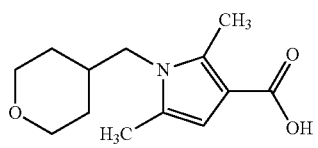 |
| 124 | 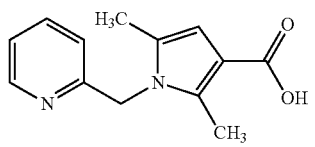 [SMILES: Cc1cc(C(=O)O)c(C)n1Cc1ccccn1] |
TABLE 27
| 125 | 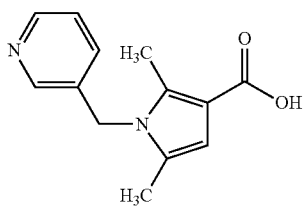 [SMILES: Cc1cc(C(=O)O)c(C)n1Cc1cccnc1] |
| --- | --- |
| 126 | 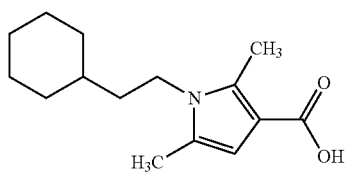 [SMILES: Cc1cc(C(=O)O)c(C)n1CCC1CCCCC1] |
| 127 | 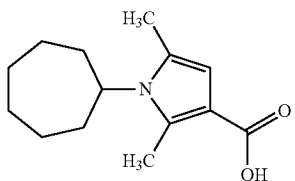 [SMILES: Cc1cc(C(=O)O)c(C)n1C1CCCCCC1] |
| 128 | 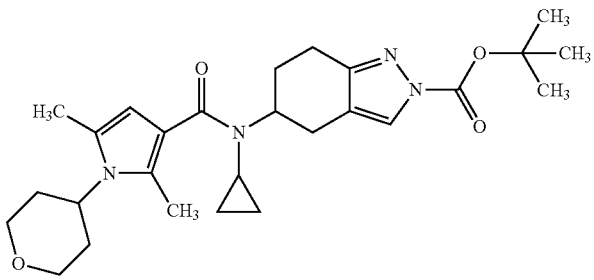 [SMILES: Cc1cc(C(=O)N(C2CC2)C2CCc3nn(C(=O)OC(C)(C)C)cc3C2)c(C)n1C1CCOCC1] |

TABLE 27-continued
129 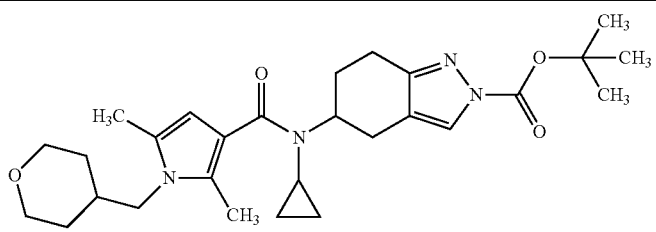
TABLE 28
130 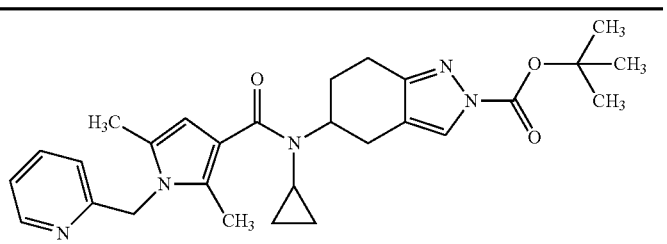
131 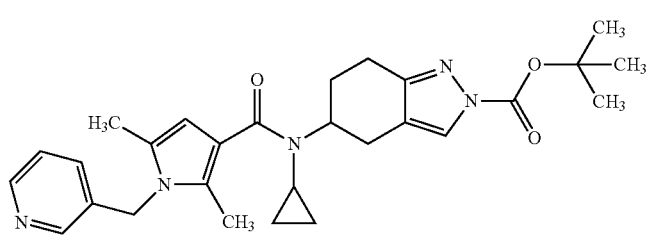 [SMILES: Cc1cc(C(=O)N(C2CC2)C2CCc3nn(C(=O)OC(C)(C)C)cc3C2)c(C)n1Cc1cccnc1]
132 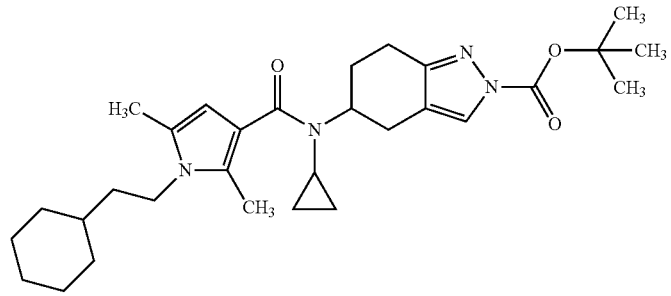 [SMILES: Cc1cc(C(=O)N(C2CC2)C2CCc3nn(C(=O)OC(C)(C)C)cc3C2)c(C)n1CCC1CCCCC1]
133 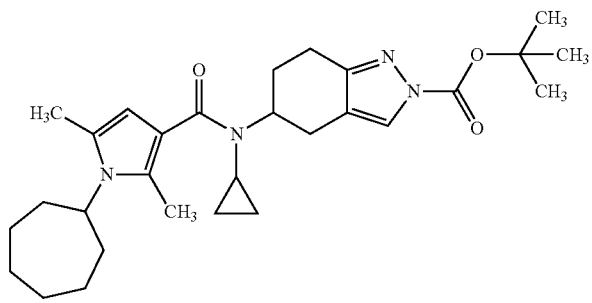 [SMILES: Cc1cc(C(=O)N(C2CC2)C2CCc3nn(C(=O)OC(C)(C)C)cc3C2)c(C)n1C1CCCCCC1]
134 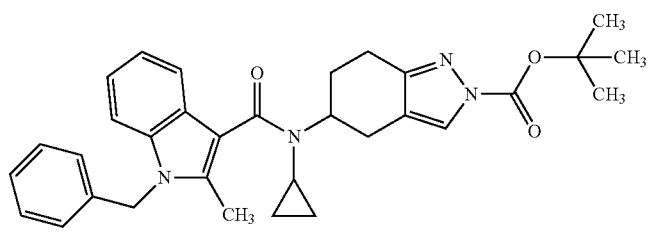 [SMILES: Cc1c(C(=O)N(C2CC2)C2CCc3nn(C(=O)OC(C)(C)C)cc3C2)c2ccccc2n1Cc1ccccc1]

TABLE 29
135 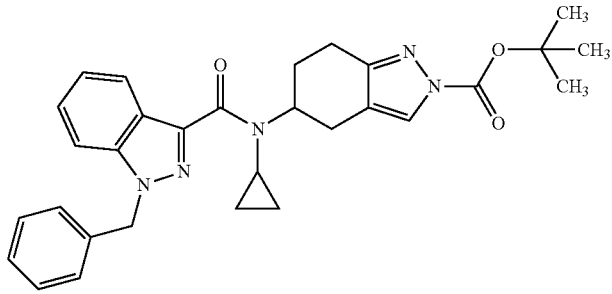 [SMILES: CC(C)(C)OC(=O)n1cc2c(n1)CCC(N(C(=O)c1nn(Cc3ccccc3)c3ccccc13)C1CC1)C2]
136 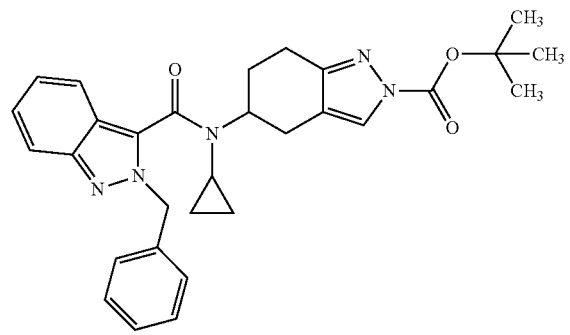 [SMILES: CC(C)(C)OC(=O)n1cc2c(n1)CCC(N(C(=O)c1c3ccccc3nn1Cc1ccccc1)C1CC1)C2]
137 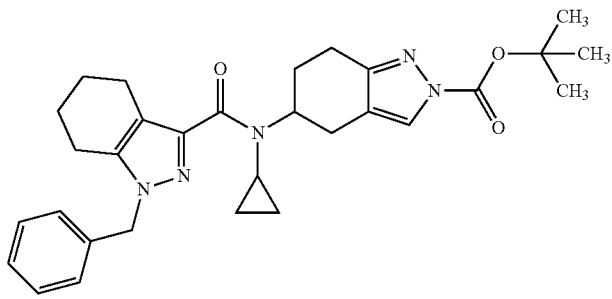 [SMILES: CC(C)(C)OC(=O)n1cc2c(n1)CCC(N(C(=O)c1nn(Cc3ccccc3)c3c1CCCC3)C1CC1)C2]
138 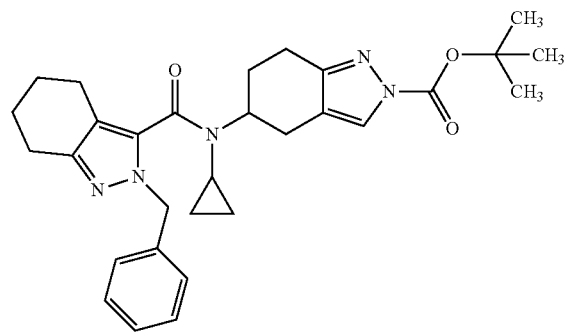 [SMILES: CC(C)(C)OC(=O)n1cc2c(n1)CCC(N(C(=O)c1c3c(nn1Cc1ccccc1)CCCC3)C1CC1)C2]
TABLE 30
139 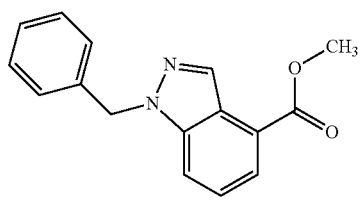 [SMILES: COC(=O)c1cccc2c1cnn2Cc1ccccc1]

TABLE 30-continued
| 140 | 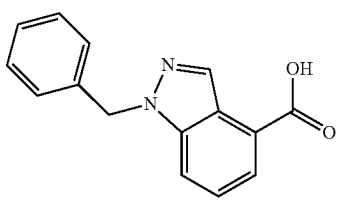 [SMILES: O=C(O)c1cccc2c1cnn2Cc1ccccc1] |
| --- | --- |
| 141 | 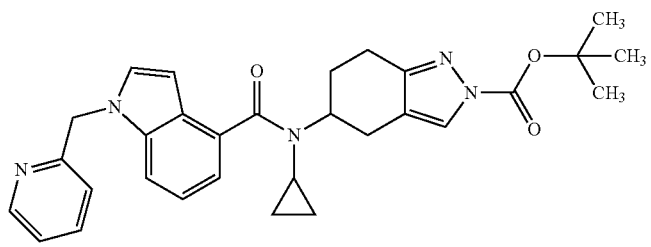 [SMILES: CC(C)(C)OC(=O)n1cc2c(n1)CCC(N(C(=O)c1cccc3c1ccn3Cc1ccccn1)C1CC1)C2] |
| 142 | 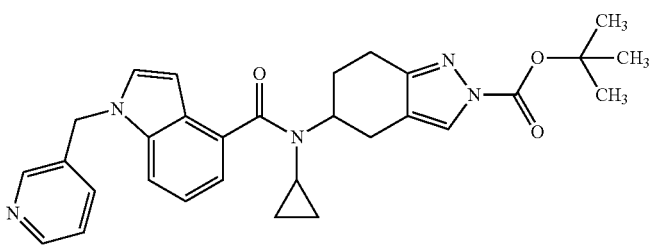 [SMILES: CC(C)(C)OC(=O)n1cc2c(n1)CCC(N(C(=O)c1cccc3c1ccn3Cc1cccnc1)C1CC1)C2] |
| 143 | 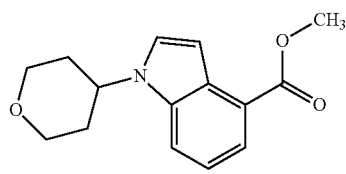 [SMILES: COC(=O)c1cccc2c1ccn2C1CCOCC1] |
TABLE 31
| 144 | 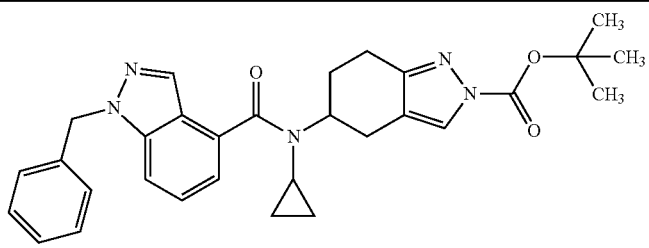 |
| --- | --- |
| 145 | 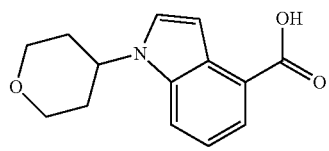 [SMILES: O=C(O)c1cccc2c1ccn2C1CCOCC1] |
| 146 | 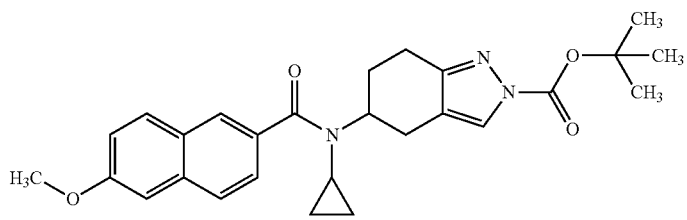 [SMILES: COc1ccc2cc(C(=O)N(C3CC3)C3CCc4nn(C(=O)OC(C)(C)C)cc4C3)ccc2c1] |

TABLE 31-continued
147
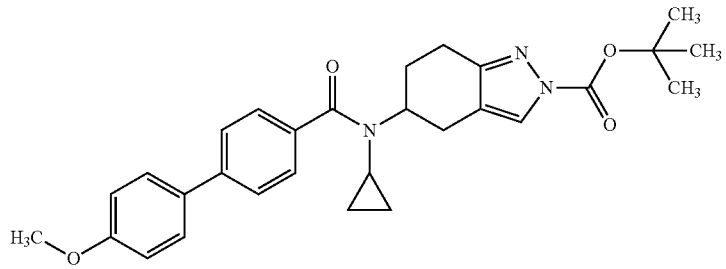 [SMILES: COc1ccc(-c2ccc(C(=O)N(C3CC3)C3CCc4nn(C(=O)OC(C)(C)C)cc4C3)cc2)cc1]
148
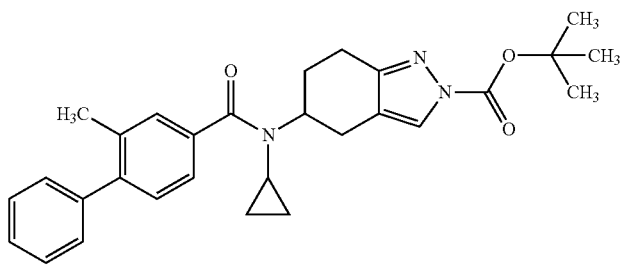
TABLE 32
149
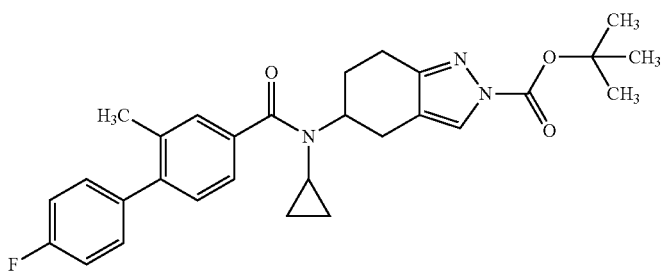 [SMILES: Cc1cc(C(=O)N(C2CC2)C2CCc3nn(C(=O)OC(C)(C)C)cc3C2)ccc1-c1ccc(F)cc1]
150
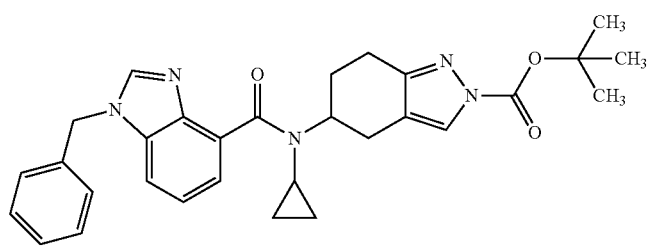 [SMILES: CC(C)(C)OC(=O)n1cc2c(n1)CCC(N(C(=O)c1cccc3c1ncn3Cc1ccccc1)C1CC1)C2]
151
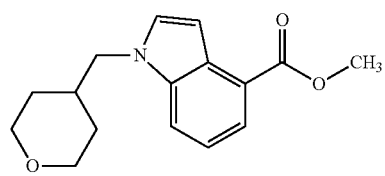 [SMILES: COC(=O)c1cccc2c1ccn2CC1CCOCC1]
152
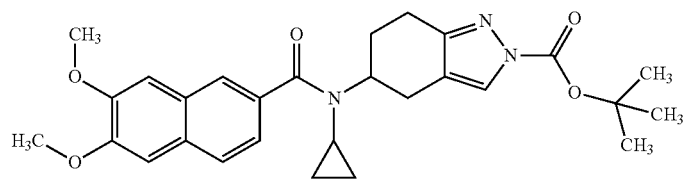 [SMILES: COc1cc2ccc(C(=O)N(C3CC3)C3CCc4nn(C(=O)OC(C)(C)C)cc4C3)cc2cc1OC]

TABLE 32-continued
153 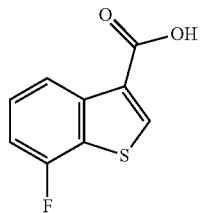 [SMILES: O=C(O)c1csc2c(F)cccc12]
TABLE 33
154 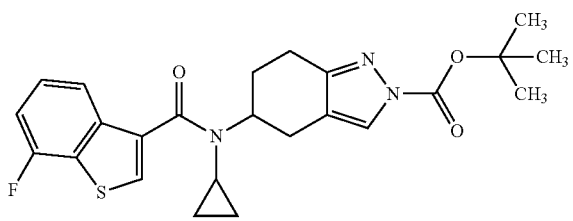 [SMILES: CC(C)(C)OC(=O)n1cc2c(n1)CCC(N(C(=O)c1csc3c(F)cccc13)C1CC1)C2]
155 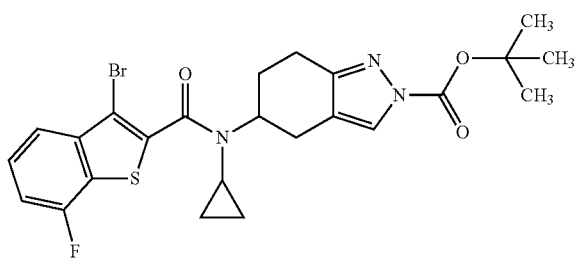 [SMILES: CC(C)(C)OC(=O)n1cc2c(n1)CCC(N(C(=O)c1sc3c(F)cccc3c1Br)C1CC1)C2]
156 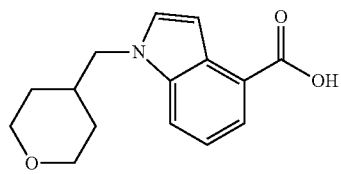 [SMILES: O=C(O)c1cccc2c1ccn2CC1CCOCC1]
157 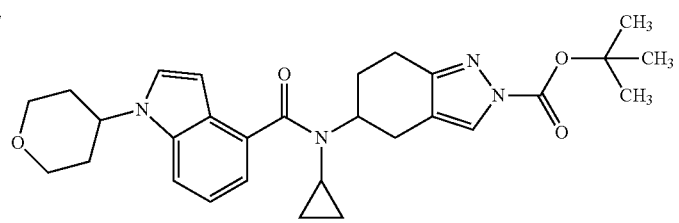
158 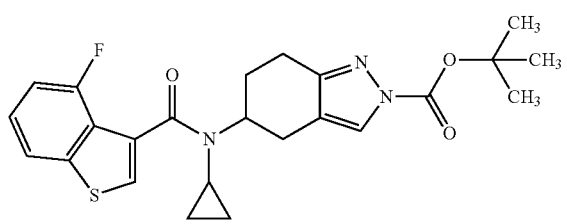 [SMILES: CC(C)(C)OC(=O)n1cc2c(n1)CCC(N(C(=O)c1csc3cccc(F)c13)C1CC1)C2]

TABLE 34
159 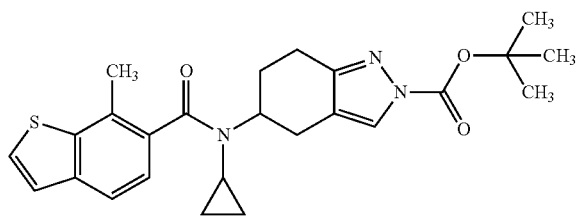 [SMILES: Cc1c(C(=O)N(C2CC2)C2CCc3nn(C(=O)OC(C)(C)C)cc3C2)ccc2ccsc12]
160 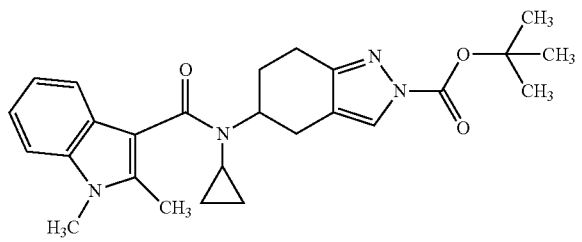 [SMILES: Cc1c(C(=O)N(C2CC2)C2CCc3nn(C(=O)OC(C)(C)C)cc3C2)c2ccccc2n1C]
161 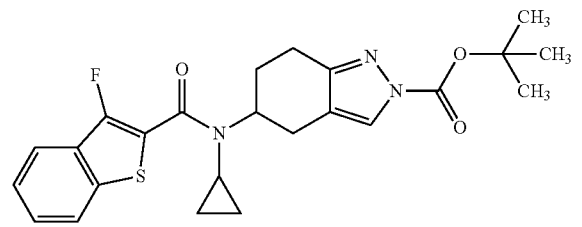 [SMILES: CC(C)(C)OC(=O)n1cc2c(n1)CCC(N(C(=O)c1sc3ccccc3c1F)C1CC1)C2]
162 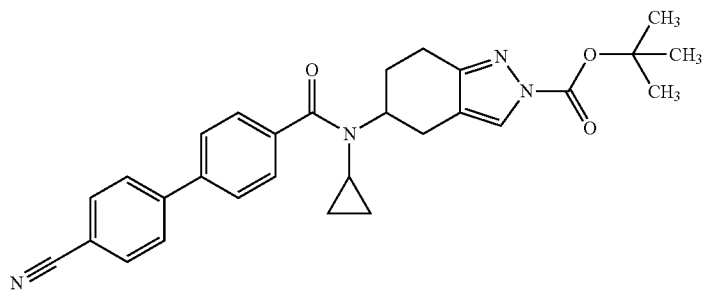 [SMILES: CC(C)(C)OC(=O)n1cc2c(n1)CCC(N(C(=O)c1ccc(-c3ccc(C#N)cc3)cc1)C1CC1)C2]
163 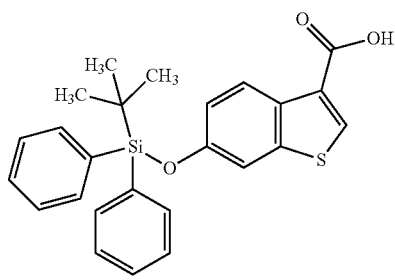 [SMILES: CC(C)(C)[Si](Oc1ccc2c(C(=O)O)csc2c1)(c1ccccc1)c1ccccc1]
TABLE 35
164 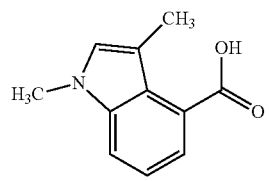

TABLE 35-continued
165 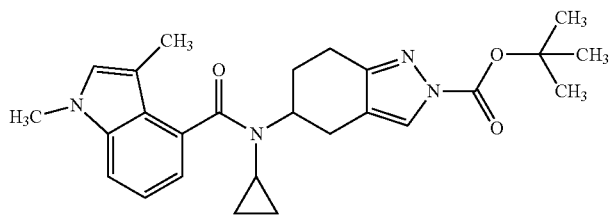 [SMILES: Cc1cn(C)c2cccc(C(=O)N(C3CC3)C3CCc4nn(C(=O)OC(C)(C)C)cc4C3)c12]
166 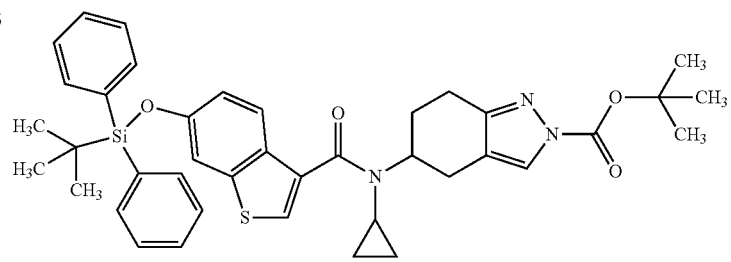
167 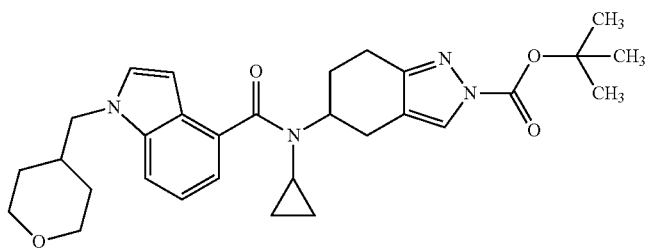 [SMILES: CC(C)(C)OC(=O)n1cc2c(n1)CCC(N(C(=O)c1cccc3c1ccn3CC1CCOCC1)C1CC1)C2]
168 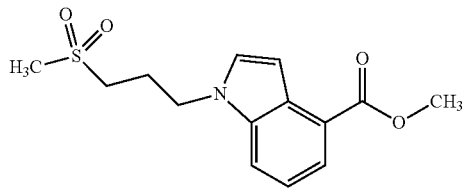
TABLE 36
169 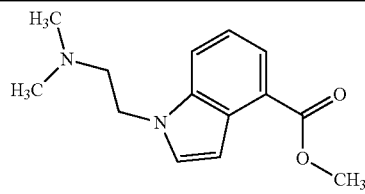
170 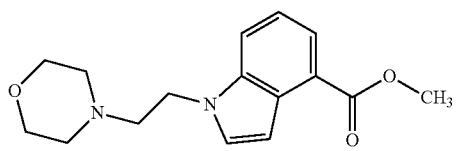 [SMILES: COC(=O)c1cccc2c1ccn2CCN1CCOCC1]
171 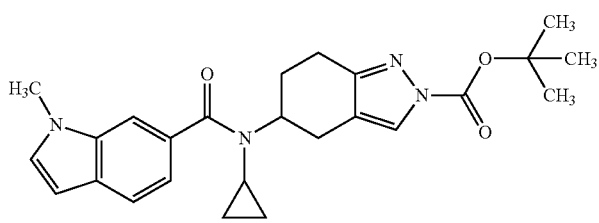 [SMILES: Cn1ccc2ccc(C(=O)N(C3CC3)C3CCc4nn(C(=O)OC(C)(C)C)cc4C3)cc21]

TABLE 36-continued
172 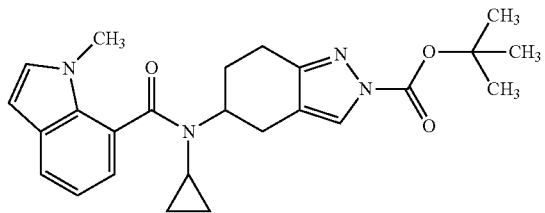 [SMILES: Cn1ccc2cccc(C(=O)N(C3CC3)C3CCc4nn(C(=O)OC(C)(C)C)cc4C3)c21]
173 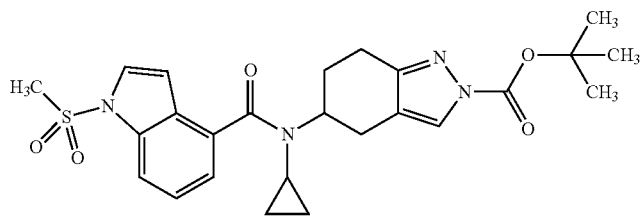 [SMILES: CC(C)(C)OC(=O)n1cc2c(n1)CCC(N(C(=O)c1cccc3c1ccn3S(C)(=O)=O)C1CC1)C2]
174 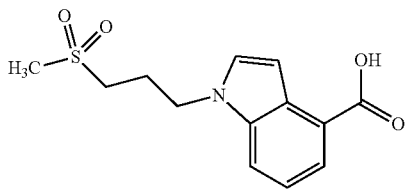 [SMILES: CS(=O)(=O)CCCn1ccc2c(C(=O)O)cccc21]
TABLE 37
175 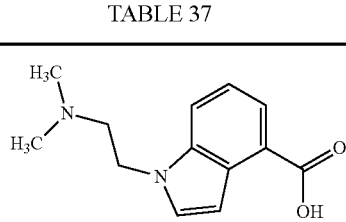
176 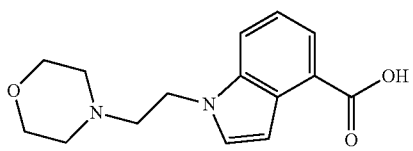 [SMILES: O=C(O)c1cccc2c1ccn2CCN1CCOCC1]
177 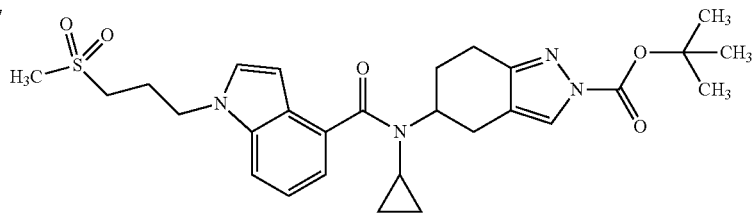
178 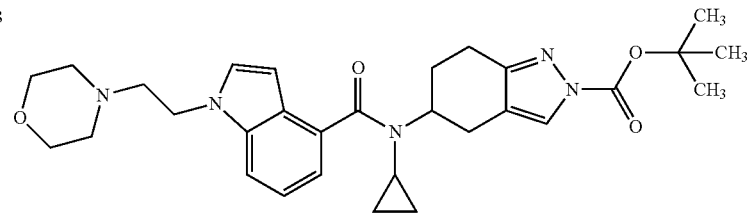

TABLE 37-continued
179
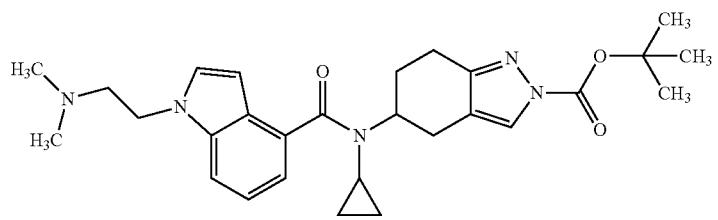 [SMILES: CN(C)CCn1ccc2c(C(=O)N(C3CC3)C3CCc4nn(C(=O)OC(C)(C)C)cc4C3)cccc21]
180
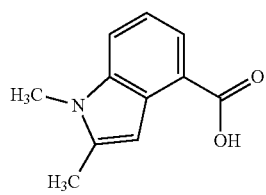
TABLE 38
181
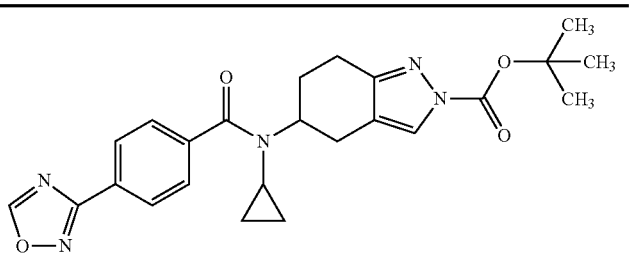
182
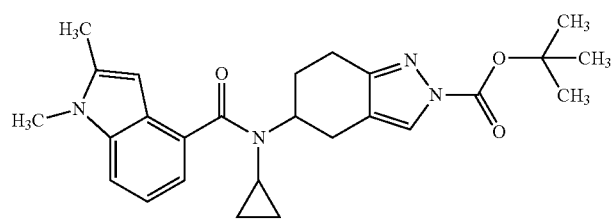 [SMILES: Cc1cc2c(C(=O)N(C3CC3)C3CCc4nn(C(=O)OC(C)(C)C)cc4C3)cccc2n1C]
183
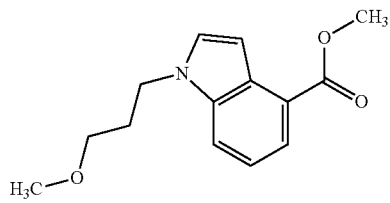
184
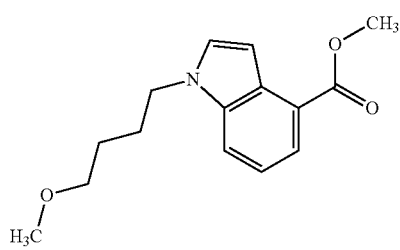
185
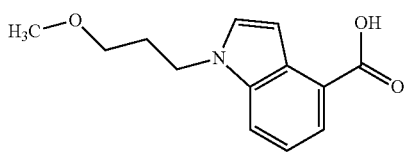 [SMILES: COCCCn1ccc2c(C(=O)O)cccc21]

TABLE 38-continued
186 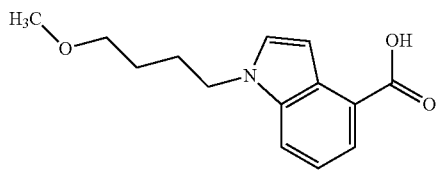 [SMILES: COCCCCn1ccc2c(C(=O)O)cccc21]
TABLE 39
187 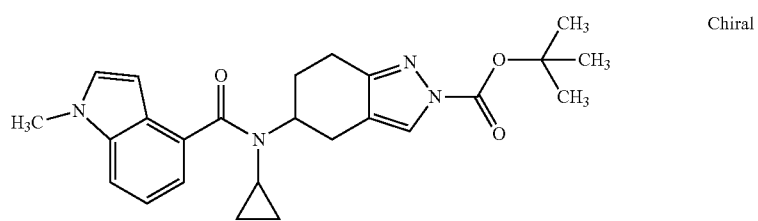 Chiral
188 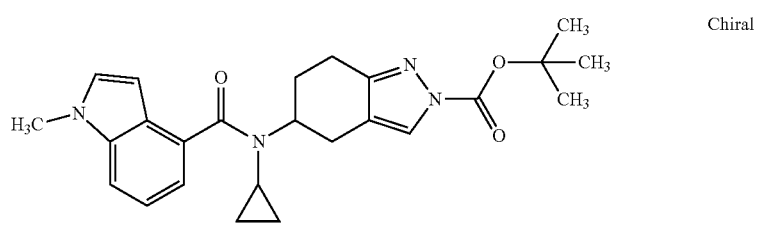 Chiral
189 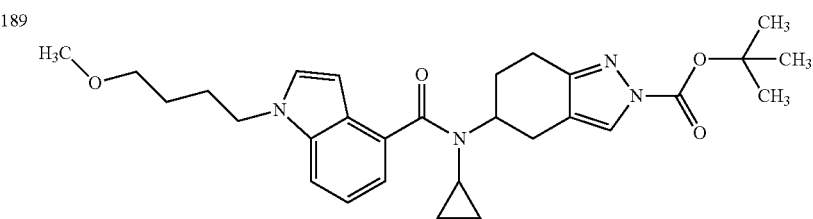
190 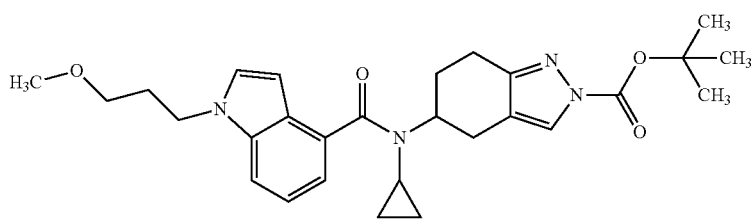 [SMILES: COCCCn1ccc2c(C(=O)N(C3CC3)C3CCc4nn(C(=O)OC(C)(C)C)cc4C3)cccc21]
191 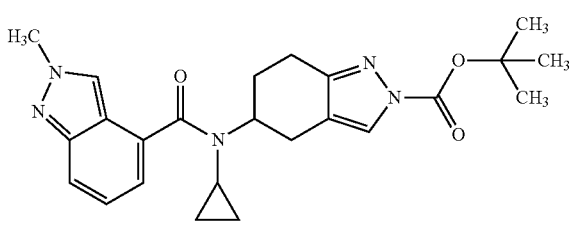 [SMILES: Cn1cc2c(C(=O)N(C3CC3)C3CCc4nn(C(=O)OC(C)(C)C)cc4C3)cccc2n1]

TABLE 40
192 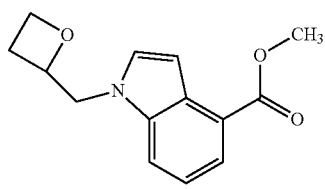 [SMILES: COC(=O)c1cccc2c1ccn2CC1CCO1]
193 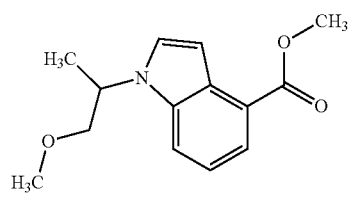 [SMILES: COCC(C)n1ccc2c(C(=O)OC)cccc21]
194 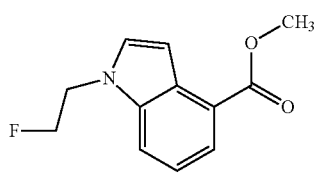 [SMILES: COC(=O)c1cccc2c1ccn2CCF]
195 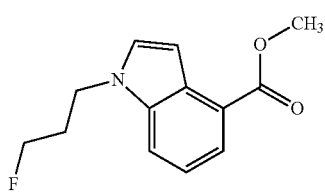 [SMILES: COC(=O)c1cccc2c1ccn2CCCF]
196 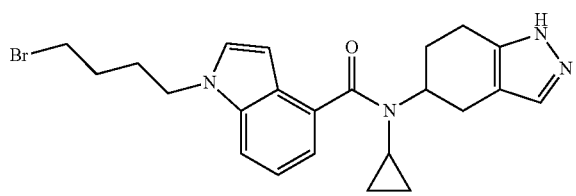 [SMILES: O=C(c1cccc2c1ccn2CCCCBr)N(C1CC1)C1CCc2[nH]ncc2C1]
197 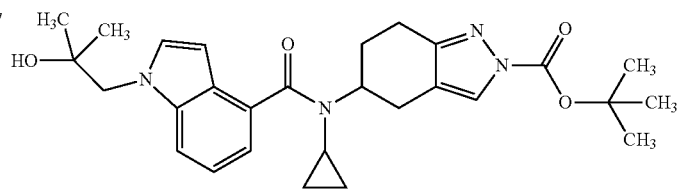
TABLE 41
198 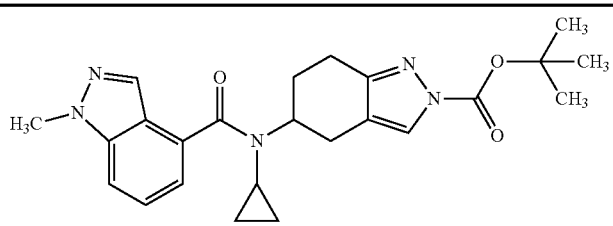

TABLE 41-continued
199 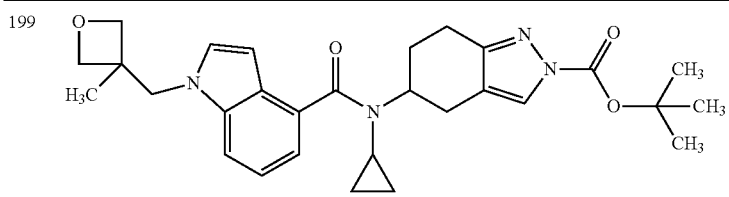
200 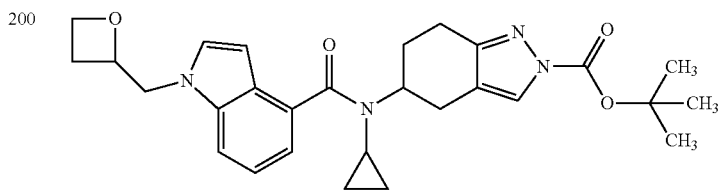
201 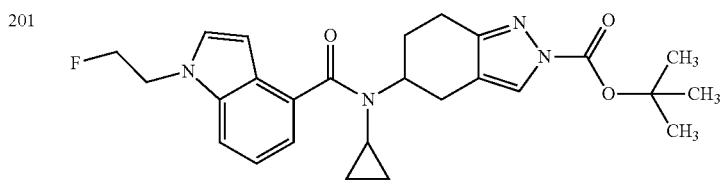
202 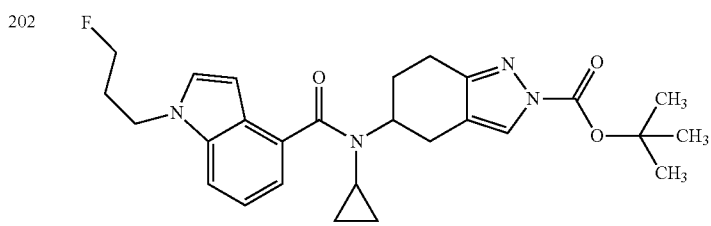
203 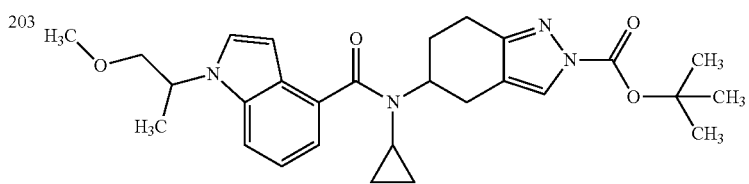
TABLE 42
204 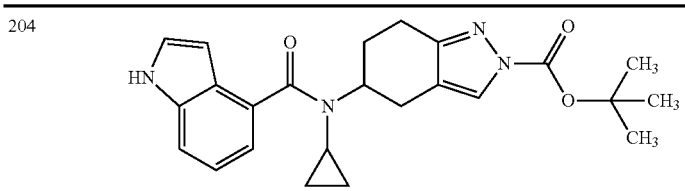
205 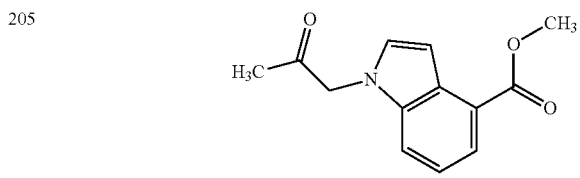
206 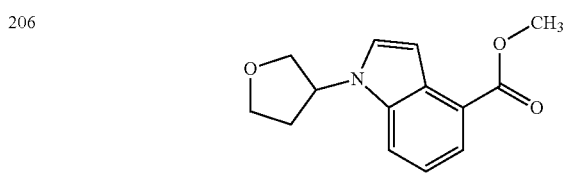

TABLE 42-continued
207 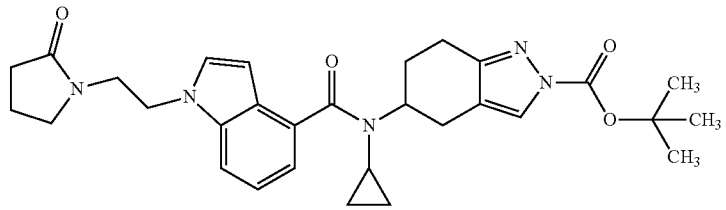 [SMILES: CC(C)(C)OC(=O)n1cc2c(n1)CCC(N(C(=O)c1cccc3c1ccn3CCN1CCCC1=O)C1CC1)C2]
208 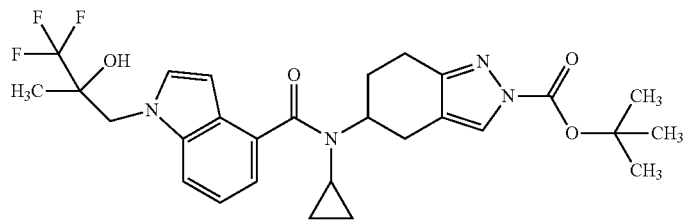 [SMILES: CC(C)(C)OC(=O)n1cc2c(n1)CCC(N(C(=O)c1cccc3c1ccn3CC(C)(O)C(F)(F)F)C1CC1)C2]
209 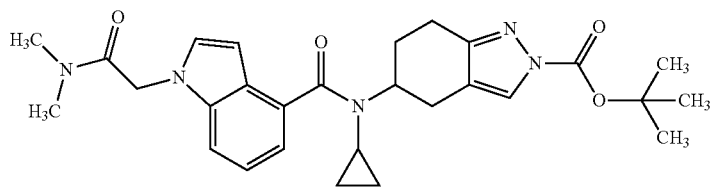 [SMILES: CN(C)C(=O)Cn1ccc2c(C(=O)N(C3CC3)C3CCc4nn(C(=O)OC(C)(C)C)cc4C3)cccc21]
TABLE 43
210 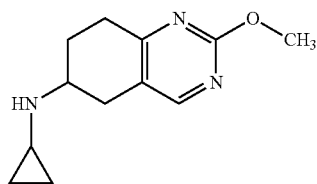 [SMILES: COc1ncc2c(n1)CCC(NC1CC1)C2]
211 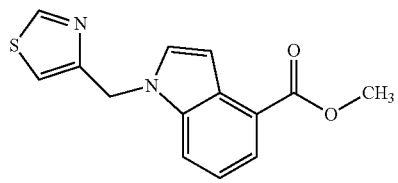 [SMILES: COC(=O)c1cccc2c1ccn2Cc1cscn1]
212 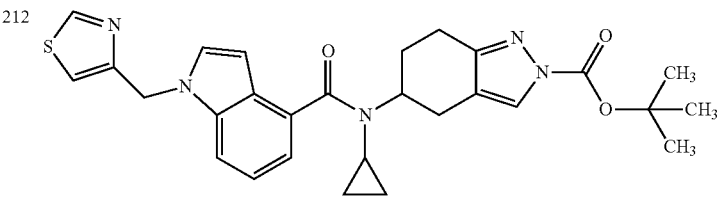
213 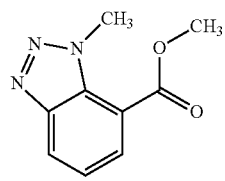

TABLE 43-continued
214 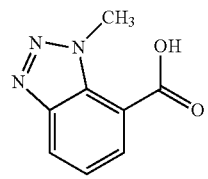
215 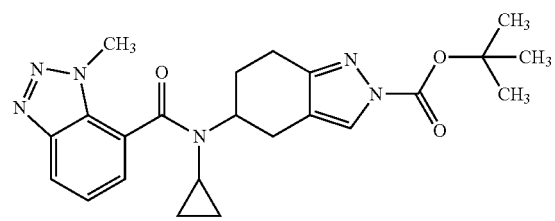 [SMILES: Cn1nnc2cccc(C(=O)N(C3CC3)C3CCc4nn(C(=O)OC(C)(C)C)cc4C3)c21]
TABLE 44
216 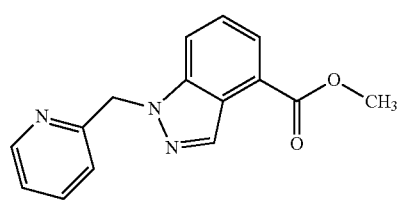 [SMILES: COC(=O)c1cccc2c1cnn2Cc1ccccn1]
217 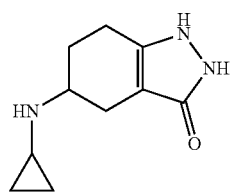 [SMILES: O=c1[nH][nH]c2c1CC(NC1CC1)CC2]
218 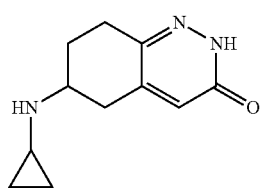 [SMILES: O=c1cc2c(n[nH]1)CCC(NC1CC1)C2]
219 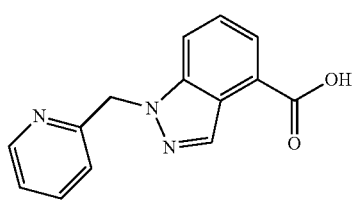 [SMILES: O=C(O)c1cccc2c1cnn2Cc1ccccn1]
220 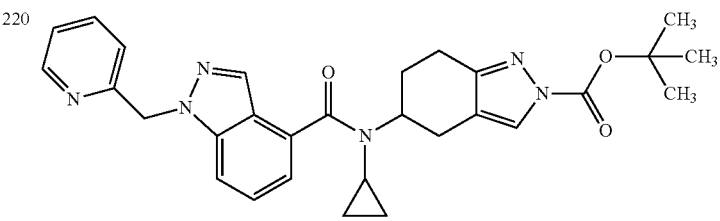

TABLE 44-continued
| 221 | 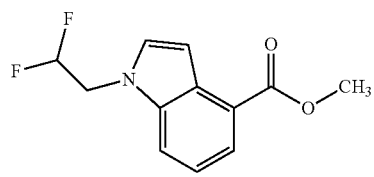 [SMILES: COC(=O)c1cccc2c1ccn2CC(F)F] | |
TABLE 45
| 222 | 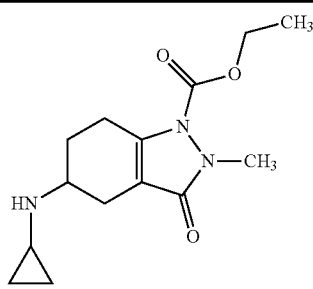 | |
| 223 | 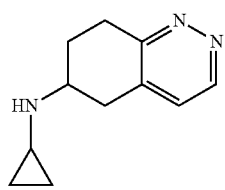 [SMILES: c1cc2c(nn1)CCC(NC1CC1)C2] | Sal: HCl |
| 224 | 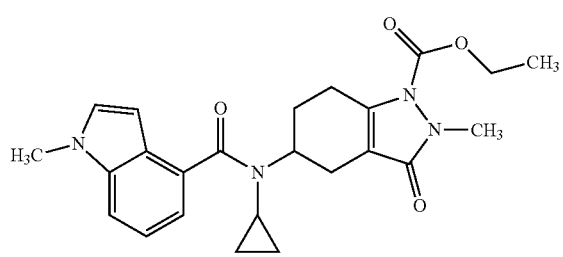 [SMILES: CCOC(=O)n1c2c(c(=O)n1C)CC(N(C(=O)c1cccc3c1ccn3C)C1CC1)CC2] | |
| 225 | 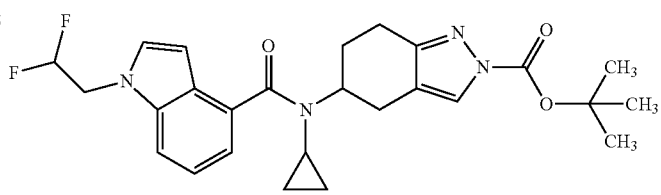 [SMILES: CC(C)(C)OC(=O)n1cc2c(n1)CCC(N(C(=O)c1cccc3c1ccn3CC(F)F)C1CC1)C2] | |
| 226 | 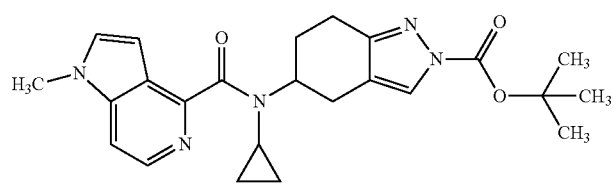 [SMILES: Cn1ccc2c(C(=O)N(C3CC3)C3CCc4nn(C(=O)OC(C)(C)C)cc4C3)nccc21] | |
| 227 | 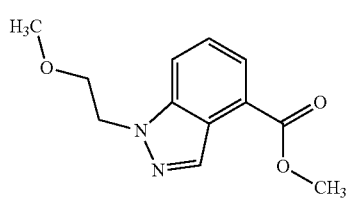 | |

TABLE 46
| | |
|---|---|
| 228 | 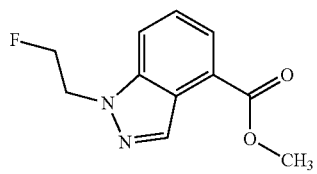 [SMILES: COC(=O)c1cccc2c1cnn2CCF] |
| 229 | 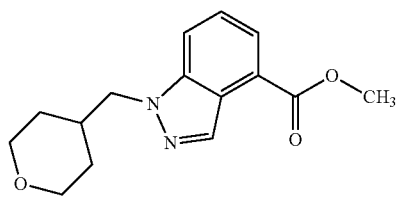 [SMILES: COC(=O)c1cccc2c1cnn2CC1CCOCC1] |
| 230 | 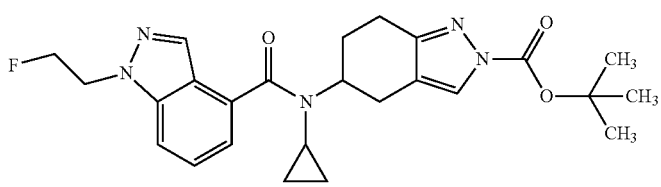 [SMILES: CC(C)(C)OC(=O)n1cc2c(n1)CCC(N(C(=O)c1cccc3c1cnn3CCF)C1CC1)C2] |
| 231 | 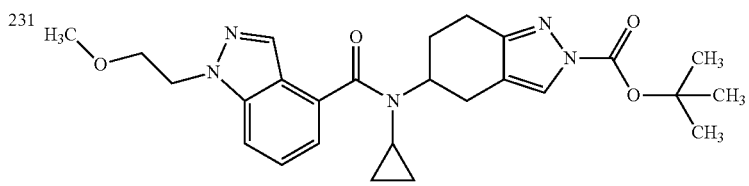 |
| 232 | 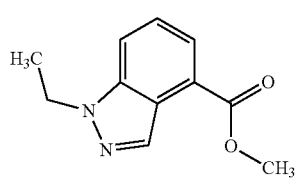 |
| 233 | 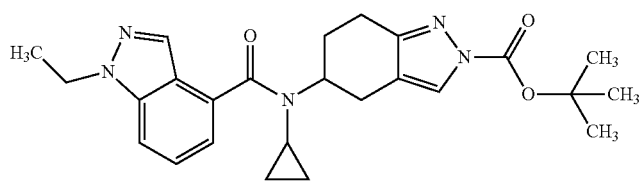 [SMILES: CCn1ncc2c(C(=O)N(C3CC3)C3CCc4nn(C(=O)OC(C)(C)C)cc4C3)cccc21] |
TABLE 47
| | |
|---|---|
| 234 | 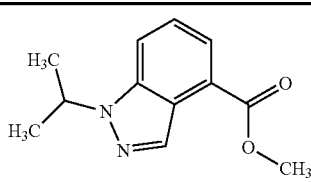 |
| 235 | 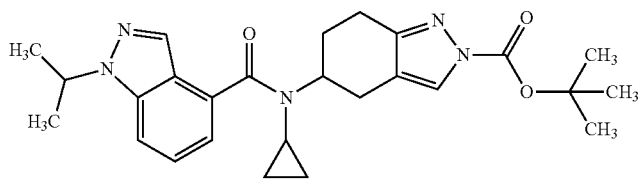 [SMILES: CC(C)n1ncc2c(C(=O)N(C3CC3)C3CCc4nn(C(=O)OC(C)(C)C)cc4C3)cccc21] |

TABLE 47-continued
236 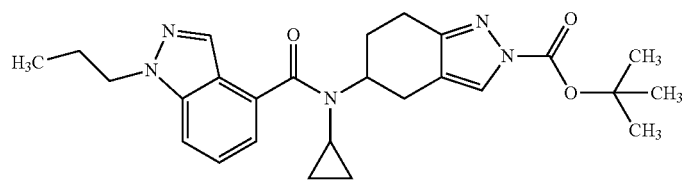 [SMILES: CCCn1ncc2c(C(=O)N(C3CC3)C3CCc4nn(C(=O)OC(C)(C)C)cc4C3)cccc21]
237 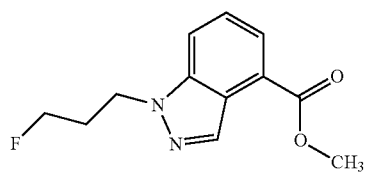 [SMILES: COC(=O)c1cccc2c1cnn2CCCF]
238 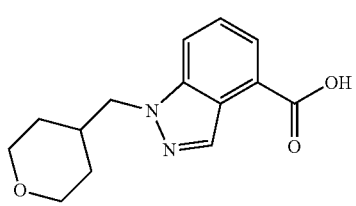 [SMILES: O=C(O)c1cccc2c1cnn2CC1CCOCC1]
239 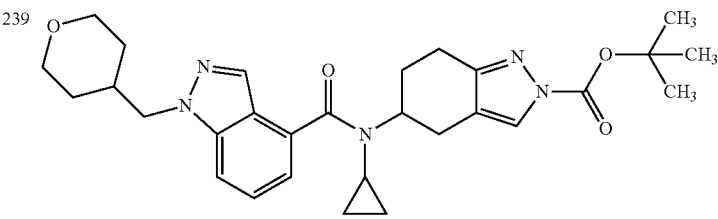
TABLE 48
240 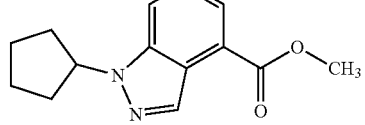
241 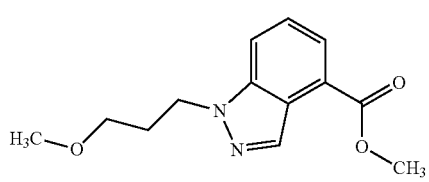
242 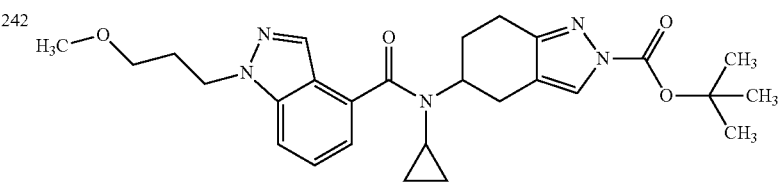
243 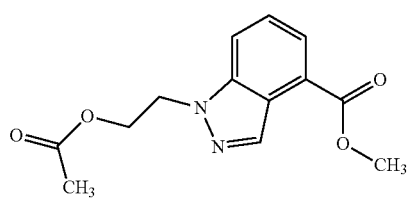 [SMILES: COC(=O)c1cccc2c1cnn2CCOC(C)=O]

| TABLE 48-continued |
|---|
| 244 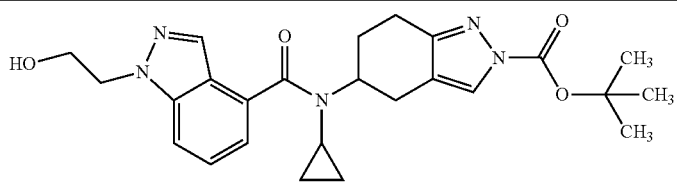 |
| 245 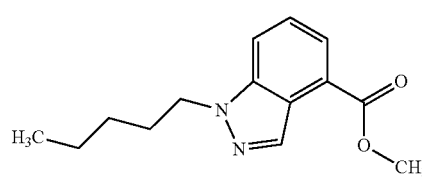 |
| TABLE 49 | TABLE 49-continued |
|---|---|
| 246 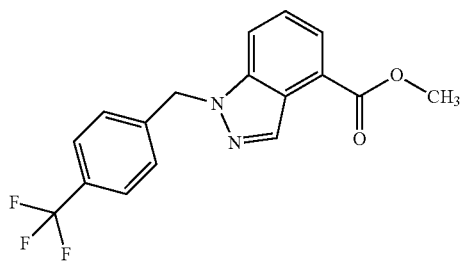 [SMILES: COC(=O)c1cccc2c1cnn2Cc1ccc(C(F)(F)F)cc1] | 249 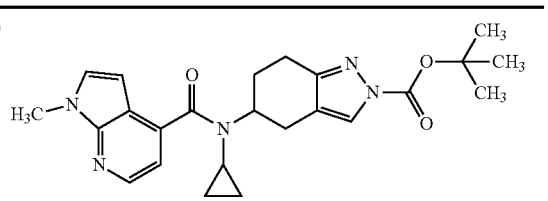 |
| 247 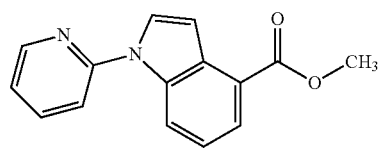 [SMILES: COC(=O)c1cccc2c1ccn2-c1ccccn1] | 250 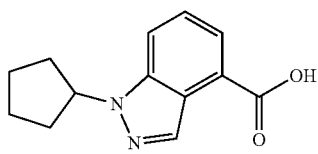 |
| 248 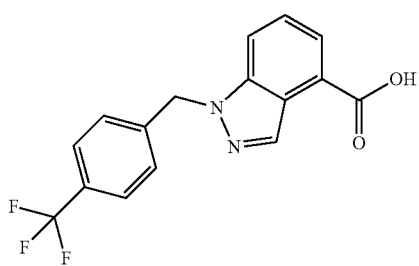 [SMILES: O=C(O)c1cccc2c1cnn2Cc1ccc(C(F)(F)F)cc1] | 251 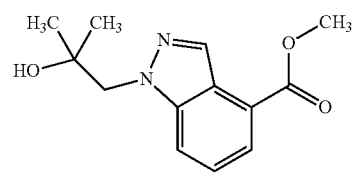 [SMILES: COC(=O)c1cccc2c1cnn2CC(C)(C)O] |
| TABLE 50 |
|---|
| 252 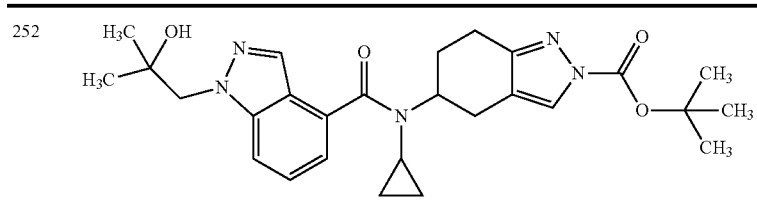 |

TABLE 50-continued
253 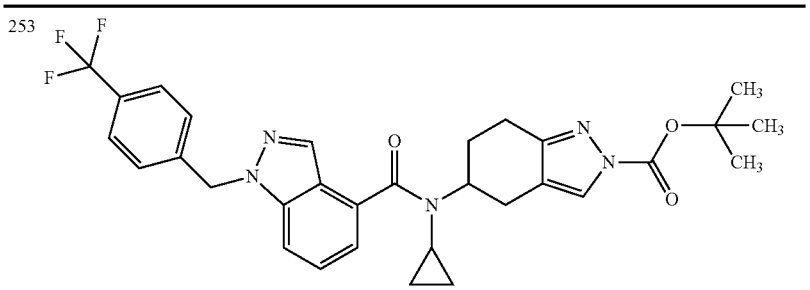
254 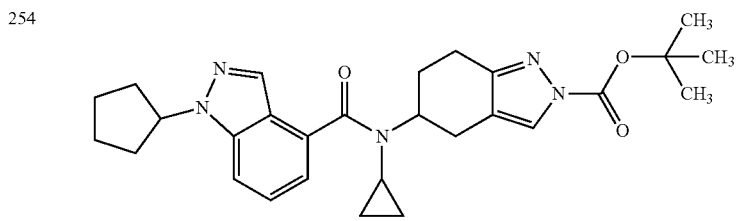
255 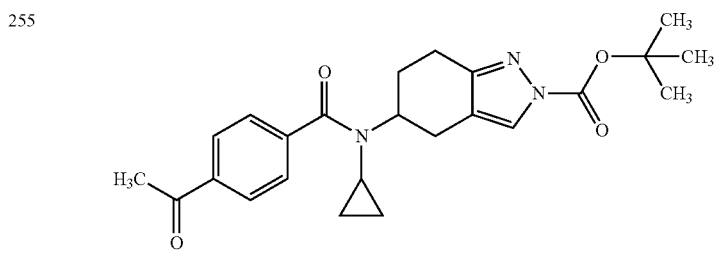
256 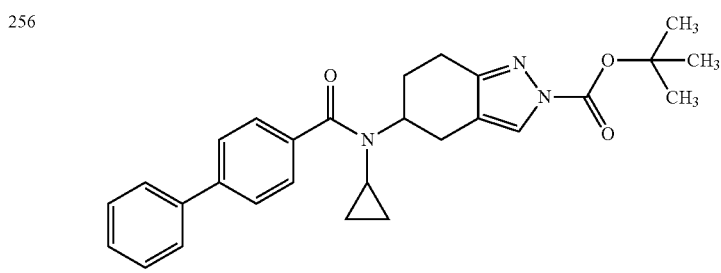
TABLE 51
257 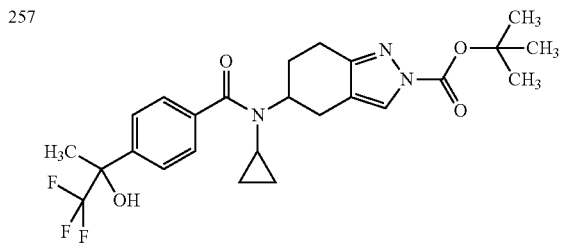
258 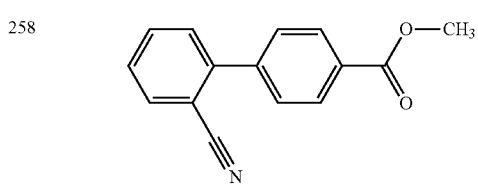
TABLE 51-continued
259 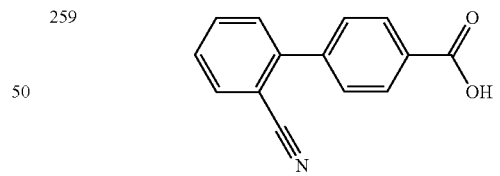
260 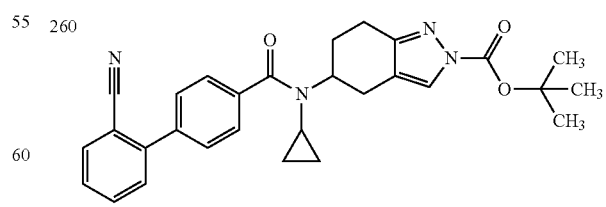

TABLE 51-continued
261 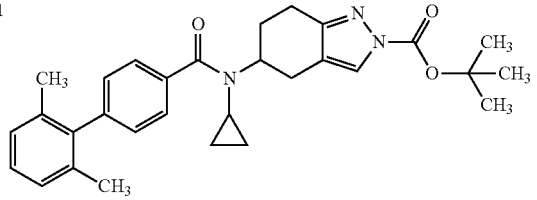
262 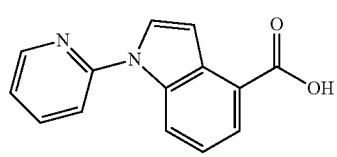 [SMILES: O=C(O)c1cccc2c1ccn2-c1ccccn1]
TABLE 52
263 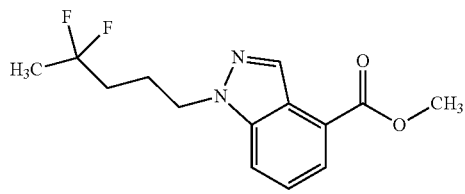 [SMILES: COC(=O)c1cccc2c1cnn2CCCC(C)(F)F]
264 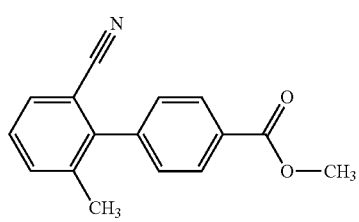 [SMILES: COC(=O)c1ccc(-c2c(C)cccc2C#N)cc1]
TABLE 52-continued
265 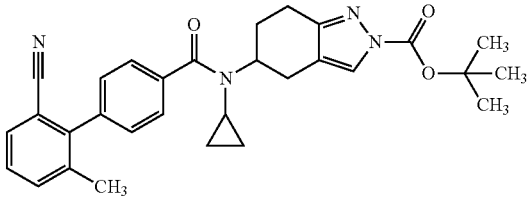 [SMILES: Cc1cccc(C#N)c1-c1ccc(C(=O)N(C2CC2)C2CCc3nn(C(=O)OC(C)(C)C)cc3C2)cc1]
266 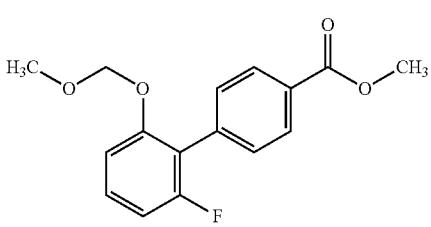
267 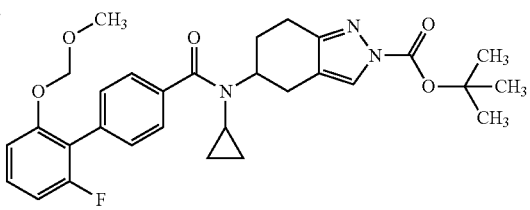 [SMILES: COCOc1cccc(F)c1-c1ccc(C(=O)N(C2CC2)C2CCc3nn(C(=O)OC(C)(C)C)cc3C2)cc1]
268 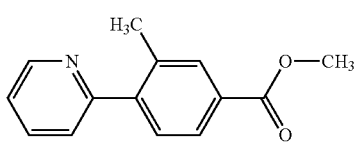 [SMILES: COC(=O)c1ccc(-c2ccccn2)c(C)c1]
TABLE 53
269 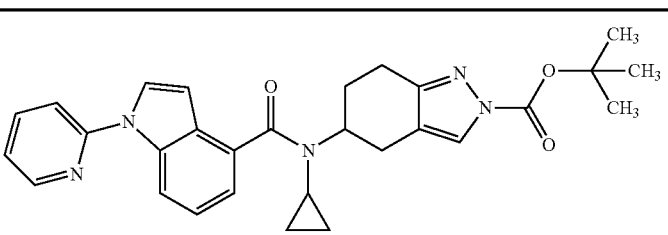
270 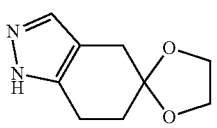 [SMILES: c1n[nH]c2c1CC1(CC2)OCCO1]
271 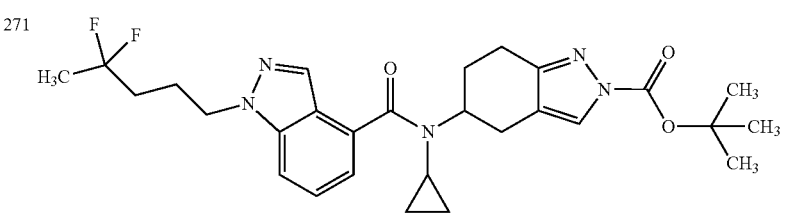

TABLE 53-continued
272 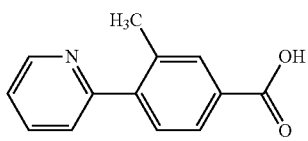
273 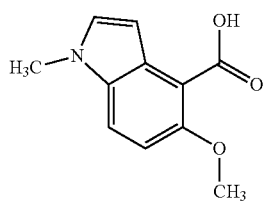
274 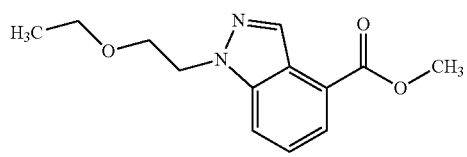 [SMILES: CCOCCn1ncc2c(C(=O)OC)cccc21]
275 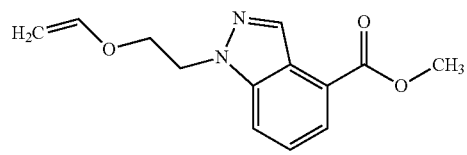 [SMILES: C=COCCn1ncc2c(C(=O)OC)cccc21]
TABLE 54
276 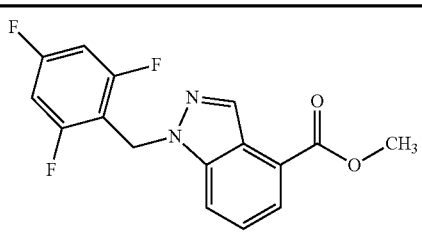
277 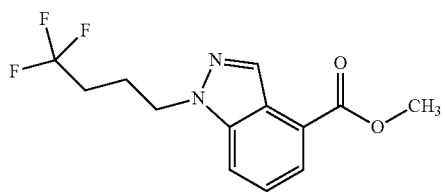 [SMILES: COC(=O)c1cccc2c1cnn2CCCC(F)(F)F]
278 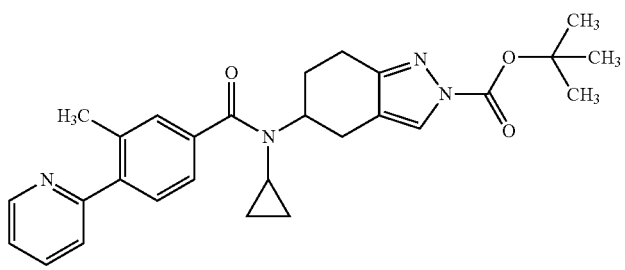 [SMILES: Cc1cc(C(=O)N(C2CC2)C2CCc3nn(C(=O)OC(C)(C)C)cc3C2)ccc1-c1ccccn1]

TABLE 54-continued
279 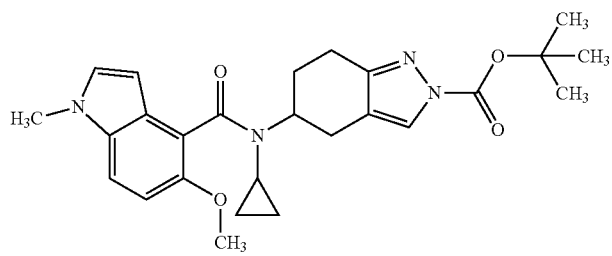 [SMILES: COc1ccc2c(ccn2C)c1C(=O)N(C1CC1)C1CCc2nn(C(=O)OC(C)(C)C)cc2C1]
280 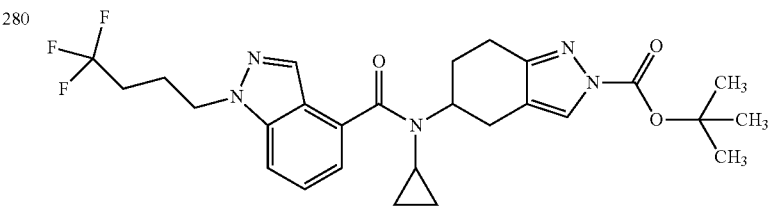
281 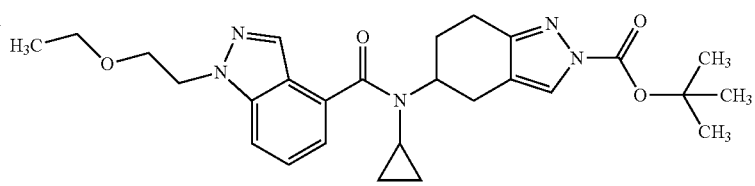
282 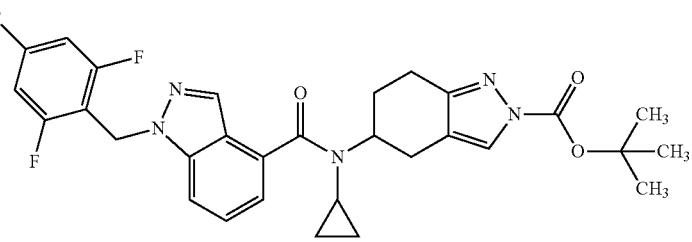
283 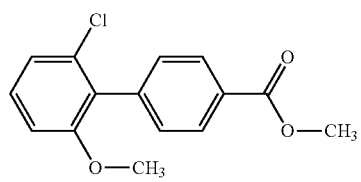
284 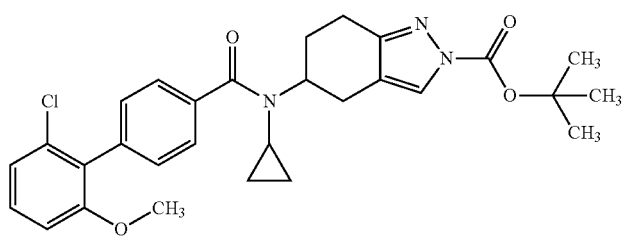 [SMILES: COc1cccc(Cl)c1-c1ccc(C(=O)N(C2CC2)C2CCc3nn(C(=O)OC(C)(C)C)cc3C2)cc1]
285 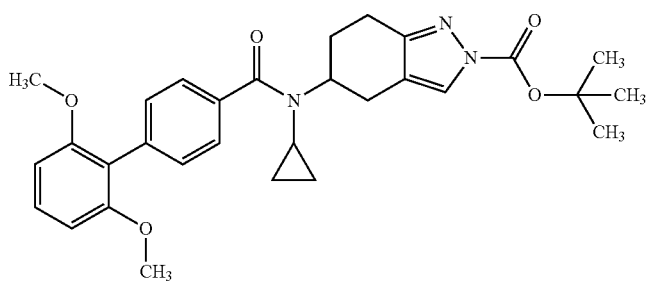 [SMILES: COc1cccc(OC)c1-c1ccc(C(=O)N(C2CC2)C2CCc3nn(C(=O)OC(C)(C)C)cc3C2)cc1]

TABLE 55
286 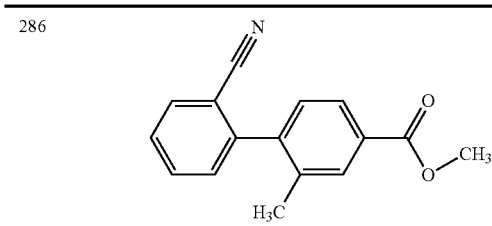
287 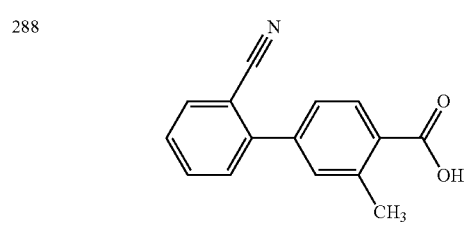
288 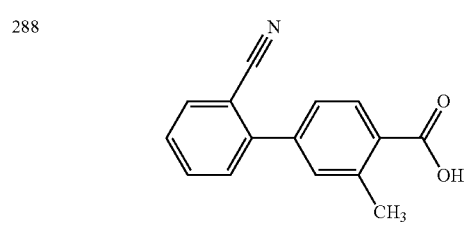
TABLE 55-continued
289 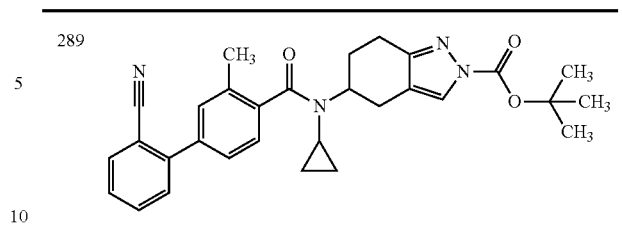
290 
TABLE 56
291 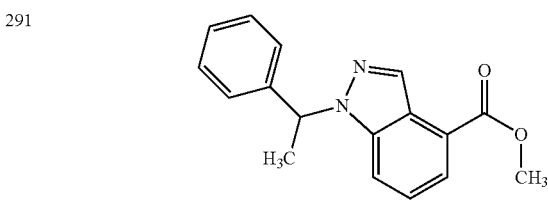
292 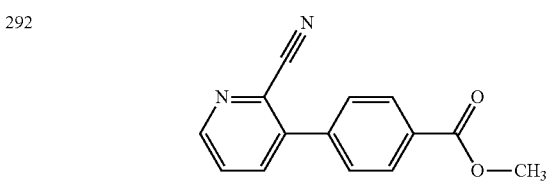
293 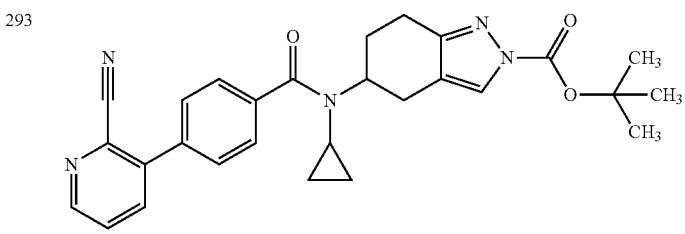
294 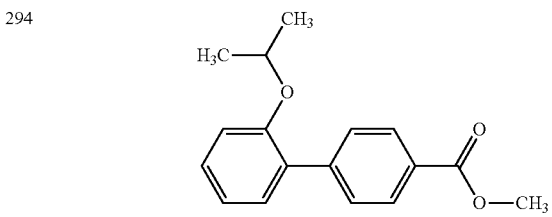

TABLE 56-continued
295 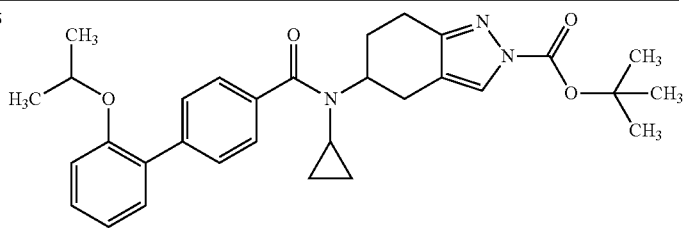
296 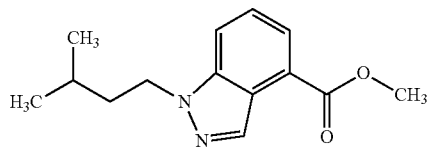 [SMILES: COC(=O)c1cccc2c1cnn2CCC(C)C]
TABLE 57
297 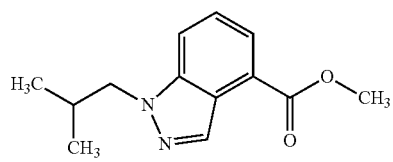 [SMILES: COC(=O)c1cccc2c1cnn2CC(C)C]
298 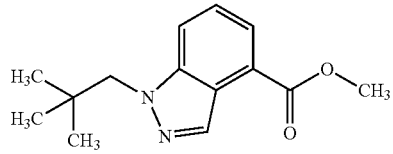 [SMILES: COC(=O)c1cccc2c1cnn2CC(C)(C)C]
299 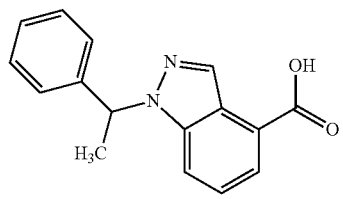 [SMILES: CC(c1ccccc1)n1ncc2c(C(=O)O)cccc21]
300 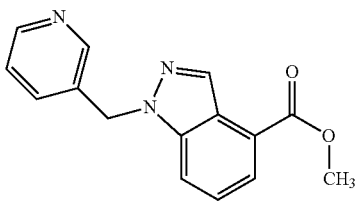 [SMILES: COC(=O)c1cccc2c1cnn2Cc1cccnc1]
301 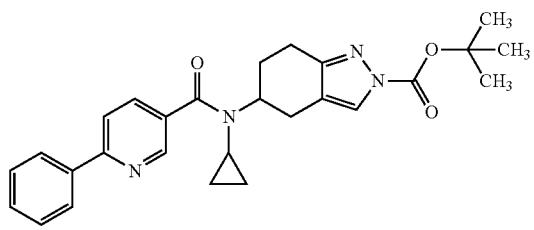 [SMILES: CC(C)(C)OC(=O)n1cc2c(n1)CCC(N(C(=O)c1ccc(-c3ccccc3)nc1)C1CC1)C2]
TABLE 58
302 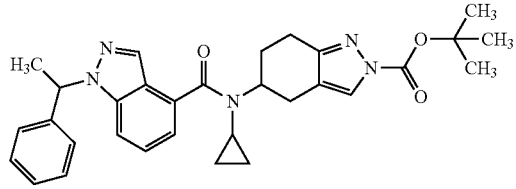 [SMILES: CC(c1ccccc1)n1ncc2c(C(=O)N(C3CC3)C3CCc4nn(C(=O)OC(C)(C)C)cc4C3)cccc21]
303 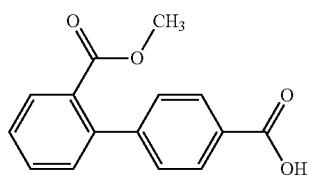 [SMILES: COC(=O)c1ccccc1-c1ccc(C(=O)O)cc1]
304 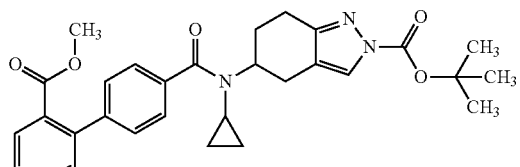
305 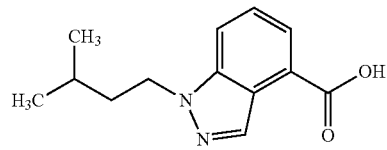 [SMILES: CC(C)CCn1ncc2c(C(=O)O)cccc21]
306 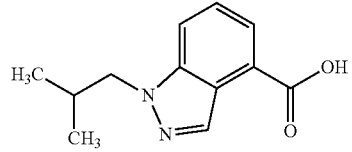
307 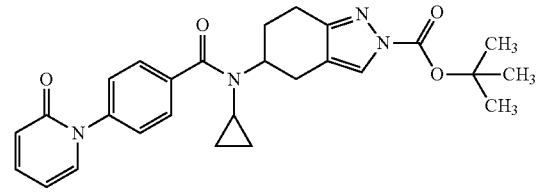 [SMILES: CC(C)(C)OC(=O)n1cc2c(n1)CCC(N(C(=O)c1ccc(-n3ccccc3=O)cc1)C1CC1)C2]

TABLE 60
308 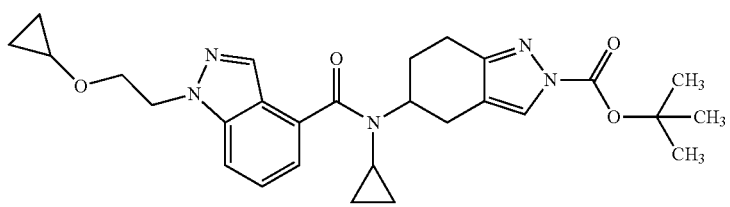 [SMILES: CC(C)(C)OC(=O)n1cc2c(n1)CCC(N(C(=O)c1cccc3c1cnn3CCOC1CC1)C1CC1)C2]
309 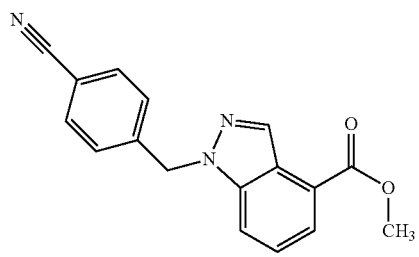 [SMILES: COC(=O)c1cccc2c1cnn2Cc1ccc(C#N)cc1]
310 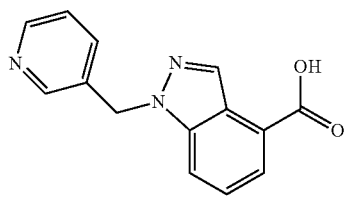 [SMILES: O=C(O)c1cccc2c1cnn2Cc1cccnc1]
311 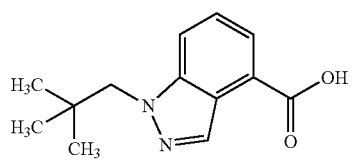
312 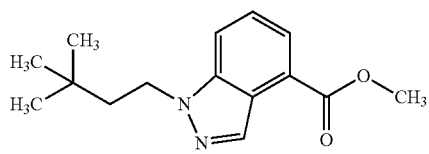 [SMILES: COC(=O)c1cccc2c1cnn2CCC(C)(C)C]
313 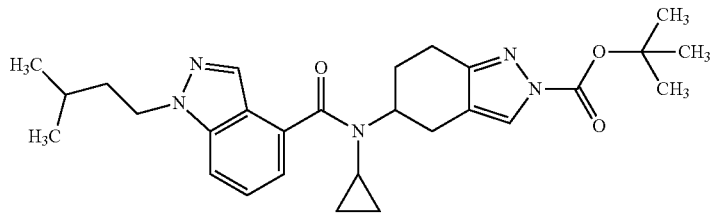 [SMILES: CC(C)CCn1ncc2c(C(=O)N(C3CC3)C3CCc4nn(C(=O)OC(C)(C)C)cc4C3)cccc21]
TABLE 61
314 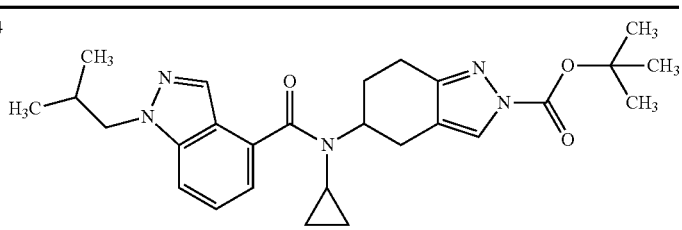

TABLE 61-continued
315 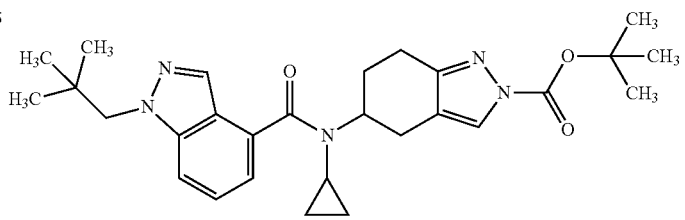
316 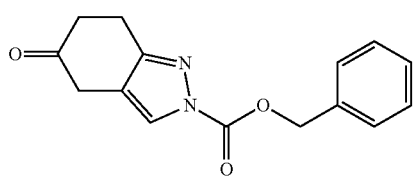 [SMILES: O=C1CCc2nn(C(=O)OCc3ccccc3)cc2C1]
317 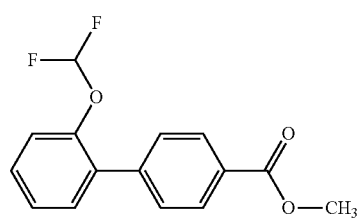 [SMILES: COC(=O)c1ccc(-c2ccccc2OC(F)F)cc1]
318 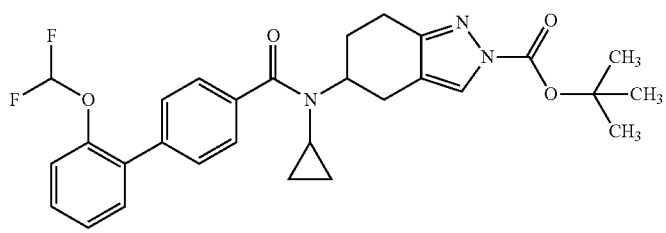 [SMILES: CC(C)(C)OC(=O)n1cc2c(n1)CCC(N(C(=O)c1ccc(-c3ccccc3OC(F)F)cc1)C1CC1)C2]
319 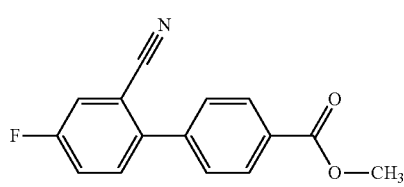
TABLE 62
320 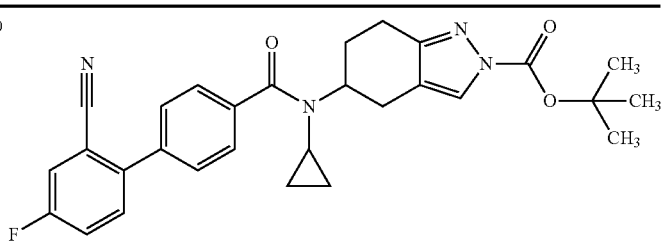
321 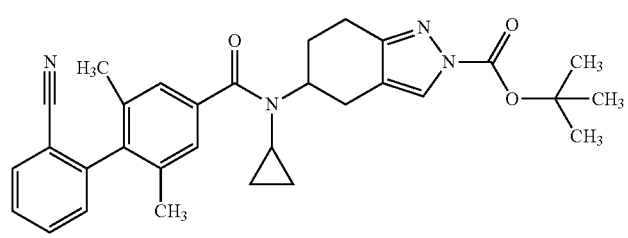 [SMILES: Cc1cc(C(=O)N(C2CC2)C2CCc3nn(C(=O)OC(C)(C)C)cc3C2)cc(C)c1-c1ccccc1C#N]

TABLE 62-continued
322 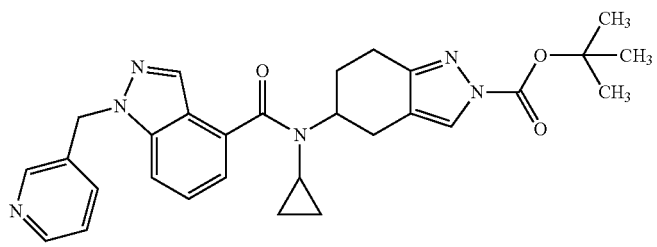
323 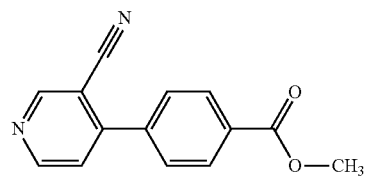 [SMILES: COC(=O)c1ccc(-c2ccncc2C#N)cc1]
324 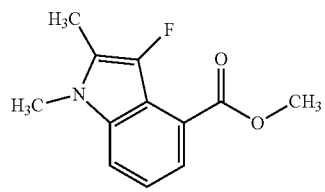
325 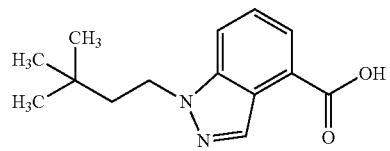 [SMILES: CC(C)(C)CCn1ncc2c(C(=O)O)cccc21]
TABLE 63
326 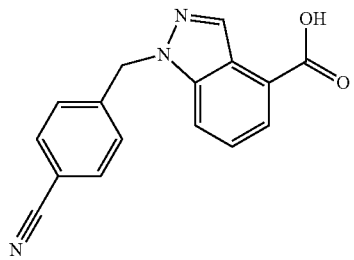 [SMILES: N#Cc1ccc(Cn2ncc3c(C(=O)O)cccc32)cc1]
327 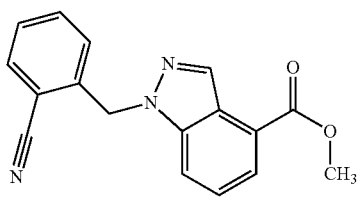 [SMILES: COC(=O)c1cccc2c1cnn2Cc1ccccc1C#N]

TABLE 63-continued
328 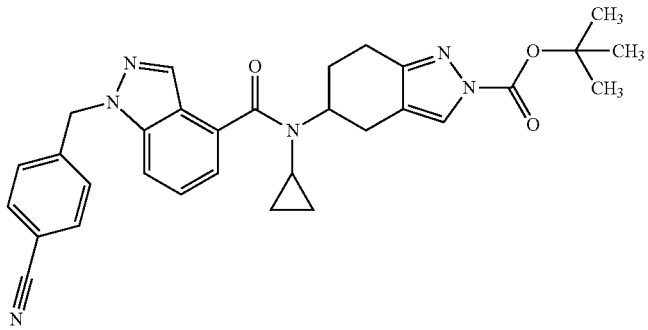 [SMILES: CC(C)(C)OC(=O)n1cc2c(n1)CCC(N(C(=O)c1cccc3c1cnn3Cc1ccc(C#N)cc1)C1CC1)C2]
329 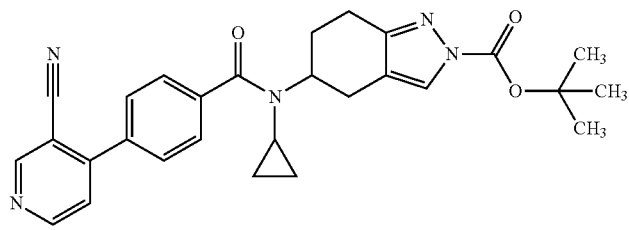 [SMILES: CC(C)(C)OC(=O)n1cc2c(n1)CCC(N(C(=O)c1ccc(-c3ccncc3C#N)cc1)C1CC1)C2]
330 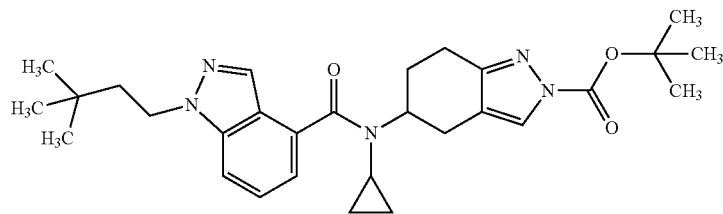 [SMILES: CC(C)(C)CCn1ncc2c(C(=O)N(C3CC3)C3CCc4nn(C(=O)OC(C)(C)C)cc4C3)cccc21]
TABLE 64
331 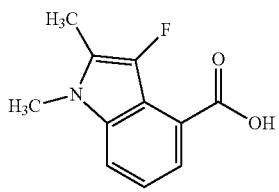
332 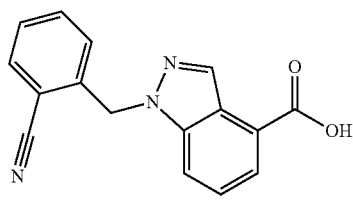 [SMILES: N#Cc1ccccc1Cn1ncc2c(C(=O)O)cccc21]
333 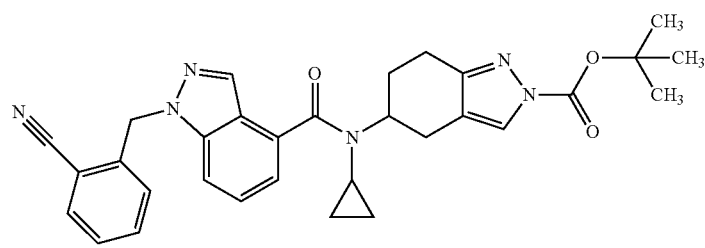 [SMILES: CC(C)(C)OC(=O)n1cc2c(n1)CCC(N(C(=O)c1cccc3c1cnn3Cc1ccccc1C#N)C1CC1)C2]

TABLE 64-continued
| 334 | 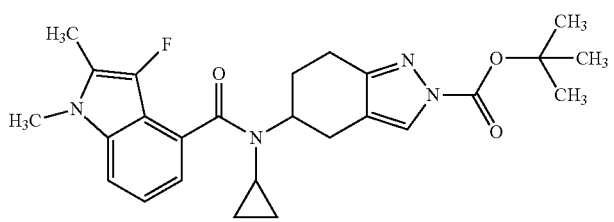 [SMILES: Cc1c(F)c2c(C(=O)N(C3CC3)C3CCc4nn(C(=O)OC(C)(C)C)cc4C3)cccc2n1C] | |
| --- | --- | --- |
| 335 | 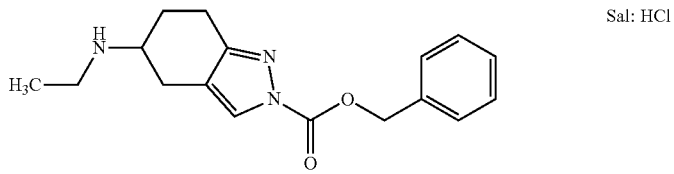 | Sal: HCl |
| 336 | 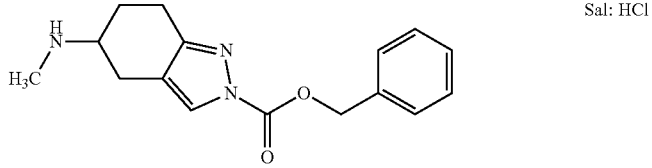 | Sal: HCl |
TABLE 65
| 337 | 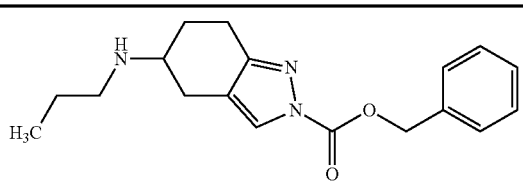 | Sal: HCl |
| --- | --- | --- |
| 338 | 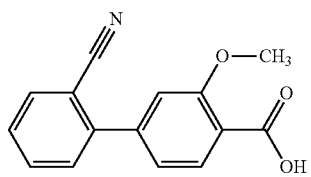 [SMILES: COc1cc(-c2ccccc2C#N)ccc1C(=O)O] | |
| 339 | 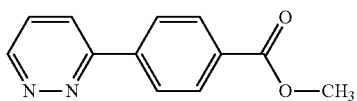 | |
| 340 | 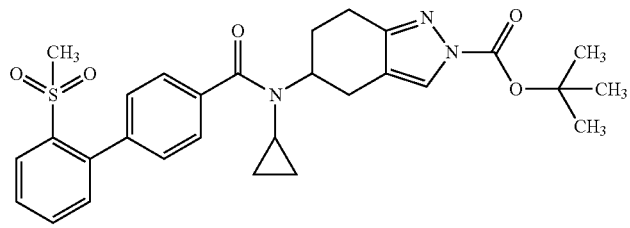 [SMILES: CC(C)(C)OC(=O)n1cc2c(n1)CCC(N(C(=O)c1ccc(-c3ccccc3S(C)(=O)=O)cc1)C1CC1)C2] | |
| 341 | 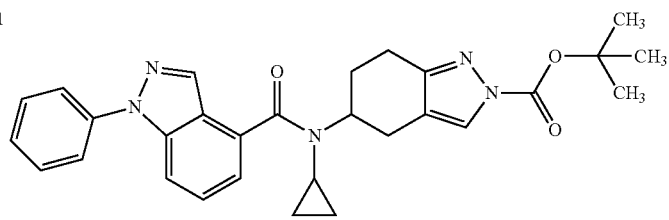 | |

TABLE 65-continued
| 342 | 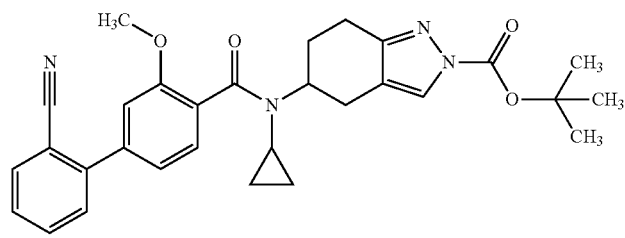 [SMILES: COc1cc(-c2ccccc2C#N)ccc1C(=O)N(C1CC1)C1CCc2nn(C(=O)OC(C)(C)C)cc2C1] |
TABLE 66
| 343 | 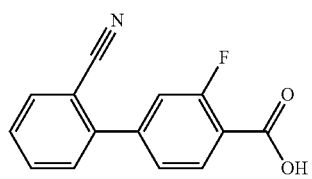 [SMILES: N#Cc1ccccc1-c1ccc(C(=O)O)c(F)c1] |
| 344 | 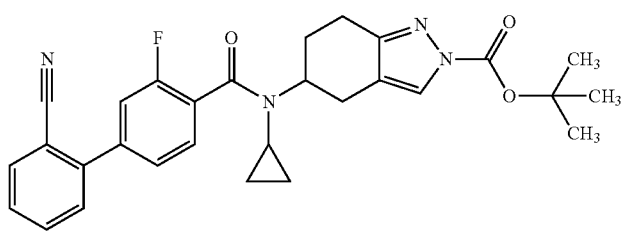 [SMILES: CC(C)(C)OC(=O)n1cc2c(n1)CCC(N(C(=O)c1ccc(-c3ccccc3C#N)cc1F)C1CC1)C2] |
| 345 | 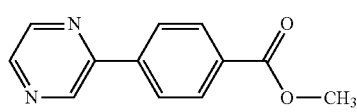 |
| 346 | 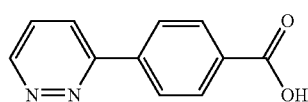 |
| 347 | 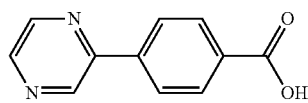 |
| 348 | 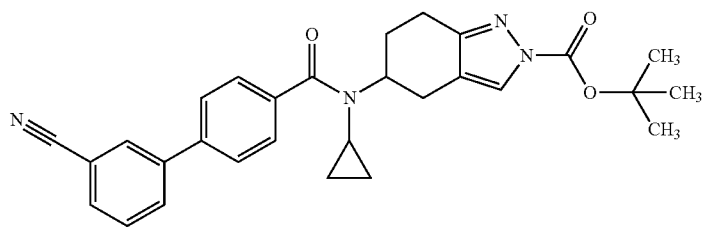 [SMILES: CC(C)(C)OC(=O)n1cc2c(n1)CCC(N(C(=O)c1ccc(-c3cccc(C#N)c3)cc1)C1CC1)C2] |
| 349 | 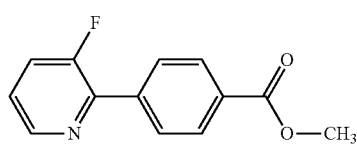 [SMILES: COC(=O)c1ccc(-c2ncccc2F)cc1] |

TABLE 67
350 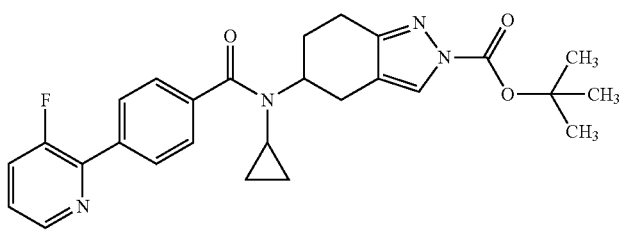 [SMILES: CC(C)(C)OC(=O)n1cc2c(n1)CCC(N(C(=O)c1ccc(-c3ncccc3F)cc1)C1CC1)C2]
351 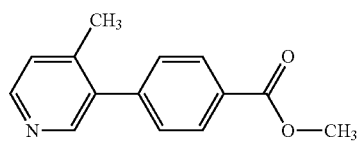
352 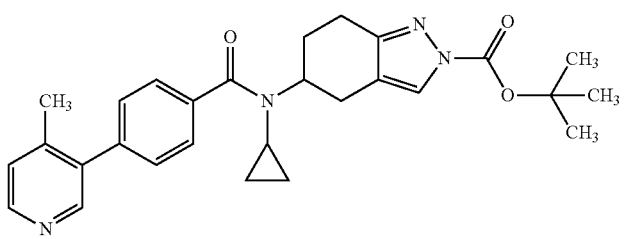 [SMILES: Cc1ccncc1-c1ccc(C(=O)N(C2CC2)C2CCc3nn(C(=O)OC(C)(C)C)cc3C2)cc1]
353 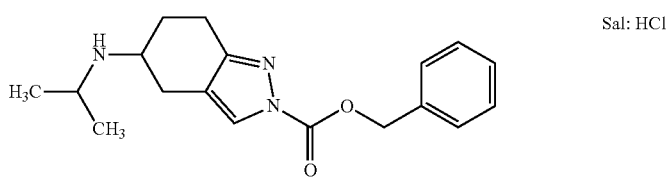  Sal: HCl
354 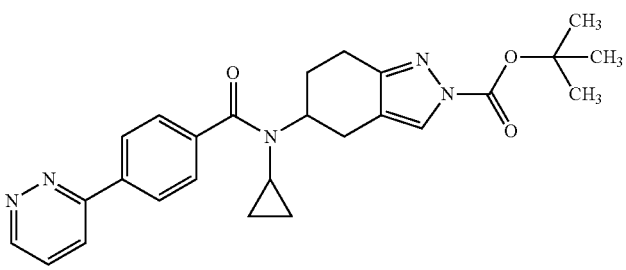 [SMILES: CC(C)(C)OC(=O)n1cc2c(n1)CCC(N(C(=O)c1ccc(-c3cccnn3)cc1)C1CC1)C2]
355 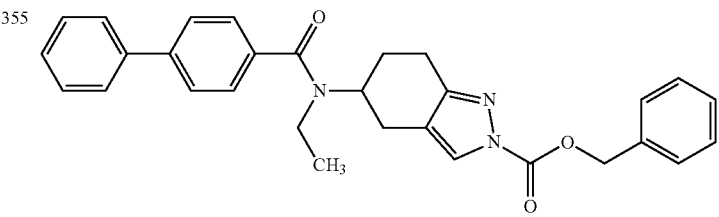
TABLE 68
356 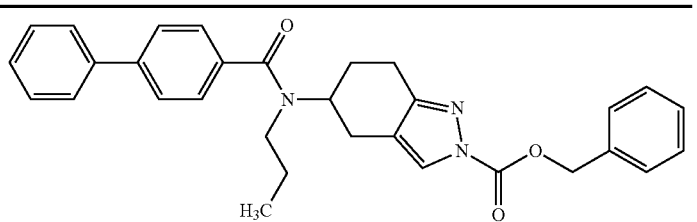

TABLE 68-continued
| | |
|---|---|
| 357 | 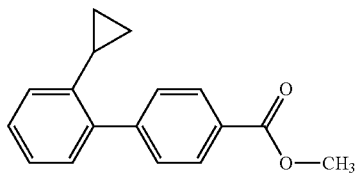 [SMILES: COC(=O)c1ccc(-c2ccccc2C2CC2)cc1] |
| 358 | 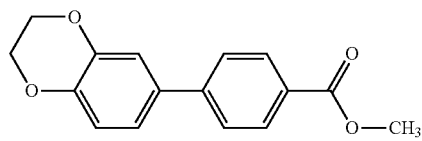 |
| 359 | 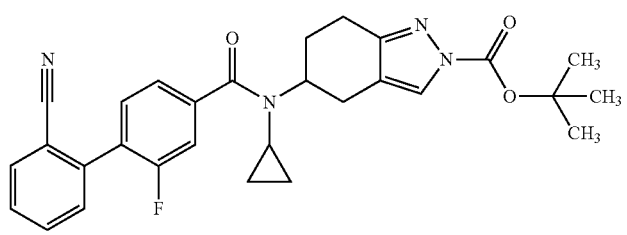 [SMILES: CC(C)(C)OC(=O)n1cc2c(n1)CCC(N(C(=O)c1ccc(-c3ccccc3C#N)c(F)c1)C1CC1)C2] |
| 360 | 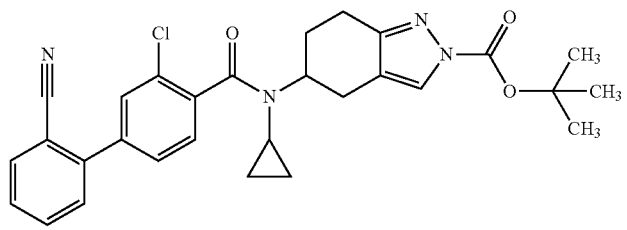 |
| 361 | 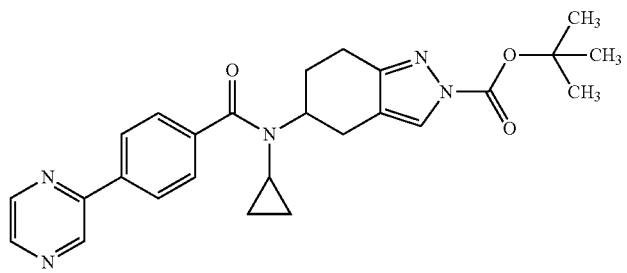 [SMILES: CC(C)(C)OC(=O)n1cc2c(n1)CCC(N(C(=O)c1ccc(-c3cnccn3)cc1)C1CC1)C2] |
TABLE 69
| | |
|---|---|
| 362 | 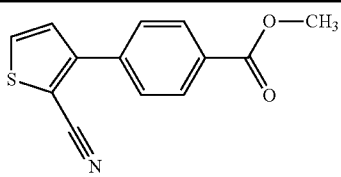 |
| 363 | 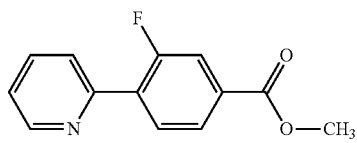 |

TABLE 69-continued
364 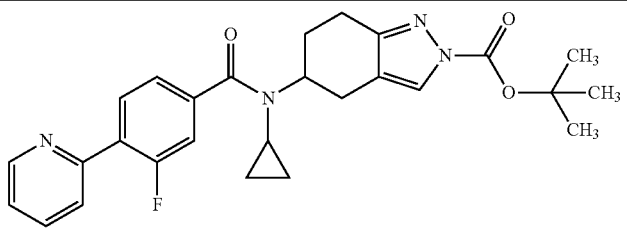
365 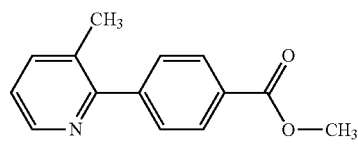
366 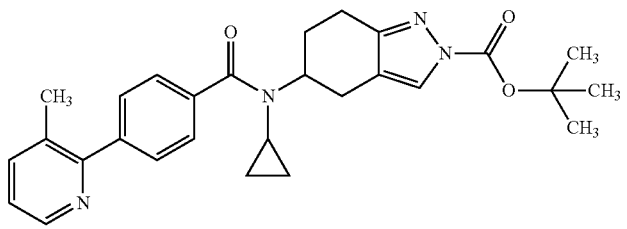 [SMILES: Cc1cccnc1-c1ccc(C(=O)N(C2CC2)C2CCc3nn(C(=O)OC(C)(C)C)cc3C2)cc1]
367 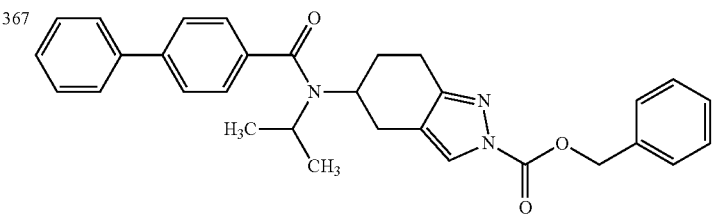
TABLE 70
368 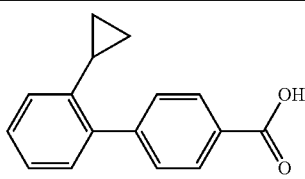
369 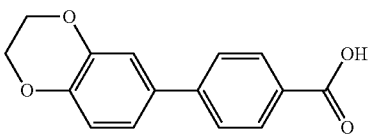 [SMILES: O=C(O)c1ccc(-c2ccc3c(c2)OCCO3)cc1]
370 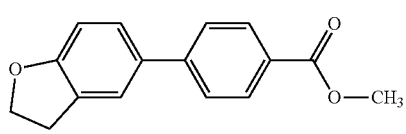 [SMILES: COC(=O)c1ccc(-c2ccc3c(c2)CCO3)cc1]
TABLE 70-continued
371 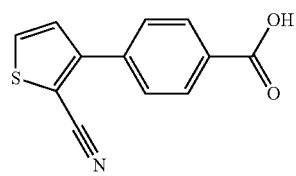 [SMILES: N#Cc1sccc1-c1ccc(C(=O)O)cc1]
372 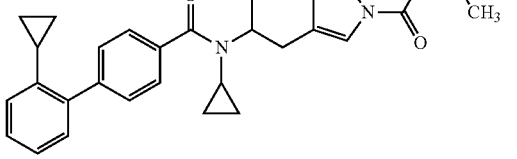
373 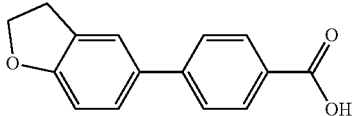 [SMILES: O=C(O)c1ccc(-c2ccc3c(c2)CCO3)cc1]

TABLE 71
| 374 | 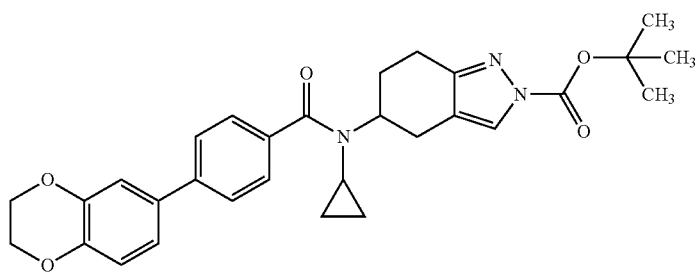 [SMILES: CC(C)(C)OC(=O)n1cc2c(n1)CCC(N(C(=O)c1ccc(-c3ccc4c(c3)OCCO4)cc1)C1CC1)C2] |
| 375 | 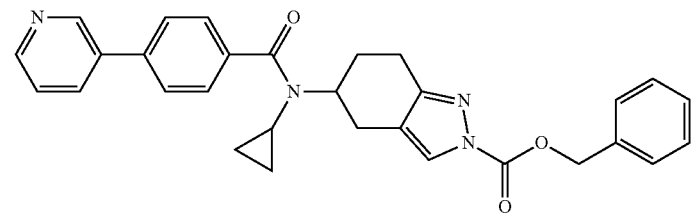 [SMILES: O=C(c1ccc(-c2cccnc2)cc1)N(C1CC1)C1CCc2nn(C(=O)OCc3ccccc3)cc2C1] |
| 376 | 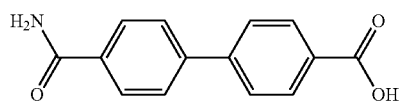 |
| 377 | 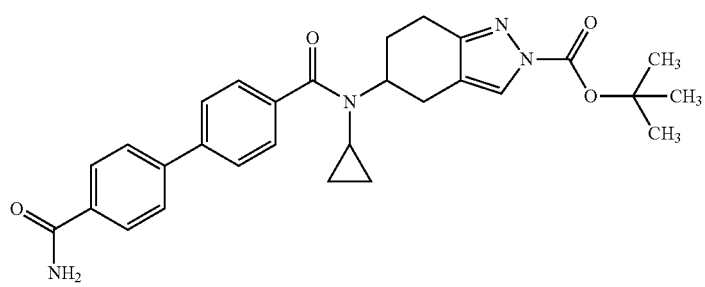 [SMILES: CC(C)(C)OC(=O)n1cc2c(n1)CCC(N(C(=O)c1ccc(-c3ccc(C(N)=O)cc3)cc1)C1CC1)C2] |
| 378 | 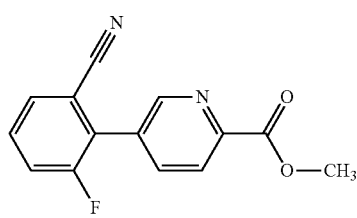 [SMILES: COC(=O)c1ccc(-c2c(F)cccc2C#N)cn1] |
| 379 | 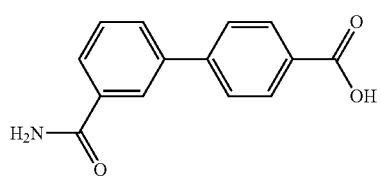 [SMILES: NC(=O)c1cccc(-c2ccc(C(=O)O)cc2)c1] |

TABLE 72
380 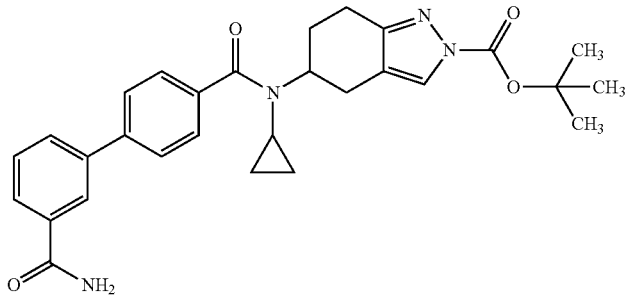 [SMILES: CC(C)(C)OC(=O)n1cc2c(n1)CCC(N(C(=O)c1ccc(-c3cccc(C(N)=O)c3)cc1)C1CC1)C2]
381 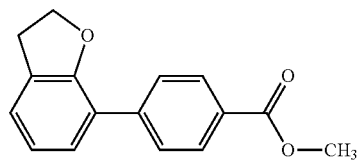 [SMILES: COC(=O)c1ccc(-c2cccc3c2OCC3)cc1]
382 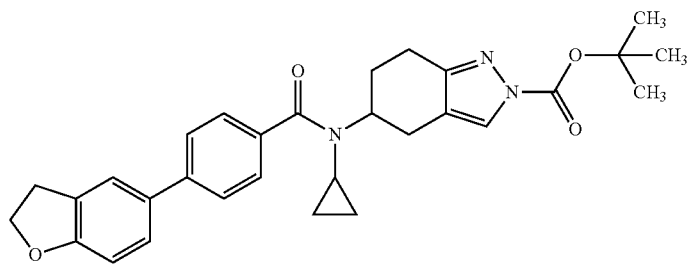 [SMILES: CC(C)(C)OC(=O)n1cc2c(n1)CCC(N(C(=O)c1ccc(-c3ccc4c(c3)CCO4)cc1)C1CC1)C2]
383 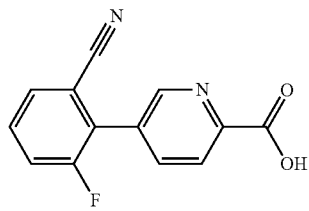 [SMILES: N#Cc1cccc(F)c1-c1ccc(C(=O)O)nc1]
384 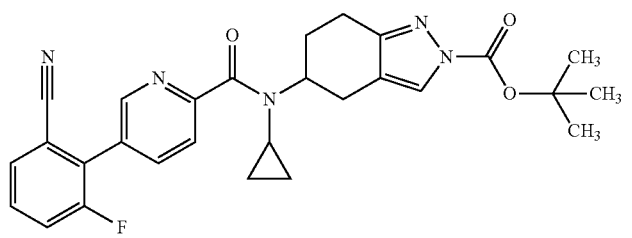 [SMILES: CC(C)(C)OC(=O)n1cc2c(n1)CCC(N(C(=O)c1ccc(-c3c(F)cccc3C#N)cn1)C1CC1)C2]

TABLE 73
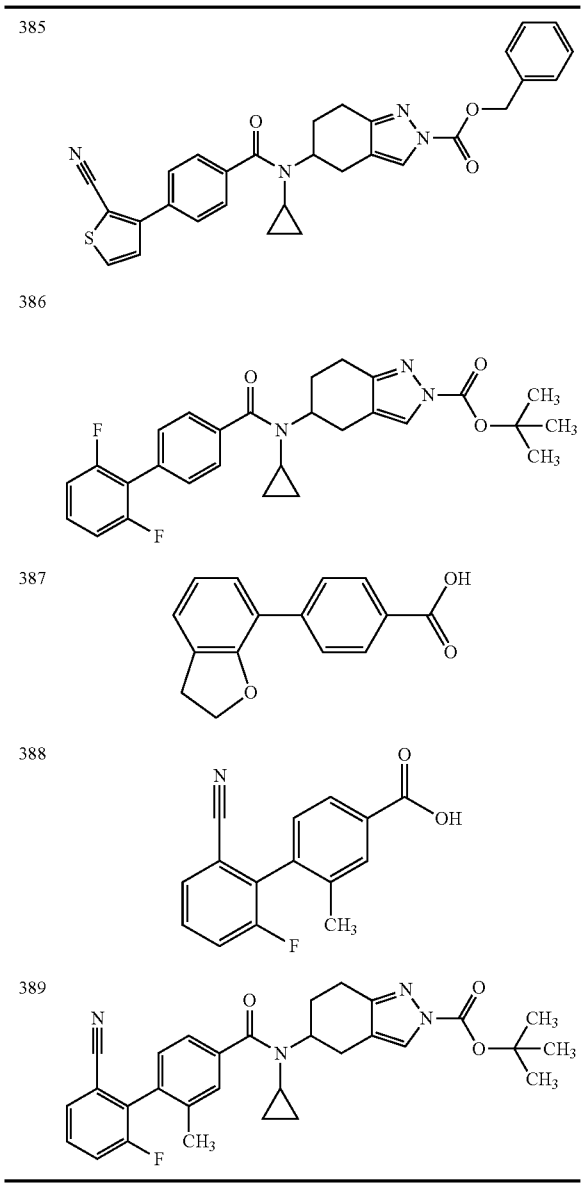
TABLE 74
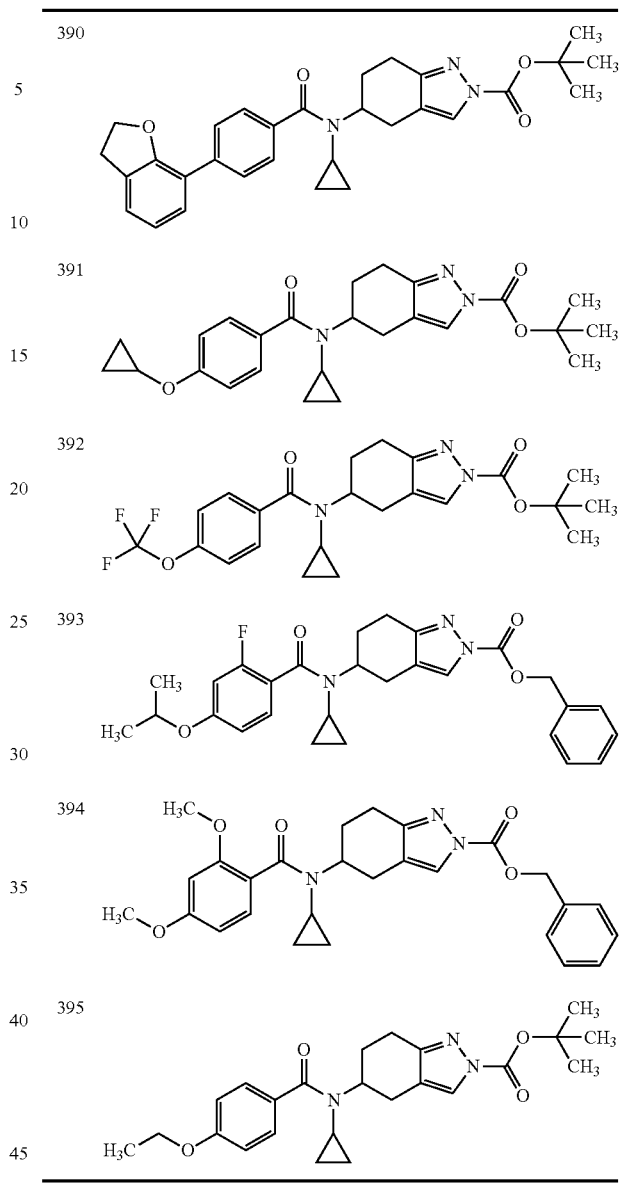
TABLE 75
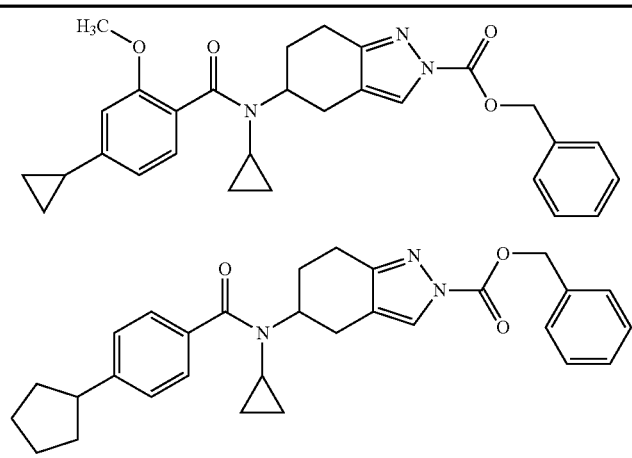

TABLE 75-continued
398 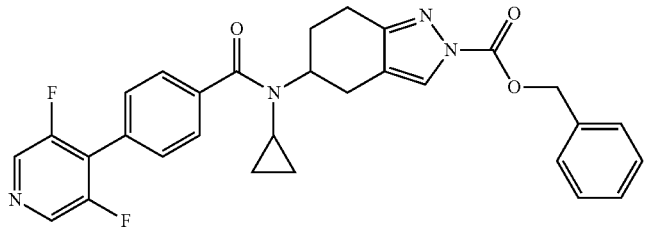 [SMILES: O=C(c1ccc(-c2c(F)cncc2F)cc1)N(C1CC1)C1CCc2nn(C(=O)OCc3ccccc3)cc2C1]
399 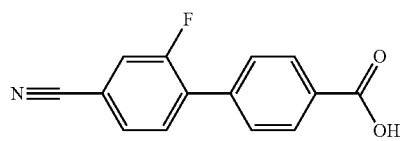
400 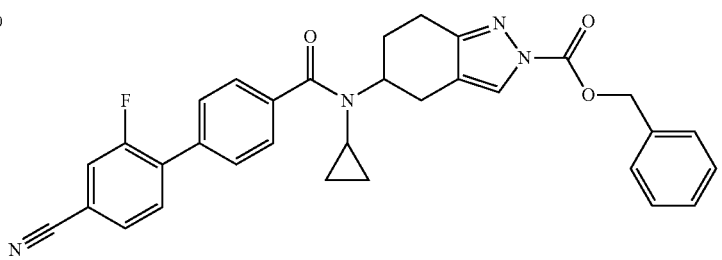
401 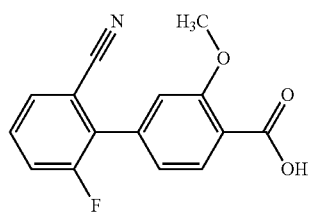 [SMILES: COc1cc(-c2c(F)cccc2C#N)ccc1C(=O)O]
TABLE 76
402 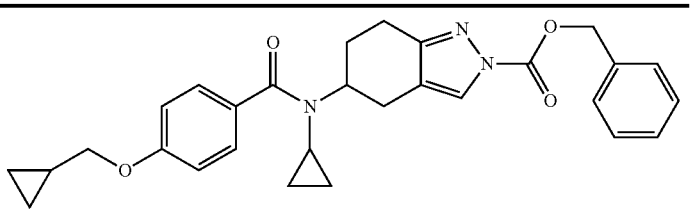
403 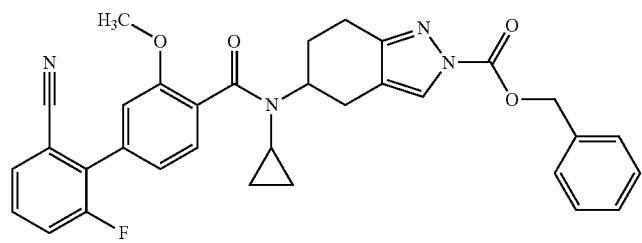 [SMILES: COc1cc(-c2c(F)cccc2C#N)ccc1C(=O)N(C1CC1)C1CCc2nn(C(=O)OCc3ccccc3)cc2C1]
404 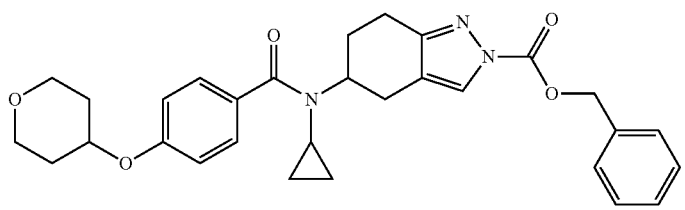 [SMILES: O=C(c1ccc(OC2CCOCC2)cc1)N(C1CC1)C1CCc2nn(C(=O)OCc3ccccc3)cc2C1]

TABLE 76-continued
405 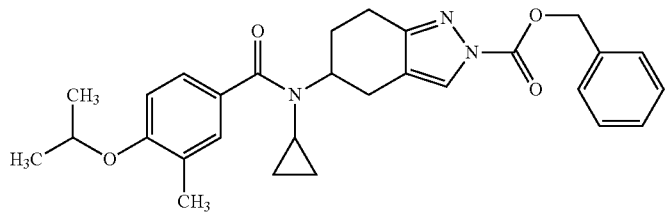 [SMILES: Cc1cc(C(=O)N(C2CC2)C2CCc3nn(C(=O)OCc4ccccc4)cc3C2)ccc1OC(C)C]
406 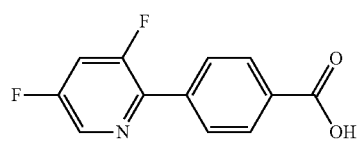 [SMILES: O=C(O)c1ccc(-c2ncc(F)cc2F)cc1]
407 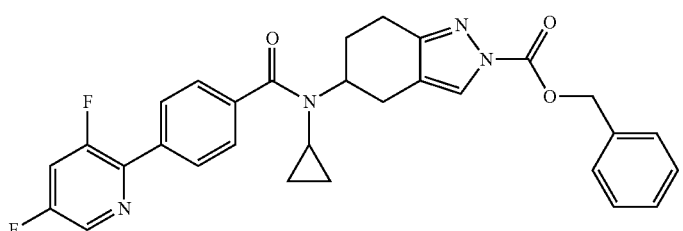
TABLE 77
408 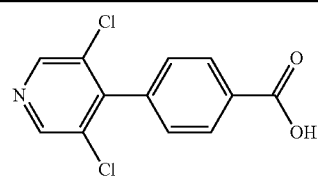
409 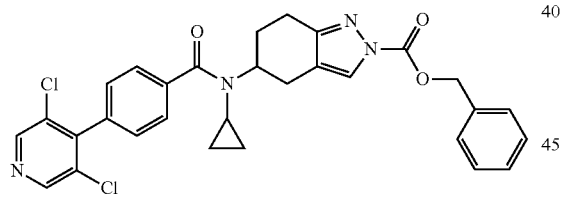
410 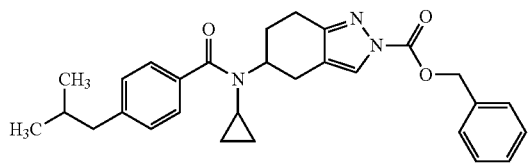 [SMILES: CC(C)Cc1ccc(C(=O)N(C2CC2)C2CCc3nn(C(=O)OCc4ccccc4)cc3C2)cc1]
TABLE 77-continued
411 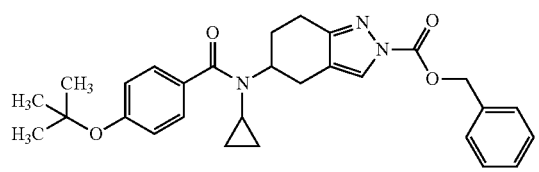 [SMILES: CC(C)(C)Oc1ccc(C(=O)N(C2CC2)C2CCc3nn(C(=O)OCc4ccccc4)cc3C2)cc1]
412 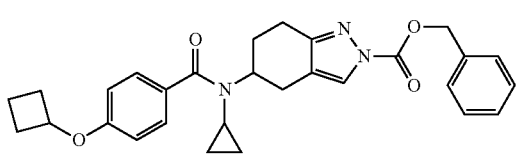 [SMILES: O=C(c1ccc(OC2CCC2)cc1)N(C1CC1)C1CCc2nn(C(=O)OCc3ccccc3)cc2C1]
413 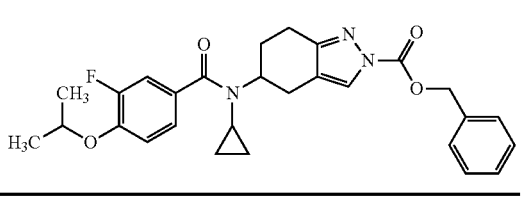
TABLE 78
414 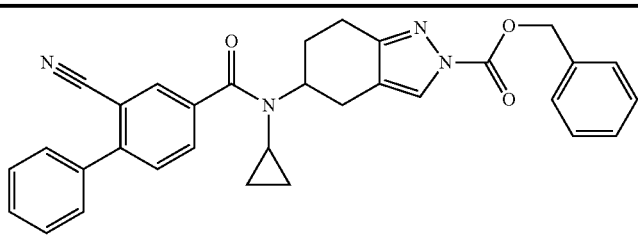

TABLE 78-continued
415 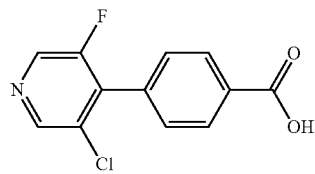
416 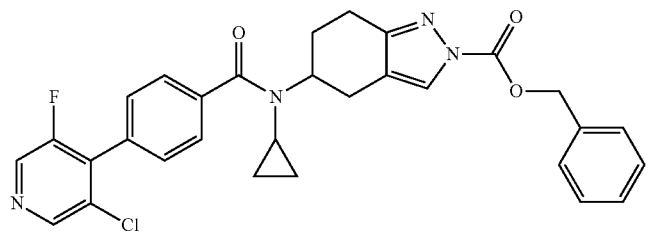 [SMILES: O=C(c1ccc(-c2c(F)cncc2Cl)cc1)N(C1CC1)C1CCc2nn(C(=O)OCc3ccccc3)cc2C1]
417 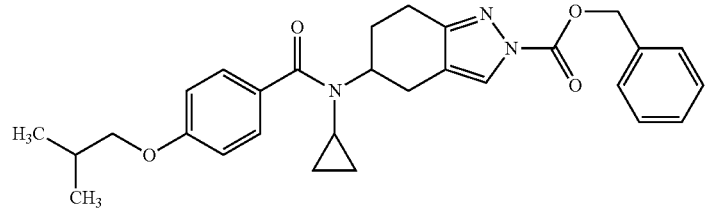 [SMILES: CC(C)COc1ccc(C(=O)N(C2CC2)C2CCc3nn(C(=O)OCc4ccccc4)cc3C2)cc1]
418 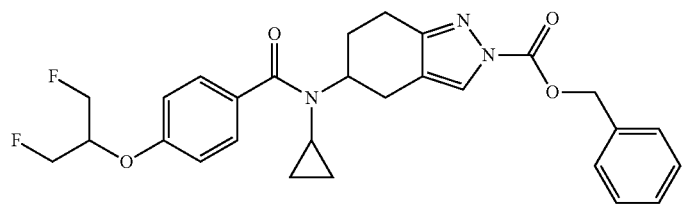 [SMILES: O=C(c1ccc(OC(CF)CF)cc1)N(C1CC1)C1CCc2nn(C(=O)OCc3ccccc3)cc2C1]
TABLE 79
419 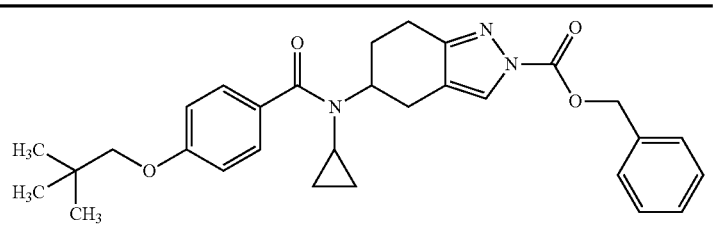
420 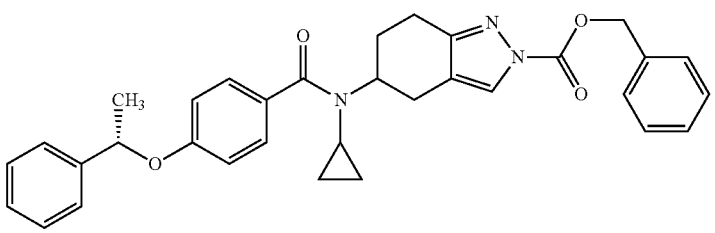 [SMILES: C[C@H](Oc1ccc(C(=O)N(C2CC2)C2CCc3nn(C(=O)OCc4ccccc4)cc3C2)cc1)c1ccccc1]
421 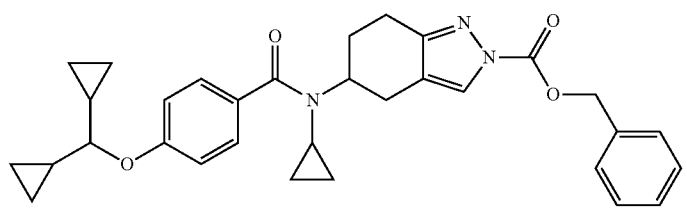 [SMILES: O=C(c1ccc(OC(C2CC2)C2CC2)cc1)N(C1CC1)C1CCc2nn(C(=O)OCc3ccccc3)cc2C1]

TABLE 79-continued
422
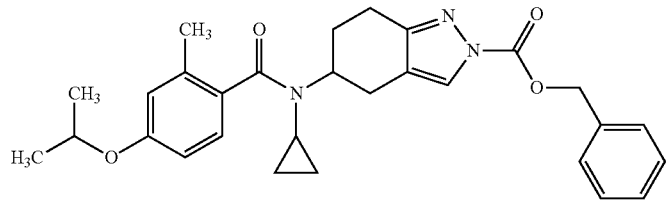 [SMILES: Cc1cc(OC(C)C)ccc1C(=O)N(C1CC1)C1CCc2nn(C(=O)OCc3ccccc3)cc2C1]
423
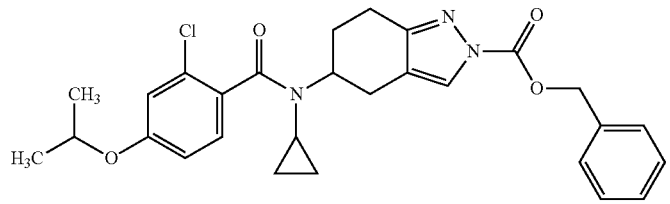 [SMILES: CC(C)Oc1ccc(C(=O)N(C2CC2)C2CCc3nn(C(=O)OCc4ccccc4)cc3C2)c(Cl)c1]
424
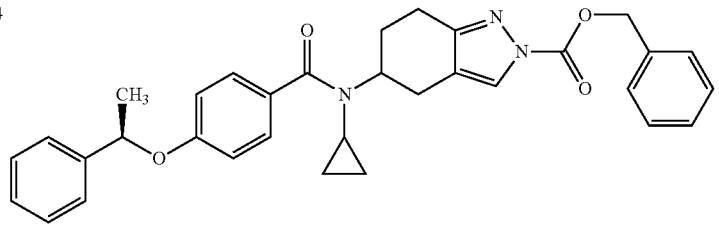
TABLE 80
425
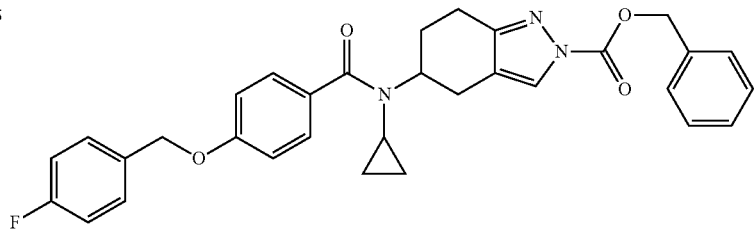
426
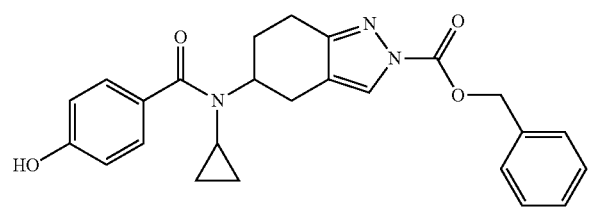 [SMILES: O=C(c1ccc(O)cc1)N(C1CC1)C1CCc2nn(C(=O)OCc3ccccc3)cc2C1]
427
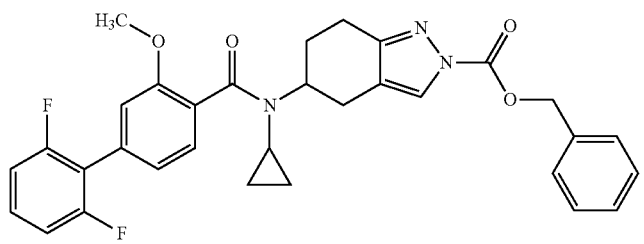 [SMILES: COc1cc(-c2c(F)cccc2F)ccc1C(=O)N(C1CC1)C1CCc2nn(C(=O)OCc3ccccc3)cc2C1]

TABLE 80-continued

| | | |
|---|---|---|
| 428 | 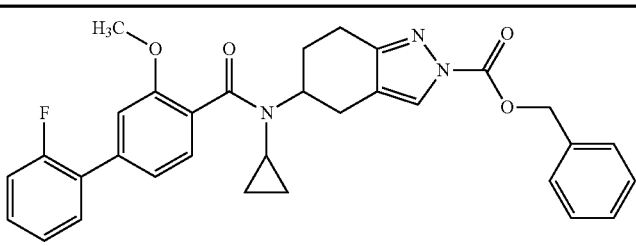 | |
| 429 | 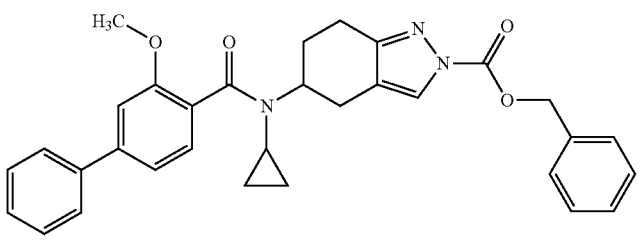 [SMILES: COc1cc(-c2ccccc2)ccc1C(=O)N(C1CC1)C1CCc2nn(C(=O)OCc3ccccc3)cc2C1] | |

TABLE 81

| | |
|---|---|
| 430 | 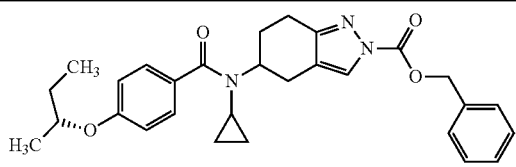 |
| 431 | 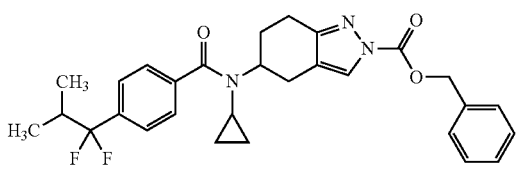 [SMILES: CC(C)C(F)(F)c1ccc(C(=O)N(C2CC2)C2CCc3nn(C(=O)OCc4ccccc4)cc3C2)cc1] |
| 432 | 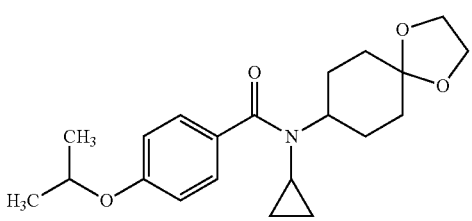 [SMILES: CC(C)Oc1ccc(C(=O)N(C2CC2)C2CCC3(CC2)OCCO3)cc1] |

TABLE 82

| PEx | PSyn | Data |
|---|---|---|
| 1 | 1 | ESI+: 504 |
| 2 | 2 | ESI+: 501.4 |
| 3 | 3 | ESI+: 479 |
| 4 | 4 | ESI+: 256.2 |
| 5 | 5 | ESI+: 270 |
| 6 | 6 | ESI+: 282, 284, 286 |
| 7 | 7 | ESI+: 266 |
| 8 | 8 | ESI+: 264 |
| 9 | 9 | ESI+: 280, 282 |
| 10 | 10 | ESI+: 260.1 |
| 11 | 11 | ESI+: 287.2 |
| 12 | 12 | ESI+: 219.2 |
| 13 | 13 | ESI+: 248.1 |
| 14 | 14 | NMR-CDCl3: 3.94 (s, 3H), 3.98 (s, 3H), 4.06 (s, 3H), 6.61 (d, J = 8 Hz, 1H), 7.04 (m, 2H), 7.84 (d, J = 8 Hz, 1H). |
| 15 | 15 | ESI+: 468 |
| 16 | 16 | ESI+: 220 |

TABLE 82-continued

| PEx | PSyn | Data |
|---|---|---|
| 17 | 17 | ESI+: 294 |
| 18 | 18 | ESI+: 312 |
| 19 | 19 | ESI+: 256 |
| 20 | 20 | ESI−: 240.1 |
| 21 | 21 | ESI+: 302.1 |
| 22 | 22 | ESI+: 197 |
| 23 | 23 | ESI+: 441, 443 |
| 24 | 24 | ESI+: 312 |
| 25 | 25 | ESI+: 250 |
| 26 | 26 | ESI+: 312 |
| 27 | 27 | ESI+: 310 (M + Na)+ |
| 28 | 28 | ESI+: 315 |
| 29 | 29 | ESI+: 354 (M + Na)+ |
| 30 | 30 | ESI+: 278 |
| 31 | 31 | ESI+: 412 |
| 32 | 32 | APCI/ESI+: 529 |
| 33 | 33 | ESI+: 208 |
| 34 | 34 | ESI+: 315 |
| 35 | 35 | ESI+: 195 |
| 36 | 36 | ESI+: 358 |
| 37 | 37 | ESI+: 488 |
| 38 | 38 | ESI+: 454 |
| 39 | 39 | ESI+: 253 |
| 40 | 40 | ESI+: 261.1 |

TABLE 83

| PEx | PSyn | Data |
|---|---|---|
| 41 | 41 | CI+: 466, 468 |
| 42 | 42 | EI: 388 |
| 43 | 43 | APCI/ESI+: 402 |
| 44 | 44 | ESI+: 342 |
| 45 | 45 | NMR-CDCl3: 0.37-0.70 (4H, m), 1.15-1.35 (6H, m), 1.60-3.10 (16H, m), 3.95-4.70 (2H, m), 7.10-7.50 (4H, m) |
| 46 | 46 | ESI+: 259 |
| 47-1 | 47 | ESI+: 278 |
| 47-2 | 47 | ESI+: 278 |
| 48 | 48 | ESI+: 354 |
| 49 | 49 | ESI+: 360 |
| 50 | 50 | ESI+: 340 |
| 51 | 51 | ESI+: 414 |
| 52 | 52 | ESI+: 342 |
| 53 | 53 | NMR-CDCl3: 1.14 (18H, d, J = 4.0 Hz), 1.60-1.73 (3H, m), 3.93 (3H, s), 6,65 (1H, d, J = 4.0 Hz), 6.85 (1H, d, J = 8.0 Hz), 7.29 (1H, d, J = 4.0 Hz), 7.38 (1H, d, J = 8.0 Hz) |
| 54 | 54 | ESI+: 362 |
| 55 | 55 | ESI+: 328 |
| 56 | 56 | ESI+: 204 |
| 57 | 57 | ESI−: 256 |

TABLE 83-continued

| | | |
|---|---|---|
| 58 | 2 | ESI+: 344 |
| 59 | 27 | ESI+: 300 |
| 60 | 31 | ESI+: 266 |
| 61 | 2 | ESI+: 412 |
| 62 | 2 | ESI+: 426 |
| 63 | 17 | ESI+: 284 |
| 64 | 20 | ESI−: 264 |
| 65 | 17 | ESI+: 294 |
| 66 | 46 | ESI+: 245 |
| 67 | 20 | ESI+: 266 |
| 68 | 20 | ESI+: 284, 286 |
| 69 | 20 | ESI+: 231 |
| 70 | 20 | ESI+: 217 |
| 71 | 2 | ESI+: 490 |
| 72 | 2 | ESI+: 476 |
| 73 | 17 | ESI+: 258 |
| 74 | 35 | ESI+: 209 |
| 75 | 20 | ESI+: 230 |
| 76 | 17 | ESI+: 272 |
| 77 | 17 | ESI+: 250 |
| 78 | 17 | ESI+: 264 |

TABLE 84

| | | |
|---|---|---|
| 79 | 20 | ESI+: 244 |
| 80 | 17 | ESI+: 326 |
| 81 | 17 | ESI+: 326 |
| 82 | 17 | ESI+: 326 |
| 83 | 17 | ESI+: 288 |
| 84 | 17 | ESI+: 288 |
| 85 | 17 | ESI+: 288 |
| 86 | 20 | ESI+: 222 |
| 87 | 20 | ESI+: 236 |
| 88 | 20 | ESI−: 296 |
| 89 | 20 | ESI−: 296 |
| 90 | 34 | ESI−: 329 |
| 91 | 17 | ESI+: 292, 294 |
| 92 | 17 | ESI+: 292 |
| 93 | 17 | ESI+: 292, 294 |
| 94 | 2 | ESI+: 495 |
| 95 | 2 | ESI+: 481 |
| 96 | 20 | ESI−: 296 |
| 97 | 20 | ESI−: 258 |
| 98 | 20 | ESI+: 264, 266 |
| 99 | 20 | ESI+: 264, 266 |
| 100 | 2 | ESI+: 557 |
| 101 | 2 | ESI+: 579 (M + Na)+ |
| 102 | 20 | ESI−: 258 |
| 103 | 20 | ESI−: 258 |
| 104 | 20 | ESI+: 264, 266 |
| 105 | 27 | ESI+: 271 |
| 106 | 27 | ESI+: 285 |
| 107 | 26 | ESI+: 312 |
| 108 | 26 | ESI+: 326 |
| 109 | 2 | ESI+: 579 (M + Na)+ |
| 110 | 2 | ESI+: 519 |
| 111 | 2 | ESI+: 519 |
| 112 | 2 | ESI+: 519 |
| 113 | 2 | ESI+: 523 |
| 114 | 2 | ESI+: 550 |
| 115 | 2 | ESI+: 564 |
| 116 | 17 | ESI+: 252 |
| 117 | 17 | ESI+: 266 |
| 118 | 17 | ESI+: 259 |
| 119 | 17 | ESI+: 259 |
| 120 | 17 | ESI+: 264 |

TABLE 85

| | | |
|---|---|---|
| 121 | 17 | ESI+: 278 |
| 122 | 20 | ESI−: 222 |
| 123 | 20 | ESI+: 238 |
| 124 | 20 | ESI+: 231 |
| 125 | 20 | ESI+: 231 |
| 126 | 20 | ESI+: 250 |

TABLE 85-continued

| | | |
|---|---|---|
| 127 | 20 | ESI+: 236 |
| 128 | 2 | ESI+: 383 (M − Boc + H)+ |
| 129 | 2 | ESI+: 397 (M − Boc + H)+ |
| 130 | 2 | ESI+: 390 (M − Boc + H)+ |
| 131 | 2 | ESI+: 490 |
| 132 | 2 | ESI+: 409 (M − Boc + H)+ |
| 133 | 2 | ESI+: 395 (M − Boc + H)+ |
| 134 | 2 | ESI+: 525 |
| 135 | 2 | ESI+: 512 |
| 136 | 2 | ESI+: 512 |
| 137 | 2 | ESI+: 516 |
| 138 | 2 | ESI+: 516 |
| 139 | 12 | ESI+: 267 |
| 140 | 20 | ESI+: 253 |
| 141 | 2 | ESI+: 512 |
| 142 | 2 | ESI+: 512 |
| 143 | 10 | ESI+: 260 |
| 144 | 2 | ESI+: 512 |
| 145 | 20 | ESI+: 246 |
| 146 | 2 | ESI+: 462 |
| 147 | 2 | ESI+: 488 |
| 148 | 2 | ESI+: 472 |
| 149 | 2 | ESI+: 490 |
| 150 | 2 | ESI+: 512 |
| 151 | 11 | ESI+: 274 |
| 152 | 2 | ESI+: 492 |
| 153 | 22 | ESI−: 195 |
| 154 | 2 | ESI+: 456 |
| 155 | 2 | ESI+: 534, 536 |
| 156 | 20 | ESI+: 260 |
| 157 | 2 | ESI+: 505 |
| 158 | 2 | ESI+: 456 |
| 159 | 2 | ESI+: 452 |
| 160 | 2 | ESI+: 449 |
| 161 | 2 | ESI+: 456 |
| 162 | 3 | ESI+: 483 |

TABLE 86

| | | |
|---|---|---|
| 163 | 22 | ESI+: 433 |
| 164 | 20 | ESI+: 190 |
| 165 | 1 | ESI+: 449 |
| 166 | 1 | ESI+: 692 |
| 167 | 1 | ESI+: 519 |
| 168 | 14 | ESI+: 296 |
| 169 | 10 | ESI+: 247 |
| 170 | 10 | ESI+: 289 |
| 171 | 1 | ESI+: 435 |
| 172 | 1 | ESI+: 435 |
| 173 | 1 | ESI+: 499 |
| 174 | 20 | ESI+: 282 |
| 175 | 20 | ESI+: 233 |
| 176 | 20 | ESI+: 275 |
| 177 | 1 | ESI+: 541 |
| 178 | 1 | NMR-CDCl3: 0.42-0.58 (4H, m), 1.64 (s, 9H), 2.19-2.27 (m, 1H), 2.33-2.50 (m, 5H), 2.61-2.67 (m, 1H), 2.72-3.30 (m, 6H), 3.67 (t, 4H), 4.25 (t, 2H), 4.40-4.53 (m, 1H), 6.49-6.51 (m, 1H), 7.13-7.79 (m, 5H) |
| 179 | 1 | ESI+: 492 |
| 180 | 20 | ESI+: 190 |
| 181 | 1 | ESI+: 450 |
| 182 | 1 | ESI+: 449 |
| 183 | 10 | ESI+: 248 |
| 184 | 10 | ESI+: 262 |
| 185 | 20 | ESI+: 234 |
| 186 | 20 | ESI+: 248 |
| 187 | 1 | ESI+: 435 |
| 188 | 1 | ESI+: 435 |
| 189 | 1 | ESI+: 507 |
| 190 | 1 | ESI+: 493 |
| 191 | 2 | ESI+: 436 |
| 192 | 10 | ESI+: 246.1 |
| 193 | 10 | ESI+: 248.2 |
| 194 | 10 | ESI+: 222.1 |
| 195 | 10 | ESI+: 236.1 |
| 196 | 23 | ESI+: 455, 457 |

TABLE 86-continued

| | | |
|---|---|---|
| 197 | 20, 1 | ESI+: 493.0 |
| 198 | 1 | ESI+: 436 |
| 199 | 20, 1 | ESI+: 505.0 |
| 200 | 20, 1 | ESI+: 491.4 |

TABLE 87

| | | |
|---|---|---|
| 201 | 20, 1 | ESI+: 467.3 |
| 202 | 20, 1 | ESI+: 481.0 |
| 203 | 20, 1 | ESI+: 493.3 |
| 204 | 1 | NMR-CDCl3: 0.40-0.56 (m, 4H), 1.64 (s, 9H), 2.20-3.31 (m, 7H), 4.43-4.54 (m, 1H), 6.55 (m, 1H), 7.14-8.39 (m, 5H), 8.33-8.50 (m, 1H) |
| 205 | 12 | NMR-DMSOd6: 2.17 (s, 3H), 3.90 (s, 3H), 5.26 (s, 2H), 7.00 (m, 1H), 7.22 (t, J = 8 Hz, 1H), 7.43 (m, 1H), 7.66 (d, J = 8 Hz, 1H), 7.76 (d, J = 8 Hz, 1H). |
| 206 | 10 | ESI+: 246.1 |
| 207 | 20, 1 | ESI+: 532.4 |
| 208 | 20, 1 | ESI+: 547.3 |
| 209 | 1 | ESI+: 506.3 |
| 210 | 30 | ESI+: 220 |
| 211 | 14 | NMR-CDCl3: 3.99 (s, 3H), 5.15 (s, 2H), 6.79 (m, 1H), 7.19-7.36 (m, 4H), 7.55 (d, J = 8 Hz, 1H), 7.91 (d, J = 8 Hz, 1H), 8.80 (m, 1H). |
| 212 | 20, 1 | ESI+: 518.4 |
| 213 | 12 | ESI+: 192 |
| 214 | 20 | NMR-DMSOd6: 4.49 (3H, s), 7.49 (1H, t, J = 8.0 Hz), 8.09 (1H, d, J = 8.0 Hz), 8.30 (1H, d, J = 8.0 Hz), 13.6 (1H, br s) |
| 215 | 1 | ESI+: 437 |
| 216 | 12 | ESI+: 268 |
| 217 | 30 | ESI+: 194 |
| 218 | 30 | ESI+: 206 |
| 219 | 20 | ESI−: 252 |
| 220 | 1 | ESI+: 513 |
| 221 | 10 | NMR-CDCl3: 3.99 (s, 3H), 4.45-4.55 (m, 2H), 5.84-6.15 (m, 1H), 7.20-7.33 (m, 3H), 7.56 (d, J = 8 Hz, 1H), 7.92-7.94 (m, 1H). |
| 222 | 30 | ESI+: 280 |
| 223 | 30 | ESI+: 190 |
| 224 | 1 | ESI+: 437 |
| 225 | 20, 1 | ESI+: 485.2 |
| 226 | 1 | ESI+: 436.2 |
| 227 | 14 | ESI+: 235.2 |
| 228 | 14 | ESI+: 223.2 |
| 229 | 12 | ESI+: 275 |
| 230 | 20, 1 | ESI+: 468.3 |
| 231 | 20, 1 | ESI+: 480.3 |
| 232 | 14 | ESI+: 205.2 |
| 233 | 20, 1 | ESI+: 450.4 |

TABLE 88

| | | |
|---|---|---|
| 234 | 14 | ESI+: 219.2 |
| 235 | 20, 1 | ESI+: 464.4 |
| 236 | 20, 1 | ESI+: 464.4 |
| 237 | 14 | ESI+: 237.2 |
| 238 | 20 | ESI+: 261 |
| 239 | 1 | ESI+: 520 |
| 240 | 12 | ESI+: 245 |
| 241 | 14 | ESI+: 249.2 |
| 242 | 20, 1 | ESI+: 494.4 |
| 243 | 14 | ESI+: 263.2 |
| 244 | 20, 1 | ESI+: 466.3 |
| 245 | 12 | ESI+: 247.1 |
| 246 | 12 | ESI+: 335 |
| 247 | 39 | ESI+: 253 |
| 248 | 20 | ESI+: 321 |
| 249 | 1 | ESI+: 436 |
| 250 | 20 | ESI+: 231 |
| 251 | 12 | ESI+: 249.1 |
| 252 | 20, 1 | ESI+: 494.3 |
| 253 | 1 | ESI+: 580 |
| 254 | 1 | ESI+: 490 |
| 255 | 1 | ESI+: 424.2 |
| 256 | 1 | ESI+: 458.2 |
| 257 | 21 | ESI+: 494.3 |
| 258 | 4 | ESI+: 238.1 |
| 259 | 20 | ESI+: 224 |
| 260 | 1 | ESI+: 483.3 |
| 261 | 1 | ESI+: 486.4 |
| 262 | 20 | ESI+: 239 |
| 263 | 12 | ESI+: 283.1 |
| 264 | 4 | ESI+: 252.2 |
| 265 | 20, 1 | ESI+: 497.4 |
| 266 | 4 | ESI+: 291.2 |
| 267 | 20, 1 | ESI+: 536.4 |
| 268 | 4 | ESI+: 228 |
| 269 | 1 | ESI+: 498 |
| 270 | 24 | ESI+: 181 |
| 271 | 20, 1 | ESI+: 528.4 |
| 272 | 20 | ESI+: 214 |
| 273 | 20 | ESI+: 206 |
| 274 | 12 | ESI+: 249.2 |
| 275 | 12 | ESI+: 247.2 |

TABLE 89

| | | |
|---|---|---|
| 276 | 12 | ESI+: 321.2 |
| 277 | 12 | ESI+: 287.2 |
| 278 | 1 | ESI+: 473 |
| 279 | 1 | ESI+: 465 |
| 280 | 20, 1 | ESI+: 532.3 |
| 281 | 20, 1 | ESI+: 494.2 |
| 282 | 20, 1 | ESI+: 566.2 |
| 283 | 57 | ESI+: 277.2 |
| 284 | 20, 1 | ESI+: 522.3 |
| 285 | 1 | ESI+: 518.4 |
| 286 | 4 | ESI+: 252 |
| 287 | 20, 1 | ESI+: 497 |
| 288 | 57 | ESI−: 236 |
| 289 | 1 | ESI+: 497 |
| 290 | 1 | ESI+: 517, 519 |
| 291 | 12 | ESI+: 281 |
| 292 | 4 | ESI+: 239 |
| 293 | 20, 1 | ESI+: 484.2 |
| 294 | 4 | ESI+: 271.2 |
| 295 | 20, 1 | ESI+: 516.4 |
| 296 | 12 | ESI+: 247 |
| 297 | 12 | ESI+: 233 |
| 298 | 12 | ESI+: 247 |
| 299 | 20 | ESI−: 265 |
| 300 | 14 | ESI+: 268 |
| 301 | 1 | ESI+: 459 |
| 302 | 1 | ESI+: 526 |
| 303 | 4 | ESI+: 257 |
| 304 | 1 | ESI+: 516 |
| 305 | 20 | ESI+: 233 |
| 306 | 20 | ESI+: 219 |
| 307 | 1 | ESI+: 475.3 |
| 308 | 20, 1 | ESI+: 506.3 |
| 309 | 14 | ESI+: 292 |
| 310 | 20 | ESI+: 254 |
| 311 | 20 | ESI+: 233 |
| 312 | 12 | ESI+: 261 |
| 313 | 1 | ESI+: 492 |
| 314 | 1 | ESI+: 478 |
| 315 | 1 | ESI+: 492 |
| 316 | 27 | ESI+: 271 |
| 317 | 4 | ESI+: 279.1 |

TABLE 90

| | | |
|---|---|---|
| 318 | 20, 1 | ESI+: 524.3 |
| 319 | 4 | ESI+: 256.1 |
| 320 | 20, 1 | ESI+: 501.4 |
| 321 | 20, 1 | ESI+: 511 |
| 322 | 1 | ESI+: 513 |
| 323 | 4 | ESI+: 239.1 |

TABLE 90-continued

| | | |
|---|---|---|
| 324 | 14 | ESI+: 222 |
| 325 | 20 | ESI+: 247 |
| 326 | 20 | ESI+: 278 |
| 327 | 12 | ESI+: 292 |
| 328 | 1 | ESI+: 537 |
| 329 | 20, 1 | ESI+: 484.3 |
| 330 | 1 | ESI+: 506 |
| 331 | 20 | ESI+: 208 |
| 332 | 20 | ESI+: 278 |
| 333 | 1 | ESI+: 537 |
| 334 | 1 | ESI+: 467 |
| 335 | 26 | ESI+: 300 |
| 336 | 26 | ESI+: 286 |
| 337 | 26 | ESI+: 314 |
| 338 | 4 | ESI+: 254.1 |
| 339 | 4 | ESI+: 215 |
| 340 | 1 | ESI+: 536 |
| 341 | 20, 1 | ESI+: 498 |
| 342 | 1 | ESI+: 513.3 |
| 343 | 4 | ESI+: 242.1 |
| 344 | 1 | ESI+: 501.2 |
| 345 | 4 | ESI+: 215 |
| 346 | 20 | ESI+: 201 |
| 347 | 20 | ESI−: 201 |
| 348 | 1 | ESI+: 483.2 |
| 349 | 4 | ESI+: 232.1 |
| 350 | 20, 1 | ESI+: 477.3 |
| 351 | 4 | ESI+: 228.2 |
| 352 | 20, 1 | ESI+: 473.3 |
| 353 | 26 | ESI+: 314 |
| 354 | 1 | ESI+: 460 |
| 355 | 1 | ESI+: 480 |
| 356 | 1 | ESI+: 494 |
| 357 | 57 | EI: 252 |
| 358 | 4 | EI: 270 |

TABLE 91

| | | |
|---|---|---|
| 359 | 4, 20, 1 | ESI+: 501.4 |
| 360 | 4, 20, 1 | ESI+: 417.3, 417.9 |
| 361 | 1 | ESI+: 460 |
| 362 | 4 | EI: 243 |
| 363 | 4 | ESI+: 232.1 |
| 364 | 20, 1 | ESI+: 477.2 |
| 365 | 4 | ESI+: 228.2 |
| 366 | 20, 1 | ESI+: 473.3 |
| 367 | 2 | ESI+: 494 |
| 368 | 20 | ESI−: 237 |
| 369 | 20 | ESI−: 255 |
| 370 | 57 | ESI+: 255 |
| 371 | 20 | ESI−: 228 |
| 372 | 1 | ESI+: 498 |
| 373 | 20 | ESI−: 239 |
| 374 | 1 | ESI+: 516 |
| 375 | 1 | ESI+: 493 |
| 376 | 4 | ESI−: 240 |
| 377 | 1 | ESI+: 501 |
| 378 | 5 | ESI+: 257 |
| 379 | 4 | ESI+: 242 |
| 380 | 1 | APCI/ESI+: 401 [M-Boc] |
| 381 | 4 | ESI+: 255 |
| 382 | 1 | APCI/ESI+: 500 |
| 383 | 20 | ESI+: 243 |
| 384 | 1 | ESI+: 502 |
| 385 | 1 | ESI+: 523 |
| 386 | 1 | ESI+: 494.0 |
| 387 | 20 | ESI+: 241 |
| 388 | 20 | ESI+: 256 |
| 389 | 1 | ESI+: 515 |
| 390 | 1 | APCI/ESI+: 400 [M-Boc] |
| 391 | 1 | APCI/ESI+: 438.1 |
| 392 | 1 | APCI/ESI+: 466.0 |
| 393 | 1 | APCI/ESI+: 492.1 |
| 394 | 1 | APCI/ESI+: 476.0 |
| 395 | 1 | APCI/ESI+: 326 [M-Boc] |
| 396 | 1 | APCI/ESI+: 486.1 |

TABLE 91-continued

| | | |
|---|---|---|
| 397 | 1 | APCI/ESI+: 484 |
| 398 | 20, 1 | ESI+: 529 |

TABLE 92

| | | |
|---|---|---|
| 399 | 4 | ESI−: 240 |
| 400 | 1 | ESI+: 535 |
| 401 | 4 | ESI+: 272.0 |
| 402 | 1 | ESI+: 486 |
| 403 | 1 | ESI+: 565.3 |
| 404 | 1 | ESI+: 516.1 |
| 405 | 1 | ESI+: 488 |
| 406 | 20 | ESI+: 236 |
| 407 | 1 | ESI+: 529 |
| 408 | 20 | ESI+: 268, 270 |
| 409 | 1 | ESI+: 561, 563 |
| 410 | 1 | ESI+: 472 |
| 411 | 1 | ESI+: 488 |
| 412 | 1 | ESI+: 486 |
| 413 | 1 | ESI+: 492.1 |
| 414 | 1 | ESI+: 517 |
| 415 | 20 | ESI+: 252, 254 |
| 416 | 1 | ESI+: 545, 547 |
| 417 | 1 | ESI+: 488 |
| 418 | 1 | ESI+: 510 |
| 419 | 1 | ESI+: 502 |
| 420 | 1 | ESI+: 536 |
| 421 | 20, 1 | ESI+: 526 |
| 422 | 1 | ESI+: 488.4 |
| 423 | 1 | ESI+: 508.1 |
| 424 | 1 | ESI+: 536 |
| 425 | 1 | ESI+: 540 |
| 426 | 1, 38 | ESI+: 432 |
| 427 | 1 | ESI+: 558.4 |
| 428 | 4, 1 | ESI+: 540.1 |
| 429 | 4, 1 | ESI+: 522.0 |
| 430 | 37 | ESI+: 488 |
| 431 | 1 | ESI+: 508 |
| 432 | 2 | ESI+: 360.3 |

TABLE 93

| Ex | Structure | Note |
|---|---|---|
| 1 | 2'-cyano-N-cyclopropyl-N-(4,5,6,7-tetrahydro-1H-indazol-5-yl)biphenyl-4-carboxamide structure | |
| 2 | 1-(2-fluoroethyl)-N-cyclopropyl-N-(4,5,6,7-tetrahydro-1H-indazol-5-yl)-1H-indole-4-carboxamide structure | Sal: HCl |
| 3 | 1-(1-phenylethyl)-N-cyclopropyl-N-(4,5,6,7-tetrahydro-1H-indazol-5-yl)-1H-indazole-4-carboxamide structure | Sal: HCl |

TABLE 93-continued

| Ex | Structure | Note |
|---|---|---|
| 4 | 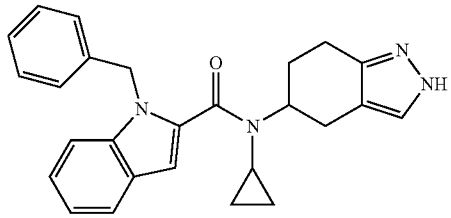 [SMILES: O=C(c1cc2ccccc2n1Cc1ccccc1)N(C1CC1)C1CCc2n[nH]cc2C1] | |
| 5 | 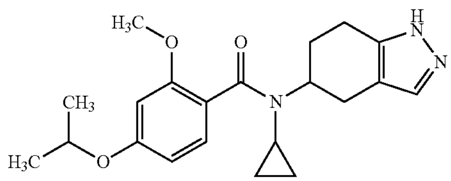 [SMILES: COc1cc(OC(C)C)ccc1C(=O)N(C1CC1)C1CCc2[nH]ncc2C1] | |

TABLE 94

| Ex | Structure | Note |
|---|---|---|
| 6 | 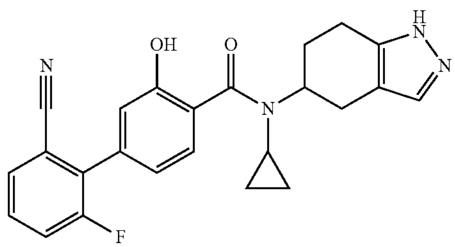 [SMILES: N#Cc1cccc(F)c1-c1ccc(C(=O)N(C2CC2)C2CCc3[nH]ncc3C2)c(O)c1] | |
| 7-1 | 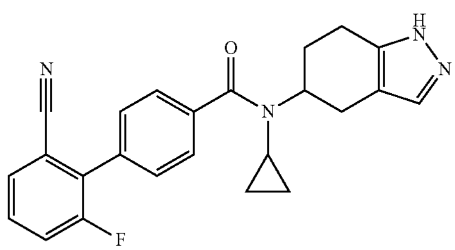 [SMILES: N#Cc1cccc(F)c1-c1ccc(C(=O)N(C2CC2)C2CCc3[nH]ncc3C2)cc1] | Chiral |
| 7-2 | 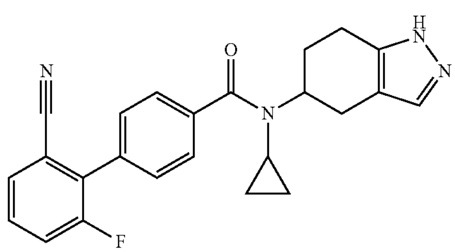 [SMILES: N#Cc1cccc(F)c1-c1ccc(C(=O)N(C2CC2)C2CCc3[nH]ncc3C2)cc1] | Chiral |
| 8-1 | 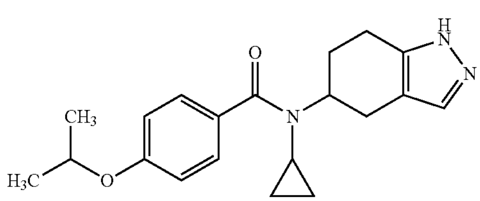 [SMILES: CC(C)Oc1ccc(C(=O)N(C2CC2)C2CCc3[nH]ncc3C2)cc1] | Chiral |

TABLE 94-continued

| Ex | Structure | Note |
|---|---|---|
| 8-2 | 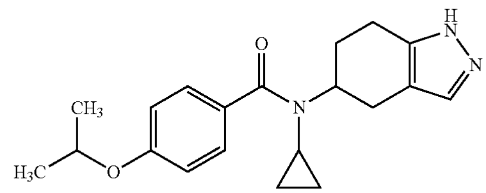 [SMILES: CC(C)Oc1ccc(C(=O)N(C2CC2)C2CCc3[nH]ncc3C2)cc1] | Chiral |

TABLE 95

| Ex | Structure | Note |
|---|---|---|
| 9 | 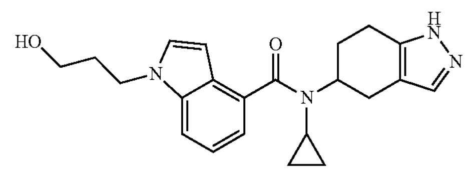 [SMILES: O=C(c1cccc2c1ccn2CCCO)N(C1CC1)C1CCc2[nH]ncc2C1] | |
| 10 | 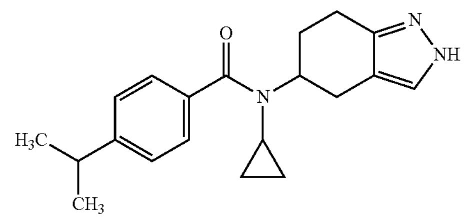 [SMILES: CC(C)c1ccc(C(=O)N(C2CC2)C2CCc3n[nH]cc3C2)cc1] | |
| 11 | 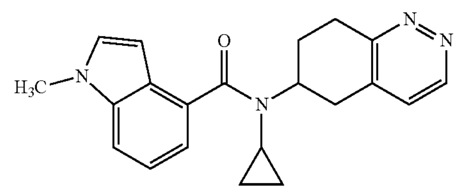 [SMILES: Cn1ccc2c(C(=O)N(C3CC3)C3CCc4nnccc4C3)cccc21] | |
| 12 | 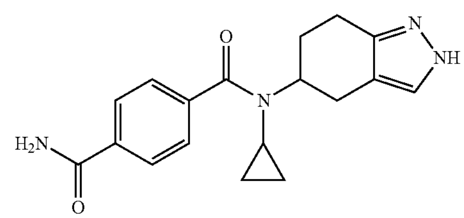 [SMILES: NC(=O)c1ccc(C(=O)N(C2CC2)C2CCc3n[nH]cc3C2)cc1] | |
| 13 | 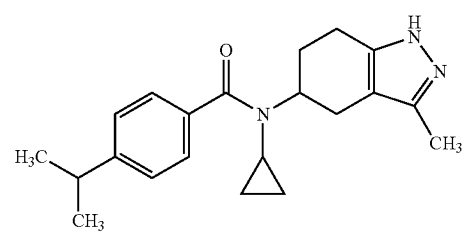 [SMILES: Cc1n[nH]c2c1CC(N(C(=O)c1ccc(C(C)C)cc1)C1CC1)CC2] | Sal: HCl |
| 14 | 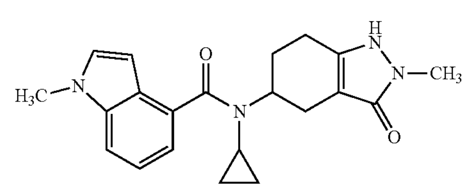 | |

TABLE 96

TABLE 97

TABLE 97-continued

TABLE 98

TABLE 98-continued
28 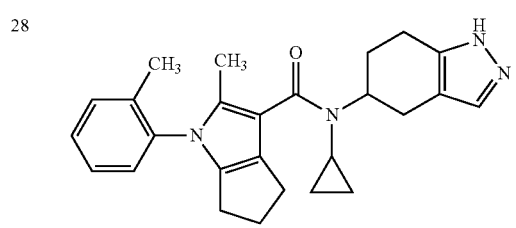
29 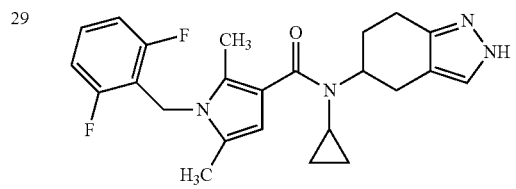
TABLE 99
30 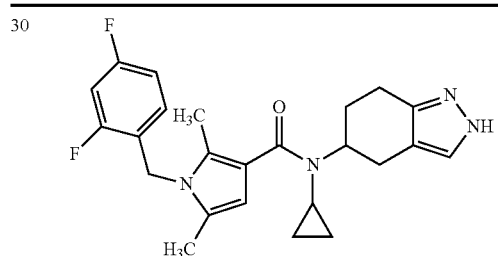
31 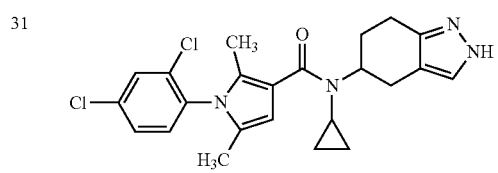
32 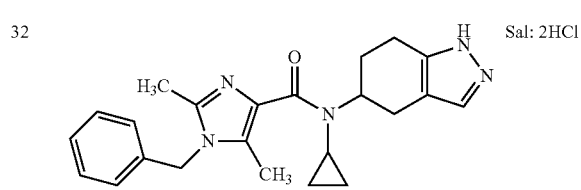  Sal: 2HCl
33 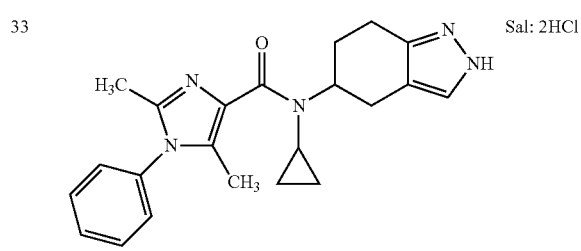  Sal: 2HCl
34 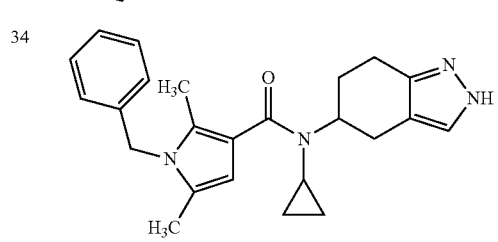
TABLE 100
35 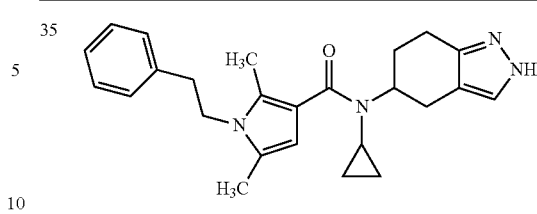
36 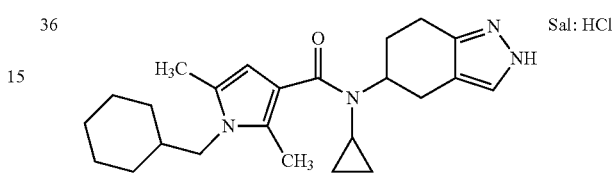  Sal: HCl
37 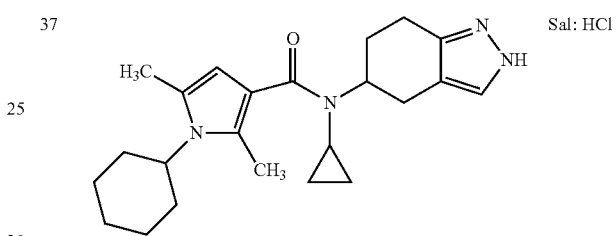  Sal: HCl
38 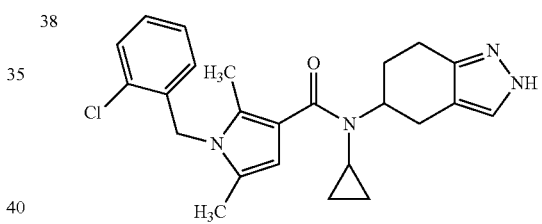
39 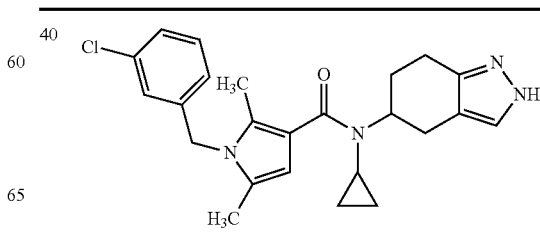
TABLE 101
40 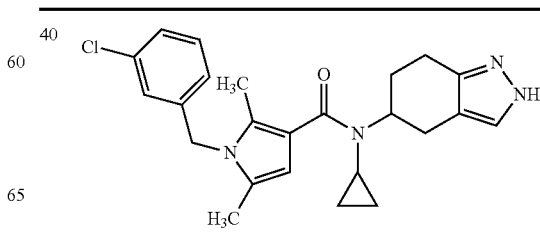

TABLE 101-continued
| 41 | 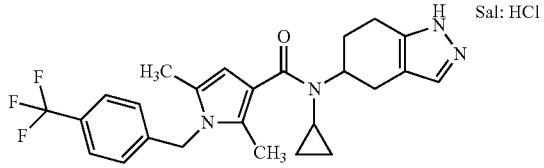 | Sal: HCl |
|---|---|---|
| 42 | 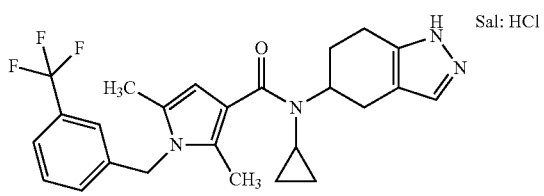 | Sal: HCl |
TABLE 101-continued
| 43 | 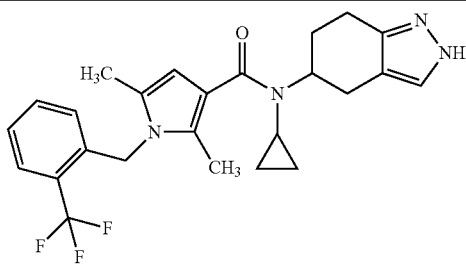 | Sal: HCl |
|---|---|---|
| 44 | 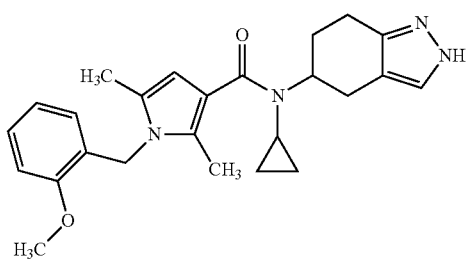 [SMILES: COc1ccccc1Cn1c(C)cc(C(=O)N(C2CC2)C2CCc3n[nH]cc3C2)c1C] | Sal: HCl |
TABLE 102
| 45 | 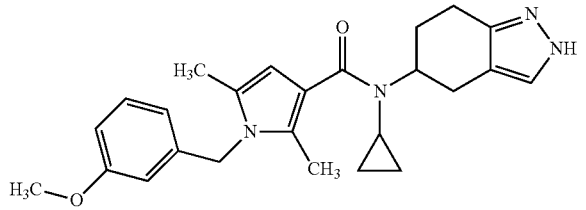 [SMILES: COc1cccc(Cn2c(C)cc(C(=O)N(C3CC3)C3CCc4n[nH]cc4C3)c2C)c1] | Sal: HCl |
|---|---|---|
| 46 | 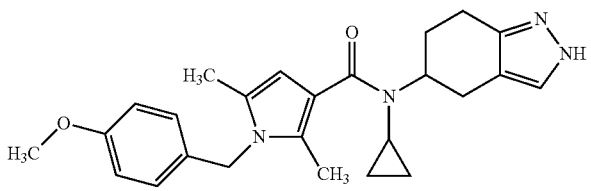 [SMILES: COc1ccc(Cn2c(C)cc(C(=O)N(C3CC3)C3CCc4n[nH]cc4C3)c2C)cc1] | Sal: HCl |
| 47 | 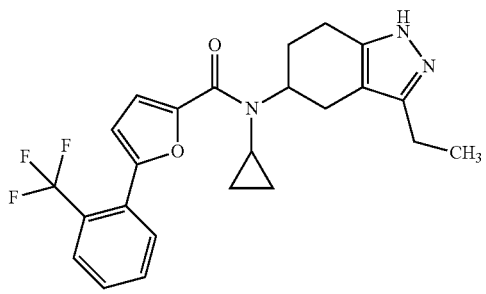 [SMILES: CCc1n[nH]c2c1CC(N(C(=O)c1ccc(-c3ccccc3C(F)(F)F)o1)C1CC1)CC2] | Sal: HCl |
| 48 | 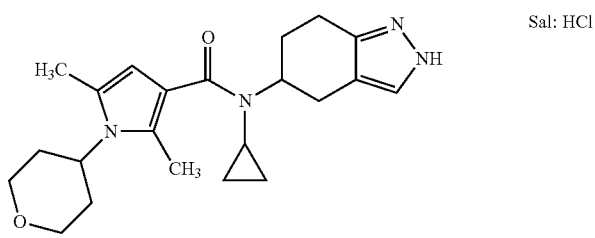 | Sal: HCl |

TABLE 102-continued
| 49 | 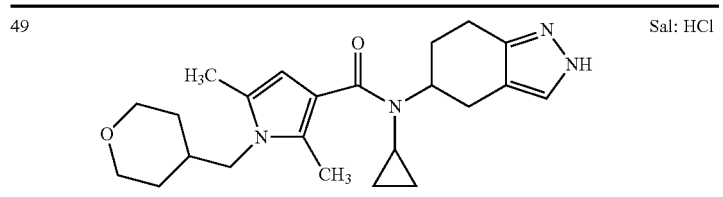 | Sal: HCl |
|---|---|---|
TABLE 103
| 50 | 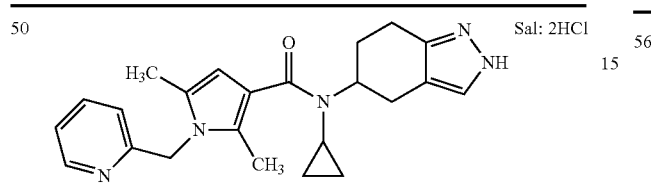 | Sal: 2HCl |
|---|---|---|
| 51 | 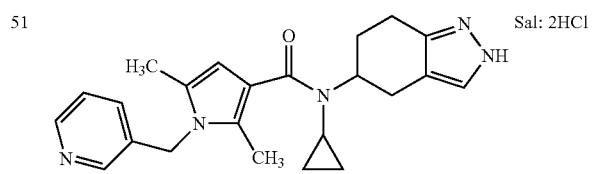 | Sal: 2HCl |
| 52 | 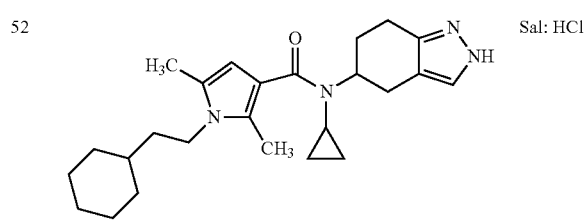 | Sal: HCl |
| 53 | 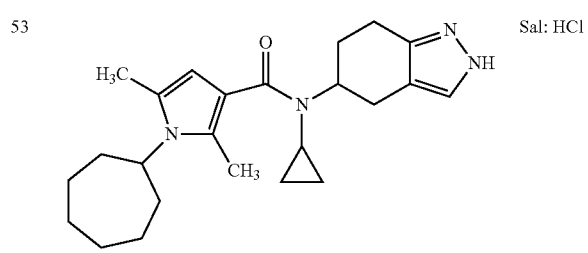 | Sal: HCl |
| 54 | 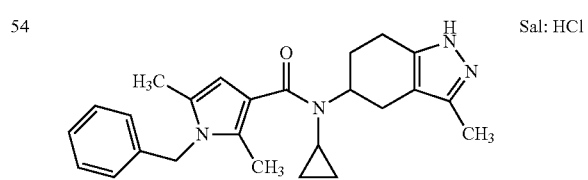 | Sal: HCl |
TABLE 104
| 55 | 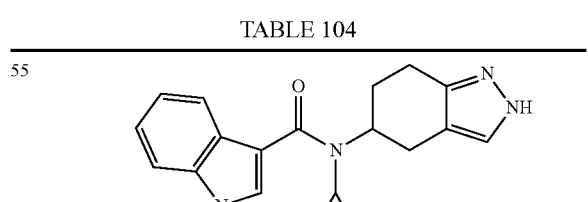 | |
|---|---|---|
TABLE 104-continued
| 56 | 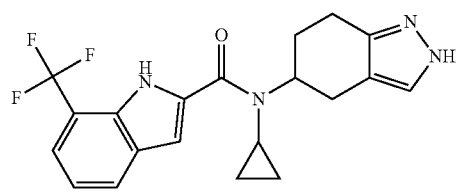 [SMILES: O=C(c1cc2cccc(C(F)(F)F)c2[nH]1)N(C1CC1)C1CCc2n[nH]cc2C1] | |
|---|---|---|
| 57 | 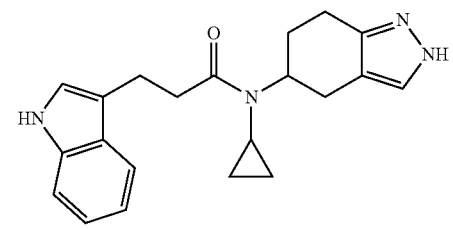 [SMILES: O=C(CCc1c[nH]c2ccccc12)N(C1CC1)C1CCc2n[nH]cc2C1] | |
| 58 | 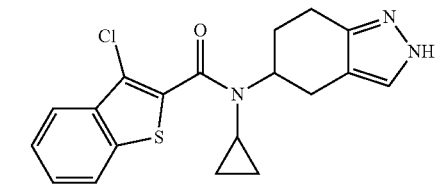 [SMILES: O=C(c1sc2ccccc2c1Cl)N(C1CC1)C1CCc2n[nH]cc2C1] | |
| 59 | 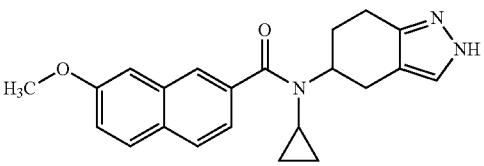 [SMILES: COc1ccc2ccc(C(=O)N(C3CC3)C3CCc4n[nH]cc4C3)cc2c1] | |
| 60 | 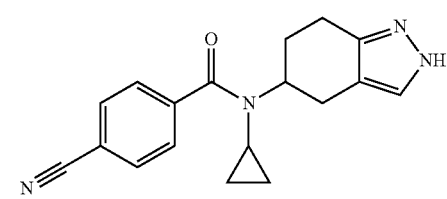 [SMILES: N#Cc1ccc(C(=O)N(C2CC2)C2CCc3n[nH]cc3C2)cc1] | |
TABLE 105
| 61 | 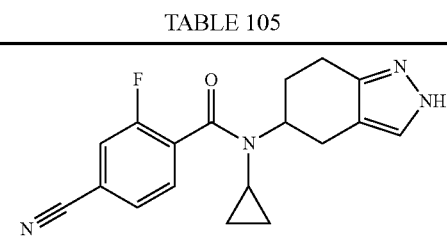 | |
|---|---|---|

TABLE 105-continued
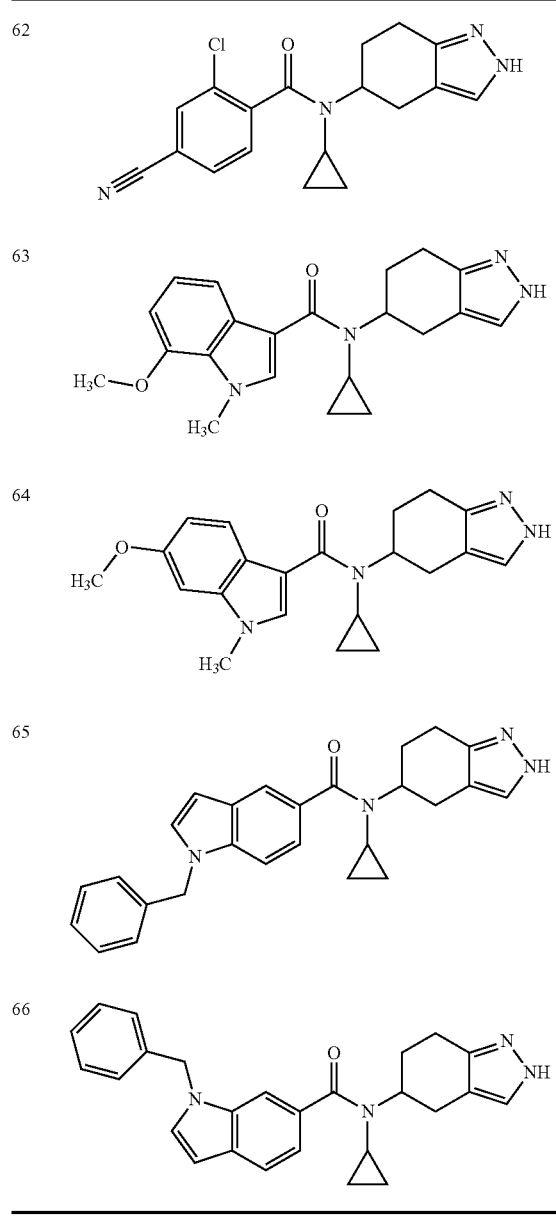
TABLE 106
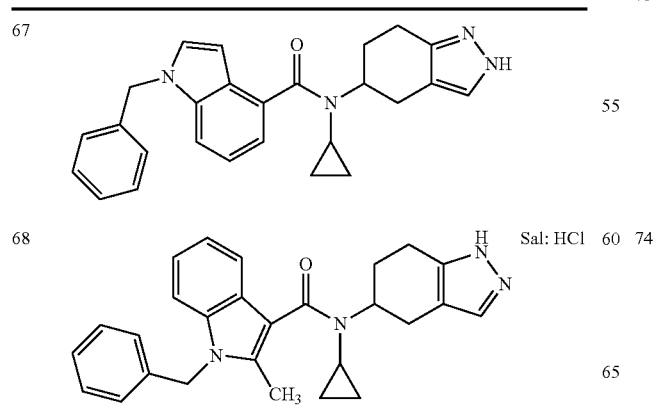
TABLE 106-continued
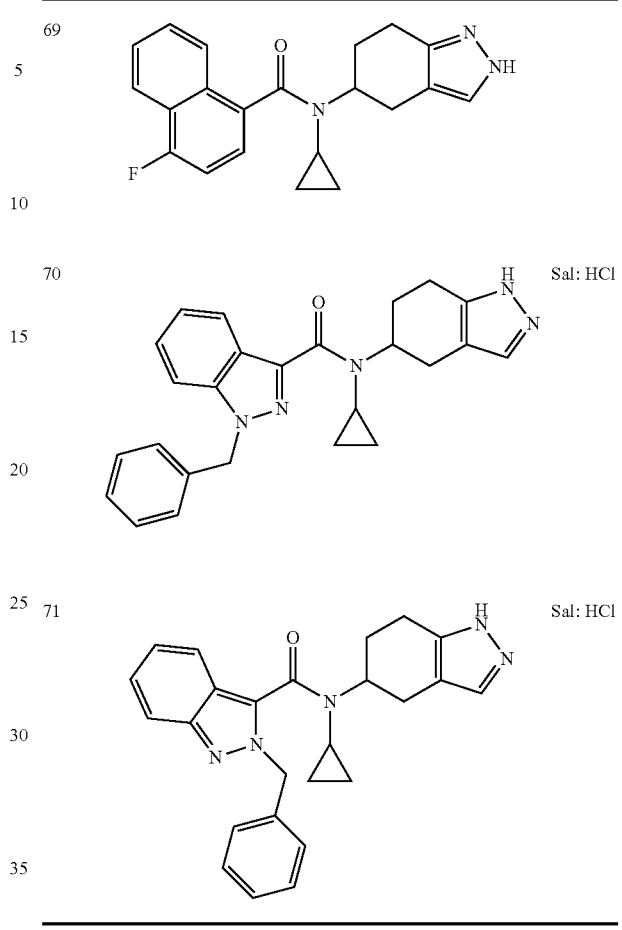
TABLE 107
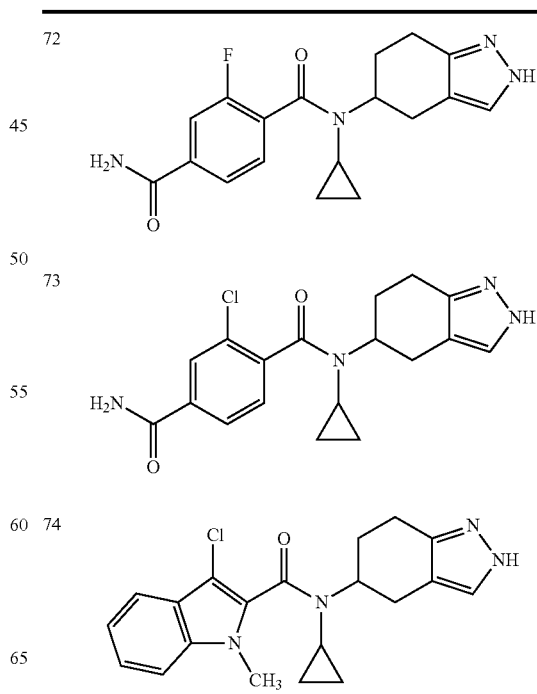

TABLE 107-continued
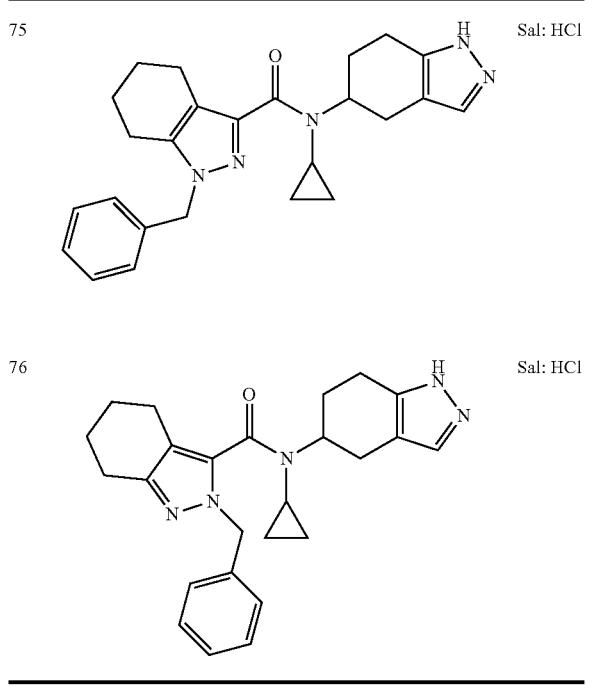
TABLE 108
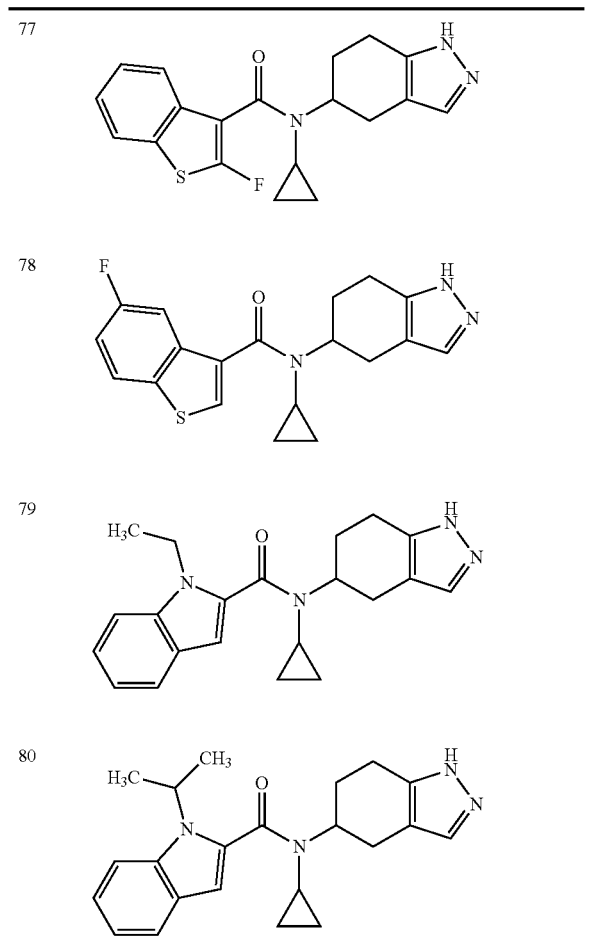
TABLE 108-continued
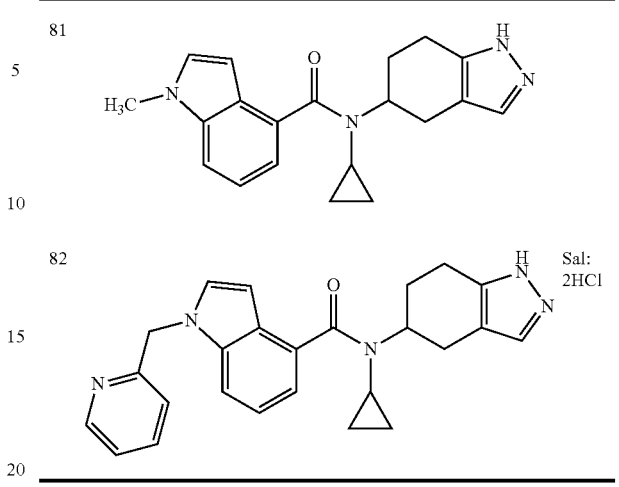
TABLE 109
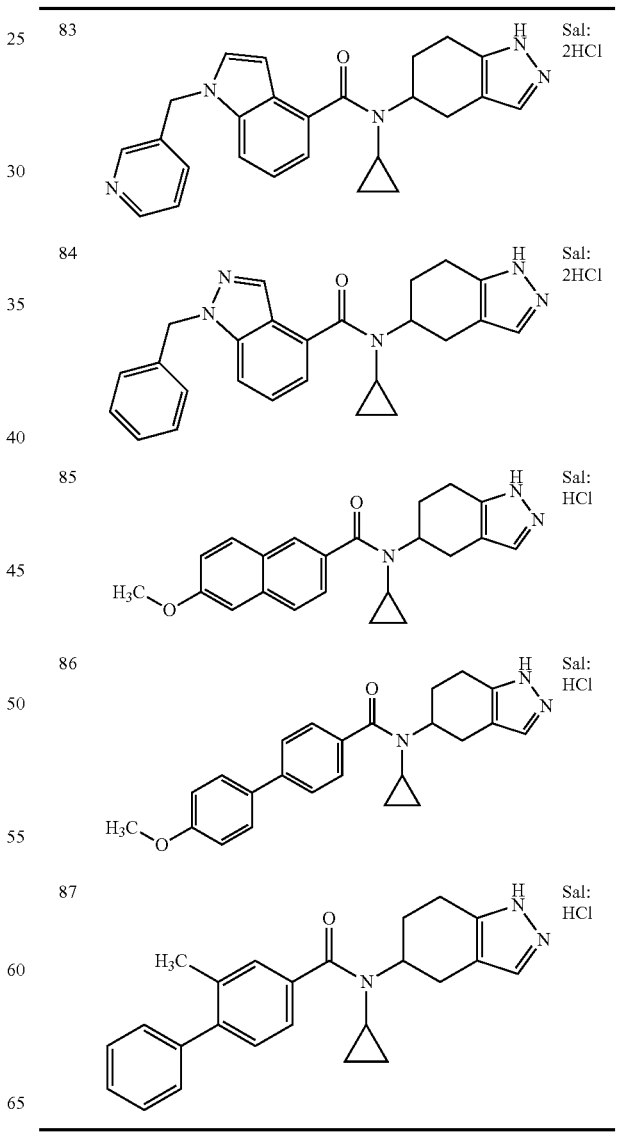

TABLE 110
| | | |
|---|---|---|
| 88 | 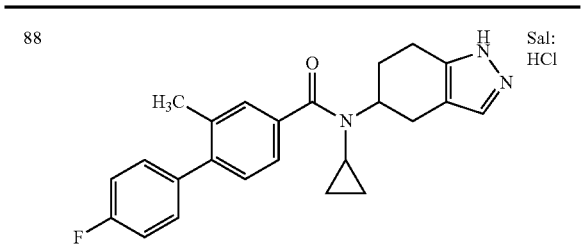 | Sal: HCl |
| 89 | 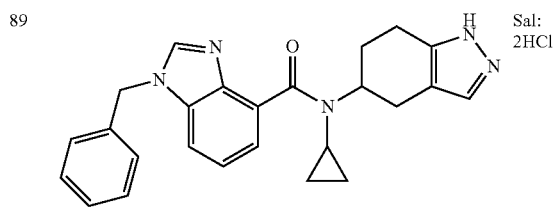 | Sal: 2HCl |
| 90 | 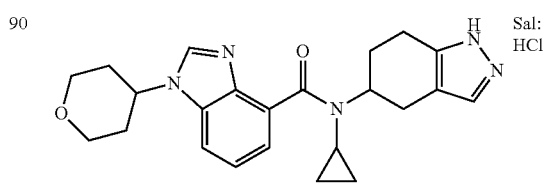 | Sal: HCl |
| 91 | 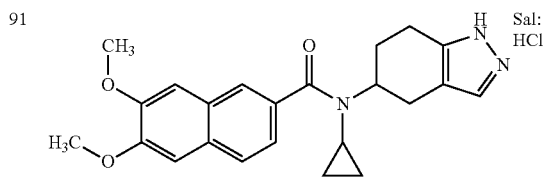 | Sal: HCl |
| 92 | 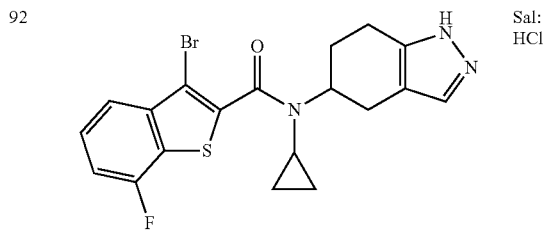 | Sal: HCl |
TABLE 111
| | | |
|---|---|---|
| 93 | 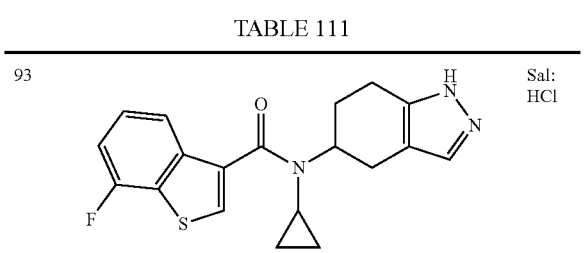 | Sal: HCl |
| 94 | 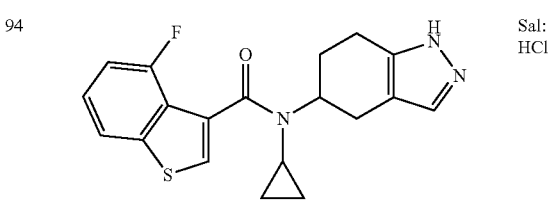 | Sal: HCl |
TABLE 111-continued
| | | |
|---|---|---|
| 95 | 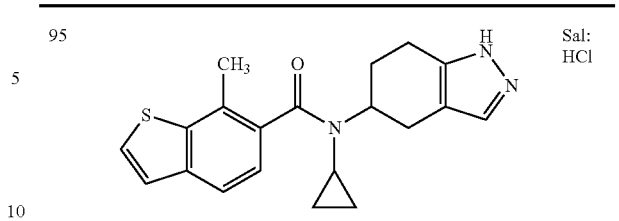 | Sal: HCl |
| 96 | 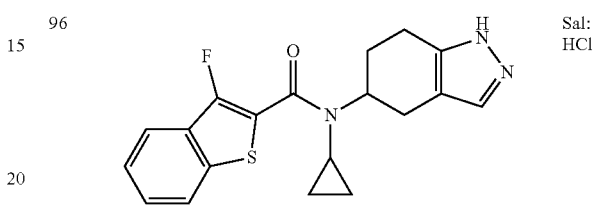 | Sal: HCl |
| 97 | 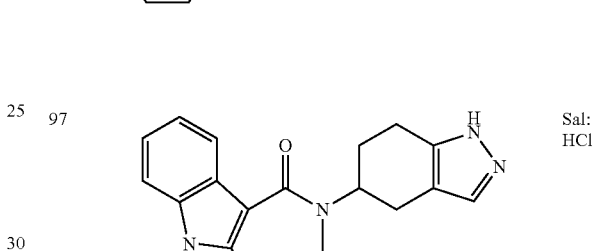 | Sal: HCl |
| 98 | 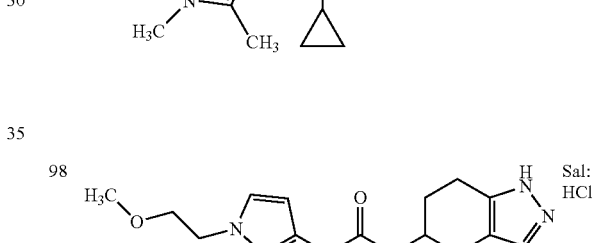 | Sal: HCl |
TABLE 112
| | | |
|---|---|---|
| 99 | 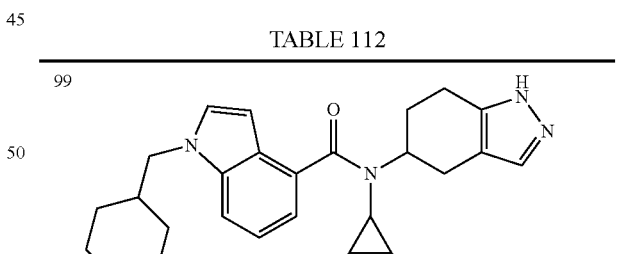 | Sal: HCl |
| 100 | 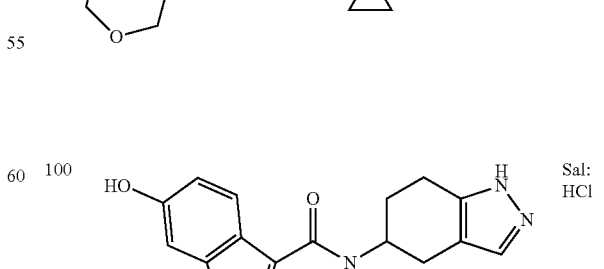 | Sal: HCl |

TABLE 112-continued
| | | |
|---|---|---|
| 101 | 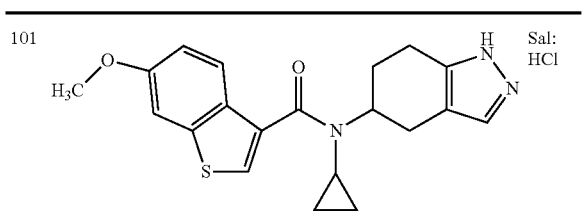 | Sal: HCl |
| 102 | 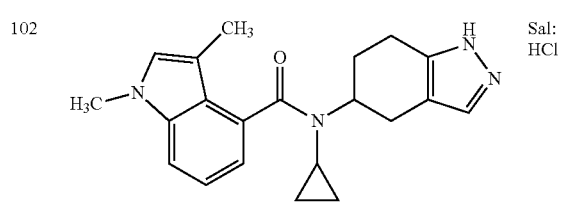 | Sal: HCl |
| 103 | 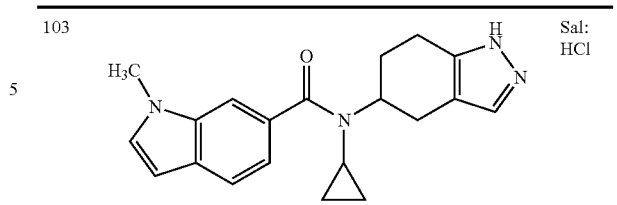 | Sal: HCl |
| 104 | 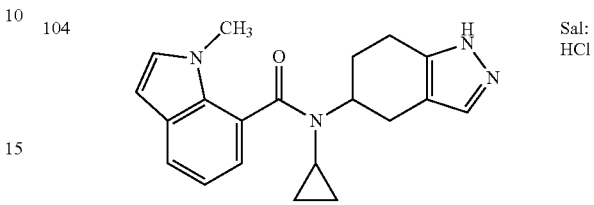 | Sal: HCl |
TABLE 113
| | | |
|---|---|---|
| 105 | 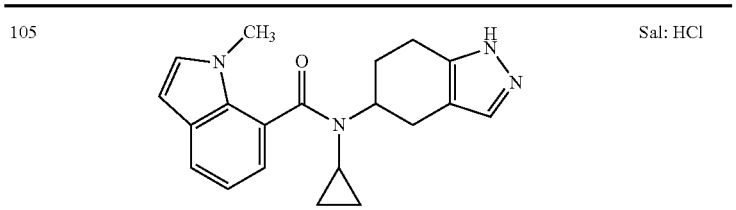 | Sal: HCl |
| 106 | 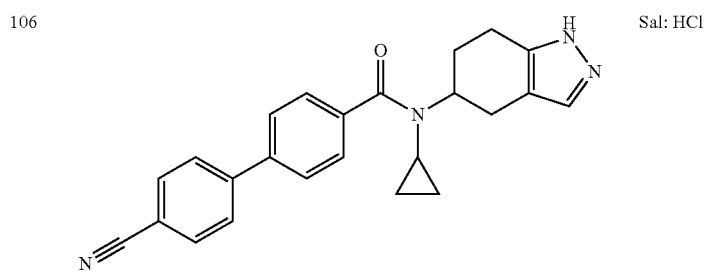 | Sal: HCl |
| 107 | 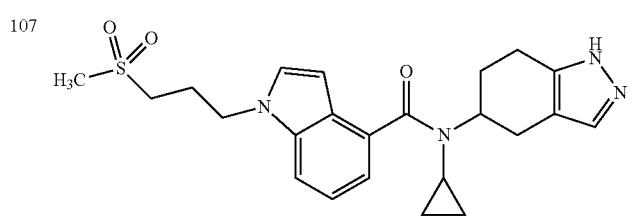 | Sal: HCl |
| 108 | 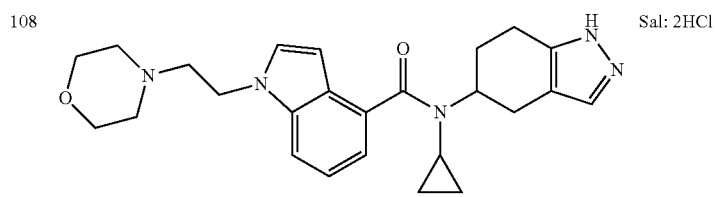 | Sal: 2HCl |
| 109 | 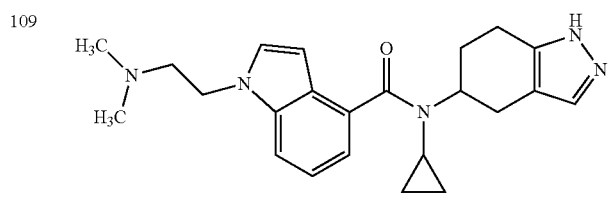 | |

TABLE 114
110 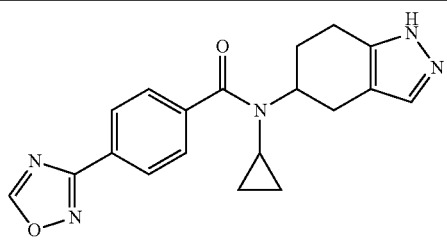
111 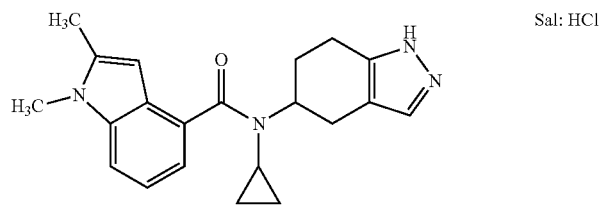 Sal: HCl
112 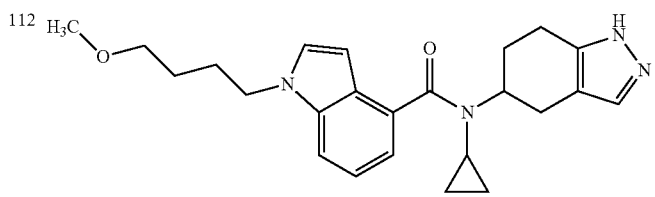
113 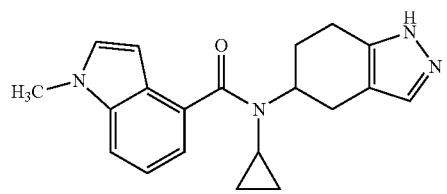 [SMILES: Cn1ccc2c(C(=O)N(C3CC3)C3CCc4[nH]ncc4C3)cccc21]
114 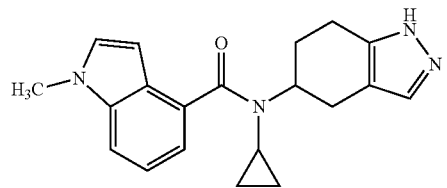 [SMILES: Cn1ccc2c(C(=O)N(C3CC3)C3CCc4[nH]ncc4C3)cccc21]
115 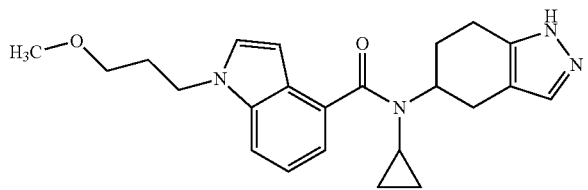 [SMILES: COCCCn1ccc2c(C(=O)N(C3CC3)C3CCc4[nH]ncc4C3)cccc21]
TABLE 115
116 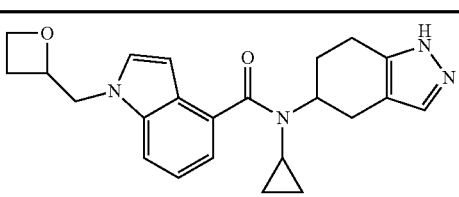
TABLE 115-continued
117 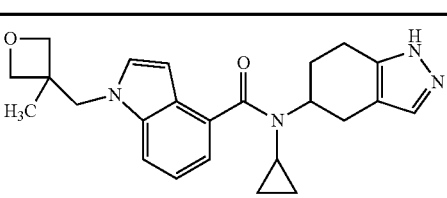

TABLE 115-continued
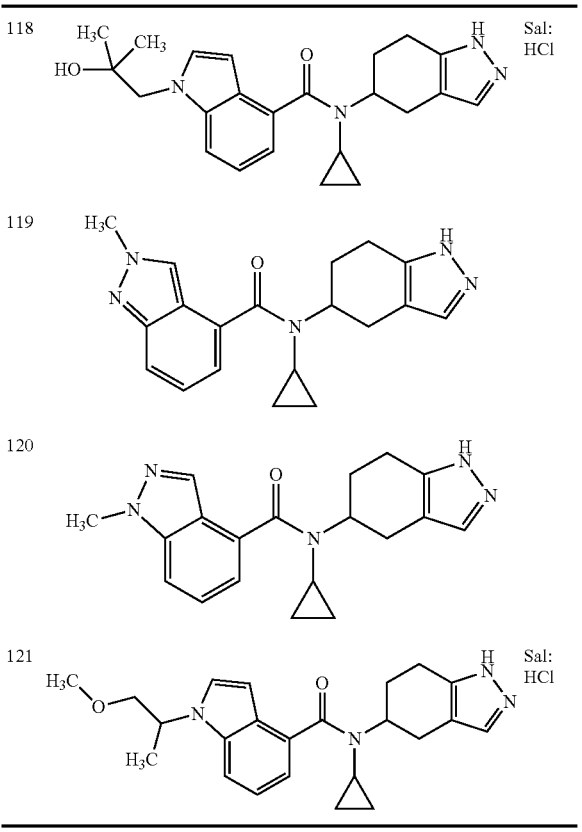
TABLE 116
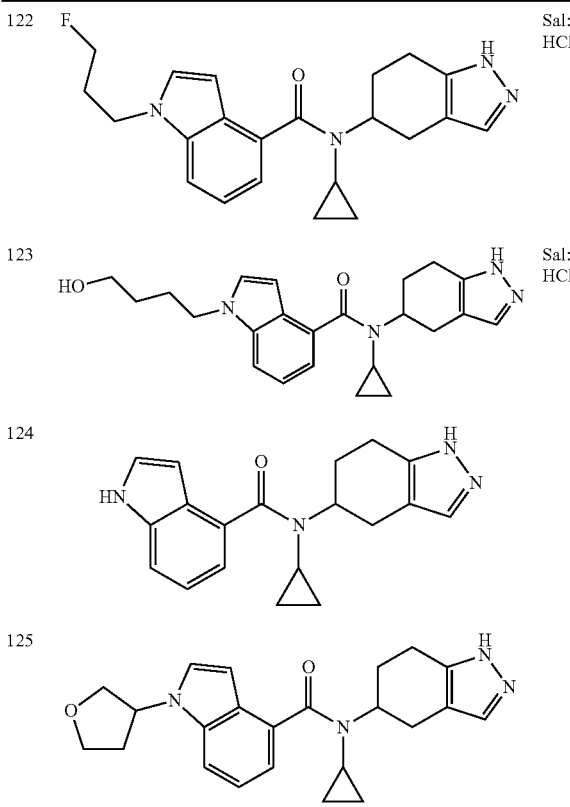
TABLE 116-continued
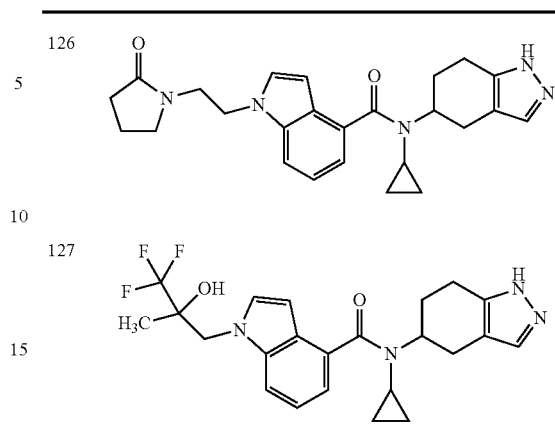
TABLE 117
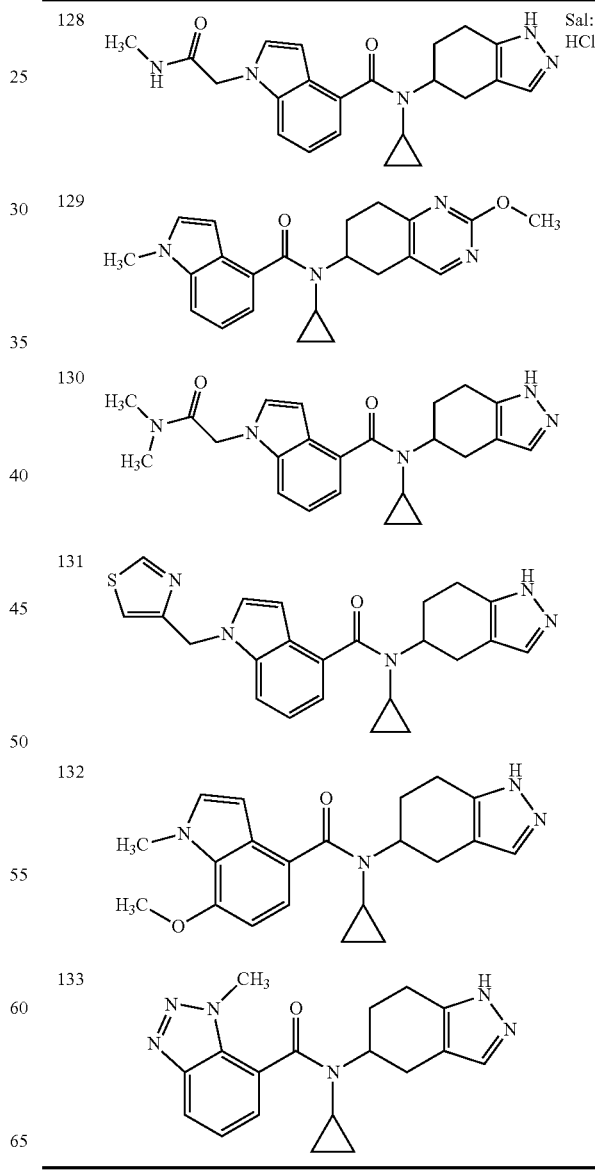

TABLE 118
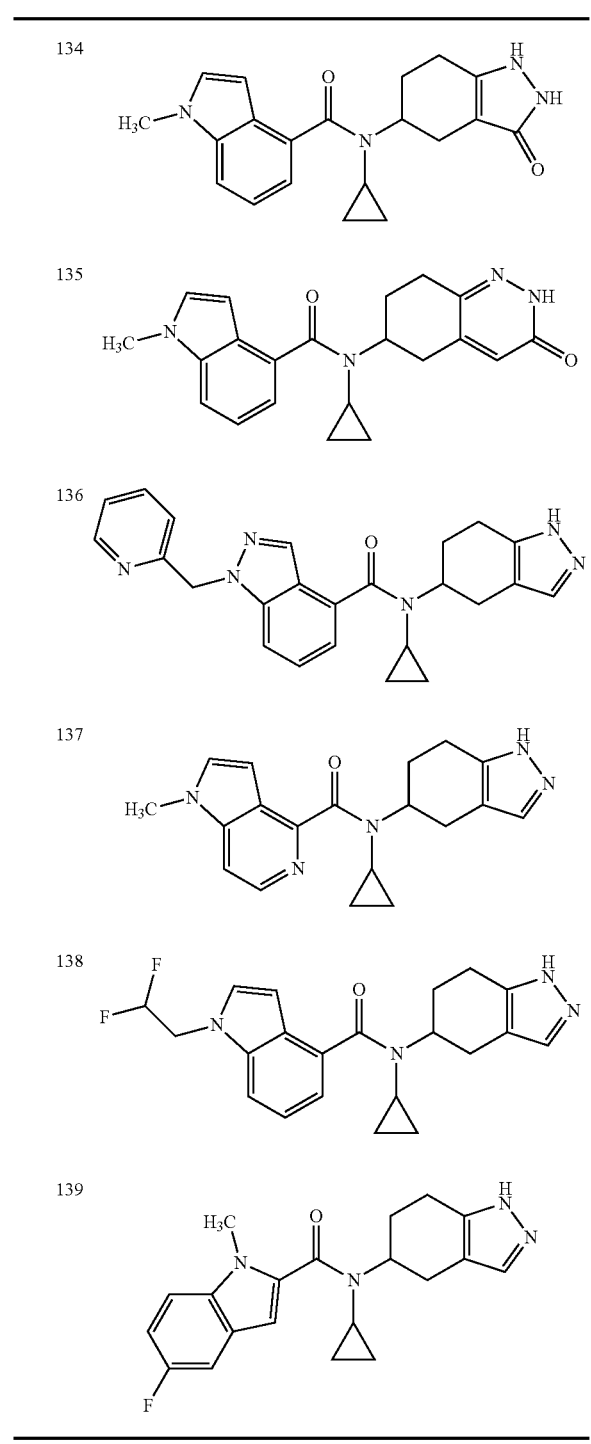
TABLE 119
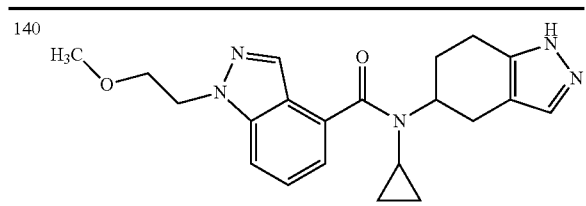
TABLE 119-continued
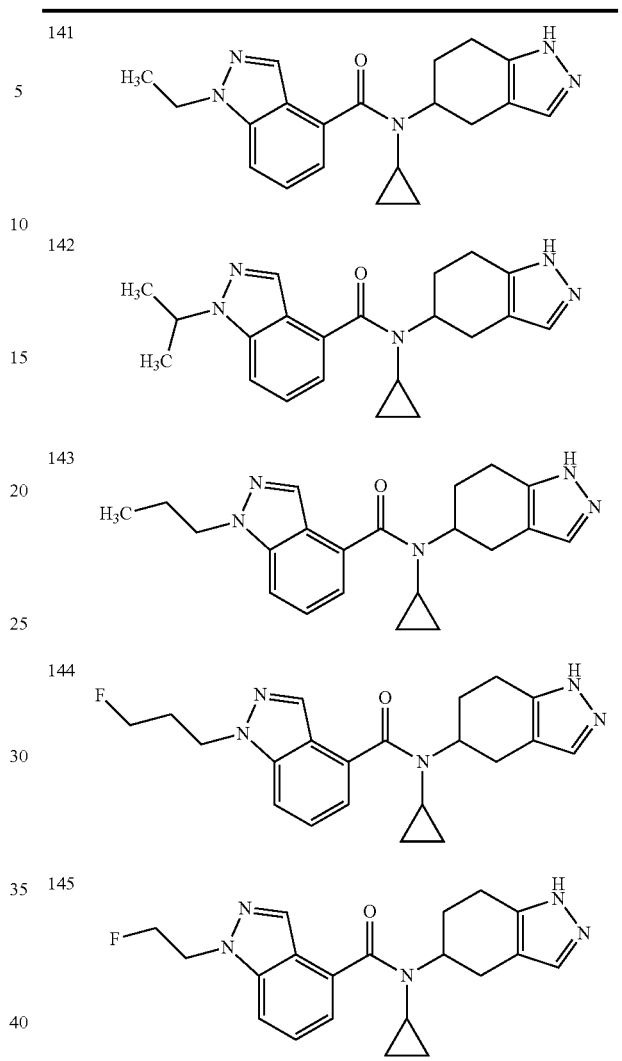
TABLE 120
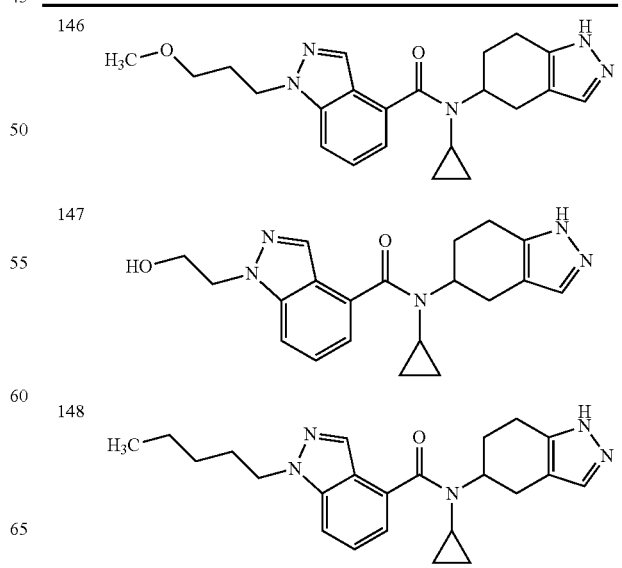

TABLE 120-continued
149 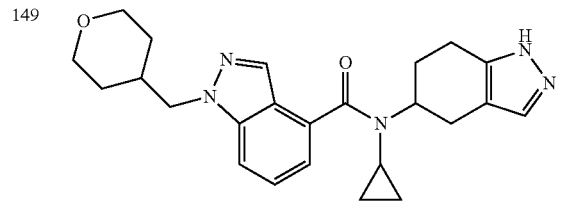
150 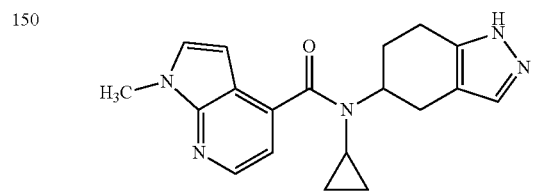
151 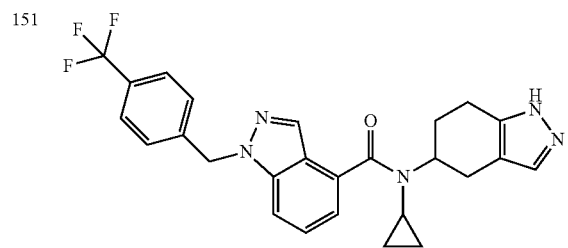
TABLE 121
152 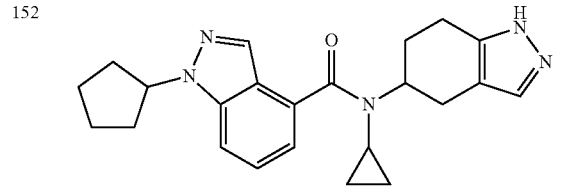
153 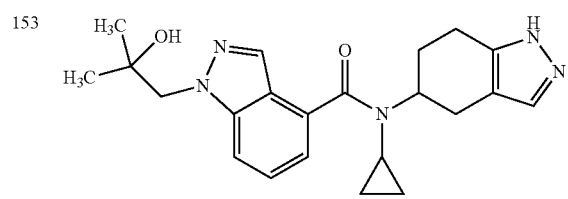
154 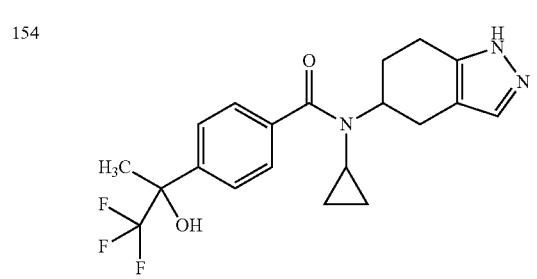
TABLE 121-continued
155 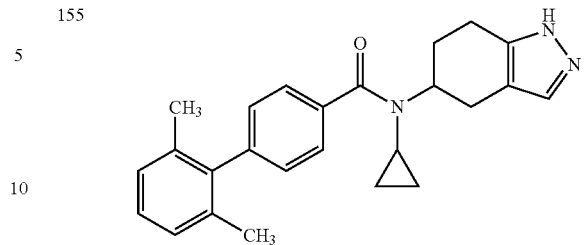
156 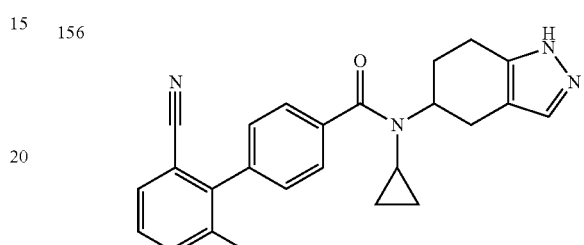
TABLE 122
157 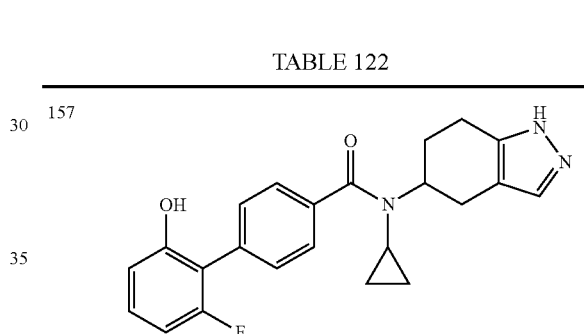
158 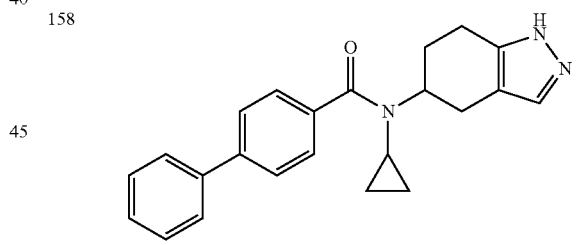
159 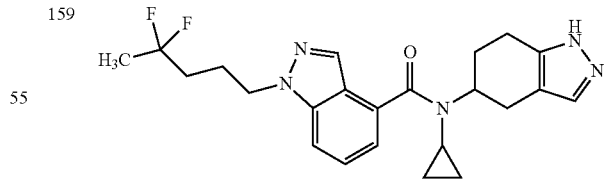
160 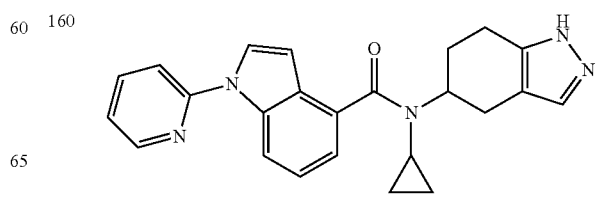

TABLE 122-continued
161 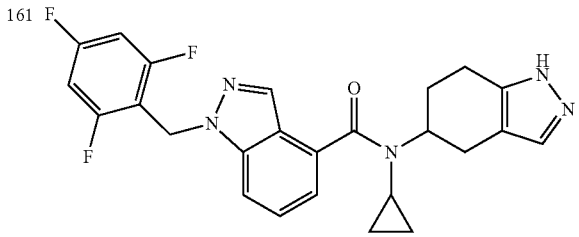
TABLE 123
162 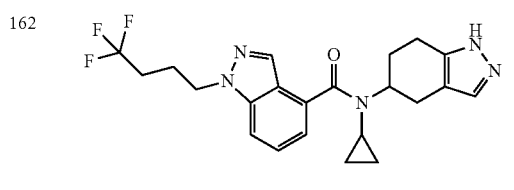
163 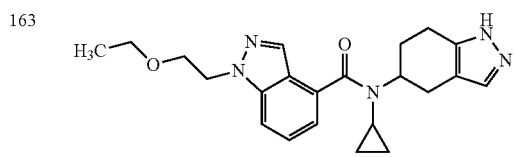
164 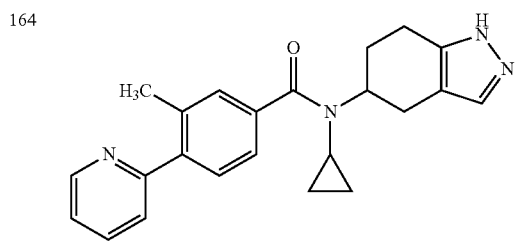
165 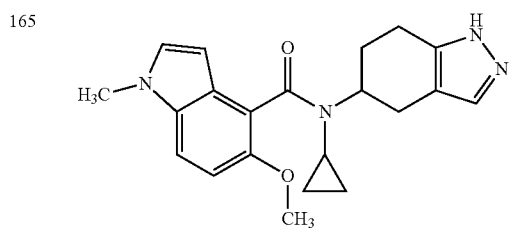
166 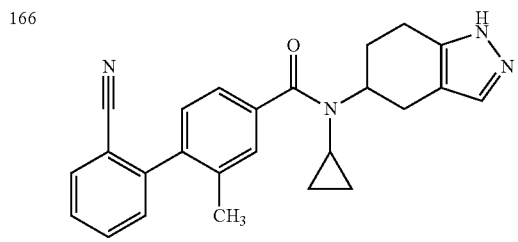
TABLE 124
167 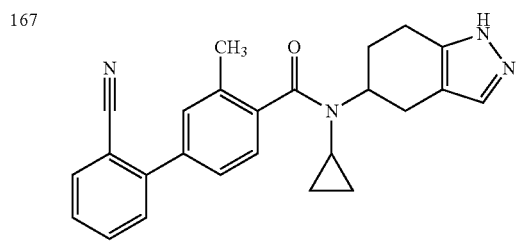
168 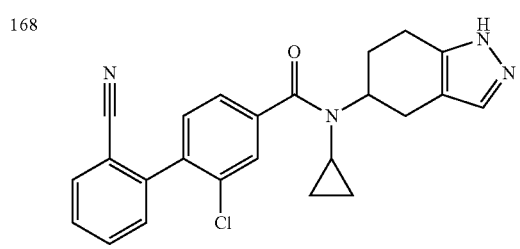
169 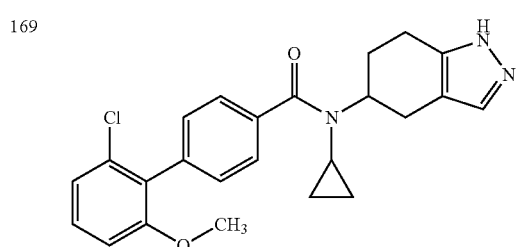
170 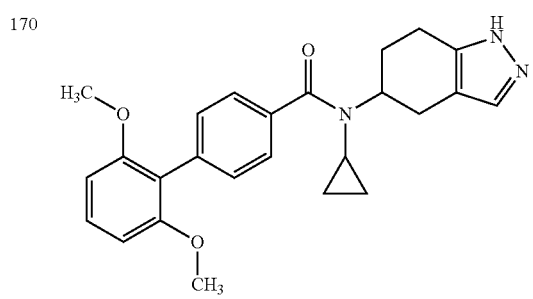
171 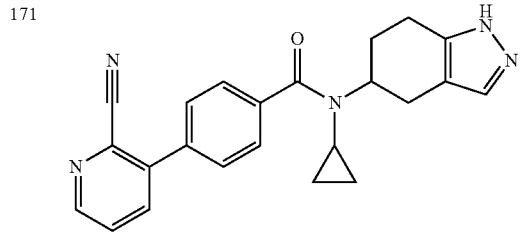
TABLE 125
172 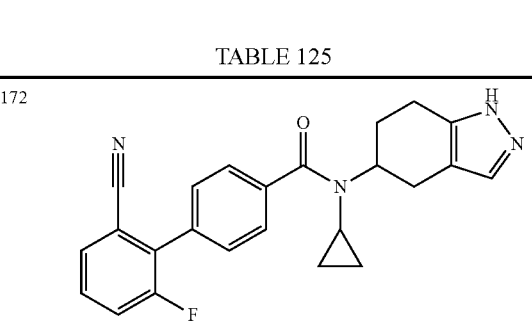

TABLE 125-continued
173 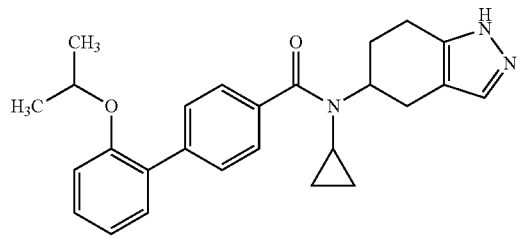 [SMILES: CC(C)Oc1ccccc1-c1ccc(C(=O)N(C2CC2)C2CCc3[nH]ncc3C2)cc1]
174 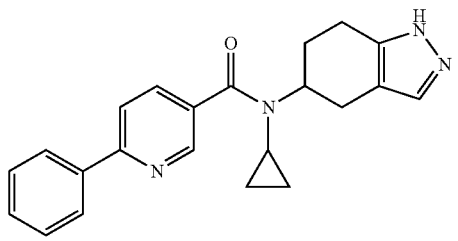 [SMILES: O=C(c1ccc(-c2ccccc2)nc1)N(C1CC1)C1CCc2[nH]ncc2C1]
175 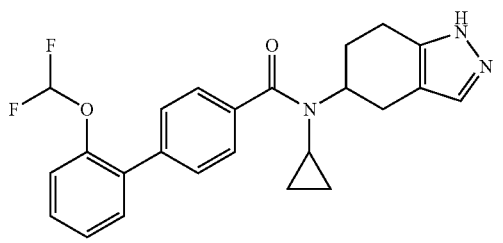 [SMILES: O=C(c1ccc(-c2ccccc2OC(F)F)cc1)N(C1CC1)C1CCc2[nH]ncc2C1]
176 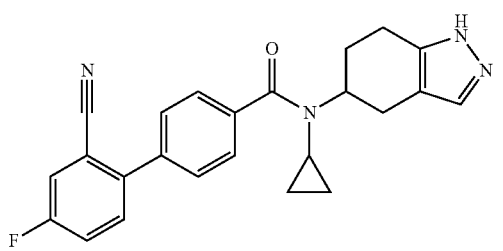 [SMILES: N#Cc1cc(F)ccc1-c1ccc(C(=O)N(C2CC2)C2CCc3[nH]ncc3C2)cc1]
TABLE 126
177 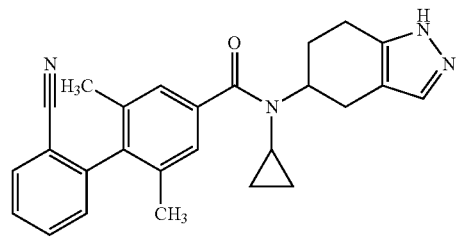 [SMILES: Cc1cc(C(=O)N(C2CC2)C2CCc3[nH]ncc3C2)cc(C)c1-c1ccccc1C#N]
178 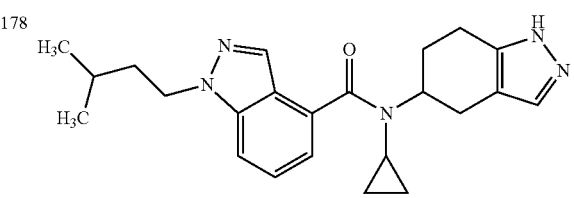
TABLE 126-continued
179 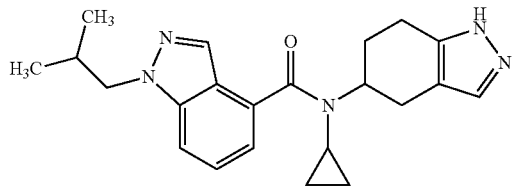 [SMILES: CC(C)Cn1ncc2c(C(=O)N(C3CC3)C3CCc4[nH]ncc4C3)cccc21]
180 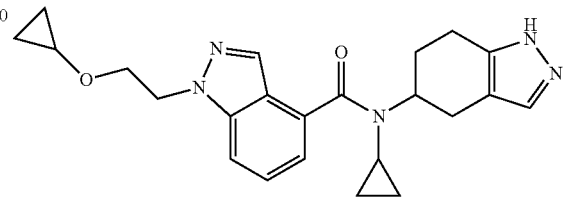
181 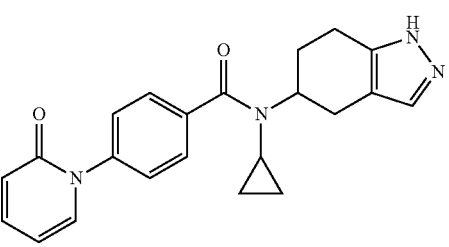 [SMILES: O=C(c1ccc(-n2ccccc2=O)cc1)N(C1CC1)C1CCc2[nH]ncc2C1]
TABLE 127
182 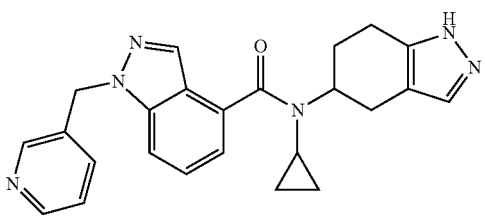 [SMILES: O=C(c1cccc2c1cnn2Cc1cccnc1)N(C1CC1)C1CCc2[nH]ncc2C1]
183 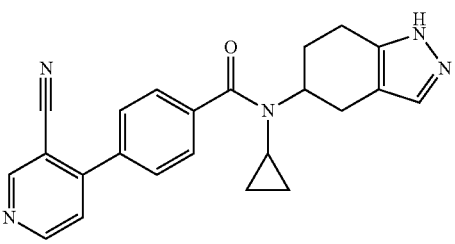 [SMILES: N#Cc1cnccc1-c1ccc(C(=O)N(C2CC2)C2CCc3[nH]ncc3C2)cc1]
184 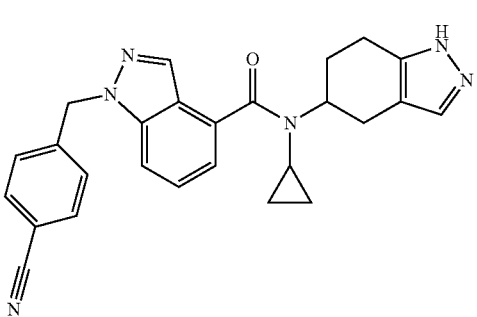 [SMILES: N#Cc1ccc(Cn2ncc3c(C(=O)N(C4CC4)C4CCc5[nH]ncc5C4)cccc32)cc1]

TABLE 127-continued
185 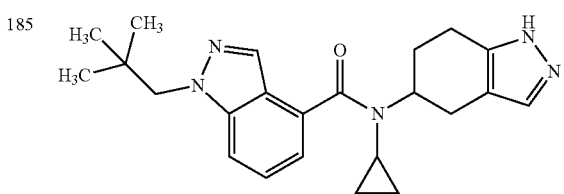
186 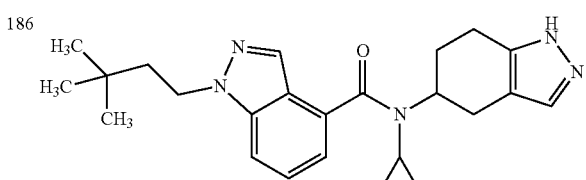
TABLE 128
187 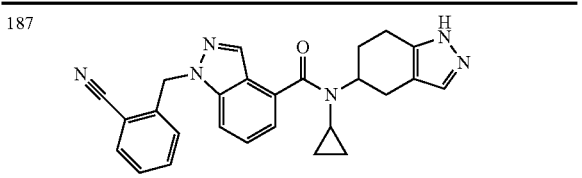
188 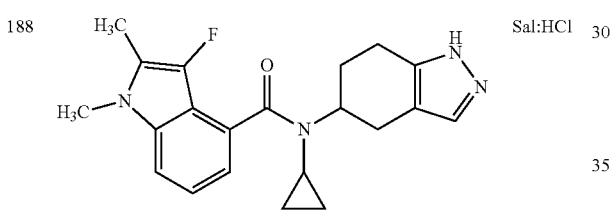 Sal:HCl
189 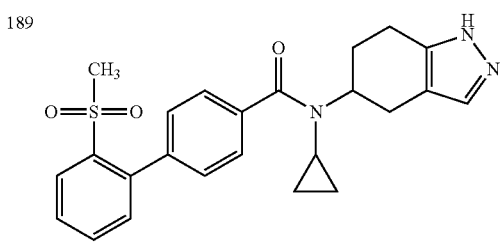
190 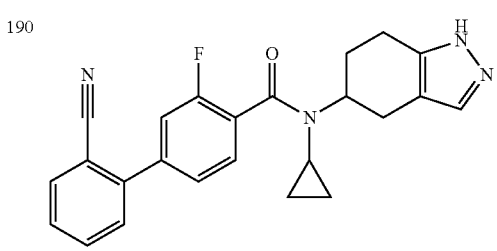
191 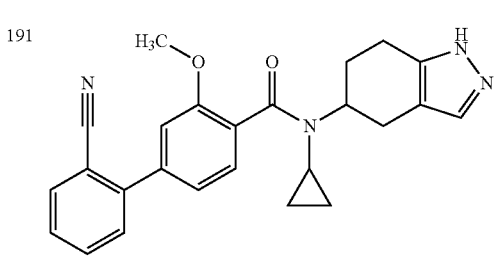
TABLE 129
192 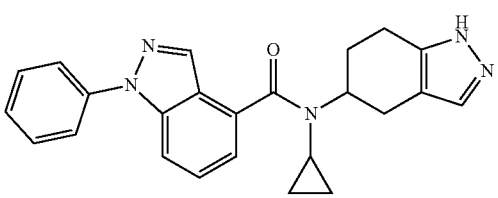 [SMILES: O=C(c1cccc2c1cnn2-c1ccccc1)N(C1CC1)C1CCc2[nH]ncc2C1]
193 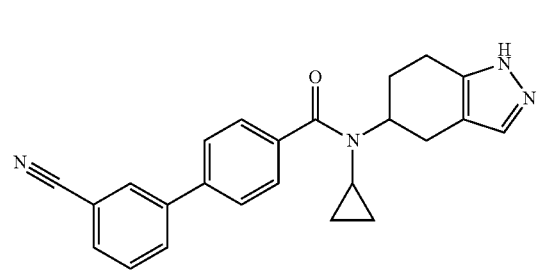 [SMILES: N#Cc1cccc(-c2ccc(C(=O)N(C3CC3)C3CCc4[nH]ncc4C3)cc2)c1]
194 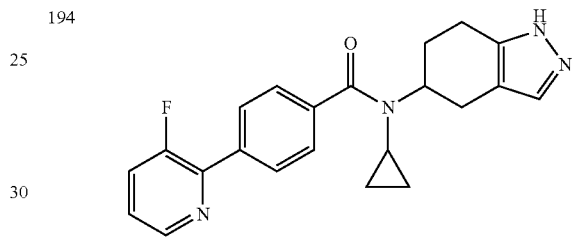
195 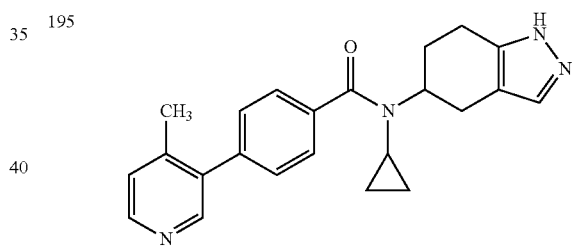
196 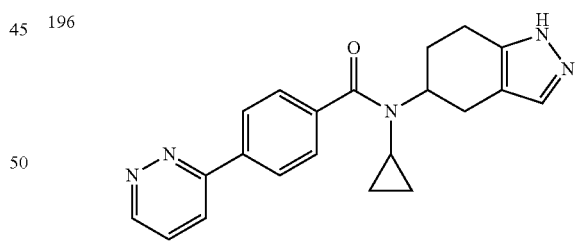
TABLE 130
197 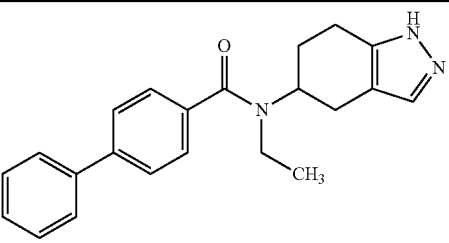

TABLE 130-continued
198 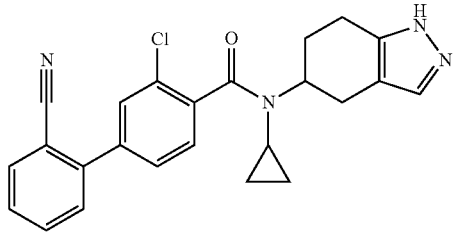 [SMILES: N#Cc1ccccc1-c1ccc(C(=O)N(C2CC2)C2CCc3[nH]ncc3C2)c(Cl)c1]
199 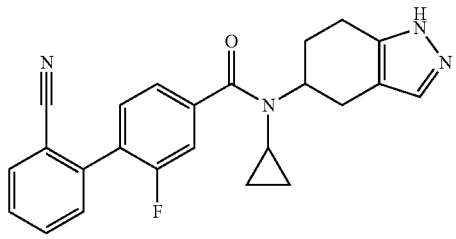 [SMILES: N#Cc1ccccc1-c1ccc(C(=O)N(C2CC2)C2CCc3[nH]ncc3C2)cc1F]
200 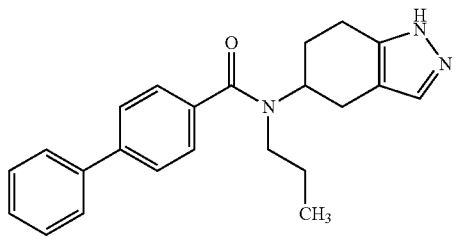 [SMILES: CCCN(C(=O)c1ccc(-c2ccccc2)cc1)C1CCc2[nH]ncc2C1]
201 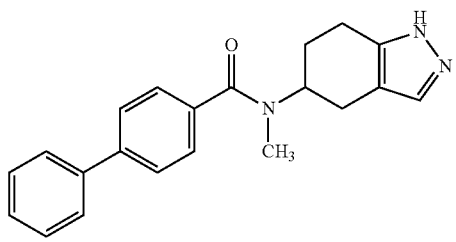 [SMILES: CN(C(=O)c1ccc(-c2ccccc2)cc1)C1CCc2[nH]ncc2C1]
TABLE 131
202 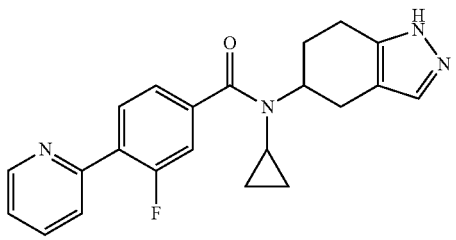 [SMILES: O=C(c1ccc(-c2ccccn2)c(F)c1)N(C1CC1)C1CCc2[nH]ncc2C1]
203 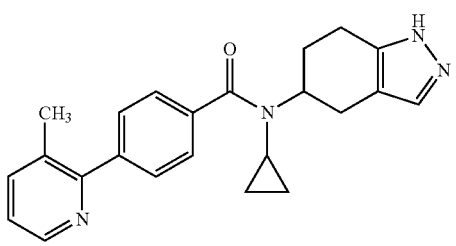 [SMILES: Cc1cccnc1-c1ccc(C(=O)N(C2CC2)C2CCc3[nH]ncc3C2)cc1]
TABLE 131-continued
204 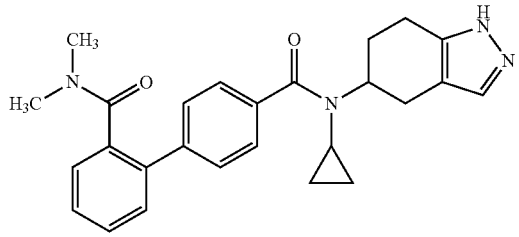 [SMILES: CN(C)C(=O)c1ccccc1-c1ccc(C(=O)N(C2CC2)C2CCc3[nH]ncc3C2)cc1]
205 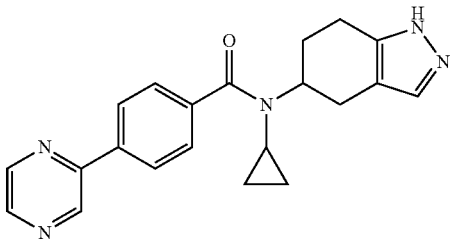 [SMILES: O=C(c1ccc(-c2cnccn2)cc1)N(C1CC1)C1CCc2[nH]ncc2C1]
206 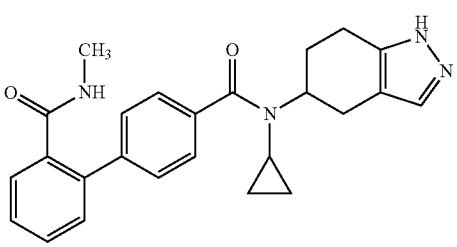 [SMILES: CNC(=O)c1ccccc1-c1ccc(C(=O)N(C2CC2)C2CCc3[nH]ncc3C2)cc1]
TABLE 132
207 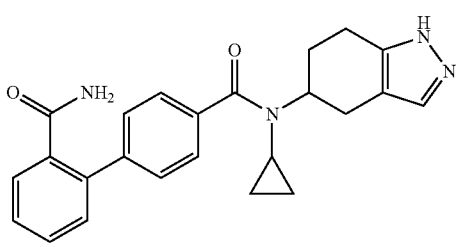 [SMILES: NC(=O)c1ccccc1-c1ccc(C(=O)N(C2CC2)C2CCc3[nH]ncc3C2)cc1]
208 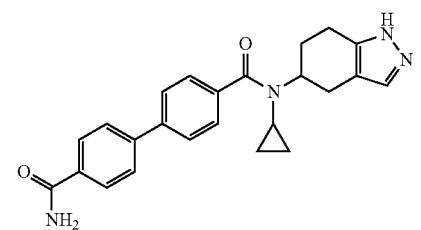 [SMILES: NC(=O)c1ccc(-c2ccc(C(=O)N(C3CC3)C3CCc4[nH]ncc4C3)cc2)cc1]
209 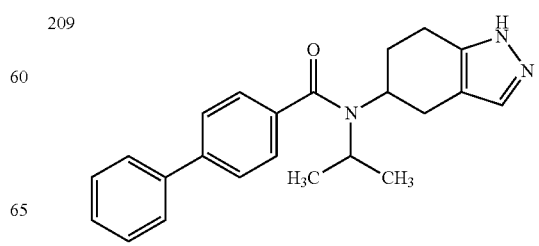

TABLE 132-continued
210 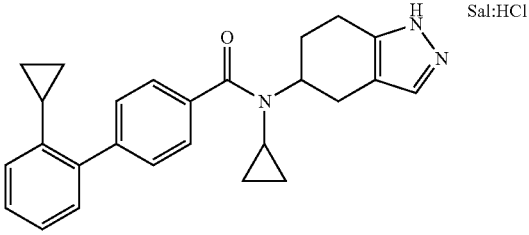 Sal:HCl
TABLE 133
211 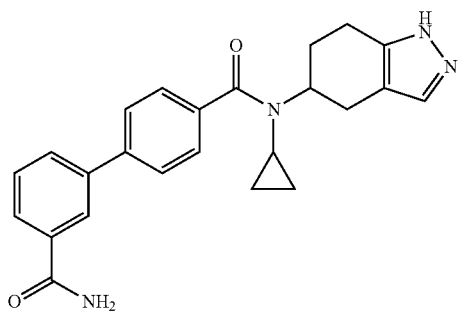 [SMILES: NC(=O)c1cccc(-c2ccc(C(=O)N(C3CC3)C3CCc4[nH]ncc4C3)cc2)c1]
212 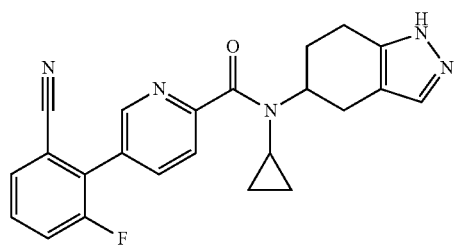 [SMILES: N#Cc1cccc(F)c1-c1ccc(C(=O)N(C2CC2)C2CCc3[nH]ncc3C2)nc1]
213 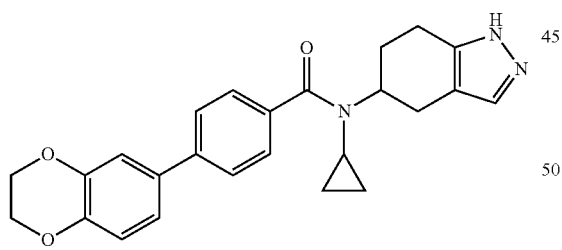
214 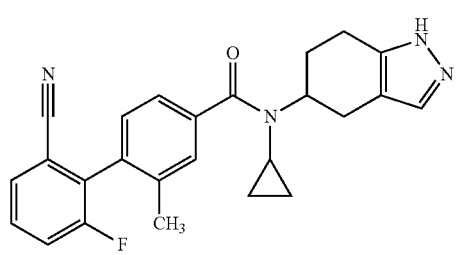 [SMILES: Cc1cc(C(=O)N(C2CC2)C2CCc3[nH]ncc3C2)ccc1-c1c(F)cccc1C#N]
TABLE 134
215 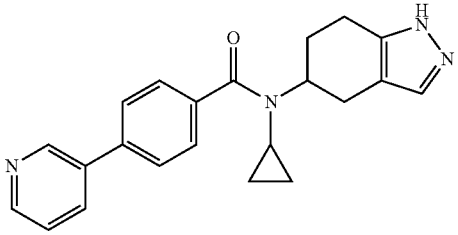 [SMILES: O=C(c1ccc(-c2cccnc2)cc1)N(C1CC1)C1CCc2[nH]ncc2C1]
216 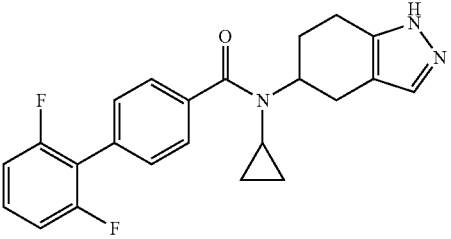 [SMILES: O=C(c1ccc(-c2c(F)cccc2F)cc1)N(C1CC1)C1CCc2[nH]ncc2C1]
217 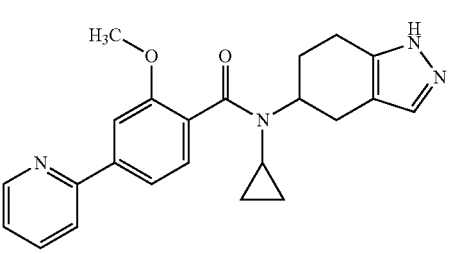 [SMILES: COc1cc(-c2ccccn2)ccc1C(=O)N(C1CC1)C1CCc2[nH]ncc2C1]
218 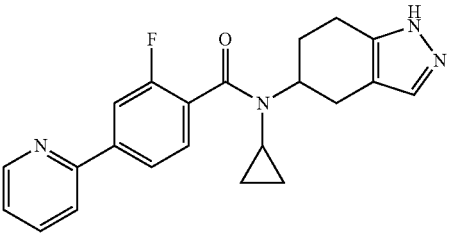 [SMILES: O=C(c1ccc(-c2ccccn2)cc1F)N(C1CC1)C1CCc2[nH]ncc2C1]
219 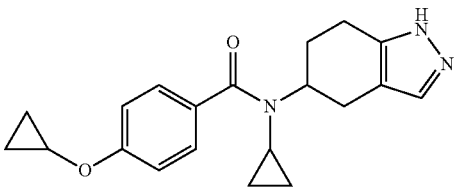 [SMILES: O=C(c1ccc(OC2CC2)cc1)N(C1CC1)C1CCc2[nH]ncc2C1]
TABLE 135
220 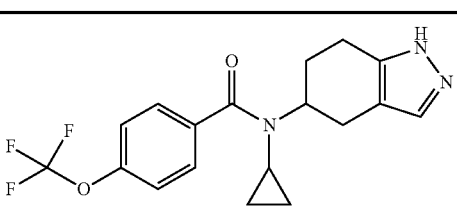

TABLE 135-continued
221 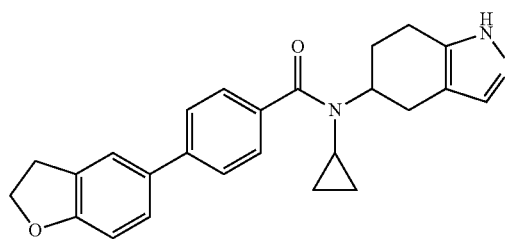
222 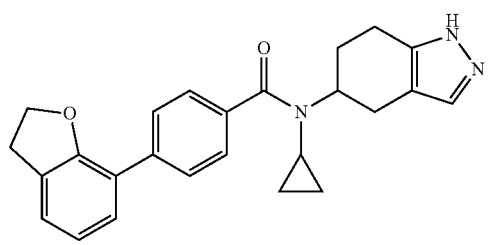 [SMILES: O=C(c1ccc(-c2cccc3c2OCC3)cc1)N(C1CC1)C1CCc2[nH]ncc2C1]
223 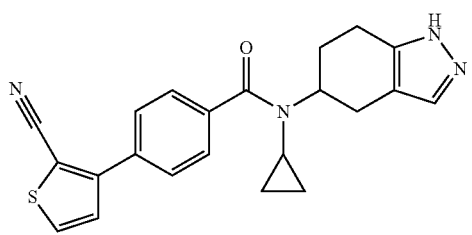 [SMILES: N#Cc1sccc1-c1ccc(C(=O)N(C2CC2)C2CCc3[nH]ncc3C2)cc1]
224 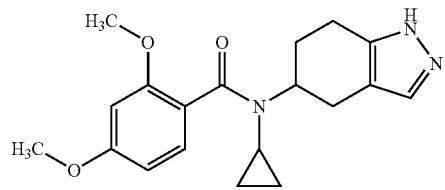 [SMILES: COc1ccc(C(=O)N(C2CC2)C2CCc3[nH]ncc3C2)c(OC)c1]
TABLE 136
225 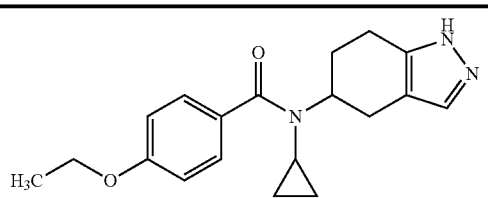
226 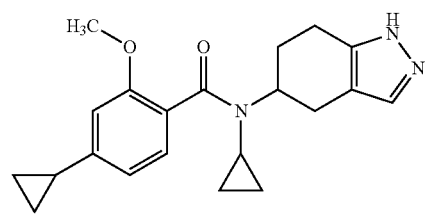 [SMILES: COc1cc(C2CC2)ccc1C(=O)N(C1CC1)C1CCc2[nH]ncc2C1]
227 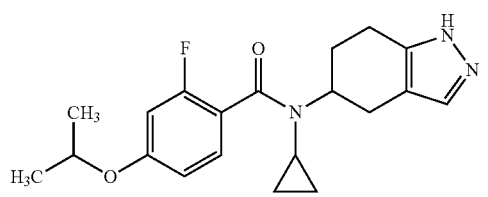 [SMILES: CC(C)Oc1ccc(C(=O)N(C2CC2)C2CCc3[nH]ncc3C2)c(F)c1]
TABLE 136-continued
228 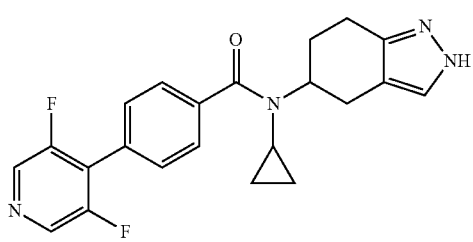 [SMILES: O=C(c1ccc(-c2c(F)cncc2F)cc1)N(C1CC1)C1CCc2n[nH]cc2C1]
229 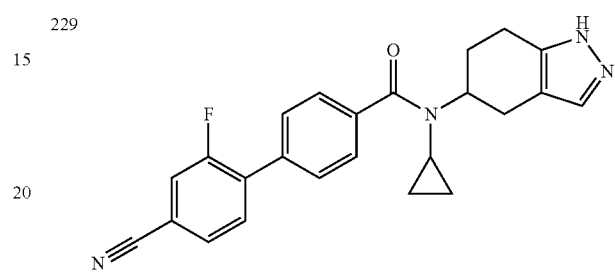
TABLE 137
230 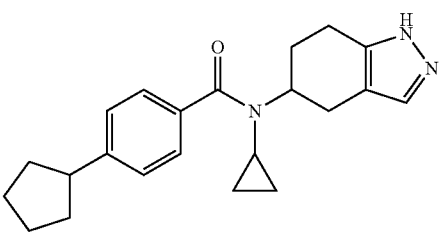 [SMILES: O=C(c1ccc(C2CCCC2)cc1)N(C1CC1)C1CCc2[nH]ncc2C1]
231 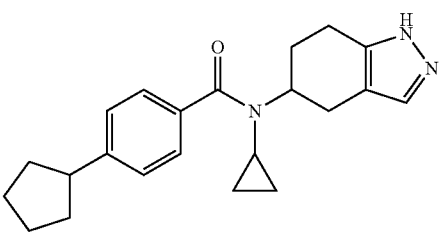 [SMILES: O=C(c1ccc(C2CCCC2)cc1)N(C1CC1)C1CCc2[nH]ncc2C1]
232 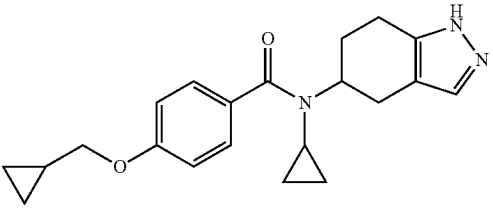 [SMILES: O=C(c1ccc(OCC2CC2)cc1)N(C1CC1)C1CCc2[nH]ncc2C1]
233 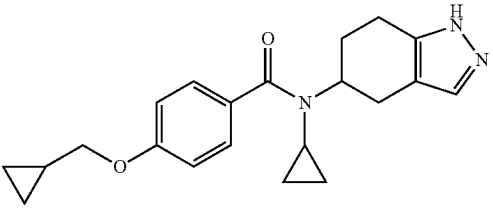 [SMILES: O=C(c1ccc(OCC2CC2)cc1)N(C1CC1)C1CCc2[nH]ncc2C1]

TABLE 137-continued
234
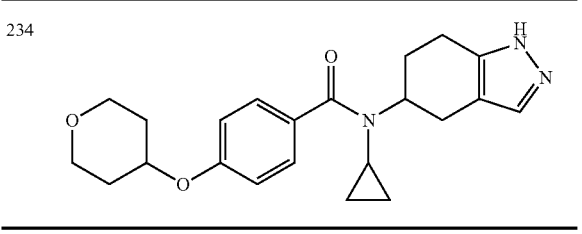
TABLE 138
235
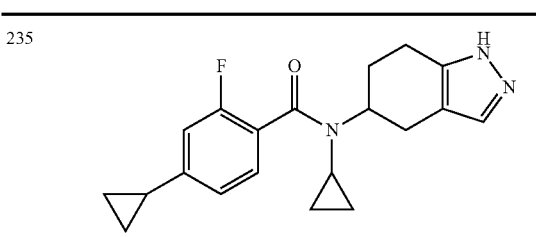
236
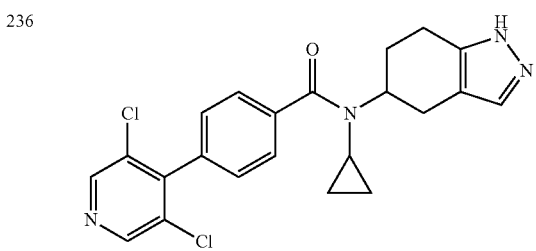
237
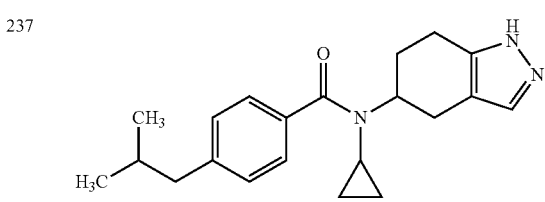
238
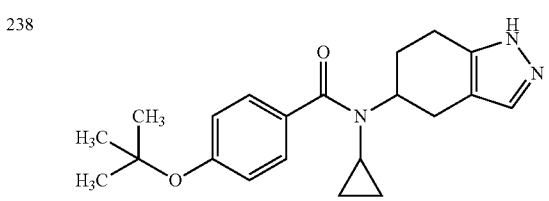
239
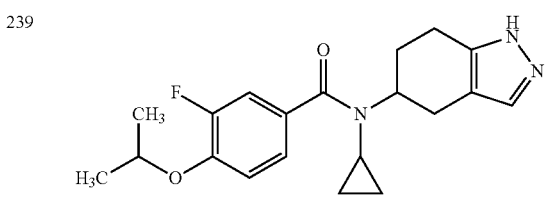
240
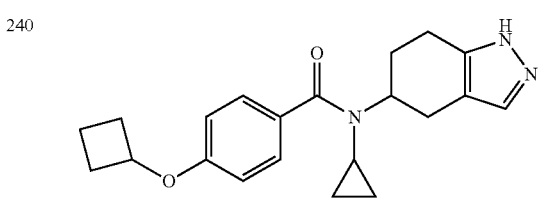
TABLE 139
241
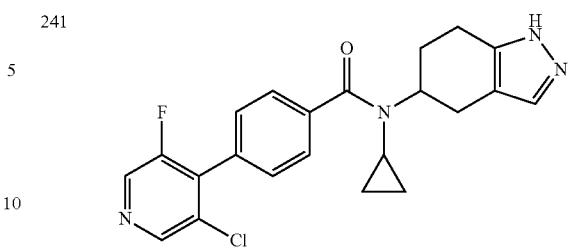
242
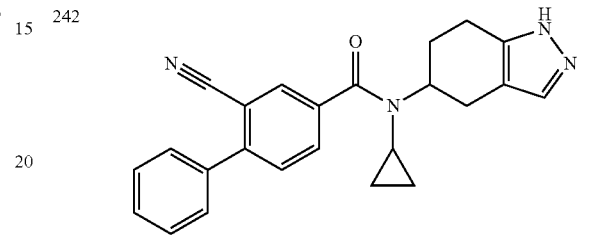
243
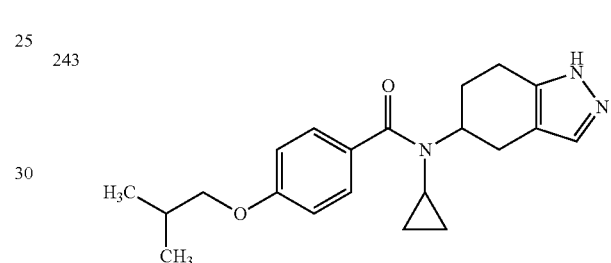
244
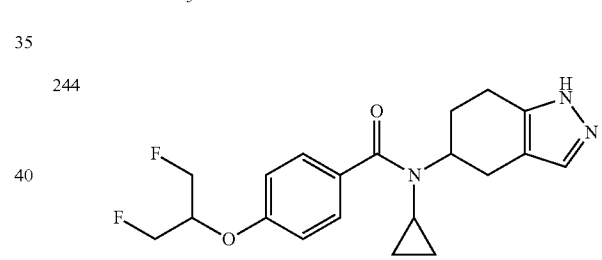
245
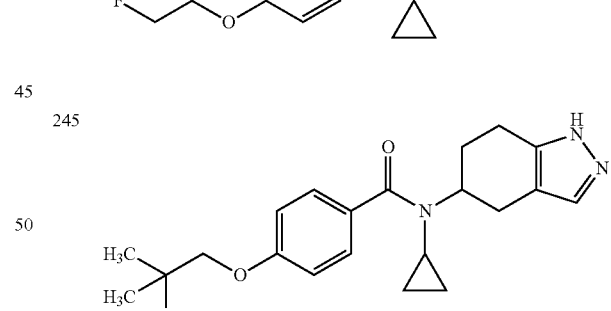
TABLE 140
246
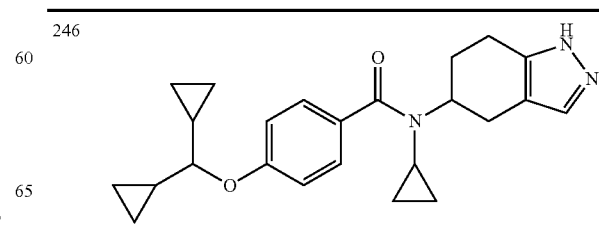

TABLE 140-continued
247 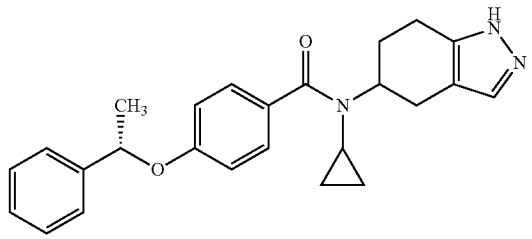 [SMILES: C[C@H](Oc1ccc(C(=O)N(C2CC2)C2CCc3[nH]ncc3C2)cc1)c1ccccc1]
248 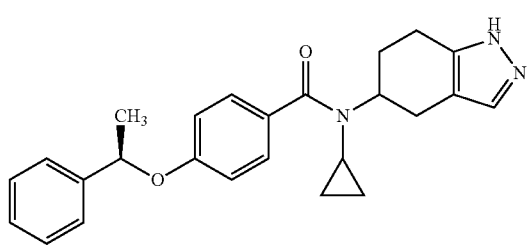 [SMILES: C[C@@H](Oc1ccc(C(=O)N(C2CC2)C2CCc3[nH]ncc3C2)cc1)c1ccccc1]
249 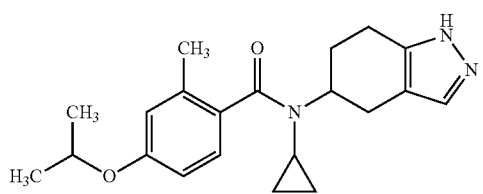 [SMILES: Cc1cc(OC(C)C)ccc1C(=O)N(C1CC1)C1CCc2[nH]ncc2C1]
250 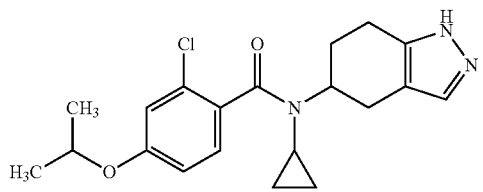 [SMILES: CC(C)Oc1ccc(C(=O)N(C2CC2)C2CCc3[nH]ncc3C2)c(Cl)c1]
TABLE 141
251 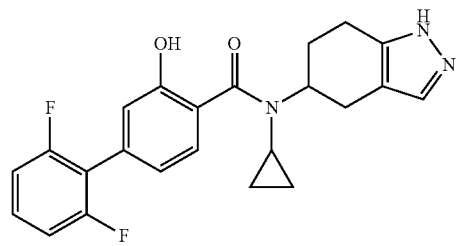 [SMILES: O=C(c1ccc(-c2c(F)cccc2F)cc1O)N(C1CC1)C1CCc2[nH]ncc2C1]
252 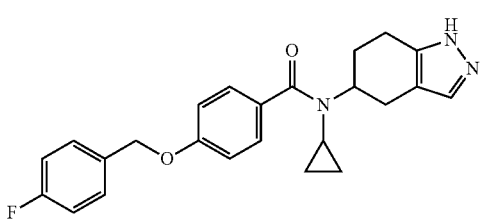 [SMILES: O=C(c1ccc(OCc2ccc(F)cc2)cc1)N(C1CC1)C1CCc2[nH]ncc2C1]
TABLE 141-continued
253 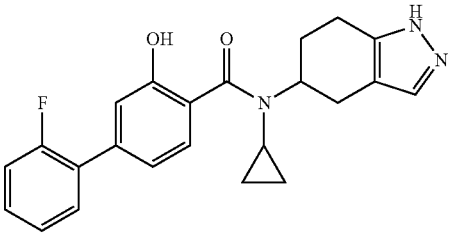 [SMILES: O=C(c1ccc(-c2ccccc2F)cc1O)N(C1CC1)C1CCc2[nH]ncc2C1]
254 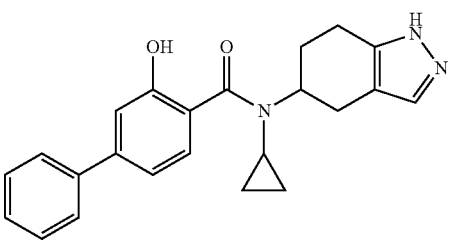 [SMILES: O=C(c1ccc(-c2ccccc2)cc1O)N(C1CC1)C1CCc2[nH]ncc2C1]
255 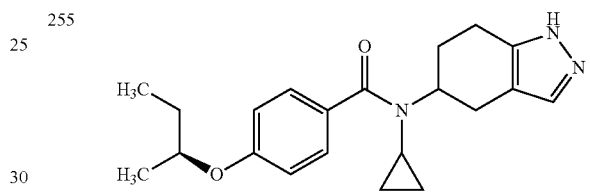
TABLE 142
256 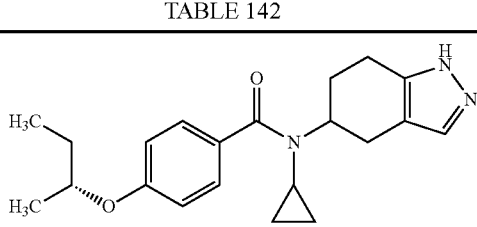
257 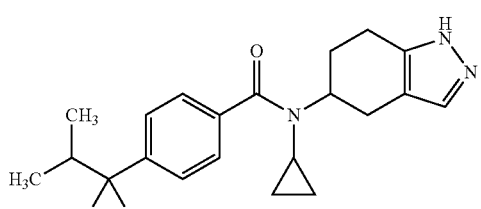
258 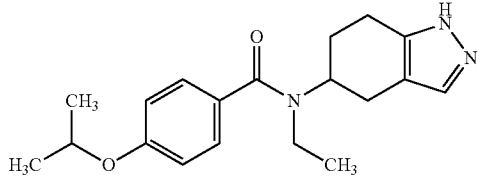 [SMILES: CCN(C(=O)c1ccc(OC(C)C)cc1)C1CCc2[nH]ncc2C1]
259 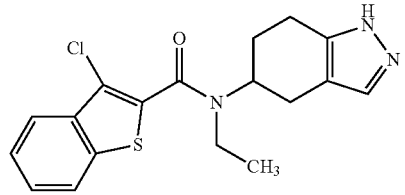 [SMILES: CCN(C(=O)c1sc2ccccc2c1Cl)C1CCc2[nH]ncc2C1]

TABLE 142-continued
260 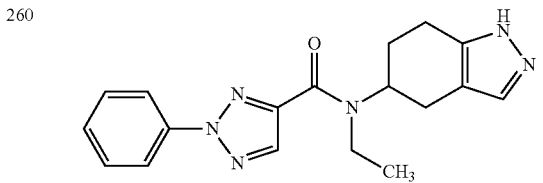
261 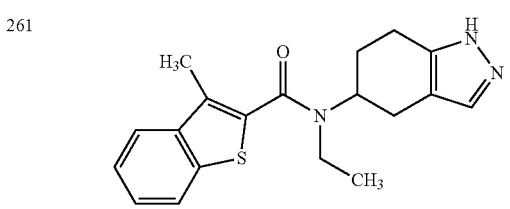
TABLE 143
262 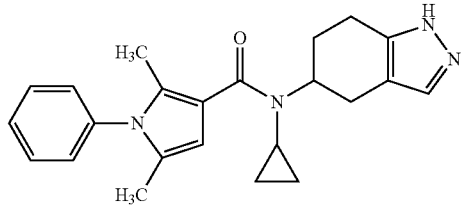 [SMILES: Cc1cc(C(=O)N(C2CC2)C2CCc3[nH]ncc3C2)c(C)n1-c1ccccc1]
263 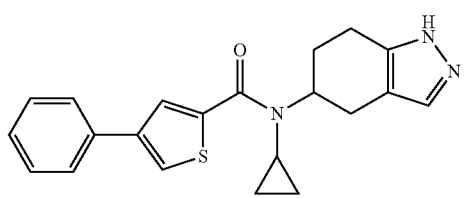 [SMILES: O=C(c1cc(-c2ccccc2)cs1)N(C1CC1)C1CCc2[nH]ncc2C1]
264 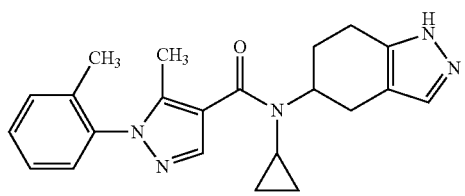 [SMILES: Cc1ccccc1-n1ncc(C(=O)N(C2CC2)C2CCc3[nH]ncc3C2)c1C]
266 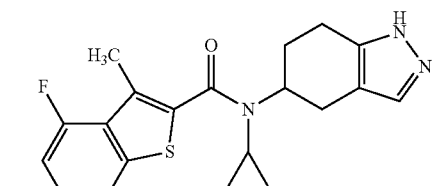
266 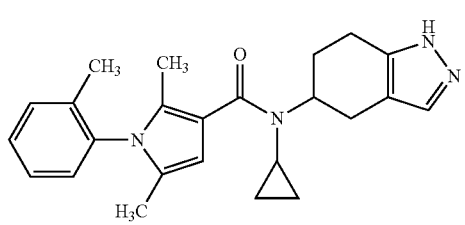
TABLE 143-continued
267 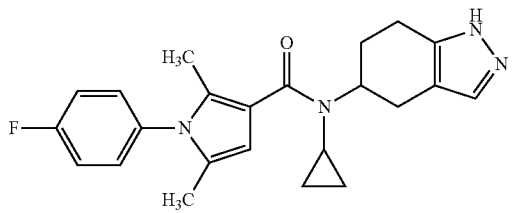 [SMILES: Cc1cc(C(=O)N(C2CC2)C2CCc3[nH]ncc3C2)c(C)n1-c1ccc(F)cc1]
TABLE 144
268 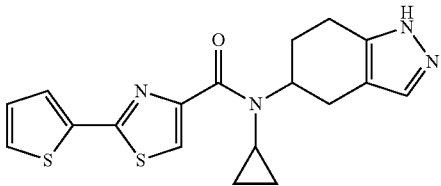 [SMILES: O=C(c1csc(-c2cccs2)n1)N(C1CC1)C1CCc2[nH]ncc2C1]
269 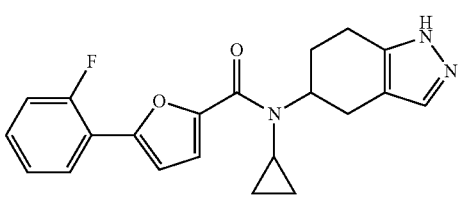 [SMILES: O=C(c1ccc(-c2ccccc2F)o1)N(C1CC1)C1CCc2[nH]ncc2C1]
270 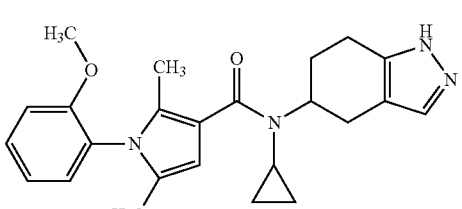
271 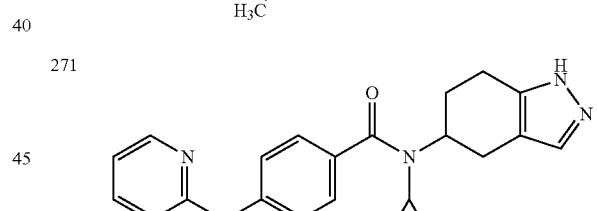
272 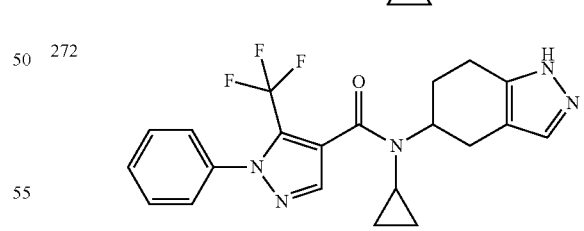
273 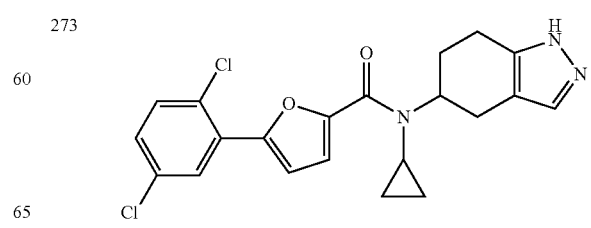

TABLE 145
274 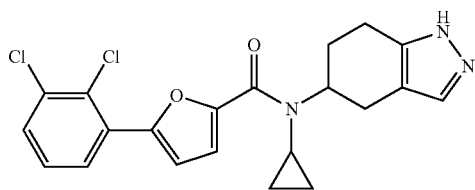 [SMILES: O=C(c1ccc(-c2cccc(Cl)c2Cl)o1)N(C1CC1)C1CCc2[nH]ncc2C1]
275 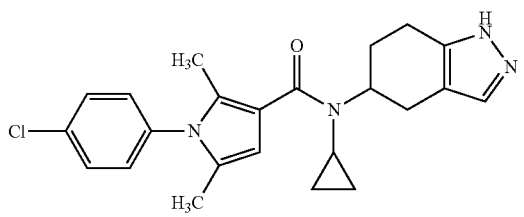 [SMILES: Cc1cc(C(=O)N(C2CC2)C2CCc3[nH]ncc3C2)c(C)n1-c1ccc(Cl)cc1]
276 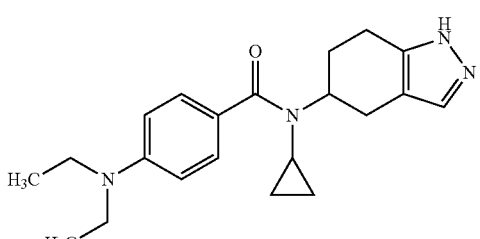
277 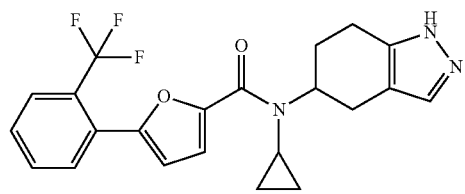 [SMILES: O=C(c1ccc(-c2ccccc2C(F)(F)F)o1)N(C1CC1)C1CCc2[nH]ncc2C1]
278 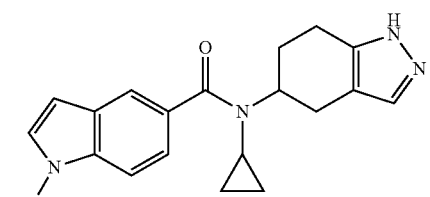
TABLE 146
279 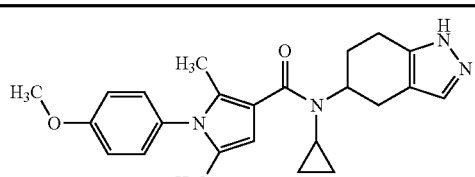
280 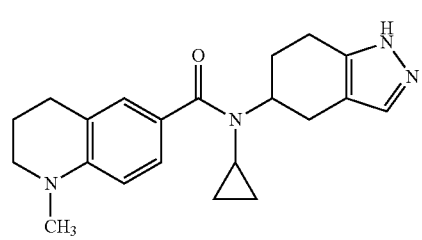 [SMILES: CN1CCCc2cc(C(=O)N(C3CC3)C3CCc4[nH]ncc4C3)ccc21]
TABLE 146-continued
281 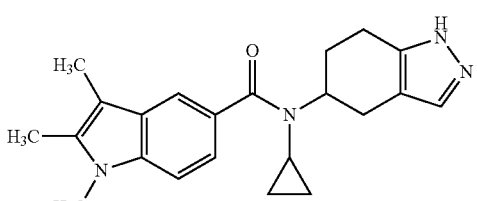
282 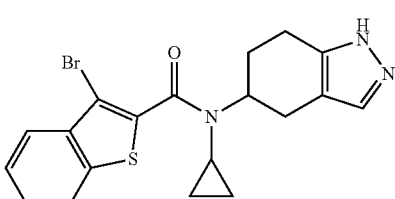
283 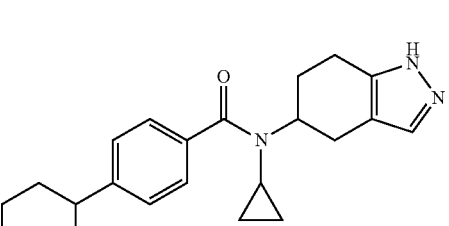
TABLE 147
284 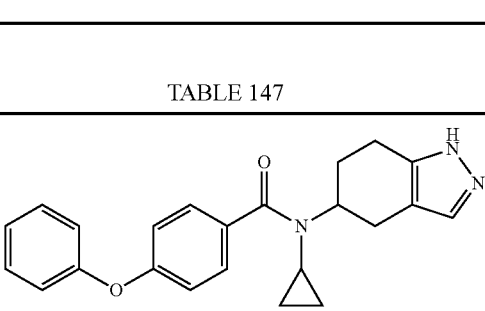
285 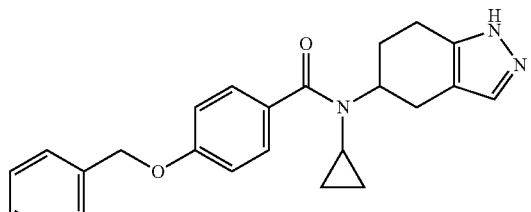
286 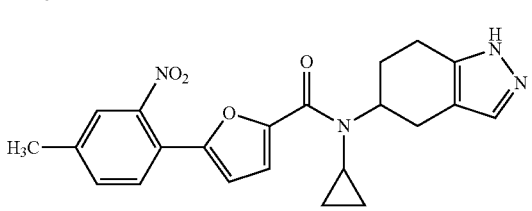 [SMILES: Cc1ccc(-c2ccc(C(=O)N(C3CC3)C3CCc4[nH]ncc4C3)o2)c([N+](=O)[O-])c1]
287 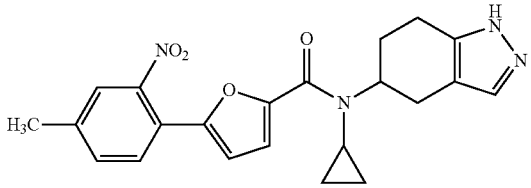 [SMILES: Cc1ccc(-c2ccc(C(=O)N(C3CC3)C3CCc4[nH]ncc4C3)o2)c([N+](=O)[O-])c1]

TABLE 147-continued
288 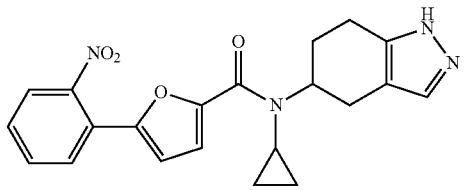 [SMILES: O=C(c1ccc(-c2ccccc2[N+](=O)[O-])o1)N(C1CC1)C1CCc2[nH]ncc2C1]
289 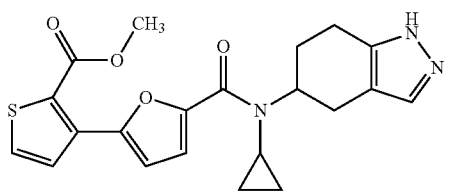 [SMILES: COC(=O)c1sccc1-c1ccc(C(=O)N(C2CC2)C2CCc3[nH]ncc3C2)o1]
TABLE 148
290 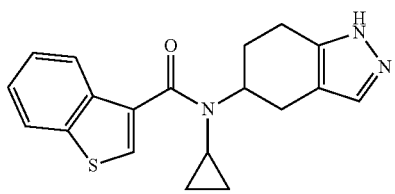 [SMILES: O=C(c1csc2ccccc12)N(C1CC1)C1CCc2[nH]ncc2C1]
291 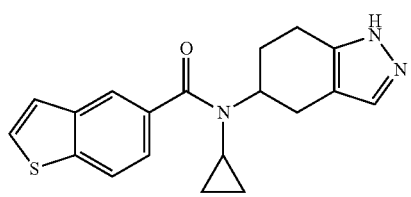 [SMILES: O=C(c1ccc2sccc2c1)N(C1CC1)C1CCc2[nH]ncc2C1]
292 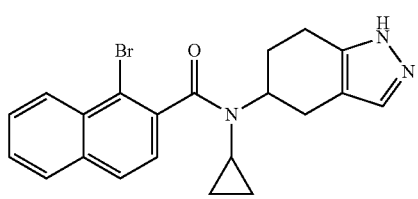 [SMILES: O=C(c1ccc2ccccc2c1Br)N(C1CC1)C1CCc2[nH]ncc2C1]
293 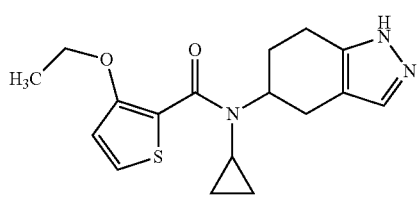 [SMILES: CCOc1ccsc1C(=O)N(C1CC1)C1CCc2[nH]ncc2C1]
294 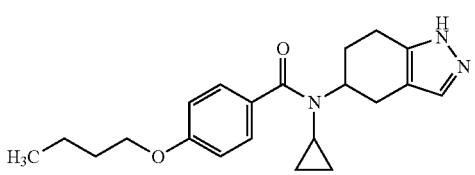 [SMILES: CCCCOc1ccc(C(=O)N(C2CC2)C2CCc3[nH]ncc3C2)cc1]
TABLE 148-continued
295 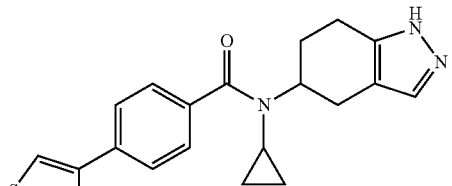
TABLE 149
296 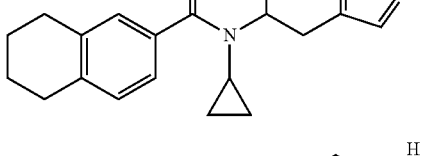
297 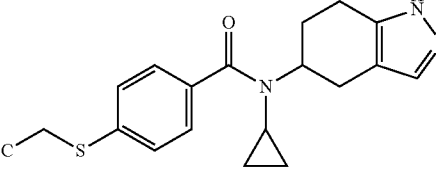
298 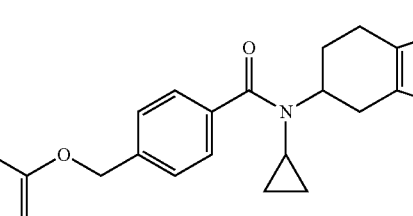
299 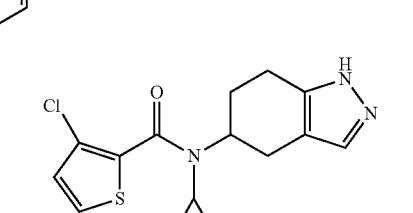
300 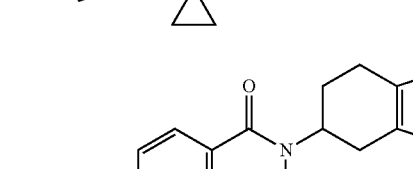
301 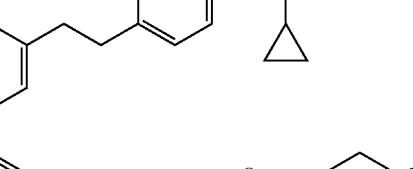

TABLE 150
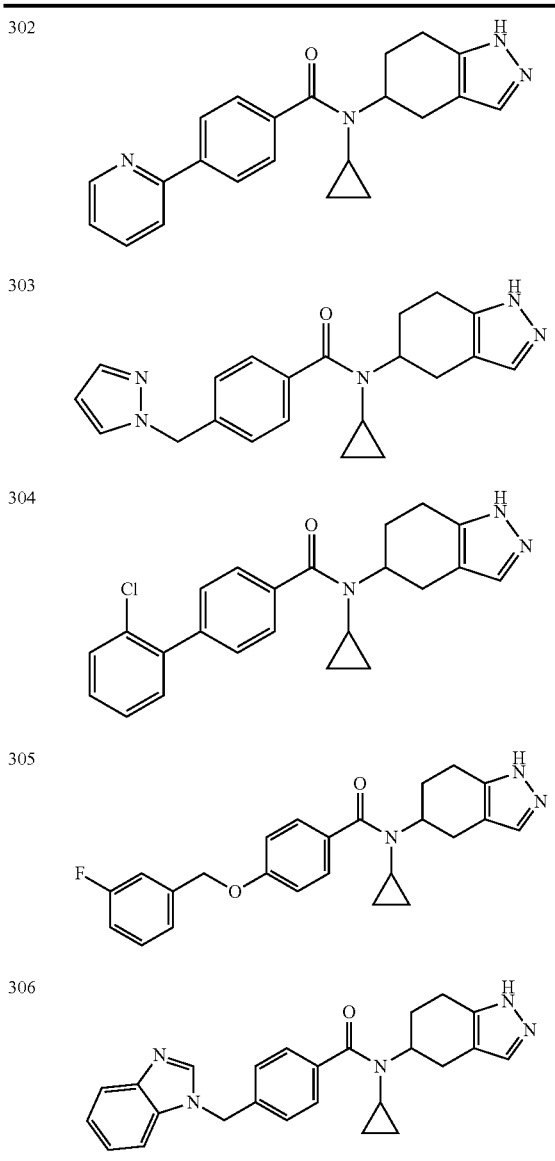
TABLE 151
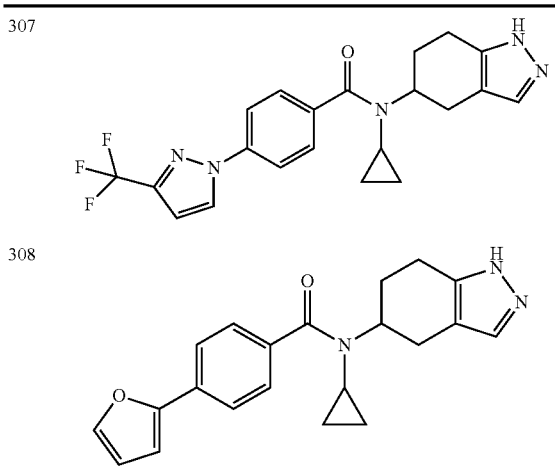
TABLE 151-continued
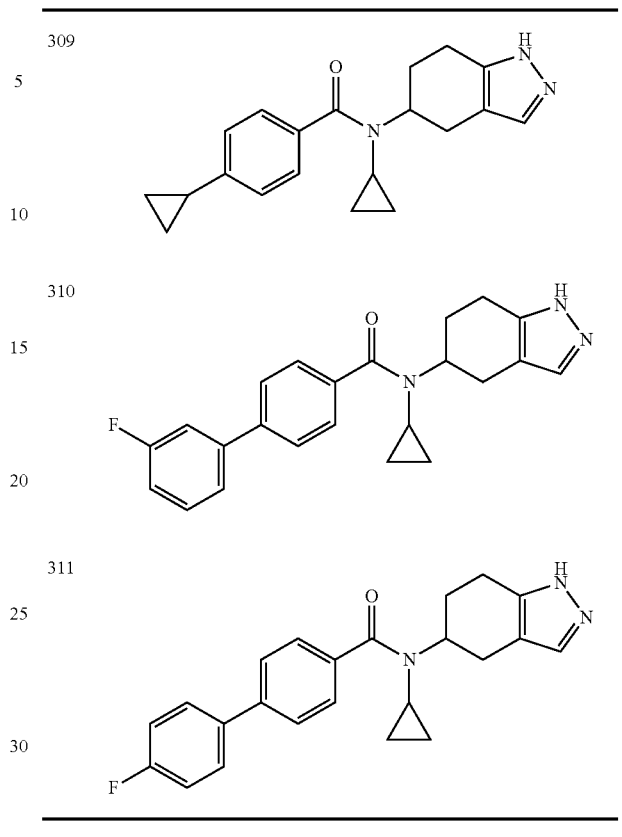
TABLE 152
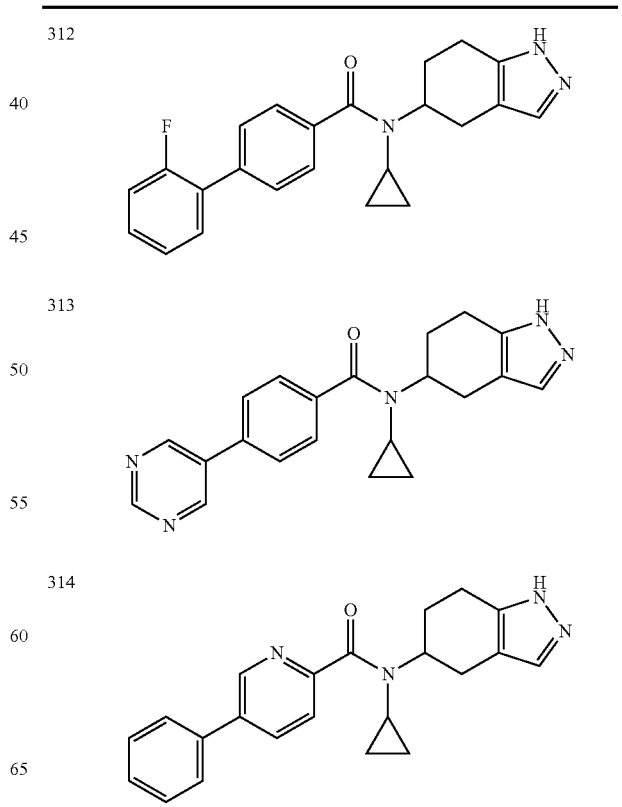

TABLE 152-continued

315

| Ex | Syn | Data |
|---|---|---|

(Structure: 4-(3-methylbutoxy)-N-cyclopropyl-N-(4,5,6,7-tetrahydro-1H-indazol-5-yl)benzamide)

TABLE 153

| Ex | Syn | Data |
|---|---|---|
| 1 | 1 | ESI+: 383.2 |
| 2 | 2 | ESI+: 367.2 |
| 3 | 3 | ESI+: 426 |
| 4 | 4 | ESI+: 411 |
| 5 | 5 | ESI+: 370.3, NMR-DMSOd6: 0.21-0.60 (m, 4H), 1.27 (d, J = 8 H, 6H), 1.93-2.34 (m, 2H), 2.57-3.00 (m, 5H), 3.78 (s, 3H), 4.16-4.31 (m, 1H), 4.62-4.71 (m, 1H), 6.50-6.53 (m, 2H), 7.06 (d, J = 8 Hz, 1H), 7.29, 12.3 (two brs, 2H). |
| 6 | 6 | ESI+: 417 |
| 7-1 | 7 | ESI+: 401.2, NMR-DMSOd6: 0.40-0.57 (m, 4H), 2.11-2.34 (m, 2H), 2.63-3.03 (m, 5H), 4.20-4.30 (m, 1H), 7.18-7.87 (m, 8H), 12.3 (brs, 1H). [□]$_D$-22.2 (CHCl3, c 0.515, 23.6° C.) |
| 7-2 | 7 | ESI+: 401.2 |
| 8-1 | 8 | ESI+: 340.2 NMR-DMSOd6: 0.35-0.59 (m, 4H), 1.28 (d, J = 8 Hz, 6H), 2.06-2.25 (m, 2H), 2.58-2.99 (m, 5H), 4.11-4.22 (m, 1H), 4.61-4.71 (m, 1H), 6.90 (d, J = 8 Hz, 2H), 7.45 (d, J = 8 Hz, 2H), 7.30, 12.3 (two brs, 2H). [□]$_D$-30.8 (CHCl3, c 0.5, 22.5° C.) |
| 8-2 | 8 | ESI+: 340.2 |
| 9 | 9 | ESI+: 379 |
| 10 | 10 | ESI+: 324 |
| 11 | 11 | ESI+: 347 |
| 12 | 12 | ESI+: 325 |
| 13 | 13 | ESI+: 338 |
| 14 | 14 | ESI+: 365 |
| 15 | 15 | ESI+: 430 |
| 16 | 16 | ESI+: 341 |
| 17 | 17 | ESI+: 395 |
| 18 | 18 | ESI+: 426 |
| 19 | 19 | ESI+: 402 |
| 20 | 20 | ESI+: 365 |
| 21 | 21 | ESI+: 374 |
| 22 | 22 | ESI+: 363 |
| 23 | 23 | ESI+: 340.2 |
| 24 | 24 | ESI+: 388 |
| 25 | 2 | ESI+: 312 |
| 26 | 2 | ESI+: 326 |
| 27 | P2, 2 | ESI+: 366 |
| 28 | P2, 2 | ESI+: 415 |
| 29 | P2, 2 | ESI+: 425 |
| 30 | P1, 2 | ESI+: 425 |
| 31 | P2, 2 | ESI+: 443, 445 |
| 32 | 2 | ESI+: 390 |

TABLE 154

| Ex | Syn | Data |
|---|---|---|
| 33 | 2 | ESI+: 376 |
| 34 | P2, 2 | ESI+: 389 |
| 35 | P2, 2 | ESI+: 403 |
| 36 | 2 | ESI+: 395 |
| 37 | 2 | ESI+: 381 |
| 38 | P2, 2 | ESI+: 423, 425 |
| 39 | P2, 2 | ESI+: 423, 425 |
| 40 | P2, 2 | ESI+: 423, 425 |
| 41 | 2 | ESI+: 457 |
| 42 | 2 | ESI+: 457 |
| 43 | 2 | ESI+: 457 |
| 44 | 2 | ESI+: 419 |
| 45 | 2 | ESI+: 419 |
| 46 | 2 | ESI+: 419 |
| 47 | 15 | ESI+: 444 |
| 48 | 2 | ESI+: 383 |
| 49 | 2 | ESI+: 397 |
| 50 | 2 | ESI+: 390 |
| 51 | 2 | ESI+: 390 |
| 52 | 2 | ESI+: 409 |
| 53 | 2 | ESI+: 395 |
| 54 | 15 | ESI+: 403 |
| 55 | 4 | ESI+: 411 |
| 56 | 4 | ESI+: 389 |
| 57 | 4 | ESI+: 349 |
| 58 | 4 | ESI+: 372 |
| 59 | 4 | ESI+: 362 |
| 60 | P2, 1 | ESI+: 307 |
| 61 | P2, 1 | ESI+: 325 |
| 62 | P2, 1 | ESI+: 341, 343 |
| 63 | P2, 1 | ESI+: 365 |
| 64 | P2, 1 | ESI+: 365 |
| 65 | P2, 1 | ESI+: 411 |
| 66 | P2, 1 | ESI+: 411 |
| 67 | P2, 1 | ESI+: 411 |
| 68 | 2 | ESI+: 425 |
| 69 | P2, 1 | ESI+: 350 |
| 70 | 2 | ESI+: 412 |
| 71 | 2 | ESI+: 412 |
| 72 | 12 | ESI+: 343 |
| 73 | 12 | ESI+: 359, 361 |
| 74 | P2, 1 | ESI+: 369, 371 |

TABLE 155

| Ex | Syn | Data |
|---|---|---|
| 75 | 2 | ESI+: 416 |
| 76 | 2 | ESI+: 416 |
| 77 | P2, 1 | ESI+: 356 |
| 78 | P2, 1 | ESI+: 356 |
| 79 | P2, 1 | ESI+: 349 |
| 80 | P2, 1 | ESI+: 363 |
| 81 | P2, 1 | ESI+: 335 |
| 82 | 2 | ESI+: 412 |
| 83 | 2 | ESI+: 412 |
| 84 | 2 | ESI+: 412 |
| 85 | 2 | ESI+: 362 |
| 86 | 2 | ESI+: 388 |
| 87 | 2 | ESI+: 372 |
| 88 | 2 | ESI+: 390 |
| 89 | 2 | ESI+: 412 |
| 90 | 2 | ESI+: 405 |
| 91 | 2 | ESI+: 392 |
| 92 | 2 | ESI+: 434, 436 |
| 93 | 2 | ESI+: 356 |
| 94 | 2 | ESI+: 356 |
| 95 | 2 | ESI+: 352 |
| 96 | 2 | ESI+: 356 |
| 97 | 2 | ESI+: 349 |
| 98 | 2 | ESI+: 379 |
| 99 | 1 | ESI+: 419 |
| 100 | 2 | ESI+: 354 |
| 101 | 2 | ESI+: 368 |
| 102 | 3 | ESI+: 349 |
| 103 | 3 | ESI+: 335 |
| 104 | 3 | ESI+: 335 |
| 105 | 3 | ESI+: 399 |
| 106 | 2 | ESI+: 383 |
| 107 | 2 | ESI+: 441 |
| 108 | 2 | ESI+: 434 |
| 109 | 1 | ESI+: 392 |
| 110 | 1 | ESI+: 350 |
| 111 | 3 | ESI+: 349 |
| 112 | 1 | ESI+: 407 |
| 113 | 1 | ESI+: 335 |
| 114 | 1 | ESI+: 335 |
| 115 | 1 | ESI+: 393 |
| 116 | 1 | ESI+: 391.2 |

TABLE 156

| | | |
|---|---|---|
| 117 | 1 | ESI+: 405.3 |
| 118 | 2 | ESI+: 393.3 |
| 119 | 1 | ESI+: 336 |
| 120 | 1 | ESI+: 336 |
| 121 | 1 | ESI+: 393.4 |
| 122 | 2 | ESI+: 381.3 |
| 123 | 9 | ESI+: 393 |
| 124 | 1 | ESI+: 321.5 |
| 125 | P20, P1, 1 | ESI+: 391.3 |
| 126 | 1 | ESI+: 432.3 |
| 127 | 1 | ESI+: 447.3 |
| 128 | P1, 2 | ESI+: 392.3 |
| 129 | 1 | ESI+: 377 |
| 130 | 1 | ESI+: 406.4 |
| 131 | 1 | ESI+: 418.2 |
| 132 | P20, P1, 1 | ESI+: 365.3, NMR-DMSOd6: 0.72-0.47 (m, 4H), 2.08-2.30 (m, 2H), 2.53-3.05 (m, 5H), 3.91 (s, 3), 4.00 (s, 3H), 4.14-4.24 (m, 1H), 6.31 (d, J = 2.8 Hz, 1H), 6.65 (d, J = 8 Hz, 1H), 7.00 (d, J = 8 Hz, 1H), 7.23 (d, J = 2.8 Hz, 1H), 7.31, 12.3 (brs, 2H). |
| 133 | 1 | ESI+: 337 |
| 134 | 11 | ESI+: 351 |
| 135 | 11 | ESI+: 363 |
| 136 | 1 | ESI+: 413 |
| 137 | 1 | ESI+: 336.2 |
| 138 | 1 | ESI+: 385.2 |
| 139 | P1, 1 | ESI+: 353.2 |
| 140 | 1 | ESI+: 380.3 |
| 141 | 1 | ESI+: 350.2 |
| 142 | 1 | ESI+: 364.2 |
| 143 | 1 | ESI+: 364.2 |
| 144 | P20, P1, 1 | ESI+: 382.2 |
| 145 | 1 | ESI+: 368.3 |
| 146 | 1 | ESI+: 394.2 |
| 147 | 1 | ESI+: 366.2 |
| 148 | P20, P1, 1 | ESI+: 392.3 |
| 149 | 1 | ESI+: 420 |
| 150 | 1 | ESI+: 336 |
| 151 | 1 | ESI+: 480 |
| 152 | 1 | ESI+: 390 |

TABLE 157

| | | |
|---|---|---|
| 153 | 1 | ESI+: 394.3 |
| 154 | 1 | ESI+: 394.2 |
| 155 | 1 | ESI+: 386.2 |
| 156 | 1 | ESI+: 397.3 |
| 157 | 1 | ESI+: 392.3 |
| 158 | 1 | ESI+: 358.3 |
| 159 | 1 | ESI+: 428.2 |
| 160 | 1 | ESI+: 398 |
| 161 | 1 | ESI+: 466.1 |
| 162 | 1 | ESI+: 432.3 |
| 163 | 1 | ESI+: 394.3 |
| 164 | 1 | ESI+: 373 |
| 165 | 1 | ESI+: 365 |
| 166 | 1 | ESI+: 397 |
| 167 | 1 | ESI+: 397 |
| 168 | 1 | ESI+: 417, 419 |
| 169 | 1 | ESI+: 422.3 |
| 170 | 1 | ESI+: 418.3 |
| 171 | 1 | ESI+: 384.2 |
| 172 | 1 | ESI+: 401.2 |
| 173 | 1 | ESI+: 416.2 |
| 174 | 1 | ESI+: 359 |
| 175 | 1 | ESI+: 424.3 |
| 176 | 1 | ESI+: 401.3, NMR-DMSOd6: 0.40-0.60 (m, 4H), 2.10-2.34 (m, 2H), 2.57-3.03 (m, 5H), 4.14-4.24 (m, 1H), 7.13-8.01 (m, 8H), 12.3 (brs, 1H). |
| 177 | 1 | ESI+: 411 |
| 178 | 1 | ESI+: 392 |
| 179 | 1 | ESI+: 378 |
| 180 | 1 | ESI+: 406.2 |

TABLE 157-continued

| | | |
|---|---|---|
| 181 | 1 | ESI+: 375.2 |
| 182 | 1 | ESI+: 413 |
| 183 | 1 | ESI+: 384.3 |
| 184 | 1 | ESI+: 437 |
| 185 | 1 | ESI+: 392 |
| 186 | 1 | ESI+: 406 |
| 187 | 1 | ESI+: 437 |
| 188 | 3 | ESI+: 367 |
| 189 | 1 | ESI+: 436 |
| 190 | 1 | ESI+: 401.2, NMR-DMSOd6: 0.46-0.60 (m, 4H), 2.04-2.34 (m, 2H), 2.63-3.05 (m, 5H), 4.24-4.39 (m, 1H), 7.17-8.00 (m, 8H), 12.3 (brs, 1H). |

TABLE 158

| | | |
|---|---|---|
| 191 | 1 | ESI+: 413.2 |
| 192 | 1 | ESI+: 398 |
| 193 | 1 | ESI+: 383.2 |
| 194 | 1 | ESI+: 377.2 |
| 195 | 1 | ESI+: 373.2 |
| 196 | 1 | ESI+: 360 |
| 197 | 5 | ESI+: 346 |
| 198 | 1 | ESI+: 417.1 |
| 199 | 1 | ESI+: 401.2 |
| 200 | 5 | ESI+: 360 |
| 201 | P1, 5 | ESI+: 332 |
| 202 | 1 | ESI+: 377.3 |
| 203 | 1 | APCI/ESI+: 373.0 |
| 204 | 1 | ESI+: 429 |
| 205 | 1 | ESI+: 360 |
| 206 | P1, 1 | ESI+: 415 |
| 207 | P1, 1 | ESI+: 401 |
| 208 | 1 | APCI/ESI+: 401 |
| 209 | 5 | ESI+: 360 |
| 210 | 1 | ESI+: 398 |
| 211 | 1 | APCI/ESI+: 401 |
| 212 | 1 | APCI/ESI+: 402 |
| 213 | 1 | ESI+: 416 |
| 214 | 1 | APCI/ESI+: 415 |
| 215 | 5 | ESI+: 359 |
| 216 | 1 | ESI+: 394.3, NMR-DMSO-d6: 0.43-0.58 (m, 4H), 2.11-2.33 (m, 2H), 2.60-3.03 (m, 5H), 4.14-4.28 (m, 1H), 7.17-7.67 (m, 8H), 12.3 (brs, 1H). |
| 217 | P4, P1, 5 | ESI+: 389.3 |
| 218 | P4, P1, 5 | ESI+: 377.3 |
| 219 | 1 | APCI/ESI+: 338.1 |
| 220 | 1 | APCI/ESI+: 366.0 |
| 221 | 1 | APCI/ESI+: 400 |
| 222 | 1 | APCI/ESI+: 400 |
| 223 | 5 | ESI+: 389 |
| 224 | 5 | APCI/ESI+: 342.1 |
| 225 | 1 | APCI/ESI+: 326 |
| 226 | 5 | APCI/ESI+: 352.1 |
| 227 | 5 | APCI/ESI+: 358.1 |
| 228 | 5 | ESI+: 395 |

TABLE 159

| | | |
|---|---|---|
| 229 | 5 | ESI+: 401 |
| 230 | 5 | ESI+: 350 |
| 231 | 5 | ESI+: 352 |
| 232 | 5 | ESI+: 354 |
| 233 | 5 | ESI+: 395 |
| 234 | 5 | ESI+: 382.3 |
| 235 | P1, 5 | ESI+: 340 |
| 236 | 5 | ESI+: 427, 429, 431 |
| 237 | 5 | ESI+: 338 |
| 238 | 5 | ESI+: 354 |
| 239 | 5 | ESI+: 358.2 |
| 240 | 5 | ESI+: 352 |
| 241 | 5 | ESI+: 411, 413 |
| 242 | 5 | ESI+: 383 |
| 243 | 5 | ESI+: 354 |

TABLE 159-continued

| 244 | 5 | ESI+: 376 |
| --- | --- | --- |
| 245 | 5 | ESI+: 368 |
| 246 | 5 | ESI+: 392 |
| 247 | 5 | ESI+: 402 |
| 248 | 5 | ESI+: 402 |
| 249 | 5 | ESI+: 354.2 |
| 250 | 5 | ESI+: 374.2 |
| 251 | 6 | ESI+: 410.1 |
| 252 | 5 | ESI+: 406 |
| 253 | 6 | ESI+: 392.3 |
| 254 | 6 | ESI+: 374.3 |
| 255 | 5 | ESI+: 354 |
| 256 | 5 | ESI+: 354 |
| 257 | 5 | ESI+: 374 |
| 258 | 16 | ESI+: 328 |
| 259 | 16 | ESI+: 360 |
| 260 | 16 | ESI+: 337 |
| 261 | 16 | ESI+: 340 |
| 262 | 17 | ESI+: 375 |
| 263 | 17 | ESI+: 364 |
| 264 | 17 | ESI+: 376 |
| 266 | 17 | ESI+: 370 |
| 266 | 17 | ESI+: 389 |
| 267 | 17 | ESI+: 393 |
| 268 | 17 | ESI+: 371 |
| 269 | 17 | ESI+: 366 |
| 270 | 17 | ESI+: 405 |

TABLE 160

| 271 | 17 | ESI+: 375 |
| --- | --- | --- |
| 272 | 17 | ESI+: 416 |
| 273 | 17 | ESI+: 416 |
| 274 | 17 | ESI+: 416 |
| 275 | 17 | ESI+: 409 |
| 276 | 17 | ESI+: 353 |
| 277 | 17 | ESI+: 416 |
| 278 | 17 | ESI+: 335 |
| 279 | 17 | ESI+: 405 |
| 280 | 17 | ESI+: 351 |
| 281 | 17 | ESI+: 363 |
| 282 | 17 | ESI+: 416 |
| 283 | 17 | ESI+: 364 |
| 284 | 17 | ESI+: 374 |
| 285 | 17 | ESI+: 388 |
| 286 | 17 | ESI+: 427 |
| 287 | 17 | ESI+: 407 |
| 288 | 17 | ESI+: 393 |
| 289 | 17 | ESI+: 412 |
| 290 | 17 | ESI+: 338 |
| 291 | 17 | ESI+: 338 |
| 292 | 17 | ESI+: 410 |
| 293 | 17 | ESI+: 332 |
| 294 | 17 | ESI+: 354 |
| 295 | 17 | ESI+: 364 |
| 296 | 17 | ESI+: 336 |
| 297 | 17 | ESI+: 342 |
| 298 | 17 | ESI+: 388 |
| 299 | 17 | ESI+: 322 |
| 300 | 17 | ESI+: 386 |
| 301 | 17 | ESI+: 388 |
| 302 | 17 | ESI+: 359 |
| 303 | 17 | ESI+: 362 |
| 304 | 18 | ESI+: 392 |
| 305 | 18 | ESI+: 406 |
| 306 | 18 | ESI+: 412 |
| 307 | 18 | ESI+: 416 |
| 308 | 18 | ESI+: 348 |
| 309 | 18 | ESI+: 322 |
| 310 | 19 | ESI+: 376 |
| 311 | 19 | ESI+: 376 |
| 312 | 19 | ESI+: 376 |

TABLE 161

| 313 | 19 | ESI+: 360 |
| --- | --- | --- |
| 314 | 19 | ESI+: 377 |
| 315 | 19 | ESI+: 368 |

INDUSTRIAL APPLICABILITY

The compound of the present invention has an excellent 11β-HSD1 inhibitory action. Therefore, the compound is useful as an active ingredient of a pharmaceutical composition for treating 11β-HSD1-related diseases such as dementia (particularly, Alzheimer's type dementia), schizophrenia, depression, pain (particularly, neuropathic pain or fibromyalgia), diabetes (particularly, type II diabetes mellitus), insulin resistance, obesity, hyperlipidemia, hypertension, osteoporosis, and glaucoma, particularly, for treating dementia (particularly, Alzheimer's type dementia), schizophrenia, depression, pain (particularly, neuropathic pain or fibromyalgia), diabetes (particularly, type II diabetes mellitus), and insulin resistance.

The invention claimed is:

1. A compound represented by formula (I) or a pharmaceutically acceptable salt thereof:

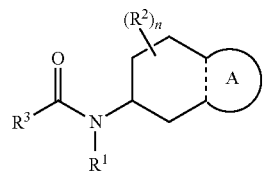

(I)

wherein:
ring A is a 5- to 6-membered monocyclic heterocycle which may be substituted and has only nitrogen atom(s) as the hetero atom; wherein the atoms in the position where the ring is fused with the adjacent ring are carbon atoms;
$R^1$ is lower alkyl, halogeno-lower alkyl, or cycloalkyl which may be substituted;
$R^2$ is halogen or lower alkyl;
$R^3$ is aryl, heteroaryl, or lower alkylene-heteroaryl; wherein each of the aryl and heteroaryl represented by $R^3$ may be substituted;
n is an integer of 0 to 3; and
a dotted line represents a single bond or a double bond.

2. The compound or pharmaceutically acceptable salt thereof according to claim 1, wherein n represents 0.

3. The compound or pharmaceutically acceptable salt therof according to claim 2, wherein $R^1$ represents cyclopropyl.

4. The compound or pharmaceutically acceptable salt thereof according to claim 3, wherein the bicyclic ring which is formed by ring A fused with the adjacent ring is 4,5,6,7-tetrahydroindazol-5-yl.

5. The compound or pharmaceutically acceptable salt thereof according to claim 4, wherein
$R^3$ represents phenyl, indolyl, or indazolyl, which may be substituted respectively with a group selected from Group Q,
Group Q is selected from the group consisting of halogen, lower alkyl, halogeno-lower alkyl, —OR$^0$, lower alkylene-OR$^0$, —S-lower alkyl, aryl, a heterocyclic group, and lower alkylene-heterocyclic group, wherein, said aryl and heterocyclic group in Group Q may be substituted with halogen, cyano, lower alkyl, —OR⁰, or oxo, and R⁰ represents —H or lower alkyl.

6. The compound or pharmaceutically acceptable salt thereof according to claim 5, wherein
   R³ represent phenyl which may be substituted with a group selected from the group consisting of
   (i) phenyl or pyridyl, which may be respectively substituted with halogen or cyano,
   (ii) halogen,
   (iii) lower alkyl, and
   (iv) —O-lower alkyl.

7. The compound or pharmaceutically acceptable salt thereof according to claim 5,
   wherein R³ represents indolyl which may be substituted with lower alkyl or —O-lower alkyl.

8. The compound or pharmaceutically acceptable salt thereof according to claim 1 which is a compound selected from the group consisting of
   (−)—N-cyclopropyl-4-isopropoxy-N-(4,5,6,7-tetrahydro-1H-indazol-5-yl) benzamide,
   (−)-2'-cyano-N-cyclopropyl-6'-fluoro-N-(4,5,6,7-tetrahydro-1H-indazol-5-yl) biphenyl-4-carboxamide,
   N-cyclopropyl-1-methyl-N-(4,5,6,7-tetrahydro-1H-indazol-5-yl)-1H-indole-4-carboxamide,
   N-cyclopropyl-7-methoxy-1-methyl-N-(4,5,6,7-tetrahydro-1H-indazol-5-yl)-1H-indole-4-carboxamide,
   2'-cyano-N-cyclopropyl-4'-fluoro-N-(4,5,6,7-tetrahydro-1H-indazol-5-yl)biphenyl-4-carboxamide,
   2'-cyano-N-cyclopropyl-3-fluoro-N-(4,5,6,7-tetrahydro-1H-indazol-5-yl)biphenyl-4-carboxamide,
   N-cyclopropyl-2',6'-difluoro-N-(4,5,6,7-tetrahydro-1H-indazol-5-yl)biphenyl-4-carboxamide,
   N-cyclopropyl-4-(3,5-difluoropyridin-4-yl)-N-(4,5,6,7-tetrahydro-2H-indazol-5-yl) benzamide, and
   N-cyclopropyl-4-isopropoxy-2-methoxy-N-(4,5,6,7-tetrahydro-1H-indazol-5-yl) benzamide,
   or a pharmaceutically acceptable salt of said compound.

9. The compound or pharmaceutically acceptable salt thereof according to claim 1, which is
   (−)—N-cyclopropyl-4-isopropoxy-N-(4,5,6,7-tetrahydro-1H-indazol-5-yl)benzamide, or a pharmaceutically acceptable salt of said compound.

10. The compound or pharmaceutically acceptable salt thereof according to claim 1, which is
    (−)-2'-cyano-N-cyclopropyl-6'-fluoro-N-(4,5,6,7-tetrahydro-1H-indazol-5-yl) biphenyl-4-carboxamide, or a pharmaceutically acceptable salt of said compound.

11. A pharmaceutical composition, comprising:
    a compound or pharmaceutically acceptable salt thereof according to claim 8; and
    at least one pharmaceutically acceptable carrier.

12. A method of treating dementia, schizophrenia, depression, or pain, comprising administering an effective amount of a compound or pharmaceutically acceptable salt thereof according to claim 8 to a patient in need thereof.

13. A method of treating dementia, comprising administering an effective amount of a compound or pharmaceutically acceptable salt thereof according to claim 8 to a patient in need thereof.

14. The method according to claim 13, wherein said dementia is Alzheimer's type dementia.

15. A method of treating or pain, comprising administering an effective amount of a compound or pharmaceutically acceptable salt thereof according to claim 8 to a patient in need thereof.

16. The method according to claim 15, wherein said pain is neuropathic pain or fibromyalgia.

* * * * *